(12) United States Patent
Trakht et al.

(10) Patent No.: US 7,820,400 B2
(45) Date of Patent: Oct. 26, 2010

(54) TUMOR-ASSOCIATED MARKER

(75) Inventors: Ilya Trakht, New York, NY (US);
Robert Canfield, Cold Spring, NY (US);
Gary Kalantarov, Fort Lee, NJ (US);
Sergei Rudchenko, Bronx, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 327 days.

(21) Appl. No.: 11/453,186

(22) Filed: Jun. 13, 2006

(65) Prior Publication Data

US 2006/0292644 A1  Dec. 28, 2006

Related U.S. Application Data

(63) Continuation of application No. 09/664,958, filed on Sep. 18, 2000, now Pat. No. 7,060,802.

(51) Int. Cl.
*G01N 33/574* (2006.01)
(52) U.S. Cl. .................................. 435/7.23; 435/7.1
(58) Field of Classification Search .............. None
See application file for complete search history.

(56) References Cited

U.S. PATENT DOCUMENTS

| | | | |
|---|---|---|---|
| 4,281,061 A * | 7/1981 | Zuk et al. ................. | 435/7.9 |
| 4,574,116 A | 3/1986 | Kaplan et al. | |
| 4,613,576 A | 9/1986 | Cote et al. | |
| 4,618,577 A | 10/1986 | Handley et al. | |
| 4,634,664 A | 1/1987 | Oestberg | |
| 4,634,666 A | 1/1987 | Engleman et al. | |
| 4,668,629 A | 5/1987 | Kaplan et al. | |
| 4,689,299 A | 8/1987 | Insel et al. | |
| 4,714,681 A | 12/1987 | Reading et al. | |
| 4,720,459 A | 1/1988 | Winkelhake | |
| 4,744,982 A | 5/1988 | Hunter et al. | |
| 4,761,377 A | 8/1988 | Glassy et al. | |
| 4,800,155 A | 1/1989 | Taniguchi et al. | |
| 4,834,976 A | 5/1989 | Rosok et al. | |
| 4,916,072 A | 4/1990 | Tsuji et al. | |
| 4,950,595 A | 8/1990 | Masuho et al. | |
| 4,954,449 A | 9/1990 | Hunter et al. | |
| 4,997,762 A | 3/1991 | Hanna, Jr. et al. | |
| 5,001,065 A | 3/1991 | Larrick et al. | |
| 5,003,046 A | 3/1991 | Neville et al. | |
| 5,006,470 A | 4/1991 | Yamaguchi et al. | |
| 5,093,261 A | 3/1992 | Hagiwara et al. | |
| 5,126,259 A | 6/1992 | Tada et al. | |
| 5,196,337 A | 3/1993 | Ochi et al. | |
| 5,215,913 A | 6/1993 | Posner | |
| 5,252,480 A | 10/1993 | Yokota et al. | |
| 5,298,419 A | 3/1994 | Masuho et al. | |
| 5,426,046 A | 6/1995 | Kaplan et al. | |
| 5,459,060 A | 10/1995 | Cotropia | |
| 5,506,132 A | 4/1996 | Lake et al. | |
| 5,565,354 A | 10/1996 | Ostberg | |
| 5,576,184 A | 11/1996 | Better et al. | |
| 5,652,114 A | 7/1997 | Chu et al. | |
| 5,879,936 A | 3/1999 | Bebbington et al. | |
| 6,197,582 B1 | 3/2001 | Trakht | |
| 6,368,826 B1 | 4/2002 | Ligensa et al. | |
| 6,455,040 B1 | 9/2002 | Wei et al. | |
| 6,913,883 B2 | 7/2005 | Ligensa et al. | |
| 7,060,802 B1 * | 6/2006 | Trakht et al. ............ | 530/388.85 |
| 2002/0146728 A1 | 10/2002 | Ligensa et al. | |
| 2007/0082382 A1 | 4/2007 | Trakht | |

FOREIGN PATENT DOCUMENTS

| | | |
|---|---|---|
| EP | 0 137 234 A | 4/1985 |
| EP | 0 695 760 A | 2/1996 |
| EP | 0 799 836 A | 10/1997 |
| EP | 1 006 184 | 6/2000 |
| WO | WO 91/09967 | 4/1991 |
| WO | WO 94/27638 | 12/1994 |
| WO | WO 99/47929 | 9/1999 |
| WO | WO 00/69898 | 11/2000 |

OTHER PUBLICATIONS

Campbell, Monoclonal Antibody technology, Chapter 1, pp. 1-32 (1984).*
Yolken Infectious Diseases vol. 4 p. 35-68 (1982).*
Antonov AS, Nikolaeva MA. Klueva TS, Romanov YA, Babaev VR, Bystrevskaya VB, Perov NA, Repin VS, Smirnov VN (1986) Primary culture of endothelial cells from atherosclerotic human aorta. Part 1. Identification, morphological and ultrastructural characteristics of two endothelial cell subpopulations. Atherosclerosis 59:1-19.

(Continued)

*Primary Examiner*—Sheela J Huff
(74) *Attorney, Agent, or Firm*—John P. White; Cooper & Dunham LLP

(57) ABSTRACT

The present invention provides monoclonal antibody-producing hybridomas designated 27.F7 and 27.B1. The invention provides a method of detecting TIP-2 antigen bearing cancer cells in a sample. The invention provides a method of detecting TIP-2 antigen on the surface of cancer cells. The invention provides a method for diagnosing cancer in a subject. The invention provides a method for delivering exogenous material to TIP-2 antigen-bearing cancer cells of a human subject. The invention provides a method for treating cancer in a human subject. The invention provides isolated peptides having the amino acid sequences Lys Leu Leu Gly Gly Gln Ile Gly Leu (SEQ. ID No.) and Ser Leu Leu Gly Cys Arg His Tyr Glu Val (SEQ. ID No.). The invention provides a method for immunohistochemical screening of a tissue section for the presence of TIP-2 antigen bearing cancer cells. The invention provides a kit for detecting the presence of TIP-2 antigen-bearing cancer cells. The invention provides a method for detecting the presence of TIP-2 antigen. The invention provides a method for immunohistochemical screening of tissue sections. The invention provides a method for monitoring progression of cancer wherein the cancer cells are TIP-2 antigen-bearing cells. The invention provides a method for diagnosing cancer associated with the expression of TIP-2.

20 Claims, 52 Drawing Sheets

OTHER PUBLICATIONS

Berman DM, Gilman AG (1998) Mammalian RGS proteins: barbarians at the gate. J Biol Chem 273:1269-1272.
Borrebaeck CA, Danielsson L, Moller SA (1987) Human monoclonal antibodies produced from L-leucine methyl ester-treated and in vitro immunized peripheral blood lymphocytes. Biochem Biophys Res Commun 148:941-946.
Brodin T, Olsson L, Sjogren HO (1983) Cloning of human hybridoma, myeloma, and lymphoma cell lines using enriched human monocytes as feeder layer. J Immunol Methods 60:1-7.
Casali P et al. (1986) Science 234:476-479.
Campbell AM (1986) Monoclonal Antibody Technology. Elsevier Publishing Co., New York, pp. 1-32.
De Vrise et al. (1998) PNAS 95:12340-45.
Galanos G et al. (1969) Eur J Biochem 9:245-249.
Glassy MC, Handley HH, Hagiwara H, Royston I (1983) UC 729-6, a human lymphoblasted B-cell line useful for generating antibody-secreting human-human hybridomas. Proc Natl Acad Sci (USA) 80:6327-6331.
Goldman-Leikin RE, Salwen HR, Herst CV, Variakojis D, Bian ML et al. (1989) Characterization of a novel myeloma cell line, MM.1. J Lab Clin Med 113:335-345.
Green et al (1994) Nature Genetics 7:13.
Greenspan et al (1999) Nature Biotechnology 17:936-37.
Harlow et al (1988) Antibodies, A laboratory manual, Cold Spring Harbor Laboratory, p. 319 and 322, 198.
Kalantarov GF, Rudchenko SA, Lobel LI, Trakht I (2002) Development of a fusion partner cell line for efficient production of human monoclonal antibodies from peripheral blood lymphocytes. Hum. Antibodies 11(3): 85-96.
Kennedy MB (1995) Origin of ODZ (DHR, GLGF) domains. Trends Biochem Sci 20:350.
Kirman I, Kalantarov GF, Lobel LI, Hibshoosh H, Estabrook A, Canfield R, Trakht I. (2002) Isolation of native human monoclonal autoantibodies to breast cancer. Hybrid Hybridomics 21(6):405-414.
Kohler G, Milstein C (1975) Continuous cultures of fused cells secreting antibody of predefined specificity. Nature 256:495-497.
Kozbor D, Roder J (1981) Requirements for the establishment of high-titered monoclonal antibodies against tetanus toxoid using the Epstein-Barr virus technique. J Immunol 127:1275-1280.
Kozbor D, Tripputi P, Roder JC, Croce CM (1984) A human hybrid myelome for production of human monoclonal antibodies. J Immunol 133: 3001-3005.
Kiyono T, Hiraiwa A, Fujita M, Hayashi Y, Akiyama T, Ishibasahi M (1997) Binding of high risk papillomavirus E6 oncoproteins to the human homologue of the Drosophila discs large tumor suppressor protein. Proc. Natl. Acad. Sci (USA) 94:11612-11616.
Lee SS, Weiss RS, Javier RT (1997) Binding of human virus oncoproteins to hdlg/SAP97, a mammalian homologue of the Drosophila discs large tumor suppressor protein. Proc Natl Acad Sci (USA) 94:6670-6675.
Levy R, Miller RA (1983) Tumor therapy with monoclonal antibodies. Fed Proc 42: 2650-2656.
Nilsson K, Ponten J 91975) Classification and biological nature of established human hematopoetic cell lines. Int J Cancer 15:321-34.
Olsson L, Kronstrom H, Cambon-De Mouzon A, Honsik C, Brodin T, Jakobsen B (1983) Antibody producing human-human hybridomas. I. Technical aspects. J Immunol Methods 61: 17-32.
Östberg L, Pursch E (1983) Human X (mouse X human) hybridomas stably producing himan antibodies. Hybridoma 2:361-367.
Paul (1993) Fundamental Immunology, Raven press, chapter 8, p. 242.
Posner MR, Schlossman SF, Lazarus H (1983) Novel approach to construction of human "myeloma analogues" for production of human monoclonal antibodies. Hybridoma 2:369-381.
Raison RL, Walker KZ, Halnan CR, Briscoe D, Basten A. (1982) Loss of secretion in mouse-human hybrids need not be due to the loss of a structural gene. J Exp. Med 156:1380-1389.
Reading CL (1982) Theory and methods for immunization in culture and monoclonal antibody production. J. Immunol Methods 53: 261-291.
Rousset et al (1998) Oncogene 16:643-54.

Sahin U, Tureci O, Schmitt H, Cochlovius B, Johannes T, Schmits R, Stenner F, Luo G, Schbert I, Pfreundschuh M (1995) Human neoplasms elicit multiple specific immune responses in the autologous host. Proc Natl Acad Sci (USA) 92: 11810-11813.
Saras J, Heldin CH (1996) PDZ domains bind carboxy-terminal sequences of target proteins. Trends Biochem Sci 21:455-458.
Scanlan MJ, Chen Y-T, Williamson B, Gure AO, Stockert JD, Gordon O, Tureci O, Sahin U, Pfreundschuh M, Old LJ (1998) Characterization of human colon cancer antigens recognized by autologous antibodies. Int J Cancer 76:652-658.
Scanlan MJ, Williamson B, Jungbluth A, Stockert E, Arden KC, Viars CS, Gure AO, Gordan JD, Chen Y-T, Old LJ (1999) Isoforms of the human PDZ-73 protein exhibit differential tissue expression. Biochem Biophys Acta 1445: 39-52.
Seabright S (1971) Lancet 2: 971-972.
Shenk T (1996) In: Fields Virology, (editors) Fields BN, Knipe DM, Howley PM (Lippincott, Philadelphia), vol. 2, pp. 2111-2148.
Shnyra AA et al (1990) In:Friedman H, Klein TW, Nakano M, Nowotny A, and Eds. Advances in Exp. Medicine & Biology Endotoxin New York: Plenum, 256:681.
Teng NN, Lam KS, Calvo Riera F, Kaplan HS (1983) Construction and treating of mouse-human heteromyelomas for human monoclonal antibody production. Proc Natl Acad Sci. (USA) 80: 7308-7312.
Weiss MC, Green H (1967) Human-mouse hybrid cell lines containing partial complements of human chromosomes and functioning human genes. Proc Natl Acad Sci (USA) 58: 1104-1111.
Westhof et al (Nature) 311:123.
Yunis JJ (1980) Cancer Genetics and Cytogenetics 2: 221-229.
Carroll WL et al. (1986) Mouse X Human heterohybridomas as fusion partners with human B cell Tumors. Journal of Immunological Methods 89:61-72.
Keaney JF et al. (1979) A new mouse myeloma cell line that has lost immunoglobulin expression but permits the construction of antibody-secreting hybrid cell lines. The Journal of Immunology 123(4):1548-1550.
Gustafsson et al. (1991) Human Antibod. Hybridomas, 2:26-32.
Final Office Action issued Mar. 11, 2004 in connection with U.S. Appl. No. 09/664,958.
Office Action issued Oct. 16, 2003 in connection with U.S. Appl. No. 09/664,958.
Final Office Action issued Apr. 30, 2003 in connection with U.S. Appl. No. 09/664,958.
Final Office Action issued Apr. 15, 2003 in connection with U.S. Appl. No. 09/664,958.
Office Action issued Sep. 26, 2002 in connection with U.S. Appl. No. 09/664,958.
Final Office Action issued Mar. 31, 2006 in connection with U.S. Appl. No. 09/767,578.
Office Action issued Oct. 11, 2005 in connection with U.S. Appl. No. 09/767,578.
Final Office Action issued Jan. 14, 2005 in connection with U.S. Appl. No. 09/767,578.
Office Action issued Apr. 23, 2004 in connection with U.S. Appl. No. 09/767,578.
Final Office Action issued Jun. 25, 2003 in connection with U.S. Appl. No. 09/767,578.
Office Action issued Jan. 9, 2003 in connection with U.S. Appl. No. 09/767,578.
Office Action issued Dec. 20, 1999 in connection with U.S. Appl. No. 09/040,833.
Office Action issued Oct. 1, 2003 in connection with U.S. Appl. No. 09/664,485.
Office Action issued May 28, 2004 in connection with U.S. Appl. No. 09/664,485.
Office Action issued Aug. 9, 2006 in connection with U.S. Appl. No. 09/664,485.
Jin Y-M et al., (1996) Protease-activated lymphoid cell and hepatocyte recognition site in the preS1 domain of the large woodchuck hepatitis virus envelope protein, Journla of General Virology, 77:1837-1846.

Zanella, I. et al. (1992) "New heteromyeloma cell lines for the production of human monoclonal antibodies," Journal of Immunological Methods, 156:205-215.

Notification of Transmittal of International Search Report dated aug. 31, 1999 issued by the International Searching Authority in connection with International Patent Application No. PCT/US99/05828.

International Search Report dated Aug. 31, 1999 issued by International Searching Authority in connection with International Patent Application No. PCT/US99/05828.

Notification of Transmittal of International Preliminary Examination Report issued Jan. 8, 2000 by the International Preliminary Examining Authority in connection with International Patent Application No. PCT/US99/05828.

International Preliminary Examination Report dated Dec. 17, 1999 issued by International Preliminary Examining Authority in connection with International Patent Application No. PCT/US99/05828.

Partial European Search Report dated Sep. 8, 2004 issued by the European Patent Office in connection with European Application No. 99913925.6.

Supplementary European Search Report dated Nov. 23, 2004 issued by the European Patent Office in connection with European Application No. 99913925.6.

Examination Report dated Jun. 27, 2005 issued by the European Patent Office in connection with European Application No. 99913925.6.

Examination Report dated Mar. 2, 2006 issued by the European Patent Office in connection with European Application No. 99913925.6.

Examination Report dated Sep. 25, 2006 issued by the European Patent Office in connection with European Application No. 99913925.6.

Examination Report dated Jul. 16, 2007 issued by the European Patent Office in connection with European Application No. 99913925.6.

Communication about Intent to Grant a European Patent dated Apr. 11, 2008 issued by the European Patent Office in connection with European Application No. 99913925.6.

International Search Report dated Feb. 7, 2003 issued by the International Searching Authority in connection with International Application No. PCT/US01/29242.

International Search Report dated Oct. 17, 2003 issued by the International Searching Authority in connection with International Application No. PCT/US01/29242.

International Search Report dated Jan. 31, 2006 issued by the International Searching Authority in connection with International Application No. PCT/US01/29242.

International Preliminary Examination Report dated Feb. 28, 2006 issued by the International Preliminary Examining Authority in connection with International Patent Application No. PCT/US01/29242.

Supplementary Partial European Search Report dated Apr. 27, 2005 issued by the European Patent Office in connection with European Application No. 01973176.9.

Supplementary Partial European Search Report dated Jul. 14, 2005 issued by the European Patent Office in connection with European Application No. 01973176.9.

Examination Report dated Oct. 17, 2005 issued by the European Patent Office in connection with European Application No. 01973176.9.

Examination Report date May 17, 2006 issued by the European Patent Office in connection with European Application No. 01973176.9.

Examination Report dated Oct. 19, 2006 issued by the European Patent Office in connection with European Application No. 01973176.9.

Communication about Intent to Grant a European Patent dated Apr. 25, 2007 issued by the European Patent Office in connection with European Application No. 01973176.9.

Decision to Grant a European Patent dated Dec. 20, 2007, issued by the European Patent Office in connection with European Application No. 01973176.9.

Notice of Allowance issued Sep. 1, 2000 in connection with U.S. Appl. No. 09/040,833.

Office Action issued Sep. 25, 2002 in connection with U.S. Appl. No. 09/767,578.

Advisory Action issued Oct. 27, 2003 in connection with U.S. Appl. No. 09/767,578.

Advisory Action issued May 6, 2005 in connection with U.S. Appl. No. 09/767,578.

Advisory Action issued Aug. 1, 2006 in connection with U.S. Appl. No. 09/767,578.

Notice of Allowance issued Jan. 5, 2007 in connection with U.S. Appl. No. 09/767,578.

Office Action issued Jul. 6, 2007 in connection with U.S. Appl. No. 11/704,925.

Office Action issued Feb. 4, 2008 in connection with U.S. Appl. No. 11/704,925.

Official Action issued Jan. 3, 2008 in connection with Canadian Patent Application No. 2,323,681.

Official Action issued Apr. 14, 2008 in connection with Canadian Patent Application No. 2,422,828; and.

Final Office Action issued Aug. 18, 2008 in connection with U.S. Appl. No. 11/704,925.

* cited by examiner

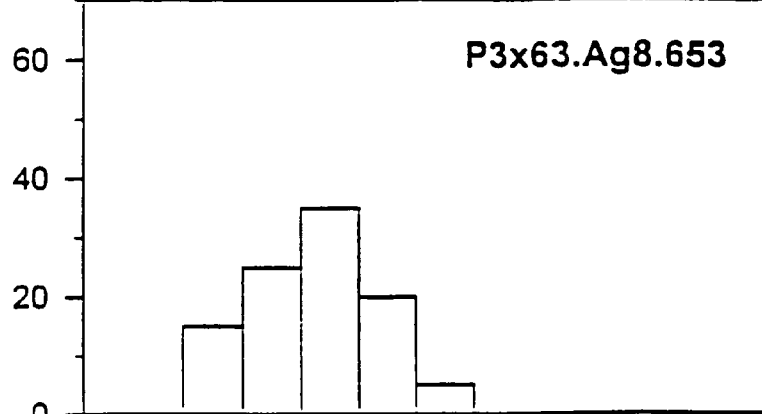
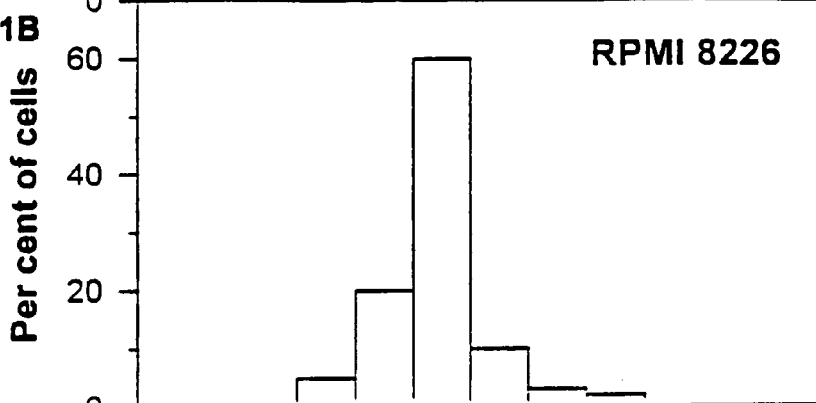
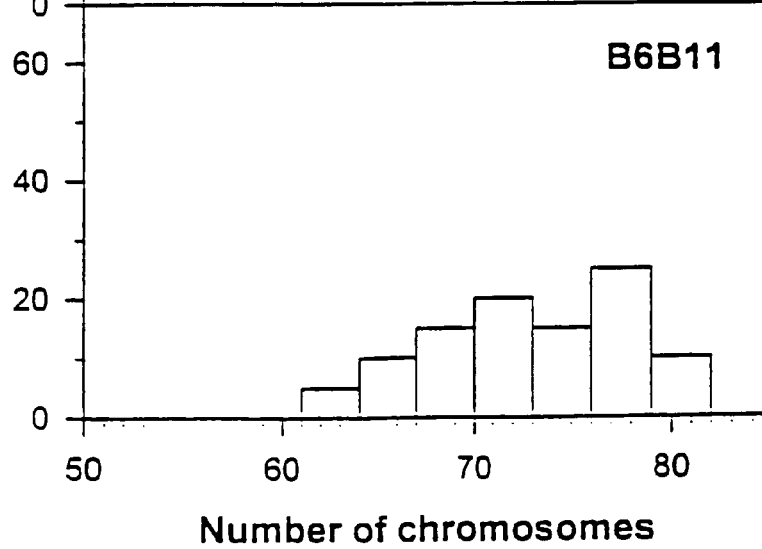

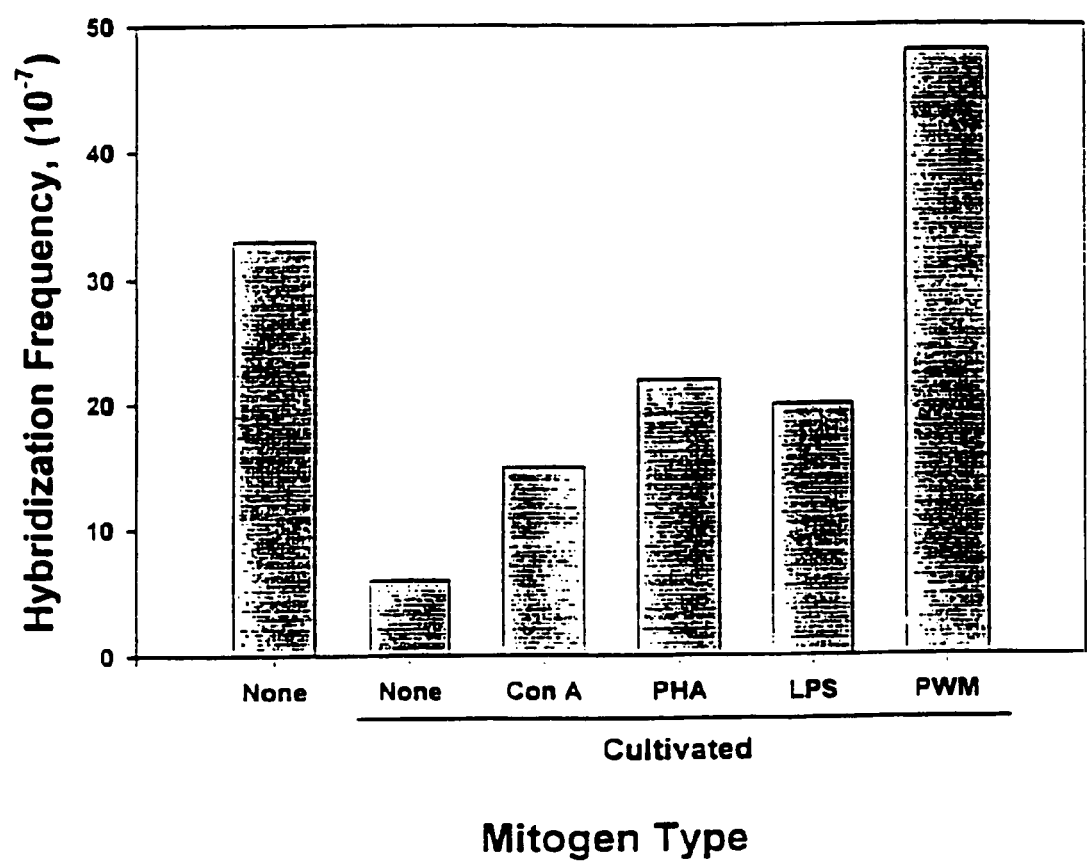

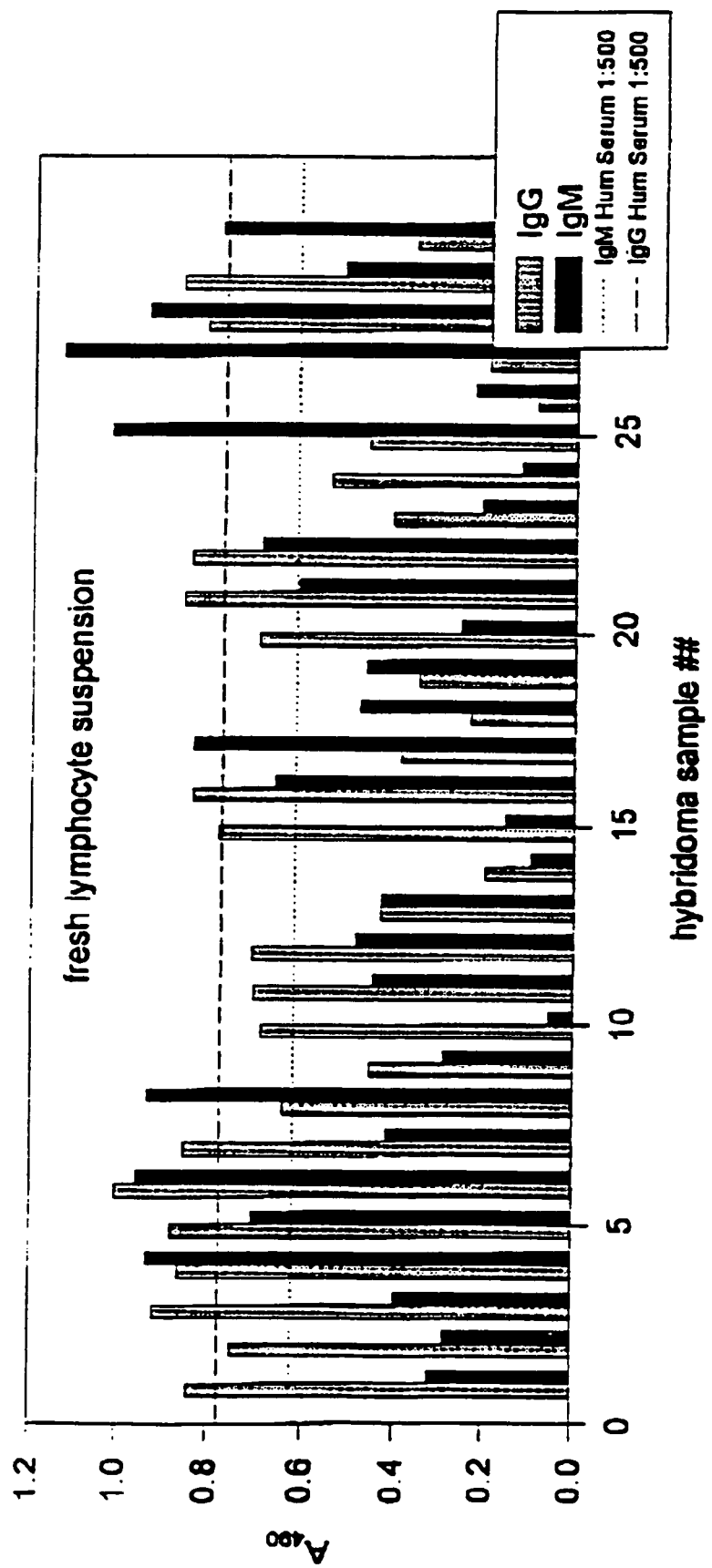

FIG. 7
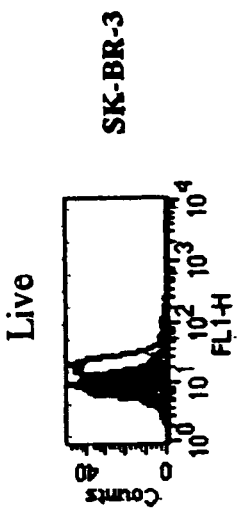
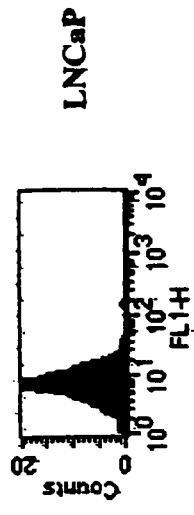
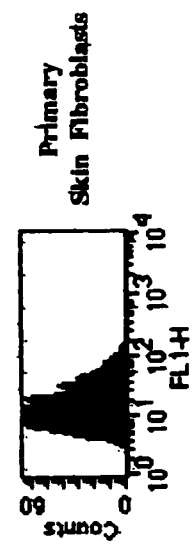
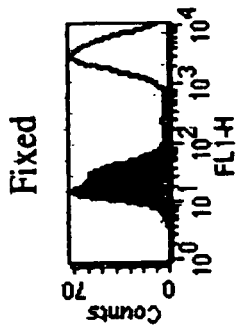
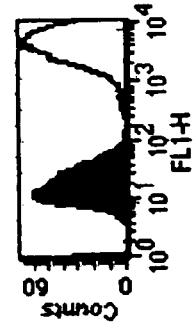
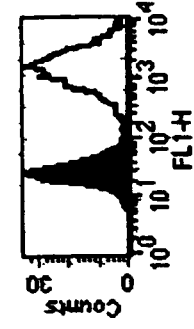
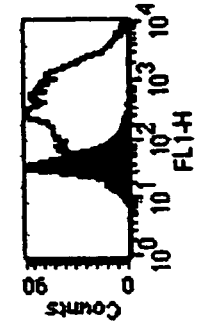
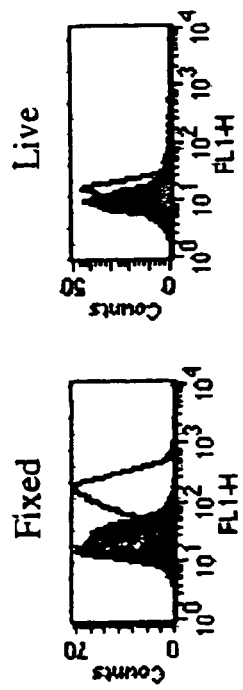
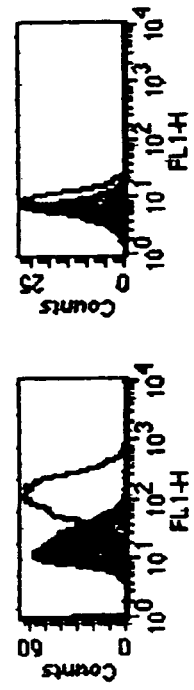
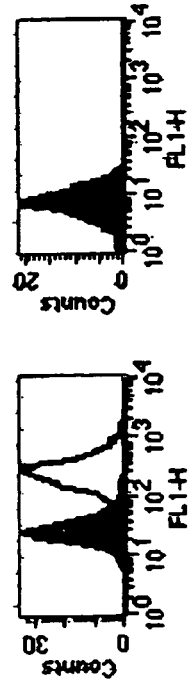
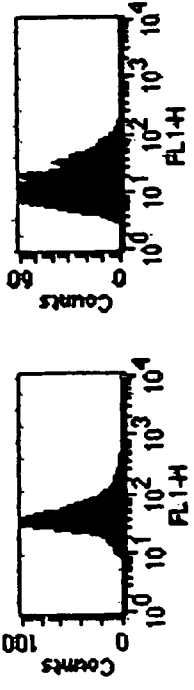

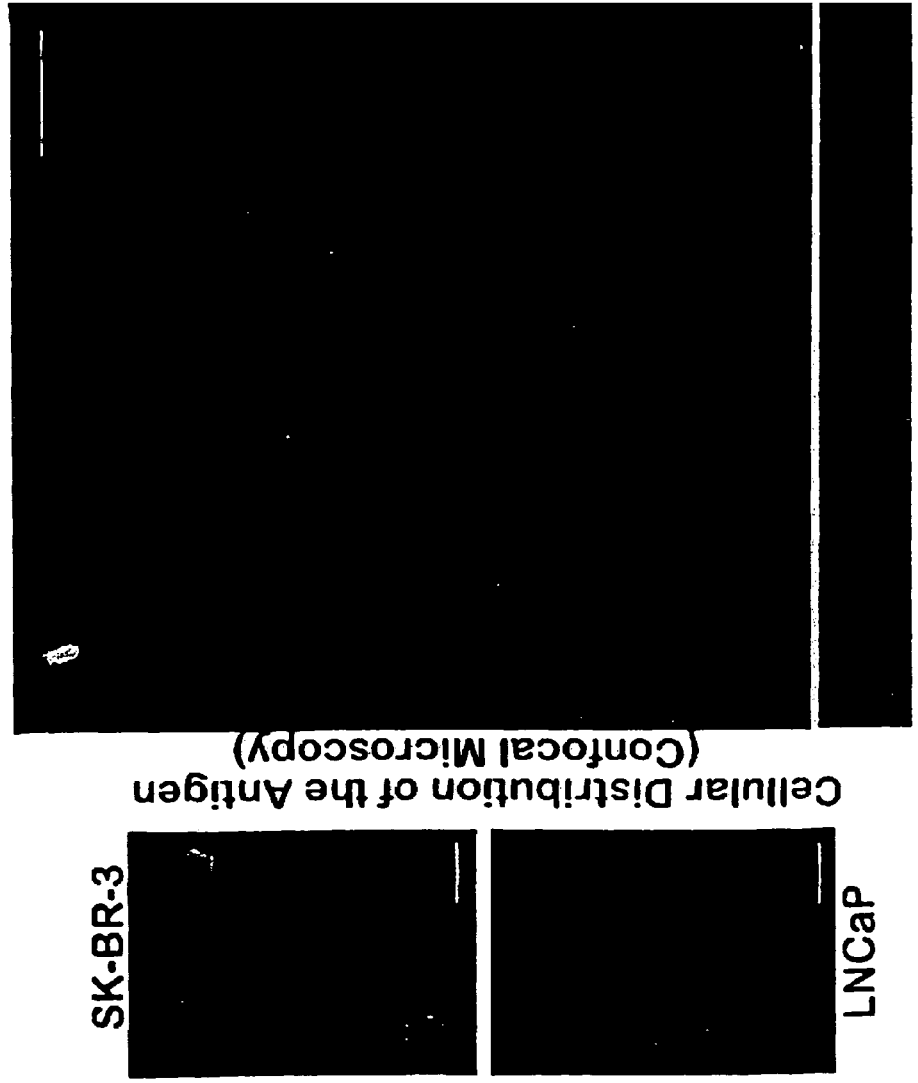
FIG. 9
Indirect Immunostaining of Cancer Cells with 27.F7
Cellular Distribution of the Antigen (Confocal Microscopy)
SK-BR-3
LNCaP
Size bars represent 20 μm
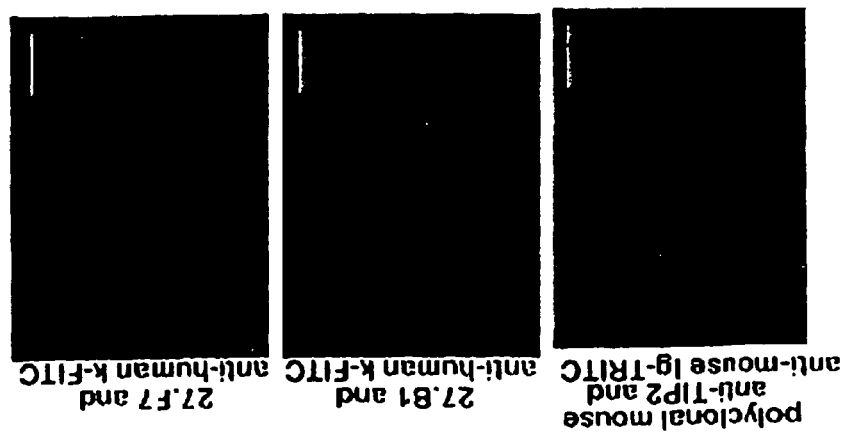
Detection of TIP2 in MCF-7 Cells using Antibodies
27.F7 and anti-human κ-FITC
27.B1 and anti-human κ-FITC
polyclonal mouse anti-TIP2 and anti-mouse Ig-TRITC FIG. 11 Indirect Immunostaining with 27.B1

Size bars represent 20 μm prostate cancer benign prostate hyperplasia

Indirect Immunostaining with 27.F7

Size bars represent 20 μm

Indirect Immunostaining with 27.F7

Size bars represent 20 μm

Regulation of G-protein Signaling System

FIG. 19 GIPC Proteins (GAIP Interacting Protein, C-terminus) - Regulators of Regulators?

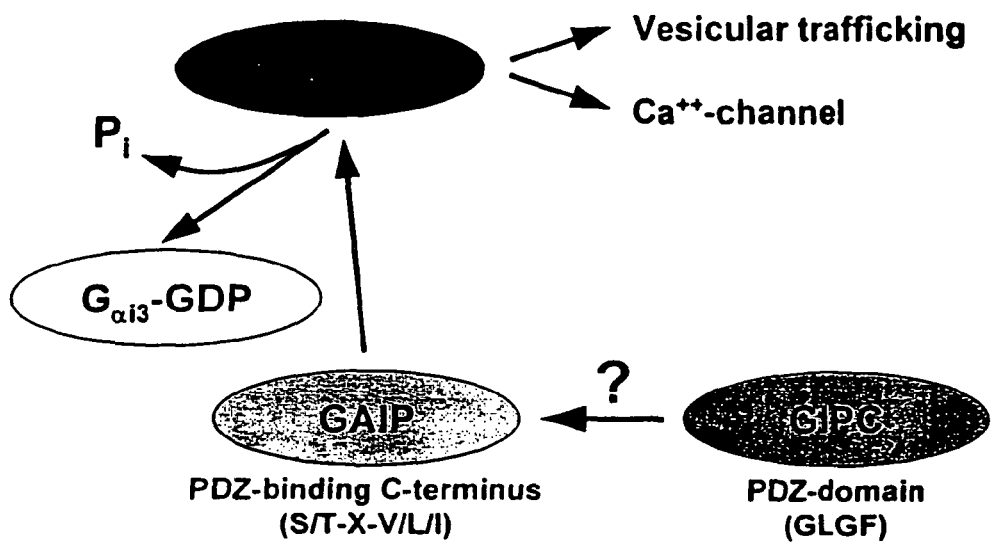

PDZ-binding C-terminus (S/T-X-V/L/I)

PDZ-domain (GLGF)

GIPC Family Proteins
- TAX interacting protein 2 (TIP-2)
- Neurophilin binding protein (NIP)
- M-Semaphorin F cytoplasmic domain associated protein (SEMCAP-1)

Other PDZ-"binders"
- NMDA
- TAX oncoprotein
- HPV E6
- AdD9 E4
- glycophorin C
- FAS
- APC
- LET-23
- CXCR2 (IL-8 RB)
- CXCR5 (coreceptor HTLV-1/HIV)

Other PDZ-"containers"
- PSD-95
- DlgA/DLG
- ZO-1
- p55
- LIN7
- PTPL1/FAP1
- RGS12
- PDZ-73 (NYCO38)

PRINCIPLE OF SEROLOGICAL RECOMBINANT EXPRESSION CLONING (SEREX) TECHNOLOGY FOR IDENTIFICATION OF TUMOR ASSOCIATED ANTIGENS

DEVELOPMENT OF MOUSE anti-TIP-2 ANTIBODIES USING HUMAN anti-TIP-2 ANTIBODY BOTH AS A CAPTURE AND A TAG Invasive Ductal Cancer Tissue Stained Indirectly with:

Analysis for Human anti-TIP-2 Antibody 27.F7 (μ, κ) on SK-BR-3 Cells

FIG. 25 Expression of TIP-2 in Normal and Cancer Breast Tissue Lysates

Release of TIP-2 into Culture Media from SK-BR-3 Cells Treated by Taxol

FIG. 29

Amino Acid Sequence of GLUT1CBP/GIPC Protein

```
         10         20         30         40         50         60
MPLGLGRRKK APPLVENEEA EPGRGGLGVG EPGPLGGGGS GGPQMGLPPP PPALRPRLVF 70         80         90        100        110        120
HTQLAHGSPT GRIEGFTNVK ELYGKIAEAF RLPTAEVMFC TLNTHKVDMD KLLGGQIGLF 130        140        150        160        170        180
DFIFAHVKGQ RKEVEVEKSE DALGLTITDN GAGYAFIKRI KEGSVIDHIH LISVGDMIEA 190        200        210        220        230        240
INGQSLLGCR HYEVARLLKE LPRGRTFTLK LTEPRKAFDM ISQRSAGGRP GSGPQLGTGR 250        260        270        280        290        300
GTLRLRSRGP ATVEDLPSAF EEKAIEKVDD LLESYMGIRD TELAATMVEL GKDKRNPDEL 310        320        330
AEALDERLGD FAFPDEFVFD VWGAIGDAKV GRY
```

TIP-2 sequence is shown in italic
HLA A*0201 binding peptides (111-119 and 185-194) are shown underlined

FIG. 30

```
1    cacggggagg cggaggcagc ggcggcggcg gcggcggcgg cggcggcggc ggagcagatc
61   ttctggtgac cccacttctc gctgctcatg ccgctgggac tgggcgccg gaaaaaggcg
121  cccctctag tggaaaatga ggaggctgag ccaggccgtg gagggctggg cgtggggag
181  ccagggcctt tgggcggagg tgggtcgggg ggcccccaaa tgggcttgcc cccctccc
241  ccagccctgc ggcccccgc tgtgttccac accagctgg cccatggcag tcccactggc
301  cgcatcgagg ggttcaccaa cgtcaaggag ctgtatggca agattgccga ggccttccgc
361  ctgccaactg ccgaggtgat gttttgcacc ctgaacaccc acaaagtgga catggacaag
421  ctcctggggg gccaaatcgg gctggaggac ttcatcttcg cccacgtgaa ggggcagcgc
481  aaggagtgg agtgttcaa gtcggaggat gcactcgggc tcaccatcac ggacaacggg
541  gctggctacg ccttcatcaa gcgcatcaa gagggcagca tgatcgacca catccacctc
601  atcagcgtgg gcgacatgat cgaggccatt aacgggcaga gcctgctggg ctgccggcac
661  tacgaagtgg cccggctgct caaggaactg ccccgaggcc gtaccttcac gctgaagctc
```

FIG. 31

Protein Antigens Identified by Natural Human Monoclonal Antibodies Developed from Breast and Prostate Cancer Patients' B-Cells

| Antibody | Antigen Name | Sequence | Molecular Weight (Calculated) | HLA A*0201-Specific MHC Binding Peptides | mRNA Expression in Tissues | Functions |
|---|---|---|---|---|---|---|
| 13.42 μ,κ | Human mRNA for KIAA0338 gene, partial cds | See Fig. 32 | 103568 (~40kD by WB) | NLLEKDYFGL (184-193) VLFDLVCEHL (174-183) KLQHPDMLV (903-911) | Brain | Unknown |
| 13.2C1 μ,κ | Human non-muscle alpha-actinin mRNA, complete cds - the second non muscle alpha-actinin isoform designated ACTN4 (actinin-4) | See Fig. 33 | 105217 | KMLDAEDIV (238-246) KMTLGMIWTI (139-148) FMPSEGKMV (374-382) KLASDLLEWI (302-311) GLVTFQAFI (825-833) CQLEINFNSV (353-362) | Adipose, Adrenal gland, Aorta, Brain, Breast, CNS, Colon, Ear, Esophagus, Foreskin, Germ Cell, Heart, Kidney, Liver, Lung, Muscle, Ovary, Pancreas, Parathyroid, Placenta, Prostate, Small intestine, Stomach, Testis, Thyroid, Tonsil, Uterus, Whole embryo, breast, colon, genitourinary tract, head_neck, lung, cell line, ovary, stomach<br><br>"…100kD alpha-actinin was found in the extracellular matrix of bone marrow stroma by Western blot and immunofluorescence microscopy." [Exp. Hematol. 1999, 27(2):345-52]. | Actin-binding protein important in organization of cytoskeleton and in cell adhesion. "An amino-terminal fragment of alpha-actinin can promote monocyte/macrophage maturation" [Exp. Hematol. 1999, 27(2):345-52]. |
| 13.2C1 μ,κ | Homo sapiens actinin, alpha 4 (ACTN4) mRNA | See Fig. 34 | 102260 | KMLDAEDIV (212-220) KMTLGMIWTI (113-122) FMPSEGKMV (345-353) KLASDLLEWI (273-282) GLVTFQAFI (797-805) | Adipose, Adrenal gland, Aorta, Brain, Breast, CNS, Colon, Ear, Esophagus, Foreskin, Germ Cell, Heart, Kidney, Liver, Lung, Muscle, Ovary, Pancreas, Parathyroid, Placenta, Prostate, Small intestine, Stomach, Testis, Thyroid, Tonsil, Uterus, Whole embryo, breast, colon, genitourinary tract, head_neck, | Actin-binding protein important in organization of cytoskeleton and in cell adhesion. "The cytoplasmic localization of actinin-4 was closely associated with an infiltrative histological phenotype and correlated significantly |

FIG. 31 (cont.)

| | | | | | |
|---|---|---|---|---|---|
| | | | | lung, cell line, ovary, stomach | with a poorer prognosis in 61 cases of breast cancer" [J.Cell.Biol. 1998, 140(6):1383-93]. Alpha-actinin-1 and 4 associate with PDZ domain of CLP-36 PDZ-LIM protein (also called hCLIM1 - high expression in epithelial cells) in actin stress fibers [JBC 2000, 275(15):11100-11105]. |
| 22.8D11 μ,λ | Human clathrin coat assembly protein 50 (AP50) mRNA | See Fig. 35 | 49662 | WLAAVTKQNV (64-73) ILPFRVTPLV (284-293) SLLAQKIEV (314-322) KLNYSDHDV (410-418) | infant brain, brain, placenta, breast, ovary (tumor), fetal heart, fetal lung, multiple sclerosis lesions, pineal gland, lymph node | Component of the adaptor complexes which link clathrin to receptors in coated vesicles clathrin-associated protein co-mplexes are believed to interact with the cyto-plasmic tails of membrane proteins, leading to their selection and concen-tration. AP50 is a subunit of the plasma membrane adaptor. |
| 27.B1 μ,κ 27.F7 μ,κ | Homo sapiens GLUT1 C-terminal binding protein (GLUT1CBP) mRNA [GIPC/TIP-2] | See Fig. 36 | 36047 | KLLGGQIGL (111-119) SLLGCRHYEV (185-194) | Adipose, Aorta, Blood, Bone, Brain, Breast, CNS, Colon, Germ Cell, Heart, Kidney, Lung, Ovary, Pancreas, Placenta, Pooled, Stomach, Testis, Thymus, Uterus, Whole embryo, brain, breast, colon, connective tissue, lung, muscle | Binds via a PDZ domain to C terminus of GLUT1 and interact with cytoskeletal proteins |
| 33.2H6 μ,λ | Homo sapiens gp130 associated protein GAM mRNA | See Fig. 37 | 21835 | YLSQEHQQQV (94-103) | placenta, breast, infant brain, uterus (pregnant), B-Cell, ovary (tumor), fetal heart, fetal liver/spleen, fetal lung, T cells (Jurkat cell line) | Has a possible role in the negative regulation of proteins containing WD-40 repeats. May be required for the initiation and maintenance of the differentiated state. |

FIG. 31 (cont.)

| | | | | |
|---|---|---|---|---|
| 33.2H6 μ,λ | Homo sapiens amino-terminal enhancer of split (AES) mRNA | See Fig. 38 | 21966 | YLSQEHQQQV (95-104) | Adrenal gland, Aorta, Blood, Bone, Brain, Breast, CNS, Colon, Esophagus, Eye, Foreskin, Germ Cell, Head and neck, Heart, Kidney, Lung, Lymph, Muscle, Nose, Ovary, Pancreas, Parathyroid, Placenta, Pooled, Prostate, Spleen, Stomach, Synovial membrane, Testis, Thymus, Thyroid, Tonsil, Uterus, Whole embryo, brain, colon, head_neck, kidney, lung, ovary, pnet | Amino-terminal enhancer of split is similar to the Drosophila enhancer of split groucho protein. The function of AES has not been determined but it has been proposed as a candidate tumor human cancer antigen. |
| 33.2H6 μ,λ | Antiquitin 1 (antiquitin=26g turgor protein homolog), mRNA | See Fig. 39 | 55357 | KVMDRPGNYV (372-381) ALIEQWNPV (149-157) ITAFNFPV (162-170) | fetal heart, infant brain, placenta, NT2 neuronal precursor, liver, HeLa (cell line), ovary, liver (HepG2 cell line), ovary (tumor), multiple sclerosis lesions | Unknown (30% identity to various eukaryotic and prokaryotic aldehyde dehydrogenases). Antiquitin has homology to a previously described protein from the green garden pea, the 26g pea turgor protein. Four human antiquitin-like sequences, possibly pseudogenes, have also been identified. |
| 39.A7 μ,λ | ARP2/3 protein complex 41 KD subunit (P41-ARC), mRNA | See Fig. 40 | 40935 | FEQENDWVV (125-133) | HeLa (cell line), fibroblast, fetal brain, infant brain, fetal liver/spleen, monocytes (stimulated), fetal heart, uterus (pregnant), olfactory epithelium, breast | Part of a complex implicated in the control of actin polymerization in cells. belongs to a complex composed of ARP2, ARP3, P41-ARC, P34-ARC, P21-ARC, P20-ARC and P16-ARC. |
| 50.1B3 μ,κ | H.sapiens seb4D mRNA H.sapiens seb4B mRNA | See Fig. 41a and 41b | seb4D-24617 | for seb4D YLGAKPWCL (100-108) CLQTGFAIGV (107-116) | thymus, Blood, Brain, Breast, Colon, Germ Cell, Heart, Kidney, Lung, Lymph, Ovary, Parathyroid, Pooled, Prostate, Testis, Thymus, Tonsil, Uterus, brain, colon, lung, muscle, ovary, | Unknown |

FIG. 31 (cont.)

| | | | seb4B-25218 | for seb4B YLGAKPWCL (101-109) CLQTGFAIGV (108-117) | stomach, thymus, pooled, whole blood | |
|---|---|---|---|---|---|---|
| 59.3G7 μλ | Homo sapiens lamin A/C (LMNA) mRNA | See Fig. 42 | 65133 | KLLEGEEERL (378-387) KLVRSVTVV (542-550) RLADALQEL (240-248) | Adipose, Adrenal gland, Bone, Brain, Breast, Colon, Esophagus, Foreskin, Germ Cell, Heart, Kidney, Larynx, Liver, Lung, Lymph, Muscle, Ovary, Pancreas, Parathyroid, Placenta, Pooled, Prostate, Spleen, Stomach, Synovial membrane, Testis, Thymus, Thyroid, Uterus, Whole embryo, brain, breast, colon, demis_dnash, head_neck, lung, cell line, ovary, stomach | Intermediate filament proteins |

FIG. 32

Human mRNA for KIAA0338 gene, partial cds

ORIGIN
```
   1 catcagcggg cggggtgtc gccgaacagg ctgctccgca gagcccgccg cgaccccgcg
  61 ccgccccgcc ccgcggcctg cctgccagag gagccgaggg ggccgcccct cgcccaacct
 121 gcccgacatg gggaacccg ggcccaggcg tgctggtcac catgacaaca gagacaggcc
 181 ccgactctga ggtgaagaaa gctcaggagg aggccccgca gcagcccgag gctgctgccg
 241 ctgtgaccac ccctgtgacc cctgcaggcc acggccaccc agaggccaac tccaatgaga
 301 agcatccatc ccagcaggac acgcggcctg ctgaacagag cctagacatg gaggagaagg
 361 actacagtga ggccgatggc ctttcggaga ggaccacgcc cagcaaggcc cagaaatcgc
 421 cccagaagat tgccaagaaa tacaagagtg ccatctgccg ggtcactctg cttgatgcct
 481 cggagtatga gtgtgaggtg gagaaacatg gccggggcca ggtgctgttt gacctggtct
 541 gtgaacacct caacctccta gagaaggact acttcggcct gacttctgt gatgctgaca
 601 gccagaagaa ctggctggac ccctccaagg agatcaagaa gcagatccgg agtagcccct
 661 ggaattttgc cttcacagtc aagttctacc cgcctgatcc tgcccagctg acagaagaca
 721 tcacaagata ctacctgtgc ctgcagctgc gggcagacat catcacgggc cggctgccat
 781 gctcctttgt cacgcatgcc ctactgggct cctacgctgt gcaggctgag ctgggtgact
 841 atgatgctga ggagcatgtg ggcaactatg tcagcgagct ccgcttcgcc cctaaccaga
 901 cccgggagct ggaggagagg atcatggagc tgcataagac atatagggg atgaccccgg
 961 gagaagcaga aatccacttc ttagagaatg ccaagaagct ttccatgtac ggagtagacc
1021 tgcaccatgc caaggactct gagggcatcg acatcatgtt aggcgtttgt gccaatggcc
1081 tgctcatcta ccgggaccgg ctgagaatca accgctttgc ctggcccaag atcctcaaga
1141 tctcctacaa gaggagtaac ttctatatca agatccggcc tggggagtat gagcaatttg
1201 agagcacaat tggctttaag ctcccaaacc accggtcagc caagagactg tggaaggtct
1261 gcatcgagca tcatacattc ttccggctgg tgtcccctga gcccccaccc aagggcttcc
1321 tggtgatggg ctccaagttc cggtacagtg ggaggaccca ggcacagact cgccaggcca
1381 gcgccctcat tgaccggcct gcacccttct ttgagcgttc ttccagcaaa cggtacacca
1441 tgtcccgcag ccttgatgga gcagagttct cccgcccagc ctcggtcagc gagaaccatg
1501 atgcagggcc tgacggtgac aagcgggatg aggatggcga gtctgggggg caacggtcag
1561 aggctgagga gggagaggtc aggactccaa ccaagatcaa ggagctaaag ccggagcagg
1621 aaaccacgcc gagacacaag caggagttct tagacaagcc agaagatgtc ttgctgaagc
1681 accaggccag catcaatgag ctcaaaagga ccctgaagga gcccaacagc aaactcatcc
```

FIG. 32 (cont.)

```
1741 accgggatcg agactgggaa cgggagcgca ggctgccctc ctcccccgcc tcccctccc
1801 ccaagggcac ccctgagaaa gccaatgaga gagcagggct gagggagggc tccgaggaga
1861 aagtcaaacc accacgtccc cgggccccag agagtgacac aggcgatgag gaccaggacc
1921 aggagaggga cacggtgttc ctgaaggaca accacctggc cattgagcgc aagtgctcca
1981 gcatcacggt cagctctacg tctagcctgg aggctgaggt ggacttcacg gtcattggtg
2041 actaccatgg cagcgccttc gaagacttct cccgcagcct gcctgagctc gaccgggaca
2101 aaagcgactc ggacactgag ggcctgctgt tctcccggga tctcaacaag ggggccccca
2161 gccaggatga tgagtctggg ggcattgagg acagcccgga tcgaggggcc tgctccaccc
2221 cggatatgcc ccagtttgag cccgtgaaaa cagaaaccat gactgtcagc agtctggcca
2281 ttagaaagaa gattgagccg gaggccgtac tgcagaccag agtctccgct atggataaca
2341 cccagcaggt tgatgggagt gcctcagtgg ggagggagtt catagcaacc actccctcca
2401 tcaccacgga gaccatatcg accaccatgg agaacagtct caagtccggg aaggggcag
2461 ctgccatgat cccaggccca cagacggtgg ccacggaaat ccgttctctt tctccgatca
2521 tcgggaaaga tgtcctcacc agcacctacg gcgccactgc ggaaaccctc tcaacctcca
2581 ccaccaccca tgtcaccaaa actgtgaaag gagggttttc tgagacaagg atcgagaagc
2641 gaatcatcat tactggggat gaagatgtcg atcaagacca ggccctggct ttggccatca
2701 aggaggccaa actgcagcat cctgatatgc tggtaaccaa agctgtcgta tacagagaaa
2761 cagacccatc cccagaggag agggacaaga agccacagga atcctgacct ctgtgaagag
2821 atcctggcat ttctggtcca acccaagcca gagaaccatt aagaaggggc cttcattctg
2881 gattctccga cgcaacactg acgtcccagc tgcgacgtac tgtcactgat gagagactgg
2941 gaagggaaaa gcatatatat atagatatat agagatatag atatatatac aggaaacacc
3001 gcatccttgc actgctgctg gggctggcag agcagttggc tgacagcaac aaccgacatc
3061 tgaacaccta catttccttt gcagacaaat tgaagaactg gtgggatttt tttcaagaaa
3121 aaaaattata taataactat aatcccttgc tcaccccttt ccccgccaa ataagaaacg
3181 caagccagac cacgatgatt gtagaagtcc ctcccgccct ggttctgcac gttacagtta
3241 gcagacgagc aattccattt gttcttctcc agcatctcta aggcccactt gaatgcaaag
3301 gaaaacactt gcacagcaaa gcaagagaag tcacagcagc aagacacgca cagtcaacca
3361 ttttccgaga aaaaagaaa attccccact tggaaagaaa gaggaggaac actggattct
3421 tactttctgg atcttgacac tgggctgcaa aacctacctt cctctctccc gcctcccctc
3481 accctcaact ctcaatgtct tgctgtcatt ttctgtctcg gctccctcct cccccttccc
3541 ccttccccca ccccacaccc ttcaccctct gtgtcctggt ccttctgagg gccactgcag
3601 atgactctcc tttgaaatga gaaaagaaa agaaagcaag aacagaaaac gaagccacag
3661 gaagggaagt agacattgta tgcttatggt ttctcattat gaaggtgcag cttgtaggag
3721 gtttgtacgg atgtgctttg aagttatgta tattacatat aacaggaaaa aatattaata
3781 aacagtgctg gtaagtatga agctgacatt ctaaaattat aattatctga ctgtgattga
3841 tgtatcctga ggttcctaga tctcactgaa ctggcccagc taaggagacc tggactctgg
3901 gtgtgggttg gctcacagta ggggctgacg ggttcagtgt agtaatactg tgtgtggtgt
```

FIG. 32 (cont.)

```
3961 ttgtaattgg ttgattggtg gggagggtg gggggcccta atggagaggt gtgggtttgg
4021 caagaaagaa gcaacacaga tgtcgtcccc aaaatgccag ttcaagacac cttctccctg
4081 cccccctggt agtaacagtc agggcctggt ctgtgctcag gtactgggtc ccagtctggg
4141 actctgctgc tgaagttgcc acagtagagg tccctggctt agtccttatc tccctacggg
4201 gcttgccttg gttttcagtc ttctctctct ttctctcttt ttttttttt tgccacattc
4261 tgcccttccc tgaccccatt gtaataacca actccatatc caaagggagg tggtgctctc
4321 agccattgta gaagatggtg gctttaacct gactgtctaa aaattcccag ctaagccttt
4381 tcctctactc tcttccttgt tctgaatcat ttcttcttct caggccaaag tagccatggt
4441 aaggaggctt catggggcag accctgaaag atcaaaactg catttgcaaa gccctcccct
4501 gtcccaggac aaagctgaga ctgacgggtg atgttgctca taggctccag ctctgcataa
4561 gaccttggct tggagacctc cctctcagtc aacagctgaa ctctgagctt gtgcccagaa
4621 attaccccaa gaccacagga acccttcaag aagctcccat cacaagcttg gcattgctct
4681 ctgccacacg tgggcttcct caggcttgtc tgccacaagc tacttctctg agctcagaaa
4741 gtgccccttg atgagggaaa atgtcccact gcactgcgaa tttctcagtt ccattttacc
4801 tcccagtcct ccttctaaac cagttaataa attcattcca caagtattta ctgattacct
4861 gcttgtgcca gggactattc tcaggctgaa gaaggtggga ggggagggcg gaacctgagg
4921 agccacctga gccagcttta tatttcaacc atggctggcc catctgagag catctcccca
4981 ctctcgccaa cctatcgggg catagcccag ggatgccccc aggcggccca ggttagatgc
5041 gtccctttgg cttgtcagtg atgacataca ccttagctgc ttagctggtg ctggcctgag
5101 gcagggcagg aaatcagaat agcatttgct tctctgggca aatgggaagt tcagcggggc
5161 agcagaatca gtggcattcc cctgtgcagg ccggtggg tccactccaa ctcccctga
5221 gtgtagcagc acactttcca tacaccaggt tctttctaca atcctggtgg aaaagccaca
5281 gaaccttctt cctgcccttc ttgagagttc ccctctttc tgggtcaaga gctggagtgg
5341 tggctccatc ctctctgggc cacttcggtc taggaactca tctttgcagg aaccaggagt
5401 cctgagcaca ctgaacacac ctcagaggga ggatccttgt tgtggatttt gcacctggct
5461 ttggggcagg ggtgaagtga ccaggcttag cttgtggagt ttatgggcca ccagggtttg
5521 gggaaatcac catcccgcgg atgctgtgac ctcccttcta cggagatgca ggcagtgcca
5581 cgagggagga ggggacctgc aaagctagaa tctagggcac tgtttcctcc ccatccttct
5641 ctttgtagag aatagagacg tttgtcttgt ctgtcttcaa cctactttc cttttctctt
5701 ttttgtttct catcctctct gtgccacctc tccacccagg aggccatgta gcatagtgga
5761 aaaagtccct gagggcggtt aggagttctg ggtgaccatc ctggctcagc tcctaactca
5821 ccatgtgaca tcaggctatc cccattcccc ctcttgggcc tcagtttccc gacttgcaaa
5881 ataagcagaa agaaccagat gctctccagg gtcttttct actttgctat ctcatgggtc
5941 ttcattttct cttatttgt tttctctgga tcttttccat ctgagggtac aggaagtacc
6001 aggacctgtt tcagttttg aatcctgcaa gcacattcca agactggcct gaaactgcat
6061 gagcaacatc actcgaaata atttttttt tcaaaagcac cttaacaacc aattgcgatg
6121 ctgtcctgtt ccttttact cacacccttc tctcctttct cgtccccatg ctcccccacc
```

FIG. 32 (cont.)

```
6181 tcagtgctcc gtgctgtatg cgtgtgctct ctgttcttgt atactcaata taagtgaaat
6241 aaatgtgttt gatgctgaac cat
```

Translation:
```
    SAGGGVAEQAAPQSPPRPRAAPPRGLPARGAEGAAPRPTCPTWGTPGPGVLVTMTTET
    GPDSEVKKAQEEAPQQPEAAAAVTTPVTPAGHGHPEANSNEKHPSQQDTRPAEQSLDM
    EEKDYSEADGLSERTTPSKAQKSPQKIAKKYKSAICRVTLLDASEYECEVEKHGRGQV
    LFDLVCEHLNLLEKDYFGLTFCDADSQKNWLDPSKEIKKQIRSSPWNFAFTVKFYPPD
    PAQLTEDITRYYLCLQLRADIITGRLPCSFVTHALLGSYAVQAELGDYDAEEHVGNYV
    SELRFAPNQTRELEERIMELHKTYRGMTPGEAEIHFLENAKKLSMYGVDLHHAKDSEG
    IDIMLGVCANGLLIYRDRLRINRFAWPKILKISYKRSNFYIKIRPGEYEQFESTIGFK
    LPNHRSAKRLWKVCIEHHTFFRLVSPEPPPKGFLVMGSKFRYSGRTQAQTRQASALID
    RPAPFFERSSSKRYTMSRSLDGAEFSRPASVSENHDAGPDGDKRDEDGESGGQRSEAE
    EGEVRTPTKIKELKPEQETTPRHKQEFLDKPEDVLLKHQASINELKRTLKEPNSKLIH
    RDRDWERERRLPSSPASPSPKGTPEKANERAGLREGSEEKVKPPRPRAPESDTGDEDQ
    DQERDTVFLKDNHLAIERKCSSITVSSTSSLEAEVDFTVIGDYHGSAFEDFSRSLPEL
    DRDKSDSDTEGLLFSRDLNKGAPSQDDESGGIEDSPDRGACSTPDMPQFEPVKTETMT
    VSSLAIRKKIEPEAVLQTRVSAMDNTQQVDGSASVGREFIATTPSITTETISTTMENS
    LKSGKGAAAMIPGPQTVATEIRSLSPIIGKDVLTSTYGATAETLSTSTTTHVTKTVKG
    GFSETRIEKRIIITGDEDVDQDQALALAIKEAKLQHPDMLVTKAVVYRETDPSPEERD
    KKPQES
```

FIG. 33

Human non-muscle alpha-actinin mRNA, complete cds -
the second non-muscle alpha-actinin isoform designated ACTN4 (actinin-4)

ORIGIN
```
   1 gcgcgccggc ggctcgggca gaggggcggg agctgaggcg ggagcggaca ggctggtggg
  61 cgagcgagag gcgcggaatg gtggactacc acgcggcgaa ccagtcgtac cagtacggcc
 121 ccagcagcgc ggcaatggct tggcggcggg ggagcatggg cgactacatg gcccaggagg
 181 acgactggga ccgggacctg ctgctggacc cggcctggga gaagcagcag cgcaagacct
 241 tcacggcatg gagcaactcc cacctgcgga aggcaggcac acagatcgag aacattgatg
 301 aggacttccg agacgggctc aagctcatgc tgctcctgga ggtcatatca ggggagcggt
 361 tacctaagcc ggagcggggg aagatgagag tgcacaaaat caacaatgtg aacaaagcgc
 421 tggactttat tgccagcaaa gggatcaagc tggacttcca tcgggcagaa gagattgtgg
 481 acggcaacgc aaagatgacc ctgggaatga tctggaccat catccttagg ttcgccatcc
 541 aggacatctc cgtggaagag acctcggcca aggaagggct ccttctctgg tgccagagaa
 601 agacagcccc atataagaac gtcaatgtgc agaacttcca catcagctgg aaggatggtc
 661 ttgccttcaa tgccctgatc caccgcaca gaccagagct gattgagtat gacaagctga
 721 ggaaggacga ccctgtcacc aacctgaaca atgccttcga agtggctgag aaatacctcg
 781 acatccccaa gatgctggat gcagaggaca tcgtgaacac ggcccggccc gacgagaagg
 841 ccataatgac ctatgtgtcc agcttctacc atgcctttc aggagcgcag aaggctgaaa
 901 ctgaaactgc cgccaaccgg atctgtaagg tgctggctgt caaccaagag aactgcagca
 961 cctcgatgga ggactacgag aagctggcca gcgacctcct ggagtggatc cggcgcacca
1021 tcccctggct ggaggaccgt gtgccccaaa agactatcca ggagatgcag cagaagctgg
1081 aggacttccg cgactaccgg cgtgtgcaca agccgcccaa ggtgcaggag aagtgccagc
1141 tggagatcaa cttcaacagc gtgcagacca agctgcgcct cagcaaccgg cccgccttca
1201 tgccctccga gggcaagatg gtctcggaca tcaacaatgg ctggcagcac ttggagcagg
1261 ctgagaaggg ctacgaggag tggctgctga atgagattcg caggctggag cggctcgacc
1321 acctggcaga gaagttccgg cagaaagcct ccatccacga ggcctggact gacgggaagg
1381 aagccatgct gaagcaccgg gactacgaga cggccacact atcggacatc aaagccctca
1441 ttcgcaagca cgaggccttc gagagcgacc tggctgcgca ccaggaccgc gtggagcaga
1501 tcgccgcctc cgcccaggag ctcaacgagc tggattacta cgactccac aatgtcaaca
1561 cccggtgcca gaagatctgt gaccagtggg acgccctcgg ctctctgaca catagtcgca
1621 gggaagccct ggagaaaaca gagaagcagc tggaggccat catcgaccag ctgcacctgg
1681 aatacgccaa gcccgcggcc cccttcaaca ctggatgga gagcgccatg gaggacctcc
1741 aggacatgtt catcgtccat accatcgagg agattgaggg cctgatctca gcccatgacc
1801 agttcaagtc caccctgccg gacgccgata gggagcgcga ggccatcctg catccacaag
1861 gaggccagag gatcgctgag agcaaccaca tcaagctgtc gggcagcaac ccctacacca
1921 ccgtcaccc gcaaatcatc aactccaagt gggagaaggt gcagcagctg gtgccaaaac
1981 gggaccatgc cctcctggag gagcagagca gcagcagca gtccaacgag cacctgcgcc
2041 gccagttcgc cagccaggcc aatgttgtgg ggccctggat ccagaccaag atggaggaga
2101 tcgcgatctc cattgagatg aacgggaccc tggaggacca gctgagccac ctgaagcagt
2161 atgaacgcag catcgtggac tacaagccca acctggacct gctggagcag cagcaccagc
2221 tcatccagga ggccctcatc ttcgacaaca gcacaccaa ctataccatg gagcacatcc
2281 gcgtgggctg ggagcagctg ctcaccacca tgcccgcac catcaacgag gtggagaacc
2341 agatccttac ccgcgacgcc aagggcatca gccaggagca gatgcaggag ttccgggcgt
2401 ccttcaacca cttcgacaag gatcatggcg gggcgctggg gcgaggagtt caaggcctgc
2461 ctcatcagcc tgggctacga cgtggagaac gaccggcagg tgaggccgag ttcaaccgca
2521 tcatgagcct ggtcgacccc aaccatagcg gccttgttac cttccaagcc ttcatcgact
2581 tcatgtcgcg ggagaccacc gacaccgaca cggctgacca ggtaatcact tccttcaagg
```

FIG. 33 (cont.)

```
2641 tcctagcagg ggacaagaac ttcatcacag ctgaggagct gcggagagag ctgcccccg
2701 accaggccga gtactgcatc gcccgcatgg cgccatacca gggccctgac ggcgtgcgcg
2761 gtgccctcga ctacaagtcc ttctccacgg ccttgtatgg cgagagcgac ctgtgaggcc
2821 ccagagacct gacccaacac ccccgacgcc tccaggagcc tgcagcccc acagtcccat
2881 tcctccactc tgtatctatg caaagcactc tctctgcagt ctccggggtg ggtgggtggg
2941 cagggagggg ctggggcagg ctctctcctc tctctctttg tgggttggcc aggaggttcc
3001 cccgaccagg ttggggagac ttggggccag cgcttctggt ctggtaaata tgtatgatgt
3061 gttgtgcttt tttaaccaag gaggggccag tggattccca cagcacaacc ggtcccttcc
3121 atgccctggg atgcctcacc acacccaggt ctcttccttt gctctgaggt cccttcaagg
3181 cctccccaat ccaggccaaa gcccatgtg ccttgtccag ggaactgcct gggccatgcg
3241 aggggccagc agagggcgcc accacctgac ggctgggacc cacccagccc ctctcccctc
3301 tctgctccag actcacttgc cattgccagg agatggcccc aacaagcacc ccgcttttgc
3361 agcagaggag ctgagttggc agaccgggcc cccctgaacc gcaccccatc ccaccagccc
3421 cggccttgct ttgtctggcc tcacgtgtct cagattttct aagaaccaaa aaaa
```

Translation:
MVDYHAANQSYQYGPSSAAMAWRRGSMGDYMAQEDDWDRDLLLDPAWEKQQRKTFTAW
SNSHLRKAGTQIENIDEDFRDGLKLMLLLEVISGERLPKPERGKMRVHKINNVNKALD
FIASKGIKLDFHRAEEIVDGNAKMTLGMIWTIILRFAIQDISVEETSAKEGLLLWCQR
KTAPYKNVNVQNFHISWKDGLAFNALIHRHRPELIEYDKLRKDDPVTNLNNAFEVAEK
YLDIPKMLDAEDIVNTARPDEKAIMTYVSSFYHAFSGAQKAETETAANRICKVLAVNQ
ENCSTSMEDYEKLASDLLEWIRRTIPWLEDRVPQKTIQEMQQKLEDFRDYRRVHKPPK
VQEKCQLEINFNSVQTKLRLSNRPAFMPSEGKMVSDINNGWQHLEQAEKGYEEWLLNE
IRRLERLDHLAEKFRQKASIHEAWTDGKEAMLKHRDYETATLSDIKALIRKHEAFESD
LAAHQDRVEQIAASAQELNELDYYDSHNVNTRCQKICDQWDALGSLTHSRREALEKTE
KQLEAIIDQLHLEYAKPAAPFNNWMESAMEDLQDMFIVHTIEEIEGLISAHDQFKSTL
PDADREREAILHPQGGQRIAESNHIKLSGSNPYTTVTPQIINSKWEKVQQLVPKRDHA
LLEEQSKQQQSNEHLRRQFASQANVVGPWIQTKMEEIAISIEMNGTLEDQLSHLKQYE
RSIVDYKPNLDLLEQQHQLIQEALIFDNKHTNYTMEHIRVGWEQLLTTIARTINEVEN
QILTRDAKGISQEQMQEFRASFNHFDKDHGGALGRGVQGLPHQPGLRRGERPAGEAEF
NRIMSLVDPNHSGLVTFQAFIDFMSRETTDTDTADQVITSFKVLAGDKNFITAEELRR
ELPPDQAEYCIARMAPYQGPDGVRGALDYKSFSTALYGESDL

FIG. 34

Homo sapiens actinin, alpha 4 (ACTN4) mRNA

ORIGIN
```
   1 cgcggccgcg tcgacctacc acgcggcgaa ccagtcgtac cagtacggcc ccagcagcgc
  61 gggcaatggc gctggcggcg ggggcagcat gggcgactac atggcccagg aggacgactg
 121 ggaccgggac ctgctgctgg acccggcctg ggagaagcag cagcgcaaga ccttcacggc
 181 atggtgcaac tcccacctgc ggaaggcagg cacacagatc gagaacattg atgaggactt
 241 ccgagacggg ctcaagctca tgctgctcct ggaggtcata tcaggggagc ggttacctaa
 301 gccggagcgg gggaagatga gagtgcacaa aatcaacaat gtgaacaaag cgctggactt
 361 tattgccagc aaaggcgtca agctggtctc catcggggca gaagagattg tggacggcaa
 421 cgcaaagatg accctgggaa tgatctggac catcatcctt aggttcgcca tccaggacat
 481 ctccgtggaa gagacctcgg ccaaggaagg gctccttctc tggtgccaga gaaagacagc
 541 cccgtataag aacgtcaatg tgcagaactt ccacatcagc tggaaggatg gtcttgcctt
 601 caatgccctg atccaccggc acagaccaga gctgattgag tatgacaagc tgaggaagga
 661 cgaccctgtc accaacctga acaatgcctt cgaagtggct gagaaatacc tcgacatccc
 721 caagatgctg gatgcagagg acatcgtgaa cacggcccgg cccgacgaga aggccataat
 781 gacctatgtg tccagcttct accatgcctt ttcaggagcg cagaaggctg aaactgccgc
 841 caaccggatc tgtaaggtgc tggctgtcaa ccaagagaac gagcacctga tggaggacta
 901 cgagaagctg gccagcgacc tcctggagtg gatccggcgc accatccccct ggctggagga
 961 ccgtgtgccc caaaagacta tccaggagat gcagcagaag ctggaggact ccgcgacta
1021 ccggcgtgtg cacaagccgc ccaaggtgca ggagaagtgc cagctggaga tcaacttcaa
1081 cacgctgcag accaagctgc gcctcagcaa ccggcccgcc ttcatgccct ccgagggcaa
1141 gatggtctcg gacatcaaca atggctggca gcacttggag caggctgaga agggctacga
1201 ggagtggctg ctgaatgaga tccgcaggct ggagcggctc gaccacctgg cagagaagtt
1261 ccggcagaag gcctccatcc acgaggcctg gactgacggg aaggaagcca tgctgaagca
1321 ccgggactac gagacggcca cactatcgga catcaaagcc ctcattcgca agcacgaggc
1381 cttcgagagc gacctggctg cgcaccagga ccgcgtggag cagatcgccg ccattgccca
1441 ggagctcaac gagctggatt actacgactc ccacaatgtc aacacccggt gccagaagat
1501 ctgtgaccag tgggacgccc tcggctctct gacacatagt cgcagggaag ccctggagaa
1561 aacagagaag cagctggagg ccatcgacca gctgcacctg gaatacgcca agcgcgcggc
1621 ccccttcaac aactggatgg agagcgccat ggaggacctc caggacatgt tcatcgtcca
1681 taccatcgag gagattgagg cctgatctc agcccatgac cagttcaagt ccaccctgcc
1741 ggacgccgat agggagcgcg aggccatcct ggccatccac aaggaggccc agaggatcgc
1801 tgagagcaac cacatcaagc tgtcgggcag caacccctac accaccgtca ccccgcaaat
```

FIG. 34 (cont.)

```
1861 catcaactcc aagtgggaga aggtgcagca gctggtgcca aaacgggacc atgccctcct
1921 ggaggagcag agcaagcagc agtccaacga gcacctgcgc cgccagttcg ccagccaggc
1981 caatgttgtg gggccctgga tccagaccaa gatggaggag atcgggcgca tctccattga
2041 gatgaacggg accctggagg accagctgag ccacctgaag cagtatgaac gcagcatcgt
2101 ggactacaag cccaacctgg acctgctgga gcagcagcac cagctcatcc aggaggccct
2161 catcttcgac aacaagcaca ccaactatac catggagcac atccgcgtgg gctgggagca
2221 gctgctcacc accattgccc gcaccatcaa cgaggtggag aaccagatcc tcacccgcga
2281 cgccaagggc atcagccagg agcagatgca ggagttccgg gcgtccttca accacttcga
2341 caaggatcat ggcggggcgc tggggcccga ggagttcaag gcctgcctca tcagcctggg
2401 ctacgacgtg gagaacgacc ggcagggtga ggccgagttc aaccgcatca tgagcctggt
2461 cgaccccaac catagcggcc ttgtgacctt ccaagccttc atcgacttca tgtcgcggga
2521 gaccaccgac acggacacgg ctgaccaggt catcgcttcc ttcaaggtct tagcagggga
2581 caagaacttc atcacagctg aggagctgcg gagagagctg ccccccgacc aggccgagta
2641 ctgcatcgcc cgcatggcgc cataccaggg ccctgacgcc gtgcccggtg ccctcgacta
2701 caagtccttc tccacggcct tgtatggcga gagcgacctg tgaggcccca gagacctgac
2761 ccaacacccc cgacggcctc caggaggggc ctgggcagcc ccacagtccc attcctccac
2821 tctgtatcta tgcaaagcac tctctgcagt cctccggggt gggtgggtgg gca
```

Translation:
```
MGDYMAQEDDWDRDLLLDPAWEKQQRKTFTAWCNSHLRKAGTQIENIDEDFRDGLKLMLL
LEVISGERLPKPERGKMRVHKINNVNKALDFIASKGVKLVSIGAEEIVDGNAKMTLGMIW
TIILRFAIQDISVEETSAKEGLLLWCQRKTAPYKNVNVQNFHISWKDGLAFNALIHRHRP
ELIEYDKLRKDDPVTNLNNAFEVAEKYLDIPKMLDAEDIVNTARPDEKAIMTYVSSFYHA
FSGAQKAETAANRICKVLAVNQENEHLMEDYEKLASDLLEWIRRTIPWLEDRVPQKTIQE
MQQKLEDFRDYRRVHKPPKVQEKCQLEINFNTLQTKLRLSNRPAFMPSEGKMVSDINNGW
QHLEQAEKGYEEWLLNEIRRLERLDHLAEKFRQKASIHEAWTDGKEAMLKHRDYETATLS
DIKALIRKHEAFESDLAAHQDRVEQIAAIAQELNELDYYDSHNVNTRCQKICDQWDALGS
LTHSRREALEKTEKQLEAIDQLHLEYAKRAAPFNNWMESAMEDLQDMFIVHTIEEIEGLI
SAHDQFKSTLPDADREREAILAIHKEAQRIAESNHIKLSGSNPYTTVTPQIINSKWEKVQ
QLVPKRDHALLEEQSKQQSNEHLRRQFASQANVVGPWIQTKMEEIGRISIEMNGTLEDQL
SHLKQYERSIVDYKPNLDLLEQQHQLIQEALIFDNKHTNYTMEHIRVGWEQLLTTIARTI
NEVENQILTRDAKGISQEQMQEFRASFNHFDKDHGGALGPEEFKACLISLGYDVENDRQG
EAEFNRIMSLVDPNHSGLVTFQAFIDFMSRETTDTDTADQVIASFKVLAGDKNFITAEEL
RRELPPDQAEYCIARMAPYQGPDAVPGALDYKSFSTALYGESDL
```

FIG. 35

CLATHRIN COAT ASSEMBLY PROTEIN AP50

ORIGIN
```
   1 caggtctgtt ctcagagcga tgggccgcag agactgatct gccgccatga ttggaggctt
  61 attcatctat aatcacaagg gggaggtgct catctcccga gtctaccgag atgacatcgg
 121 gaggaacgca gtggatgcct ttcgggtcaa tgttatccat gcccggcagc aggtgcgcag
 181 cccrgtcacc aacattgctc gcaccagctt cttccacgtt aagcggtcca acatttggct
 241 ggcagcagtc accaagcaga atgtcaacgc tgccatggtc ttcgaattcc tctataagat
 301 gtgtgacgtg atggccgctt actttggcaa gatcagcgag gaaaacatca gaacaatttc
 361 tttgctcata tatgagctgc tggatgagat tctagacttt ggctaccac agaattccga
 421 gacaggcgcg ctgaaaacct tcatcacgca gcagggcatc aagagtcagc atcagacaaa
 481 agaagagcag tcacagatca ccagccaggt aactgggcag attggctggc ggcgagaggg
 541 catcaagtat cgtcggaatg agctcttcct ggatgtgctg gagagtgtga acctgctcat
 601 gtccccacaa gggcaggtgc tgagtgccca tgtgtcgggc cgggtggtga tgaagagcta
 661 cctgagtggc atgcctgaat gcaagtttgg gatgaatgac aagattgtta ttgaaaagca
 721 gggcaaggc acagctgatg aaacaagcaa gagcgggaag caatcaattg ccattgatga
 781 ctgcaccttc accagtgtg tgcgactcag caagtttgac tctgaacgca gcatcagctt
 841 tatcccgcca gatggagagt ttgagcttat gaggtatcgc acaaccaagg acatcatcct
 901 tccccttccgg gtgatcccgc tagtgcgaga gtgggacgc accaaactgg aggtcaaggt
 961 ggtcatcaag tccaacttta aaccctcact gctggctcag aagattgagg tgaggatccc
1021 aacccactg aacacaagcg gggtgcaggt gatctgcatg aaggggaagg ccaagtacaa
1081 ggccagcgag aatgccatcg tgtggaagat caagcgcatg gcaggcatga aggaatcgca
1141 gatcagcgca gagattgagc ttctgcctac caacgacaag aagaaatggg ctcgaccccc
1201 catttccatg aactttgagg tgccattcgc gccctctggc ctcaaggtgc gctacttgaa
1261 ggtgtttgaa ccgaagctga actacagcga ccatgatgtc atcaaatggg tgcgctacat
1321 tggccgcagt ggcatttatg aaactcgctg ctagctgcca ctaggcagct agcccacctc
1381 cccagccacc ctcctccaca ggtccaggtg ccgctccctc cccaccaca catcagtgtc
1441 tcctccctcc tgctttgctg ccttcccttt gcaccagccc gagtctaggt ctgggccaag
1501 cacattacaa gtgggaccgg tggagcagcc cctgggctcc ctgggcaggg gagttctgag
1561 gctcctgctc tcccatccac ctgtctgtcc tggcctaatg ccaggctctg agttctgtga
1621 ccaaagccag gtgggttccc ttccttcc accctgtgg ccacagctct ggagtgggag
1681 ggttggttgc ccctcacctc agagctcccc caaaggccag taatggatcc ccggcctcag
1741 tccctactct gctttgggat agtgtgagct tcatttgta cacgtgttgc ttcgtccagt
1801 tacaaaccca ataaactctg tagagtgg
```

Translation:
MIGGLFIYNHKGEVLISRVYRDDIGRNAVDAFRVNVIHARQQVRSPVTNIARTSFFHV
KRSNIWLAAVTKQNVNAAMVFEFLYKMCDVMAAYFGKISEENIKNNFLLIYELLDEIL
DFGYPQNSETGALKTFITQQGIKSQHQTKEEQSQITSQVTGQIGWRREGIKYRRNELF
LDVLESVNLLMSPQGQVLSAHVSGRVVMKSYLSGMPECKFGMNDKIVIEKQGKGTADE
TSKSGKQSIAIDDCTFHQCVRLSKFDSERSISFIPPDGEFELMRYRTTKDIILPFRVI
PLVREVGRTKLEVKVVIKSNFKPSLLAQKIEVRIPTPLNTSGVQVICMKGKAKYKASE
NAIVWKIKRMAGMKESQISAEIELLPTNDKKKWARPPISMNFEVPFAPSGLKVRYLKV
FEPKLNYSDHDVIKWVRYIGRSGIYETRC

FIG. 36

Homo sapiens GLUT1 C-terminal binding protein (GLUT1CBP) mRNA

ORIGIN
```
   1 cacggggagg cggaggcagc ggcggcggcg gcggcggcgg cggcggcggc ggagcagatc
  61 ttctggtgac cccacttctc gctgctcatg ccgctgggac tggggcgccg gaaaaaggcg
 121 cccctctag tggaaaatga ggaggctgag ccaggccgtg gagggctggg cgtgggggag
 181 ccagggcctt gggcggagg tgggtcgggg ggccccaaa tgggcttgcc cccccctccc
 241 ccagccctgc ggccccgcct tgtgttccac acccagctgg cccatggcag tcccactggc
 301 cgcatcgagg ggttcaccaa cgtcaaggag ctgtatggca agattgccga ggccttccgc
 361 ctgccaactg ccgaggtgat gttttgcacc ctgaacaccc acaaagtgga catggacaag
 421 ctcctggggg gccaaatcgg gctggaggac ttcatcttcg cccacgtgaa ggggcagcgc
 481 aaggaggtgg aggtgttcaa gtcggaggat gcactcgggc tcaccatcac ggacaacggg
 541 gctggctacg ccttcatcaa gcgcatcaag gagggcagcg tgatcgacca catccacctc
 601 atcagcgtgg gcgacatgat cgaggccatt aacgggcaga gcctgctggg ctgccggcac
 661 tacgaagtgg cccggctgct caaggaactg ccccgaggcc gtaccttcac gctgaagctc
 721 acggagcctc gcaaggcctt cgacatgatc agccagcgtt cagcgggtgg ccgccctggc
 781 tctggcccac aactgggcac tggccgaggg accctgcggc tccgatcccg gggccccgcc
 841 acggtggagg atctgccctc tgcctttgaa gagaaggcca ttgagaaggt ggatgacctg
 901 ctggagagtt acatgggtat cagggacacg gagctggcgg ccaccatggt ggagctggga
 961 aaggacaaaa ggaacccgga tgagctggcc gaggccctgg acgaacggct gggtgacttt
1021 gccttccctg acgagttcgt ctttgacgtc tggggcgcca ttggggacgc caaggtcggc
1081 cgctactagg actgcccccg gaccctgcga tgatgacccg ggcgcaacct ggtgggggcc
1141 cccagcaggg acactgacgt caggacccga gcctccaagc ctgagcctag ctcagcagcc
1201 caaggacgat ggtgagggga ggtggggcca ggcccctgc cccgctccaa tcggtaccat
1261 cccctccctg gttcccagtc tggccgggt ccccggcccc cctgtgccct gttccccacc
1321 ctacctcagc tggggtcagg cacagggaag ggagggatc agccaaattt gggcggccac
1381 ccccgcctcc accactttcc accatcagct gccaaactgg tccctctgtc tccctgggc
1441 cttgggttct gtttgggggt catgaccttc ctagtttcct gacgcaggga atacagggga
1501 gagggttgtc cttcccccca gcaaatgcaa taatgccctc accctcctg agaggagccc
1561 cctccctgtg gagcctgtta cctccgcatt tgacacgagt tgctgtgaac cccgcaacct
1621 cctccccacc tcccatctct ccttccaggc ccatccctgg cccagagcag gagggaggga
1681 gggacgatgg cggtgggttt ttgtatctga atttgctgtc ttgaacataa agaatctatc
1741 tgctgttaaa aaaaaaaaaa aaaaa
```

Translation:
MPLGLGRRKKAPPLVENEEAEPGRGGLGVGEPGPLGGGGSGGPQMGLPPPPPALRPRL
VFHTQLAHGSPTGRIEGFTNVKELYGKIAEAFRLPTAEVMFCTLNTHKVDMDKLLGGQ
IGLEDFIFAHVKGQRKEVEVFKSEDALGLTITDNGAGYAFIKRIKEGSVIDHIHLISV
GDMIEAINGQSLLGCRHYEVARLLKELPRGRTFTLKLTEPRKAFDMISQRSAGGRPGS
GPQLGTGRGTLRLRSRGPATVEDLPSAFEEKAIEKVDDLLESYMGIRDTELAATMVEL
GKDKRNPDELAEALDERLGDFAFPDEFVFDVWGAIGDAKVGRY

FIG. 37 gp130 associated protein GAM

ORIGIN
```
   1 ggccgcccgg cgcccccagc agnccgagcc ggggcgcaca gncggggngc agaccgcgcc
  61 ccccgccgcg attgacatga tgtttccaca aagcaggcat tcgggctcct cgcacctacc
 121 ccagcaactc aaattcacca cctcggactc ctgcgaccgc atcaaagacg aatttcagct
 181 actgcaagct cagtaccaca gcctcaagct cgaatgtgac aagttggcca gtgagaagtc
 241 agagatgcag cgtcactatg tgatgtacta cgagatgtcc tacggcttga acatcgagat
 301 gcacaaacag gctgagatcg tcaaaaggct gaacgggatt tgtgcccagg tcctgcccta
 361 cctctcccaa gagcaccagc agcaggtctt gggagccatt gagagggcca agcaggtcac
 421 cgctcccgag ctgaactcta tcatccgaca gcagctccaa gcccaccagc tgtcccagct
 481 gcaggccctg gccctgccct tgacccact acccgtgggg ctgcagccgc cttcgctgcc
 541 ggcggtcagc gcaggcaccg gcctcctctc gctgtccgcg ctgggttccc aggcccacct
 601 ctccaaggaa gacaagaacg ggcacgatgg tgacacccac caggaggatg atggcgagaa
 661 gtcggattag caggggggccg ggacggggag gttgggaggg gggacagagg ggagacagag
 721 gcacggagag aaaggaatgt ttagcacaag acacagcgga gctcgggatg ggctaaactc
 781 ccatagtatt tatggtggcc gccggcgggg gccccagccc agcttgcagg ccacctctag
 841 ctttcttccc tacccattc ccggcttccc tcctcctccc tgcagcctgg ttaggtggat
 901 acctgccctg acatgtgagg caagctaagg cctggaggga cagctgggag accaggtccc
 961 aagggagcaa gacctcgcga agcgcagcag acccggccct ttccccgttt taggcatgtg
1021 taaccgacag tctgcctggg ccacagccct ctcaacctgg tactgcatgc acgcaatgct
1081 agctgcccct ttcccgtcct gggnaccccg agtctccccc gaccccgggt cccaggtatg
1141 ctcccacctc cacctgcccc actcaccacc tctgctagtt ccagacacct ccacgcccac
1201 ctggtcctct cctaccgcac acaaaagggg gggaacgagg gacgagctta gctgagctgg
1261 gaggagcagg gtgagggtgg gcgacccagg attcccctc cccttcccaa ataaccc
```

Translation:
MFPQSRHSGSSHLPQQLKFTTSDSCDRIKDEFQLLQAQYHSLKLECDKLASEKSEMQR
HYVMYYEMSYGLNIEMHKQAEIVKRLNGICAQVLPYLSQEHQQQVLGAIERAKQVTAP
ELNSIIRQQLQAHQLSQLQALALPLTPLPVGLQPPSLPAVSAGTGLLSLSALGSQAHL
SKEDKNGHDGDTHQEDDGEKSD

FIG. 38

Homo sapiens amino-terminal enhancer of split (AES) mRNA

ORIGIN
```
         1 ggccgcccgg cgcccccagc agnccgagcc ggggcgcaca gncggggcgc agcccgcgcc
        61 ccccgccgcg attgacatga tgtttccaca aagcaggcat tcgggctcct cgcacctacc
       121 ccagcaactc aaattcacca cctcggactc ctgcgaccgc atcaaagacg aatttcagct
       181 actgcaagct cagtaccaca gcctcaagct cgaatgtgac aagttggcca gtgagaagtc
       241 agagatgcag cgtcactatg tgatgtacta cgagatgtcc tacggcttga acatcgagat
       301 gcacaaacag gctgagatcg tcaaaaggct gaacgggatt tgtgcccagg tcctgcccta
       361 cctctcccaa gagcaccagc agcaggtctt gggagccatt gagagggcca agcaggtcac
       421 cgctcccgag ctgaactcta tcatccgaca gcagctccaa gcccaccagc tgtcccagct
       481 gcaggccctg gccctgccct tgaccccact acccgtgggg ctgcagccgc cttcgctgcc
       541 ggcggtcagc gcaggcaccg gcctcctctc gctgtccgcg ctgggttccc aggcccacct
       601 ctccaaggaa gacaagaacg ggcacgatgg tgacacccac caggaggatg atggcgagaa
       661 gtcggattag cagggggccg ggacagggag gttgggaggg gggacagagg ggagacagag
       721 gcacggagag aaaggaatgt ttagcacaag acacagcgga gctcgggatt ggctaatctc
       781 ccatagtatt tatggtggcg ccggcgggc cccagcccag cttgcaggcc acctctagct
       841 ttcttcctac cccattccgg cttccctcct cctcccctgc agcctggtta ggtggatacc
       901 tgccctgaca tgtgaggcaa gctaaggcct ggagggtcag atgggagacc aggtcccaag
       961 ggagcaagac ctgcgaagcg cagcagcccc ggcccttccc ccgttttgaa catgtgtaac
      1021 cgacagtctg ccctgggcca cagccctctc accctggtac tgcatgcacg caatgctagc
      1081 tgccccttcc ccgtcctggg caccccgagt ctccccgac cccgggtccc aggtatgctc
      1141 ccacctccac ctgccccact caccacctct gctagttcca gacacctcca cgcccacctg
      1201 gtcctctccc atcgcccaca aaggggggg cacgagggac gagcttagct gagctgggag
      1261 gagcagggtg agggtgggcg acccaggatt ccccctcccc ttcccaaata aagatgaggg
      1321 tact
```

Translation:
MMFPQSRHSGSSHLPQQLKFTTSDSCDRIKDEFQLLQAQYHSLKLECDKLASEKSEMQ
RHYVMYYEMSYGLNIEMHKQAEIVKRLNGICAQVLPYLSQEHQQQVLGAIERAKQVTA
PELNSIIRQQLQAHQLSQLQALALPLTPLPVGLQPPSLPAVSAGTGLLSLSALGSQAH
LSKEDKNGHDGDTHQEDDGEKSD

FIG. 39

Antiquitin 1 (antiquitin=26g turgor protein homolog), mRNA

ORIGIN
```
   1 cctgctccaa ggtccagaga gctttctggt ctttgcagca ggcctgccgc cttcatgtcc
  61 actctcctca tcaatcagcc ccagtatgcg tggctgaaag agctggggct ccgcgaggaa
 121 aacgagggcg tgtataatgg aagctgggga ggccggggag aggttattac gacctattgc
 181 cccgctaaca acgagccaat agcaagagtc cgacaggcca gtgtggcaga ctatgaagaa
 241 actgtaaaga aagcaagaga agcatggaaa atctgggcag atattcctgc tccaaaacga
 301 ggagaaatag taagacagat tggcgatgcc ttgcgggaga agatccaagt actaggaagc
 361 ttggtgtctt tggagatggg gaaaatctta gtggaaggtg tgggtgaagt tcaggagtat
 421 gtggatatct gtgactatgc tgttggttta tcaaggatga ttggaggacc tatcttgcct
 481 tctgaaagat ctggccatgc actgattgag cagtggaatc ccgtaggcct ggttggaatc
 541 atcacggcat tcaatttccc tgtggcagtg tatggttgga acaacgccat cgccatgatc
 601 tgtggaaatg tctgcctctg gaaggagct ccaaccactt ccctcattag tgtggctgtc
 661 acaaagataa tagccaaggt tctggaggac aacaagctgc ctggtgcaat tgttccttg
 721 acttgtggtg gagcagatat tggcacagca atggccaaag atgaacgagt gaacctgctg
 781 tccttcactg ggagcactca ggtgggaaaa caggtgggcc tgatggtgca ggagaggttt
 841 gggagaagtc tgttggaact tggaggaaac aatgccatta ttgcctttga agatgcagac
 901 ctcagcttag ttgttccatc agctctcttc gctgctgtgg aacagctgg ccagaggtgt
 961 accactgcga ggcgactgtt tatacatgaa agcatccatg atgaggttgt aaacagactt
1021 aaaaaggcct atgcacagat ccgagttggg aacccatggg accctaatgt tctctatggg
1081 ccactccaca ccaagcaggc agtgagcatg tttcttggag cagtggaaga agcaaagaaa
1141 gaaggtggca cagtggtcta tgggggcaag gttatggatc gccctggaaa ttatgtagaa
1201 ccgacaattg tgacaggtct tggccacgat gcgtccattg cacacacaga gactttcgct
1261 ccgattctct atgtctttaa attcaagaat gaagaagagg tctttgcatg gaataatgaa
1321 gtaaaacagg gactttcaag tagcatcttt accaaagatc tgggcagaat cttcgctgg
1381 cttggaccta aggatcaga ctgtggcatt gtaaatgtca acattccaac aagtggggct
1441 gagattggag gtgcctttgg aggagaaaag cacactggtg gtggcaggga gtctggcagt
1501 gatgcctgga acagtacat gagaaggtct acttgtacta tcaactacag taaagacctt
1561 cctctggccc aaggaatcaa gtttcagtaa aggtgtttta gatgaacatc ccttaatttg
1621 aggtgttcca gcagctgttt ttggagaaga caaagaagat taaagttttc cctgaataaa
1681 tgcattatta tgactgtgac agtgactaat cccctatga ccccaaagcc ctgattaaat
1741 caagagattc ctttttaaa aatcaaaata aaattgttac aacatagcca tagttactaa
1801 aaaaaaaaa
```

Translation:
MSTLLINQPQYAWLKELGLREENEGVYNGSWGGRGEVITTYCPANNEPIARVRQASVA
DYEETVKKAREAWKIWADIPAPKRGEIVRQIGDALREKIQVLGSLVSLEMGKILVEGV
GEVQEYVDICDYAVGLSRMIGGPILPSERSGHALIEQWNPVGLVGIITAFNFPVAVYG
WNNAIAMICGNVCLWKGAPTTSLISVAVTKIIAKVLEDNKLPGAICSLTCGGADIGTA
MAKDERVNLLSFTGSTQVGKQVGLMVQERFGRSLLELGGNNAIIAFEDADLSLVVPSA
LFAAVGTAGQRCTTARRLFIHESIHDEVVNRLKKAYAQIRVGNPWDPNVLYGPLHTKQ
AVSMFLGAVEEAKKEGGTVVYGGKVMDRPGNYVEPTIVTGLGHDASIAHTETFAPILY
VFKFKNEEEVFAWNNEVKQGLSSSIFTKDLGRIFRWLGPKGSDCGIVNVNIPTSGAEI
GGAFGGEKHTGGGRESGSDAWKQYMRRSTCTINYSKDLPLAQGIKFQ

FIG. 40

ARP2/3 protein COMPLEX 41 KD SUBUNIT (P41-ARC), mRNA

ORIGIN
```
        1 ggcacgaggg agcccagagc cggttcggcg cgtcgactgc ccagagtccg cggccggggc
       61 gcgggaggag ccaagccgcc atggcctacc acagcttcct ggtggagccc atcagctgcc
      121 acgcctggaa caaggaccgc acccagattg ccatctgccc caacaaccat gaggtgcata
      181 tctatgaaaa gagcggtgcc aaatggacca aggtgcacga gctcaaggag cacaacgggc
      241 aggtgacagg catcgactgg ccccccgaga gtaaccgtat tgtgacctgc ggcacagacc
      301 gcaacgccta cgtgtggacg ctgaagggcc gcacatggaa gcccacgctg gtcatcctgc
      361 ggatcaaccg ggctgcccgc tgcgtgcgct gggcccccaa cgagaacaag tttgctgtgg
      421 gcagcggctc tcgtgtgatc tccatctgtt atttcgagca ggagaatgac tggtgggttt
      481 gcaagcacat caagaagccc atccgctcca ccgtcctcag cctggactgg caccccaaca
      541 atgtgctgct ggctgccggc tcctgtgact tcaagtgtcg gatcttttca gcctacatca
      601 aggaggtgga ggaacggccg gcacccaccc cgtggggctc caagatgccc tttggggaac
      661 tgatgttcga atccagcagt agctgcggct gggtacatgg cgtctgtttc tcagccagcg
      721 ggagccgcgt ggcctgggta agccacgaca gcaccgtctg cctggctgat gccgacaaga
      781 agatggccgt cgcgactctg gcctctgaaa cactaccact gctggcgctg accttcatca
      841 cagacaacag cctggtggca gcgggccacg actgcttccc ggtgctgttc acctatgacg
      901 ccgccgcggg gatgctgagc ttcggcgggc ggctggacgt tcctaagcag agctcgcagc
      961 gtggcttgac ggcccgcgag cgcttccaga acctggacaa gaaggcgagc tccgagggtg
     1021 gcacggctgc gggcgcgggc ctagactcgc tgcacaagaa cagcgtcagc cagatctcgg
     1081 tgctcagcgg cggcaaggcc aagtgctcgc agttctgcac cactggcatg gatggcggca
     1141 tgagtatctg ggatgtgaag agcttggagt cagccttgaa ggacctcaag atcaaatgac
     1201 ctgtgaggaa tatgttgcct tcatcctaac tgctggggaa gcggggagag gggtcaggga
     1261 ggctaatggt tgctttgctg aatgtttctg gggtaccaat acgagttccc ataggggctg
     1321 ctccctcaaa aagggagggg acagatgggg agcttttctt acctattcaa ggaatacgtg
     1381 ccttttctt aaatgctttc atttattgaa aaaaaaaaa aaaaaaa
```

Translation:
MAYHSFLVEPISCHAWNKDRTQIAICPNNHEVHIYEKSGAKWTKVHELKEHNGQVTGI
DWAPESNRIVTCGTDRNAYVWTLKGRTWKPTLVILRINRAARCVRWAPNENKFAVGSG
SRVISICYFEQENDWWVCKHIKKPIRSTVLSLDWHPNNVLLAAGSCDFKCRIFSAYIK
EVEERPAPTPWGSKMPFGELMFESSSSCGWVHGVCFSASGSRVAWVSHDSTVCLADAD
KKMAVATLASETLPLLALTFITDNSLVAAGHDCFPVLFTYDAAAGMLSFGGRLDVPKQ
SSQRGLTARERFQNLDKKASSEGGTAAGAGLDSLHKNSVSQISVLSGGKAKCSQFCTT
GMDGGMSIWDVKSLESALKDLKIK

FIG. 41a

H.sapiens seb4D mRNA

ORIGIN
```
   1 gagcgcgggt tctcgcggc ccctggccgc ccccggcgtc atgtacggct cgcagaaggg
  61 caccacgttc accaagatct tcgtgggcgg cctgccgtac cacactaccg acgcctcgct
 121 caggaagtac ttcgagggct tcggcgacat cgaggaggcc gtggtcatca ccgaccgcca
 181 gacgggcaag tcccgcggct acggcttcgt gaccatggcc gaccgggcgg cagctgagag
 241 ggcttgcaaa gaccctaacc ccatcatcga cggccgcaag gccaacgtga acctggcata
 301 tctgggcgcc aagccttggt gtctccagac gggctttgcc attggcgtgc agcagctgca
 361 ccccaccttg atccagcgga cttacgggct gacccccgcac tacatctacc caccagccat
 421 cgtgcagccc agcgtggtga tcccagccgc ccctgtcccg tcgctgtcct cgccctacat
 481 tgagtacacg ccggccagcc cggtctacgc ccagtaccca ccggccaccct atgaccagta
 541 cccatacgcc gcctcgcctg ccacggctga cagcttcgtg ggctacagct accctgccgc
 601 cgtgcaccag gccctctcag ccgcagcacc cgcgggcacc actttcgtgc agtaccaggc
 661 gccgcagctg cagcctgaca ggatgcagtg aggggcgttc ctgccccgag gactgtggca
 721 ttgtcacctt cacagcagac agagctgcca ggccatgatg ggctggcgac agcccggctg
 781 agcttcagtg aggtgccacc agcacccgtg cctccgaaga ccgctcgggc attccgcctg
 841 cgccctggga cagcggagag acggcttctc tttaatctag gtcccattgt gtcttgaggg
 901 aggacttta agaatgactg agaactattt aaagacgcaa tcccaggttc cttgcacacc
 961 atggcagcct ctccttgcac cttctcctgc ctctccacac tccaggttcc ctcaggcttg
1021 tgtccccact gctgcatcgt ggcggggtgt cacagaccct ctgcagcccc tggctgccct
1081 ggactgtgca gagatgcctg actccaggga aacctgaaag caagaagtta atggactgtt
1141 tattgtaact tgatcctccc gagctgtgag cgcagtctga ggtctgagga cacggcctcc
1201 tgttggagtc ccattttctc catcagggca cgtgggcggc ttcctcaagc ccggaggagc
1261 tcccaggcgc acaggggccg ccggtaacag gggccgccgg ccaaaggccc ctttccagtc
1321 atagcactga agttgcaact ttttcttgt aattgttttg ctactaagat aatttcagaa
1381 gttcagtcta ttttttcagc ggatactgcc gccaccaaga atccaaacct aggaa
```

Translation:
SAGFSRPLAAPGVMYGSQKGTTFTKIFVGGLPYHTTDASLRKYFEGFGDIEEAVVITD
RQTGKSRGYGFVTMADRAAAERACKDPNPIIDGRKANVNLAYLGAKPWCLQTGFAIGV
QQLHPTLIQRTYGLTPHYIYPPAIVQPSVVIPAAPVPSLSSPYIEYTPASPVYAQYPP
ATYDQYPYAASPATADSFVGYSYPAAVHQALSAAAPAGTTFVQYQAPQLQPDRMQ

FIG. 41b

H.sapiens seb4B mRNA

ORIGIN
```
   1 gcggcggatg cagtacaacc ggcgctttgt caacgttgtg cccacctttg gcaagaagaa
  61 gggcaccacg ttcaccaaga tcttcgtggg cggcctgccg taccacacta ccgacgcctc
 121 gctcaggaag tacttcgagg gcttcggcga catcgaggag gccgtggtca tcaccgaccg
 181 ccagacgggc aagtcccgcg gctacggctt cgtgaccatg gccgaccggg cggcagctga
 241 gagggcttgc aaagacccta accccatcat cgacggccgc aaggccaacg tgaacctggc
 301 atatctgggc gccaagcctt ggtgtctcca gacgggcttt gccattggcg tgcagcagct
 361 gcaccccacc ttgatccagc ggacttacgg gctgacccc g cactacatct acccaccagc
 421 catcgtgcag cccagcgtgg tgatcccagc cgcccctgtc ccgtcgctgt cctcgcccta
 481 cattgagtac acgccggcca gccggtcta cgcccagtac ccaccggcca cctatgacca
 541 gtacccatac gccgcctcgc ctgccacggc tgacagcttc gtgggctaca gctaccctgc
 601 cgccgtgcac caggccctct cagccgcagc acccgcgggc accactttcg tgcagtacca
 661 ggcgccgcag ctgcagcctg acaggatgca gtgaggggcg ttcctgcccc gaggactgtg
 721 gcattgtcac cttcacagca gacagagctg ccaggccatg atgggctggc gacagcccgg
 781 ctgagcttca gtgaggtgcc accagcaccc gtgcctccga agaccgctcg ggcattccgc
 841 ctgcgccctg ggacagcgga gagacggctt ctctttaatc taggtccat tgtgtcttga
 901 gggaggactt ttaagaatga ctgagaacta tttaaagacg caatcccagg ttccttgcac
 961 accatggcag cctctccttg caccttctcc tgcctctcca cactccaggt tccctcaggc
1021 ttgtgtcccc actgctgcat cgtggcgggg tgtcacagac cctctgcagc ccctggctgc
1081 cctggactgt gcagagatgc ctgactccga ggaaacctga aagcaagaag ttaatggact
1141 gtttattgta acttgatcct cccgagctgt gagcgcagtc tgaggtctga ggacacggcc
1201 tcctgttgga gtcccatttt ctccatcagg gcacgtgggc ggcttcctca agcccggagg
1261 agctcccagg cgcacagggg ccgccggtaa caggggccgc cggccaaagg cccctttcca
1321 gtcatagcac tgaagttgca acttttttct tgtaattgtt ttgctactaa gataatttca
1381 gaagttcagt ctattttttc agcggatact gccgccacca agaatccaaa cctaggaa
```

Translation:
RRMQYNRRFVNVVPTFGKKKGTTFTKIFVGGLPYHTTDASLRKYFEGFGDIEEAVVIT
DRQTGKSRGYGFVTMADRAAAERACKDPNPIIDGRKANVNLAYLGAKPWCLQTGFAIG
VQQLHPTLIQRTYGLTPHYIYPPAIVQPSVVIPAAPVPSLSSPYIEYTPASPVYAQYP
PATYDQYPYAASPATADSFVGYSYPAAVHQALSAAAPAGTTFVQYQAPQLQPDRMQ

FIG. 42

Homo sapiens lamin A/C (LMNA) mRNA

ORIGIN
```
   1 actcagtgtt cgcgggagcc gcacctacac cagccaaccc agatcccgag gtccgacagc
  61 gcccggccca gatccccacg cctgccagga gcaagccgag agccagccgg ccggcgcact
 121 ccgactccga gcagtctctg tccttcgacc cgagccccgc gcccttccg ggaccctgc
 181 cccgcgggca gcgctgccaa cctgccggcc atggagaccc cgtcccagcg gcgcgccacc
 241 cgcagcgggg cgcaggccag ctccactccg ctgtcgccca cccgcatcac ccggctgcag
 301 gagaaggagg acctgcagga gctcaatgat cgcttggcgg tctacatcga ccgtgtgcgc
 361 tcgctggaaa cggagaacgc agggctgcgc cttcgcatca ccgagtctga agaggtggtc
 421 agccgcgagg tgtccggcat caaggccgcc tacgaggccg agctcgggga tgcccgcaag
 481 acccttgact cagtagccaa ggagcgcgcc cgcctgcagc tggagctgag caaagtgcgt
 541 gaggagttta aggagctgaa agcgcgcaat accaagaagg agggtgacct gatagctgct
 601 caggctcggc tgaaggacct ggaggctctg ctgaactcca aggaggccgc actgagcact
 661 gctctcagtg agaagcgcac gctggagggc gagctgcatg atctgcgggg ccaggtggcc
 721 aagcttgagg cagccctagg tgaggccaag aagcaacttc aggatgagat gctgcggcgg
 781 gtggatgctg agaacaggct gcagaccatg aaggaggaac tggacttcca gaagaacatc
 841 tacagtgagg agctgcgtga gaccaagcgc cgtcatgaga cccgactggt ggagattgac
 901 aatgggaagc agcgtgagtt tgagagccgg ctggcggatg cgctgcagga actgcgggcc
 961 cagcatgagg accaggtgga gcagtataag aaggagctgg agaagactta ttctgccaag
1021 ctggacaatg ccaggcagtc tgctgagagg aacagcaacc tggtggggc tgcccacgag
1081 gagctgcagc agtcgcgcat ccgcatcgac agcctctctg cccagctcag ccagctccag
1141 aagcagctgg cagccaagga ggcgaagctt cgagacctgg aggactcact ggcccgtgag
1201 cgggacacca gccggcggct gctggcggaa aaggagcggg agatggccga gatgcgggca
1261 aggatgcagc agcagctgga cgagtaccag gagcttctgg acatcaagct ggcccgggac
1321 atggagatcc acgcctaccg caagctcttg gagggcgagg aggagaggct acgcctgtcc
1381 cccagcccta cctcgcagcg cagccgtggc cgtgcttcct ctcactcatc ccagacacag
1441 ggtgggggca gcgtcaccaa aaagcgcaaa ctggagtcca ctgagagccg cagcagcttc
1501 tcacagcacg cacgcactag cggggcgcgtg gccgtggagg aggtggatga ggagggcaag
1561 tttgtccggc tgcgcaacaa gtccaatgag gaccagtcca tgggcaattg gcagatcaag
1621 cgccagaatg gagatgatcc cttgctgact taccggttcc ccaccaaagtt caccctgaag
1681 gctgggcagg tggtgacgat ctgggctgca ggagctgggg ccacccacag ccccctacc
1741 gacctggtgt ggaaggcaca gaacacctgg ggctgcggga acagcctgcg tacggctctc
1801 atcaactcca ctggggaaga agtggccatg cgcaagctgg tgcgctcagt gactgtggtt
1861 gaggacgacg aggatgagga tggagatgac ctgctccatc accaccatgt gagtggtagc
1921 cgccgctgag gcgagcctg cactggggcc acccagccag gcctggggc agcctctccc
1981 cagcctcccc gtgccaaaaa tcttttcatt aaagaatgtt tggaactt
```

Translation:
MEPTPSQRRATRSGAQASSTPLSPTRITRLQEKEDLQELNDRLAVYIDRVRSLETENAG
LRLRITESEEVVSREVSGIKAAYEAELGDARKTLDSVAKERARLQLELSKVREEFKEL
KARNTKKEGDLIAAQARLKDLEALLNSKEAALSTALSEKRTLEGELHDLRGQVAKLEA
ALGEAKKQLQDEMLRRVDAENRLQTMKEELDFQKNIYSEELRETKRRHETRLVEIDNG
KQREFESRLADALQELRAQHEDVEQYKKELEKTYSAKLDNARQSAERNSNLVGAAHE
ELQQSRIRIDSLSAQLSQLQKQLAAKEAKLRDLEDSLARERDTSRRLLAEKEREMAEM
RARMQQQLDEYQELLDIKLALDMEIHAYRKLLEGEEERLRLSPSPTSQRSRGRASSHS
SQTQGGGSVTKKRKLESTESRSSFSQHARTSGRVAVEEVDEEGKFVRLRNKSNEDQSM
GNWQIKRQNGDDPLLTYRFPPKFTLKAGQVVTIWAAGAGATHSPPTDLVWKAQNTWGC
GNSLRTALINSTGEEVAMRKLVRSVTVVEDDEDEDGDDLLHHHHVSGSRR

SEQUENCE LISTING

<160> NUMBER OF SEQ ID NOS: 53

<210> SEQ ID NO 1
<211> LENGTH: 333
<212> TYPE: PRT
<213> ORGANISM: Human

<400> SEQUENCE: 1

```
Met Pro Leu Gly Leu Gly Arg Arg Lys Lys Ala Pro Pro Leu Val Glu
1               5                   10                  15

Asn Glu Glu Ala Glu Pro Gly Arg Gly Gly Leu Gly Val Gly Glu Pro
                20                  25                  30

Gly Pro Leu Gly Gly Gly Gly Ser Gly Gly Pro Gln Met Gly Leu Pro
            35                  40                  45

Pro Pro Pro Pro Ala Leu Arg Pro Arg Leu Val Phe His Thr Gln Leu
        50                  55                  60

Ala His Gly Ser Pro Thr Gly Arg Ile Glu Gly Phe Thr Asn Val Lys
65                  70                  75                  80

Glu Leu Tyr Gly Lys Ile Ala Glu Ala Phe Arg Leu Pro Thr Ala Glu
                85                  90                  95

Val Met Phe Cys Thr Leu Asn Thr His Lys Val Asp Met Asp Lys Leu
                100                 105                 110

Leu Gly Gly Gln Ile Gly Leu Glu Asp Phe Ile Phe Ala His Val Lys
            115                 120                 125

Gly Gln Arg Lys Glu Val Glu Val Phe Lys Ser Glu Asp Ala Leu Gly
        130                 135                 140

Leu Thr Ile Thr Asp Asn Gly Ala Gly Tyr Ala Phe Ile Lys Arg Ile
145                 150                 155                 160

Lys Glu Gly Ser Val Ile Asp His Ile His Leu Ile Ser Val Gly Asp
                165                 170                 175

Met Ile Glu Ala Ile Asn Gly Gln Ser Leu Leu Gly Cys Arg His Tyr
                180                 185                 190

Glu Val Ala Arg Leu Leu Lys Glu Leu Pro Arg Gly Arg Thr Phe Thr
            195                 200                 205
```

```
Leu Lys Leu Thr Glu Pro Arg Lys Ala Phe Asp Met Ile Ser Gln Arg
        210                 215                 220

Ser Ala Gly Gly Arg Pro Gly Ser Gly Pro Gln Leu Gly Thr Gly Arg
225                 230                 235                 240

Gly Thr Leu Arg Leu Arg Ser Arg Gly Pro Ala Thr Val Glu Asp Leu
                245                 250                 255

Pro Ser Ala Phe Glu Glu Lys Ala Ile Glu Lys Val Asp Asp Leu Leu
            260                 265                 270

Glu Ser Tyr Met Gly Ile Arg Asp Thr Glu Leu Ala Ala Thr Met Val
        275                 280                 285

Glu Leu Gly Lys Asp Lys Arg Asn Pro Asp Glu Leu Ala Glu Ala Leu
    290                 295                 300

Asp Glu Arg Leu Gly Asp Phe Ala Phe Pro Asp Glu Phe Val Phe Asp
305                 310                 315                 320

Val Trp Gly Ala Ile Gly Asp Ala Lys Val Gly Arg Tyr
                325                 330
```

```
<210> SEQ ID NO 2
<211> LENGTH: 720
<212> TYPE: DNA
<213> ORGANISM: Human

<400> SEQUENCE: 2
cacggggagg cggaggcagc ggcggcggcg gcggcggcgg cggcggcggc ggagcagatc      60
ttctggtgac cccacttctc gctgctcatg ccgctgggac tggggcgccg gaaaaaggcg     120 cccccctctag tggaaaatga ggaggctgag ccaggccgtg gagggctggg cgtgggggag    180
ccagggcctt tggcggagg tgggtcgggg ggcccccaaa tgggcttgcc ccccctcccc      240
ccagccctgc ggccccgcct tgtgttccac acccagctgg cccatggcag tcccactggc    300
cgcatcgagg ggttcaccaa cgtcaaggag ctgtatggca agattgccga ggccttccgc   360
ctgccaactg ccgaggtgat gttttgcacc ctgaacaccc acaaagtgga catggacaag    420
ctcctggggg gccaaatcgg gctggaggac ttcatcttcg cccacgtgaa ggggcagcgc    480
aaggaggtgg aggtgttcaa gtcggaggat gcactcgggc tcaccatcac ggacaacggg    540
gctggctacg ccttcatcaa gcgcatcaag gagggcagcg tgatcgacca catccacctc    600
atcagcgtgg gcgacatgat cgaggccatt aacgggcaga gcctgctggg ctgccggcac    660
tacgaagtgg cccggctgct caaggaactg ccccgaggcc gtaccttcac gctgaagctc    720
```

```
<210> SEQ ID NO 3
<211> LENGTH: 9
<212> TYPE: PRT
<213> ORGANISM: Human

<400> SEQUENCE: 3

Lys Leu Leu Gly Gly Gln Ile Gly Leu
1               5

<210> SEQ ID NO 4
<211> LENGTH: 10
<212> TYPE: PRT
<213> ORGANISM: Human

<400> SEQUENCE: 4

Ser Leu Leu Gly Cys Arg His Tyr Glu Val
1               5                   10
```

-continued

```
<210> SEQ ID NO 5
<211> LENGTH: 6263
<212> TYPE: DNA
<213> ORGANISM: Human

<400> SEQUENCE: 5
catcagcggg cggggtgtc gccgaacagg ctgctccgca gagcccgccg cgaccccgcg      60
ccgccccgcc ccgcggcctg cctgccagag gagccgaggg ggccgcccct cgcccaacct     120
gcccgacatg gggaaccccg ggcccaggcg tgctggtcac catgacaaca gagacaggcc     180
ccgactctga ggtgaagaaa gctcaggagg aggccccgca gcagcccgag gctgctgccg     240
ctgtgaccac ccctgtgacc cctgcaggcc acggccaccc agaggccaac tccaatgaga     300
agcatccatc ccagcaggac acgcggcctg ctgaacagag cctagacatg gaggagaagg     360
actacagtga ggccgatggc ctttcggaga ggaccacgcc cagcaaggcc cagaaatcgc     420
cccagaagat tgccaagaaa tacaagagtg ccatctgccg ggtcactctg cttgatgcct     480
cggagtatga gtgtgaggtg gagaaacatg gccggggcca ggtgctgttt gacctggtct     540
gtgaacacct caacctccta gagaaggact acttcggcct gaccttctgt gatgctgaca     600
gccagaagaa ctggctggac ccctccaagg agatcaagaa gcagatccgg agtagcccct     660
ggaattttgc cttcacagtc aagttctacc cgcctgatcc tgcccagctg acagaagaca     720
tcacaagata ctacctgtgc ctgcagctgc gggcagacat catcacgggc cggctgccat     780
gctcctttgt cacgcatgcc ctactgggct cctacgctgt gcaggctgag ctgggtgact     840
atgatgctga ggagcatgtg ggcaactatg tcagcgagct ccgcttcgcc cctaaccaga     900
cccgggagct ggaggagagg atcatggagc tgcataagac atataggggg atgccccgg      960 gagaagcaga aatccacttc ttagagaatg ccaagaagct ttccatgtac ggagtagacc    1020
tgcaccatgc caaggactct gagggcatcg acatcatgtt aggcgtttgt gccaatggcc    1080
tgctcatcta ccgggaccgg ctgagaatca accgctttgc ctggcccaag atcctcaaga    1140
tctcctacaa gaggagtaac ttctatatca agatccggcc tggggagtat gagcaatttg    1200
agagcacaat tggctttaag ctcccaaacc accggtcagc caagagactg tggaaggtct    1260
gcatcgagca tcatacattc ttccggctgg tgtcccctga gcccccaccc aagggcttcc    1320
tggtgatggg ctccaagttc cggtacagtg ggaggaccca ggcacagact cgccaggcca    1380
gcgccctcat tgaccggcct gcaccttct ttgagcgttc ttccagcaaa cggtacacca    1440
tgtcccgcag ccttgatgga gcagagttct cccgcccagc ctcggtcagc gagaaccatg    1500
atgcagggcc tgacggtgac aagcgggatg aggatggcga gtctgggggg caacggtcag    1560
aggctgagga gggagaggtc aggactccaa ccaagatcaa ggagctaaag ccggagcagg    1620
aaaccacgcc gagacacaag caggagttct tagacaagcc agaagatgtc ttgctgaagc    1680
accaggccag catcaatgag ctcaaaagga ccctgaagga gcccaacagc aaactcatcc    1740
accgggatcg agactgggaa cgggagcgca ggctgccctc ctccccccgcc tcccctccc    1800 ccaagggcac ccctgagaaa gccaatgaga gagcagggct gagggagggc tccgaggaga    1860
aagtcaaacc accacgtccc cggggcccag agagtgacac aggcgatgag gaccaggacc    1920
aggagaggga cacggtgttc ctgaaggaca accacctggc cattgagcgc aagtgctcca    1980
gcatcacggt cagctctacg tctagcctgg aggctgaggt ggacttcacg gtcattggtg    2040
actaccatgg cagcgccttc gaagacttct cccgcagcct gctgagctc gaccgggaca    2100 aaagcgactc ggacactgag ggcctgctgt tctcccggga tctcaacaag ggggccccca    2160
```

```
gccaggatga tgagtctggg ggcattgagg acagcccgga tcgagggggcc tgctccaccc    2220 cggatatgcc ccagtttgag cccgtgaaaa cagaaaccat gactgtcagc agtctggcca    2280
ttagaaagaa gattgagccg gaggccgtac tgcagaccag agtctccgct atggataaca    2340
cccagcaggt tgatgggagt gcctcagtgg ggagggagtt catagcaacc actccctcca    2400
tcaccacgga gaccatatcg accaccatgg agaacagtct caagtccggg aaggggggcag    2460 ctgccatgat cccaggccca cagacggtgg ccacggaaat ccgttctctt tctccgatca    2520
tcgggaaaga tgtcctcacc agcacctacg gcgccactgc ggaaaccctc tcaacctcca    2580
ccaccaccca tgtcaccaaa actgtgaaag gagggttttc tgagacaagg atcgagaagc    2640
gaatcatcat tactggggat gaagatgtcg atcaagacca ggccctggct ttggccatca    2700
aggaggccaa actgcagcat cctgatatgc tggtaaccaa agctgtcgta tacagagaaa    2760
cagacccatc cccagaggag agggacaaga agccacagga atcctgacct ctgtgaagag    2820
atcctggcat ttctggtcca acccaagcca gagaaccatt aagaagggggc cttcattctg    2880 gattctccga cgcaacactg acgtcccagc tgcgacgtac tgtcactgat gagagactgg    2940
gaagggaaaa gcatatatat atagatatat agagatatag atatatatac aggaaacacc    3000
gcatccttgc actgctgctg gggctggcag agcagttggc tgacagcaac aaccgacatc    3060
tgaacaccta catttccttt gcagacaaat tgaagaactg gtgggatttt tttcaagaaa    3120
aaaaattata taataactat aatcccttgc tcaccccttt ccccgccaa ataagaaacg     3180 caagccagac cacgatgatt gtagaagtcc ctcccgccct ggttctgcac gttacagtta    3240
gcagacgagc aattccattt gttcttctcc agcatctcta aggcccactt gaatgcaaag    3300
gaaaacactt gcacagcaaa gcaagagaag tcacagcagc aagacacgca cagtcaacca    3360
ttttccgaga aaaaagaaa attccccact tggaaagaaa gaggaggaac actggattct     3420
tactttctgg atcttgacac tgggctgcaa aacctacctt cctctctccc gcctcccctc    3480
accctcaact ctcaatgtct tgctgtcatt ttctgtctcg gctccctcct ccccttccc     3540 ccttccccca ccccacaccc ttcaccctct gtgtcctggt ccttctgagg gccactgcag    3600
atgactctcc tttgaaatga gaaaagaaa agaaagcaag aacagaaaac gaagccacag     3660
gaagggaagt agacattgta tgcttatggt ttctcattat gaaggtgcag cttgtaggag    3720
gtttgtacgg atgtgctttg aagttatgta tattacatat aacaggaaaa atattaata    3780 aacagtgctg gtaagtatga agctgacatt ctaaaattat aattatctga ctgtgattga    3840
tgtatcctga ggttcctaga tctcactgaa ctggcccagc taaggagacc tggactctgg    3900
gtgtgggttg gctcacagta ggggctgacg ggttcagtgt agtaatactg tgtgtggtgt    3960
ttgtaattgg ttgattggtg gggagggggtg ggggccccta atggagaggt gtgggtttgg   4020
caagaaagaa gcaacacaga tgtcgtcccc aaaatgccag ttcaagacac cttctccctg    4080 ccccccctggt agtaacagtc agggcctggt ctgtgctcag gtactgggtc ccagtctggg   4140
actctgctgc tgaagttgcc acagtagagg tccctggctt agtccttatc tccctacggg    4200
gcttgccttg gttttcagtc ttctctctct ttctctcttt ttttttttt tgccacattc     4260 tgcccttccc tgaccccatt gtaataacca actccatatc caagggagg tggtgctctc     4320 agccattgta gaagatggtg gctttaacct gactgtctaa aaattcccag ctaagccttt    4380
tcctctactc tcttccttgt tctgaatcat ttcttcttct caggccaaag tagccatggt    4440
aaggaggctt catggggcag accctgaaag atcaaaactg catttgcaaa gccctcccct    4500
gtcccaggac aaagctgaga ctgacgggtg atgttgctca taggctccag ctctgcataa    4560
```

-continued

```
gaccttggct tggagacctc cctctcagtc aacagctgaa ctctgagctt gtgcccagaa    4620 attacccccaa gaccacagga acccttcaag aagctcccat cacaagcttg gcattgctct    4680
ctgccacacg tgggcttcct caggcttgtc tgccacaagc tacttctctg agctcagaaa    4740
gtgccccttg atgagggaaa atgtcccact gcactgcgaa tttctcagtt ccattttacc    4800
tcccagtcct ccttctaaac cagttaataa attcattcca caagtattta ctgattacct    4860
gcttgtgcca gggactattc tcaggctgaa gaaggtggga ggggagggcg gaacctgagg    4920
agccacctga gccagcttta tatttcaacc atggctggcc catctgagag catctcccca    4980
ctctcgccaa cctatcgggg catagcccag ggatgccccc aggcggccca ggttagatgc    5040
gtccctttgg cttgtcagtg atgacataca ccttagctgc ttagctggtg ctggcctgag    5100
gcagggcagg aaatcagaat agcatttgct tctctgggca aatgggaagt tcagcggggc    5160
agcagaatca gtggcattcc ccctggtgca ggccggtggg tccactccaa ctcccccctga   5220 gtgtagcagc acactttcca tacaccaggt tctttctaca atcctggtgg aaaagccaca    5280
gaaccttctt cctgcccttc ttgagagttc ccctctttc tgggtcaaga gctggagtgg     5340
tggctccatc ctctctgggc cacttcggtc taggaactca tctttgcagg aaccaggagt    5400
cctgagcaca ctgaacacac ctcagaggga ggatccttgt tgtggatttt gcacctggct    5460
ttggggcagg ggtgaagtga ccaggcttag cttgtggagt ttatgggcca ccagggtttg    5520
gggaaatcac catcccgcgg atgctgtgac ctcccttcta cggagatgca ggcagtgcca    5580
cgagggagga ggggacctgc aaagctagaa tctagggcac tgtttcctcc ccatccttct    5640
ctttgtagag aatagagacg tttgtcttgt ctgtcttcaa cctactttc cttttctctt      5700 ttttgtttct catcctctct gtgccacctc tccacccagg aggccatgta gcatagtgga    5760
aaaagtccct gagggcggtt aggagttctg ggtgaccatc ctggctcagc tcctaactca    5820
ccatgtgaca tcaggctatc cccattcccc ctcttgggcc tcagtttccc gacttgcaaa    5880
ataagcagaa agaaccagat gctctccagg gtctttttct actttgctat ctcatgggtc    5940
ttcatttctc cttatttgt tttctctgga tcttttccat ctgagggtac aggaagtacc      6000
aggacctgtt tcagttttg aatcctgcaa gcacattcca agactggcct gaaactgcat      6060
gagcaacatc actcgaaata attttttttt tcaaaagcac cttaacaacc aattgcgatg    6120
ctgtcctgtt ccttttttact cacacccttc tctcctttct cgtccccatg ctcccccacc    6180
tcagtgctcc gtgctgtatg cgtgtgctct ctgttcttgt atactcaata taagtgaaat    6240
aaatgtgttt gatgctgaac cat                                             6263
```

<210> SEQ ID NO 6
<211> LENGTH: 933
<212> TYPE: PRT
<213> ORGANISM: Human

<400> SEQUENCE: 6

```
Ser Ala Gly Gly Gly Val Ala Glu Gln Ala Ala Pro Gln Ser Pro Pro
1               5                   10                  15

Arg Pro Arg Ala Ala Pro Pro Arg Gly Leu Pro Ala Arg Gly Ala Glu
            20                  25                  30

Gly Ala Ala Pro Arg Pro Thr Cys Pro Thr Trp Gly Thr Pro Gly Pro
        35                  40                  45

Gly Val Leu Val Thr Met Thr Thr Glu Thr Gly Pro Asp Ser Glu Val
    50                  55                  60
```

```
Lys Lys Ala Gln Glu Ala Pro Gln Gln Pro Glu Ala Ala Ala
 65                  70                  75                  80

Val Thr Thr Pro Val Thr Pro Ala Gly His Gly His Pro Glu Ala Asn
                 85                  90                  95

Ser Asn Glu Lys His Pro Ser Gln Asp Thr Arg Pro Ala Glu Gln Ser
            100                 105                 110

Leu Asp Met Glu Glu Lys Asp Tyr Ser Glu Ala Asp Gly Leu Ser Glu
            115                 120                 125

Arg Thr Thr Pro Ser Lys Ala Gln Lys Ser Pro Gln Lys Ile Ala Lys
        130                 135                 140

Lys Tyr Lys Ser Ala Ile Cys Arg Val Thr Leu Leu Asp Ala Ser Glu
145                 150                 155                 160

Tyr Glu Cys Glu Val Glu Lys His Gly Arg Gly Gln Val Leu Phe Asp
                165                 170                 175

Leu Val Cys Glu His Leu Asn Leu Leu Glu Lys Asp Tyr Phe Gly Leu
            180                 185                 190

Thr Phe Cys Asp Ala Asp Ser Gln Lys Asn Trp Leu Asp Pro Ser Lys
        195                 200                 205

Glu Ile Lys Lys Gln Ile Arg Ser Ser Pro Trp Asn Phe Ala Phe Thr
210                 215                 220

Val Lys Phe Tyr Pro Pro Asp Pro Ala Gln Leu Thr Glu Asp Ile Thr
225                 230                 235                 240

Arg Tyr Tyr Leu Cys Leu Gln Leu Arg Ala Asp Ile Ile Thr Gly Arg
                245                 250                 255

Leu Pro Cys Ser Phe Val Thr His Ala Leu Leu Gly Ser Tyr Ala Val
            260                 265                 270

Gln Ala Glu Leu Gly Asp Tyr Asp Ala Glu His Val Gly Asn Tyr
        275                 280                 285

Val Ser Glu Leu Arg Phe Ala Pro Asn Gln Thr Arg Glu Leu Glu Glu
290                 295                 300

Arg Ile Met Glu Leu His Lys Thr Tyr Arg Gly Met Thr Pro Gly Glu
305                 310                 315                 320

Ala Glu Ile His Phe Leu Glu Asn Ala Lys Lys Leu Ser Met Tyr Gly
                325                 330                 335

Val Asp Leu His His Ala Lys Asp Ser Glu Gly Ile Asp Ile Met Leu
            340                 345                 350

Gly Val Cys Ala Asn Gly Leu Leu Ile Tyr Arg Asp Arg Leu Arg Ile
        355                 360                 365

Asn Arg Phe Ala Trp Pro Lys Ile Leu Lys Ile Ser Tyr Lys Arg Ser
370                 375                 380

Asn Phe Tyr Ile Lys Ile Arg Pro Gly Glu Tyr Glu Gln Phe Glu Ser
385                 390                 395                 400

Thr Ile Gly Phe Lys Leu Pro Asn His Arg Ser Ala Lys Arg Leu Trp
                405                 410                 415

Lys Val Cys Ile Glu His His Thr Phe Phe Arg Leu Val Ser Pro Glu
            420                 425                 430

Pro Pro Pro Lys Gly Phe Leu Val Met Gly Ser Lys Phe Arg Tyr Ser
        435                 440                 445

Gly Arg Thr Gln Ala Gln Thr Arg Gln Ala Ser Ala Leu Ile Asp Arg
450                 455                 460

Pro Ala Pro Phe Phe Glu Arg Ser Ser Ser Lys Arg Tyr Thr Met Ser
465                 470                 475                 480
```

-continued

```
Arg Ser Leu Asp Gly Ala Glu Phe Ser Arg Pro Ala Ser Val Ser Glu
            485                 490                 495

Asn His Asp Ala Gly Pro Asp Gly Asp Lys Arg Asp Glu Asp Gly Glu
            500                 505                 510

Ser Gly Gly Gln Arg Ser Glu Ala Glu Glu Gly Glu Val Arg Thr Pro
            515                 520                 525

Thr Lys Ile Lys Glu Leu Lys Pro Glu Gln Glu Thr Thr Pro Arg His
            530                 535                 540

Lys Gln Glu Phe Leu Asp Lys Pro Glu Asp Val Leu Leu Lys His Gln
545                 550                 555                 560

Ala Ser Ile Asn Glu Leu Lys Arg Thr Leu Lys Glu Pro Asn Ser Lys
                565                 570                 575

Leu Ile His Arg Asp Arg Asp Trp Glu Arg Glu Arg Leu Pro Ser
                580                 585                 590

Ser Pro Ala Ser Pro Ser Pro Lys Gly Thr Pro Glu Lys Ala Asn Glu
                595                 600                 605

Arg Ala Gly Leu Arg Glu Gly Ser Glu Glu Lys Val Lys Pro Pro Arg
            610                 615                 620

Pro Arg Ala Pro Glu Ser Asp Thr Gly Asp Glu Asp Gln Asp Gln Glu
625                 630                 635                 640

Arg Asp Thr Val Phe Leu Lys Asp Asn His Leu Ala Ile Glu Arg Lys
                645                 650                 655

Cys Ser Ser Ile Thr Val Ser Ser Thr Ser Ser Leu Glu Ala Glu Val
                660                 665                 670

Asp Phe Thr Val Ile Gly Asp Tyr His Gly Ser Ala Phe Glu Asp Phe
                675                 680                 685

Ser Arg Ser Leu Pro Glu Leu Asp Arg Asp Lys Ser Asp Ser Asp Thr
            690                 695                 700

Glu Gly Leu Leu Phe Ser Arg Asp Leu Asn Lys Gly Ala Pro Ser Gln
705                 710                 715                 720

Asp Asp Glu Ser Gly Gly Ile Glu Asp Ser Pro Asp Arg Gly Ala Cys
                725                 730                 735

Ser Thr Pro Asp Met Pro Gln Phe Glu Pro Val Lys Thr Glu Thr Met
                740                 745                 750

Thr Val Ser Ser Leu Ala Ile Arg Lys Lys Ile Glu Pro Glu Ala Val
            755                 760                 765

Leu Gln Thr Arg Val Ser Ala Met Asp Asn Thr Gln Gln Val Asp Gly
            770                 775                 780

Ser Ala Ser Val Gly Arg Glu Phe Ile Ala Thr Thr Pro Ser Ile Thr
785                 790                 795                 800

Thr Glu Thr Ile Ser Thr Thr Met Glu Asn Ser Leu Lys Ser Gly Lys
                805                 810                 815

Gly Ala Ala Ala Met Ile Pro Gly Pro Gln Thr Val Ala Thr Glu Ile
            820                 825                 830

Arg Ser Leu Ser Pro Ile Ile Gly Lys Asp Val Leu Thr Ser Thr Tyr
            835                 840                 845

Gly Ala Thr Ala Glu Thr Leu Ser Thr Ser Thr Thr His Val Thr
            850                 855                 860

Lys Thr Val Lys Gly Gly Phe Ser Glu Thr Arg Ile Glu Lys Arg Ile
865                 870                 875                 880

Ile Ile Thr Gly Asp Glu Asp Val Asp Gln Asp Gln Ala Leu Ala Leu
                885                 890                 895
```

-continued

```
Ala Ile Lys Glu Ala Lys Leu Gln His Pro Asp Met Leu Val Thr Lys
            900                 905                 910
Ala Val Val Tyr Arg Glu Thr Asp Pro Ser Pro Glu Glu Arg Asp Lys
        915                 920                 925
Lys Pro Gln Glu Ser
    930

<210> SEQ ID NO 7
<211> LENGTH: 3474
<212> TYPE: DNA
<213> ORGANISM: Human

<400> SEQUENCE: 7
```

| | | | | | |
|---|---|---|---|---|---|
| gcgcgccggc | ggctcgggca | gaggggcggg | agctgaggcg | ggagcggaca | ggctggtggg | 60 |
| cgagcgagag | gcgcggaatg | gtggactacc | acgcggcgaa | ccagtcgtac | cagtacggcc | 120 |
| ccagcagcgc | ggcaatggct | tggcggcggg | ggagcatggg | cgactacatg | gcccaggagg | 180 |
| acgactggga | ccgggacctg | ctgctggacc | cggcctggga | gaagcagcag | cgcaagacct | 240 |
| tcacggcatg | gagcaactcc | cacctgcgga | aggcaggcac | acagatcgag | aacattgatg | 300 |
| aggacttccg | agacgggctc | aagctcatgc | tgctcctgga | ggtcatatca | ggggagcggt | 360 |
| tacctaagcc | ggagcggggg | aagatgagag | tgcacaaaat | caacaatgtg | aacaaagcgc | 420 |
| tggactttat | tgccagcaaa | gggatcaagc | tggacttcca | tcgggcagaa | gagattgtgg | 480 |
| acggcaacgc | aaagatgacc | ctgggaatga | tctggaccat | catccttagg | ttcgccatcc | 540 |
| aggacatctc | cgtggaagag | acctcggcca | aggaagggct | ccttctctgg | tgccagagaa | 600 |
| agacagcccc | atataagaac | gtcaatgtgc | agaacttcca | catcagctgg | aaggatggtc | 660 |
| ttgccttcaa | tgccctgatc | caccggcaca | gaccagagct | gattgagtat | gacaagctga | 720 |
| ggaaggacga | ccctgtcacc | aacctgaaca | atgccttcga | agtggctgag | aaataccctcg | 780 |
| acatccccaa | gatgctggat | gcagaggaca | tcgtgaacac | ggcccggccc | gacgagaagg | 840 |
| ccataatgac | ctatgtgtcc | agcttctacc | atgccttttc | aggagcgcag | aaggctgaaa | 900 |
| ctgaaactgc | cgccaaccgg | atctgtaagg | tgctggctgt | caaccaagag | aactgcagca | 960 |
| cctcgatgga | ggactacgag | aagctggcca | gcgacctcct | ggagtggatc | cggcgcacca | 1020 |
| tcccctggct | ggaggaccgt | gtgccccaaa | agactatcca | ggagatgcag | cagaagctgg | 1080 |
| aggacttccg | cgactaccgg | cgtgtgcaca | gccgcccaa | ggtgcaggag | aagtgccagc | 1140 |
| tggagatcaa | cttcaacagc | gtgcagacca | agctgcgcct | cagcaaccgg | cccgccttca | 1200 |
| tgccctccga | gggcaagatg | gtctcggaca | tcaacaatgg | ctggcagcac | ttggagcagg | 1260 |
| ctgagaaggg | ctacgaggag | tggctgctga | atgagattcg | caggctggag | cggctcgacc | 1320 |
| acctggcaga | gaagttccgg | cagaaagcct | ccatccacga | ggcctggact | gacgggaagg | 1380 |
| aagccatgct | gaagcaccgg | gactacgaga | cggccacact | atcggacatc | aaagccctca | 1440 |
| ttcgcaagca | cgaggccttc | gagagcgacc | tggctgcgca | ccaggaccgc | gtggagcaga | 1500 |
| tcgccgcctc | cgcccaggag | ctcaacgagc | tggattacta | cgactcccac | aatgtcaaca | 1560 |
| cccggtgcca | gaagatctgt | gaccagtggg | acgccctcgg | ctctctgaca | catagtcgca | 1620 |
| gggaagccct | ggagaaaaca | gagaagcagc | tggaggccat | catcgaccag | ctgcacctgg | 1680 |
| aatacgccaa | gcccgcggcc | cccttcaaca | actggatgga | gagcgccatg | gaggacctcc | 1740 |
| aggacatgtt | catcgtccat | accatcgagg | agattgaggg | cctgatctca | gcccatgacc | 1800 |
| agttcaagtc | caccctgccg | gacgccgata | gggagcgcga | ggccatcctg | catccacaag | 1860 |

| | | |
|---|---|---|
| gaggccagag gatcgctgag agcaaccaca tcaagctgtc gggcagcaac ccctacacca | 1920 | |
| ccgtcacccc gcaaatcatc aactccaagt gggagaaggt gcagcagctg gtgccaaaac | 1980 | |
| gggaccatgc cctcctggag gagcagagca agcagcagca gtccaacgag cacctgcgcc | 2040 | |
| gccagttcgc cagccaggcc aatgttgtgg ggccctggat ccagaccaag atggaggaga | 2100 | |
| tcgcgatctc cattgagatg aacgggaccc tggaggacca gctgagccac ctgaagcagt | 2160 | |
| atgaacgcag catcgtggac tacaagccca acctggacct gctggagcag cagcaccagc | 2220 | |
| tcatccagga ggccctcatc ttcgacaaca agcacaccaa ctataccatg gagcacattc | 2280 | |
| gcgtgggctg ggagcagctg ctcaccacca ttgcccgcac catcaacgag gtggagaacc | 2340 | |
| agatccttac ccgcgacgcc aagggcatca gccaggagca gatgcaggag ttccgggcgt | 2400 | |
| ccttcaacca cttcgacaag gatcatggcg gggcgctggg gcgaggagtt caaggcctgc | 2460 | |
| ctcatcagcc tgggctacga cgtggagaac gaccggcagg tgaggccgag ttcaaccgca | 2520 | |
| tcatgagcct ggtcgacccc aaccatagcg gccttgttac cttccaagcc ttcatcgact | 2580 | |
| tcatgtcgcg ggagaccacc gacaccgaca cggctgacca ggtaatcact tccttcaagg | 2640 | |
| tcctagcagg ggacaagaac ttcatcacag ctgaggagct gcggagagag ctgccccccg | 2700 | |
| accaggccga gtactgcatc gcccgcatgg cgccatacca gggccctgac ggcgtgcgcg | 2760 | |
| gtgccctcga ctacaagtcc ttctccacgg ccttgtatgg cgagagcgac ctgtgaggcc | 2820 | |
| ccagagacct gacccaacac ccccgacgcc tccaggagcc tggcagcccc acagtcccat | 2880 | |
| tcctccactc tgtatctatg caaagcactc tctctgcagt ctccggggtg ggtgggtggg | 2940 | |
| cagggagggg ctggggcagg ctctctcctc tctctctttg tgggttggcc aggaggttcc | 3000 | |
| cccgaccagg ttggggagac ttggggccag cgcttctggt ctggtaaata tgtatgatgt | 3060 | |
| gttgtgctttt tttaaccaag gaggggccag tggattccca cagcacaacc ggtcccttcc | 3120 | |
| atgccctggg atgcctcacc acacccaggt ctcttccttt gctctgaggt cccttcaagg | 3180 | |
| cctcccccaat ccaggccaaa gccccatgtg ccttgtccag ggaactgcct gggccatgcg | 3240 | |
| aggggccagc agagggcgcc accacctgac ggctgggacc cacccagccc ctctcccctc | 3300 | |
| tctgctccag actcacttgc cattgccagg agatggcccc aacaagcacc ccgcttttgc | 3360 | |
| agcagaggag ctgagttggc agaccgggcc cccctgaacc gcaccccatc ccaccagccc | 3420 | |
| cggccttgct ttgtctggcc tcacgtgtct cagattttct aagaaccaaa aaaa | 3474 | |

<210> SEQ ID NO 8
<211> LENGTH: 912
<212> TYPE: PRT
<213> ORGANISM: Human

<400> SEQUENCE: 8

Met Val Asp Tyr His Ala Ala Asn Gln Ser Tyr Gln Tyr Gly Pro Ser
1               5                   10                  15

Ser Ala Ala Met Ala Trp Arg Arg Gly Ser Met Gly Asp Tyr Met Ala
                20                  25                  30

Gln Glu Asp Asp Trp Asp Arg Asp Leu Leu Leu Asp Pro Ala Trp Glu
            35                  40                  45

Lys Gln Gln Arg Lys Thr Phe Thr Ala Trp Ser Asn Ser His Leu Arg
        50                  55                  60

Lys Ala Gly Thr Gln Ile Glu Asn Ile Asp Glu Asp Phe Arg Asp Gly
65                  70                  75                  80

Leu Lys Leu Met Leu Leu Leu Glu Phe Ile Ser Gly Glu Arg Leu Pro
                85                  90                  95

```
Lys Pro Glu Arg Gly Lys Met Arg Val His Lys Ile Asn Asn Val Asn
            100                 105                 110

Lys Ala Leu Asp Phe Ile Ala Ser Lys Gly Ile Lys Leu Asp Phe His
            115                 120                 125

Arg Ala Glu Glu Ile Val Asp Gly Asn Ala Lys Met Thr Leu Gly Met
            130                 135                 140

Ile Trp Thr Ile Ile Leu Arg Phe Ala Ile Gln Asp Ile Ser Val Glu
145                 150                 155                 160

Glu Thr Ser Ala Lys Glu Gly Leu Leu Leu Trp Cys Gln Arg Lys Thr
                165                 170                 175

Ala Pro Tyr Lys Asn Val Asn Val Gln Asn Phe His Ile Ser Trp Lys
                180                 185                 190

Asp Gly Leu Ala Phe Asn Ala Leu Ile His Arg His Arg Pro Glu Leu
                195                 200                 205

Ile Glu Tyr Asp Lys Leu Arg Lys Asp Asp Pro Val Thr Asn Leu Asn
            210                 215                 220

Asn Ala Phe Glu Val Ala Glu Lys Tyr Leu Asp Ile Pro Lys Met Leu
225                 230                 235                 240

Asp Ala Glu Asp Ile Val Asn Thr Ala Arg Pro Asp Glu Lys Ala Ile
                245                 250                 255

Met Thr Tyr Val Ser Ser Phe Tyr His Ala Phe Ser Gly Ala Gln Lys
            260                 265                 270

Ala Glu Thr Glu Thr Ala Ala Asn Arg Ile Cys Lys Val Leu Ala Val
            275                 280                 285

Asn Gln Glu Asn Cys Ser Thr Ser Met Glu Asp Tyr Glu Lys Leu Ala
            290                 295                 300

Ser Asp Leu Leu Glu Trp Ile Arg Arg Thr Ile Pro Trp Leu Glu Asp
305                 310                 315                 320

Arg Val Pro Gln Lys Thr Ile Gln Glu Met Gln Gln Lys Leu Glu Asp
                325                 330                 335

Phe Arg Asp Tyr Arg Arg Val His Lys Pro Pro Lys Val Gln Glu Lys
                340                 345                 350

Cys Gln Leu Glu Ile Asn Phe Asn Ser Val Gln Thr Lys Leu Arg Leu
            355                 360                 365

Ser Asn Arg Pro Ala Phe Met Pro Ser Glu Gly Lys Met Val Ser Asp
370                 375                 380

Ile Asn Asn Gly Trp Gln His Leu Glu Gln Ala Glu Lys Gly Tyr Glu
385                 390                 395                 400

Glu Trp Leu Leu Asn Glu Ile Arg Arg Leu Glu Arg Leu Asp His Leu
                405                 410                 415

Ala Glu Lys Phe Arg Gln Lys Ala Ser Ile His Glu Ala Trp Thr Asp
            420                 425                 430

Gly Lys Glu Ala Met Leu Lys His Arg Asp Tyr Glu Thr Ala Thr Leu
            435                 440                 445

Ser Asp Ile Lys Ala Leu Ile Arg Lys His Glu Ala Phe Glu Ser Asp
            450                 455                 460

Leu Ala Ala His Gln Asp Arg Val Glu Gln Ile Ala Ala Ser Ala Gln
465                 470                 475                 480

Glu Leu Asn Glu Leu Asp Tyr Tyr Asp Ser His Asn Val Asn Thr Arg
                485                 490                 495

Cys Gln Lys Ile Cys Asp Gln Trp Asp Ala Leu Gly Ser Leu Thr His
            500                 505                 510
```

-continued

```
Ser Arg Arg Glu Ala Leu Glu Lys Thr Glu Lys Gln Leu Glu Ala Ile
        515                 520                 525

Ile Asp Gln Leu His Leu Glu Tyr Ala Lys Pro Ala Ala Pro Phe Asn
530                 535                 540

Asn Trp Met Glu Ser Ala Met Glu Asp Leu Gln Asp Met Phe Ile Val
545                 550                 555                 560

His Thr Ile Glu Glu Ile Glu Gly Leu Ile Ser Ala His Asp Gln Phe
                565                 570                 575

Lys Ser Thr Leu Pro Asp Ala Asp Arg Glu Arg Glu Ala Ile Leu His
            580                 585                 590

Pro Gln Gly Gly Gln Arg Ile Ala Glu Ser Asn His Ile Lys Leu Ser
        595                 600                 605

Gly Ser Asn Pro Tyr Thr Thr Val Thr Pro Gln Ile Ile Asn Ser Lys
    610                 615                 620

Trp Glu Lys Val Gln Gln Leu Val Pro Lys Arg Asp His Ala Leu Leu
625                 630                 635                 640

Glu Glu Gln Ser Lys Gln Gln Ser Asn Glu His Leu Arg Arg Gln
                645                 650                 655

Phe Ala Ser Gln Ala Asn Val Val Gly Pro Trp Ile Gln Thr Lys Met
            660                 665                 670

Glu Glu Ile Ala Ile Ser Ile Glu Met Asn Gly Thr Leu Glu Asp Gln
        675                 680                 685

Leu Ser His Leu Lys Gln Tyr Glu Arg Ser Ile Val Asp Tyr Lys Pro
    690                 695                 700

Asn Leu Asp Leu Leu Glu Gln Gln His Gln Leu Ile Gln Glu Ala Leu
705                 710                 715                 720

Ile Phe Asp Asn Lys His Thr Asn Tyr Thr Met Glu His Ile Arg Val
                725                 730                 735

Gly Trp Glu Gln Leu Leu Thr Thr Ile Ala Arg Thr Ile Asn Glu Val
            740                 745                 750

Glu Asn Gln Ile Leu Thr Arg Asp Ala Lys Gly Ile Ser Gln Glu Gln
        755                 760                 765

Met Gln Glu Phe Arg Ala Ser Phe Asn His Phe Asp Lys Asp His Gly
    770                 775                 780

Gly Ala Leu Gly Arg Gly Val Gln Gly Leu Pro His Gln Pro Gly Leu
785                 790                 795                 800

Arg Arg Gly Glu Arg Pro Ala Gly Glu Ala Glu Phe Asn Arg Ile Met
                805                 810                 815

Ser Leu Val Asp Pro Asn His Ser Gly Leu Val Thr Phe Gln Ala Phe
            820                 825                 830

Ile Asp Phe Met Ser Arg Glu Thr Thr Asp Thr Asp Thr Ala Asp Gln
        835                 840                 845

Val Ile Thr Ser Phe Lys Val Leu Ala Gly Asp Lys Asn Phe Ile Thr
    850                 855                 860

Ala Glu Glu Leu Arg Arg Glu Leu Pro Pro Asp Gln Ala Glu Tyr Cys
865                 870                 875                 880

Ile Ala Arg Met Ala Pro Tyr Gln Gly Pro Asp Gly Val Arg Gly Ala
                885                 890                 895

Leu Asp Tyr Lys Ser Phe Ser Thr Ala Leu Tyr Gly Glu Ser Asp Leu
            900                 905                 910
```

<210> SEQ ID NO 9
<211> LENGTH: 2874
<212> TYPE: DNA
<213> ORGANISM: Human

<400> SEQUENCE: 9

| | | | | | |
|---|---|---|---|---|---|
| cgcggccgcg | tcgacctacc | acgcggcgaa | ccagtcgtac | cagtacggcc | ccagcagcgc | 60 |
| gggcaatggc | gctggcggcg | ggggcagcat | gggcgactac | atggcccagg | aggacgactg | 120 |
| ggaccgggac | ctgctgctgg | acccggcctg | ggagaagcag | cagcgcaaga | ccttcacggc | 180 |
| atggtgcaac | tcccacctgc | ggaaggcagg | cacacagatc | gagaacattg | atgaggactt | 240 |
| ccgagacggg | ctcaagctca | tgctgctcct | ggaggtcata | tcaggggagc | ggttacctaa | 300 |
| gccgagcgg | gggaagatga | gagtgcacaa | aatcaacaat | gtgaacaaag | cgctggactt | 360 |
| tattgccagc | aaaggcgtca | agctggtctc | catcggggca | gaagagattg | tggacggcaa | 420 |
| cgcaaagatg | accctgggaa | tgatctggac | catcatcctt | aggttcgcca | tccaggacat | 480 |
| ctccgtggaa | gagacctcgg | ccaaggaagg | gctccttctc | tggtgccaga | gaaagacagc | 540 |
| cccgtataag | aacgtcaatg | tgcagaactt | ccacatcagc | tggaaggatg | gtcttgcctt | 600 |
| caatgccctg | atccaccggc | acagaccaga | gctgattgag | tatgacaagc | tgaggaagga | 660 |
| cgaccctgtc | accaacctga | caatgccttc | gaagtggct | gagaaatacc | tcgacatccc | 720 |
| caagatgctg | gatgcagagg | acatcgtgaa | cacggcccgg | cccgacgaga | aggccataat | 780 |
| gacctatgtg | tccagcttct | accatgcctt | ttcaggagcg | cagaaggctg | aaactgccgc | 840 |
| caaccggatc | tgtaaggtgc | tggctgtcaa | ccaagagaac | gagcacctga | tggaggacta | 900 |
| cgagaagctg | gccagcgacc | tcctggagtg | gatccggcgc | accatcccct | ggctggagga | 960 |
| ccgtgtgccc | caaaagacta | tccaggagat | gcagcagaag | ctggaggact | ccgcgacta | 1020 |
| ccggcgtgtg | cacaagccgc | ccaaggtgca | ggagaagtgc | cagctggaga | tcaacttcaa | 1080 |
| cacgctgcag | accaagctgc | gcctcagcaa | ccggcccgcc | ttcatgccct | ccgagggcaa | 1140 |
| gatggtctcg | gacatcaaca | atggctggca | gcacttggag | caggctgaga | agggctacga | 1200 |
| ggagtggctg | ctgaatgaga | tccgcaggct | ggagcggctc | gaccacctgg | cagagaagtt | 1260 |
| ccggcagaag | gcctccatcc | acgaggcctg | gactgacggg | aaggaagcca | tgctgaagca | 1320 |
| ccgggactac | gagacggcca | cactatcgga | catcaaagcc | ctcattgca | agcacgaggc | 1380 |
| cttcgagatg | cgacctggct | gcgcaccagg | accgcgtgga | gcagatcgcc | gccattgccc | 1440 |
| aggagctcaa | cgagctggat | tactacgact | cccacaatgt | caacacccgg | tgccagaaga | 1500 |
| tctgtgacca | gtgggacgcc | ctcggctctc | tgacacatag | tcgcagggaa | gccctggaga | 1560 |
| aaacagagaa | gcagctggag | gccatcgacc | agctgcacct | ggaatacgcc | aagcgcgcgg | 1620 |
| ccccttcaa | caactggatg | gagagcgcca | tggaggacct | ccaggacatg | ttcatcgtcc | 1680 |
| ataccatcga | ggagattgag | ggcctgatct | cagcccatga | ccagttcaag | tccaccctgc | 1740 |
| cggacgccga | tagggagcgc | gaggccatcc | tggccatcca | aaggaggcc | cagaggatcg | 1800 |
| ctgagagcaa | ccacatcaag | ctgtcgggca | gcaacccta | caccaccgtc | accccgcaaa | 1860 |
| tcatcaactc | caagtgggag | aaggtgcagc | agctggtgcc | aaaacgggac | catgccctcc | 1920 |
| tggaggagca | gagcaagcag | cagtccaacg | agcacctgcg | ccgccagttc | gccagccagg | 1980 |
| ccaatgttgt | ggggccctgg | atccagacca | agatggagga | gatcgggcgc | atctccattg | 2040 |
| agatgaacgg | gaccctggag | gaccagctga | gccacctgaa | gcagtatgaa | cgcagcatcg | 2100 |
| tggactacaa | gcccaaccctg | gacctgctgg | agcagcagca | ccagctcatc | caggaggccc | 2160 |

-continued

```
tcatcttcga caacaagcac accaactata ccatggagca catccgcgtg ggctgggagc    2220
agctgctcac caccattgcc cgcaccatca acgaggtgga gaaccagatc ctcacccgcg    2280
acgccaaggg catcagccag gagcagatgc aggagttccg ggcgtccttc aaccacttcg    2340
acaaggatca tggcggggcg ctggggcccg aggagttcaa ggcctgcctc atcagcctgg    2400
gctacgacgt ggagaacgac cggcagggtg aggccgagtt caaccgcatc atgagcctgg    2460
tcgaccccaa ccatagcggc cttgtgacct tccaagcctt catcgacttc atgtcgcggg    2520
agaccaccga cacggacacg gctgaccagg tcatcgcttc cttcaaggtc ttagcagggg    2580
acaagaactt catcacagct gaggagctgc ggagagagct gccccccgac caggccgagt    2640
actgcatcgc ccgcatggcg ccataccagg gcctgacgc cgtgcccggt gccctcgact    2700
acaagtcctt ctccacggcc ttgtatggcg agagcgacct gtgaggcccc agagacctga    2760
cccaacaccc ccgacggcct ccaggagggg cctgggcagc ccacagtcc cattcctcca     2820 ctctgtatct atgcaaagca ctctctgcag tcctccgggg tggtgggtgg ggca          2874
```

<210> SEQ ID NO 10
<211> LENGTH: 883
<212> TYPE: PRT
<213> ORGANISM: Human

<400> SEQUENCE: 10

```
Met Gly Asp Tyr Met Ala Gln Glu Asp Asp Trp Asp Arg Asp Leu Leu
1               5                   10                  15

Leu Asp Pro Ala Trp Glu Lys Gln Gln Arg Lys Thr Phe Thr Ala Trp
                20                  25                  30

Cys Asn Ser His Leu Arg Lys Ala Gly Thr Gln Ile Glu Asn Ile Asp
            35                  40                  45

Glu Asp Phe Arg Asp Gly Leu Lys Leu Met Leu Leu Leu Glu Val Ile
        50                  55                  60

Ser Gly Glu Arg Leu Pro Lys Pro Glu Arg Gly Lys Met Arg Val His
65                  70                  75                  80

Lys Ile Asn Asn Val Asn Lys Ala Leu Asp Phe Ile Ala Ser Lys Gly
                85                  90                  95

Val Lys Leu Val Ser Ile Gly Ala Glu Glu Ile Val Asp Gly Asn Ala
            100                 105                 110

Lys Met Thr Leu Gly Met Ile Trp Thr Ile Ile Leu Arg Phe Ala Ile
        115                 120                 125

Gln Asp Ile Ser Val Glu Glu Thr Ser Ala Lys Glu Gly Leu Leu Leu
    130                 135                 140

Trp Cys Gln Arg Lys Thr Ala Pro Tyr Lys Asn Val Asn Val Gln Asn
145                 150                 155                 160

Phe His Ile Ser Trp Lys Asp Gly Leu Ala Phe Asn Ala Leu Ile His
                165                 170                 175

Arg His Arg Pro Glu Leu Ile Glu Tyr Asp Lys Leu Arg Lys Asp Asp
            180                 185                 190

Pro Val Thr Asn Leu Asn Asn Ala Phe Glu Val Ala Glu Lys Tyr Leu
        195                 200                 205

Asp Ile Pro Lys Met Leu Asp Ala Glu Asp Ile Val Asn Thr Ala Arg
    210                 215                 220

Pro Asp Glu Lys Ala Ile Met Thr Tyr Val Ser Ser Phe Tyr His Ala
225                 230                 235                 240

Phe Ser Gly Ala Gln Lys Ala Glu Thr Ala Ala Asn Arg Ile Cys Lys
                245                 250                 255
```

-continued

```
Val Leu Ala Val Asn Gln Glu Asn Glu His Leu Met Glu Asp Tyr Glu
            260                 265                 270

Lys Leu Ala Ser Asp Leu Leu Glu Trp Ile Arg Arg Thr Ile Pro Trp
            275                 280                 285

Leu Glu Asp Arg Val Pro Gln Lys Thr Ile Gln Glu Met Gln Gln Lys
            290                 295                 300

Leu Glu Asp Phe Arg Asp Tyr Arg Arg Val His Lys Pro Pro Lys Val
305                 310                 315                 320

Gln Glu Lys Cys Gln Leu Glu Ile Asn Phe Asn Thr Leu Gln Thr Lys
                325                 330                 335

Leu Arg Leu Ser Asn Arg Pro Ala Phe Met Pro Ser Glu Asp Lys Met
                340                 345                 350

Val Ser Asp Ile Asn Asn Gly Trp Gln His Leu Glu Gln Ala Glu Lys
                355                 360                 365

Gly Tyr Glu Glu Trp Leu Leu Asn Glu Ile Arg Arg Leu Glu Arg Leu
            370                 375                 380

Asp His Leu Ala Glu Lys Phe Arg Gln Lys Ala Ser Ile His Glu Trp
385                 390                 395                 400

Thr Asp Gly Lys Glu Ala Met Leu Lys His Arg Asp Tyr Glu Thr Ala
                405                 410                 415

Thr Leu Ser Asp Ile Lys Ala Leu Ile Arg Lys His Glu Ala Phe Glu
                420                 425                 430

Ser Asp Leu Ala Ala His Gln Asp Arg Val Glu Gln Ile Ala Ala Ile
                435                 440                 445

Ala Gln Glu Leu Asn Glu Leu Asp Tyr Tyr Asp Ser His Asn Val Asn
            450                 455                 460

Thr Arg Cys Gln Lys Ile Cys Asp Gln Trp Asp Ala Leu Gly Ser Leu
465                 470                 475                 480

Thr His Ser Arg Arg Glu Ala Leu Glu Lys Thr Glu Lys Gln Leu Glu
                485                 490                 495

Ala Ile Asp Gln Leu His Leu Glu Tyr Ala Lys Arg Ala Ala Pro Phe
                500                 505                 510

Asn Asn Trp Met Glu Ser Ala Met Glu Asp Leu Gln Asp Met Phe Ile
            515                 520                 525

Val His Thr Ile Glu Glu Ile Glu Gly Leu Ile Ser Ala His Asp Gln
            530                 535                 540

Phe Lys Ser Thr Leu Pro Asp Ala Asp Arg Glu Arg Glu Ala Ile Leu
545                 550                 555                 560

Ala Ile His Lys Glu Ala Gln Arg Ile Ala Glu Ser Asn His Ile Lys
                565                 570                 575

Leu Ser Gly Ser Asn Pro Tyr Thr Thr Val Thr Pro Gln Ile Ile Asn
                580                 585                 590

Ser Lys Trp Glu Lys Val Gln Gln Leu Val Pro Lys Arg Asp His Ala
                595                 600                 605

Leu Leu Glu Glu Gln Ser Lys Gln Gln Ser Asn Glu His Leu Arg Arg
            610                 615                 620

Gln Phe Ala Ser Gln Ala Asn Val Val Gly Pro Trp Ile Gln Thr Lys
625                 630                 635                 640

Met Glu Glu Ile Gly Arg Ile Ser Ile Glu Met Asn Gly Thr Leu Glu
                645                 650                 655

Asp Gln Leu Ser His Leu Lys Gln Tyr Glu Arg Ser Ile Val Asp Tyr
                660                 665                 670
```

```
Lys Pro Asn Leu Asp Leu Leu Glu Gln Gln His Gln Leu Ile Gln Glu
        675                 680                 685

Ala Leu Ile Phe Asp Asn Lys His Thr Asn Tyr Thr Met Glu His Ile
    690                 695                 700

Arg Val Gly Trp Glu Gln Leu Leu Thr Thr Ile Ala Arg Thr Ile Asn
705                 710                 715                 720

Glu Val Glu Asn Gln Ile Leu Thr Arg Asp Ala Lys Gly Ile Ser Gln
                725                 730                 735

Glu Gln Met Gln Glu Phe Arg Ala Ser Phe Asn His Phe Asp Lys Asp
            740                 745                 750

His Gly Gly Ala Leu Gly Pro Glu Glu Phe Lys Ala Cys Leu Ile Ser
        755                 760                 765

Leu Gly Tyr Asp Val Glu Asn Asp Arg Gln Gly Glu Ala Glu Phe Asn
    770                 775                 780

Arg Ile Met Ser Leu Val Asp Pro Asn His Ser Gly Leu Val Thr Phe
785                 790                 795                 800

Gln Ala Phe Ile Asp Phe Met Ser Arg Glu Thr Thr Asp Thr Asp Thr
                805                 810                 815

Ala Asp Gln Val Ile Ala Ser Phe Lys Val Leu Ala Gly Asp Lys Asn
            820                 825                 830

Phe Ile Thr Ala Glu Glu Leu Arg Arg Glu Leu Pro Pro Asp Gln Ala
        835                 840                 845

Glu Tyr Cys Ile Ala Arg Met Ala Pro Tyr Gln Gly Pro Asp Ala Val
    850                 855                 860

Pro Gly Ala Leu Asp Tyr Lys Ser Phe Ser Thr Ala Leu Tyr Gly Glu
865                 870                 875                 880

Ser Asp Leu

<210> SEQ ID NO 11
<211> LENGTH: 1828
<212> TYPE: DNA
<213> ORGANISM: Human

<400> SEQUENCE: 11
caggtctgtt ctcagagcga tgggccgcag agactgatct gccgccatga ttggaggctt      60
attcatctat aatcacaagg gggaggtgct catctcccga gtctaccgag atgacatcgg     120
gaggaacgca gtggatgcct tcgggtcaa tgttatccat gcccggcagc aggtgcgcag     180
ccccgtcacc aacattgctc gcaccagctt cttccacgtt aagcggtcca acatttggct     240
ggcagcagtc accaagcaga atgtcaacgc tgccatggtc ttcgaattcc tctataagat     300
gtgtgacgtg atggccgctt actttggcaa gatcagcgag gaaaacatca gaacaatttt     360
tttgctcata tatgagctgc tggatgagat tctagacttt ggctacccac agaattccga     420
gacaggcgcg ctgaaaacct tcatcacgca gcagggcatc aagagtcagc atcagacaaa     480
agaagagcag tcacagatca ccagccaggt aactgggcag attggctggc ggcgagaggg     540
catcaagtat cgtcggaatg agctcttcct ggatgtgctg agagtgtgaa cctgctcat      600 gtccccacaa gggcaggtgc tgagtgccca tgtgtcgggc cggtggtga tgaagagcta      660 cctgagtggc atgcctgaat gcaagtttgg gatgaatgac aagattgtta ttgaaaagca     720
gggcaaaggc acagctgatg aaacaagcaa gagcgggaag caatcaattg ccattgatga     780
ctgcaccttc caccagtgtg tgcgactcag caagtttgac tctgaacgca gcatcagctt     840
tatcccgcca gatggagagt ttgagcttat gaggtatcgc acaaccaagg acatcatcct     900
```

```
tcccttccgg gtgatcccgc tagtgcgaga agtgggacgc accaaactgg aggtcaaggt      960
ggtcatcaag tccaacttta aaccctcact gctggctcag aagattgagg tgaggatccc     1020
aaccccactg aacacaagcg gggtgcaggt gatctgcatg aaggggaagg ccaagtacaa     1080
aaccccactg aacacaagcg gggtgcaggt gatctgcatg aaggggaagg ccaagtacaa     1140
gatcagcgca gagattgagc ttctgcctac aacgacaag aagaaatggg ctcgaccccc      1200
catttccatg aactttgagg tgccattcgc gccctctggc ctcaaggtgc gctacttgaa     1260
ggtgtttgaa ccgaagctga actacagcga ccatgatgtc atcaaatggg tgcgctacat     1320
tggccgcagt ggcatttatg aaactcgctg ctagctgcca ctaggcagct agcccacctc     1380
cccagccacc ctcctccaca ggtccaggtg ccgctccctc ccccaccaca catcagtgtc     1440
tcctccctcc tgctttgctg ccttcccttt gcaccagccc gagtctaggt ctgggccaag     1500
cacattacaa gtgggaccgg tggagcagcc cctgggctcc ctgggcaggg agttctgag      1560
gctcctgctc tcccatccac ctgtctgtcc tggcctaatg ccaggctctg agttctgtga     1620
ccaaagccag gtgggttccc tttccttccc accctgtgg ccacagctct ggagtgggag      1680
ggttggttgc ccctcacctc agagctcccc caaaggccag taatggatcc ccggcctcag     1740
tccctactct gctttgggat agtgtgagct tcattttgta cacgtgttgc ttcgtccagt     1800
tacaaaccca ataaactctg tagagtgg                                        1828
```

<210> SEQ ID NO 12
<211> LENGTH: 435
<212> TYPE: PRT
<213> ORGANISM: Human

<400> SEQUENCE: 12

```
Met Ile Gly Gly Leu Phe Ile Tyr Asn His Lys Gly Glu Val Leu Ile
1               5                   10                  15

Ser Arg Val Tyr Arg Asp Asp Ile Gly Arg Asn Ala Val Asp Ala Phe
            20                  25                  30

Arg Val Asn Val Ile His Ala Arg Gln Gln Val Arg Ser Pro Val Thr
        35                  40                  45

Asn Ile Ala Arg Thr Ser Phe Phe His Val Lys Arg Ser Asn Ile Trp
    50                  55                  60

Leu Ala Ala Val Thr Lys Gln Asn Val Asn Ala Met Val Phe Glu
65                  70                  75                  80

Phe Leu Tyr Lys Met Cys Asp Val Met Ala Ala Tyr Phe Gly Lys Ile
                85                  90                  95

Ser Glu Glu Asn Ile Lys Asn Phe Leu Leu Ile Tyr Glu Leu Leu
            100                 105                 110

Asp Glu Ile Leu Asp Phe Gly Tyr Pro Gln Asn Ser Glu Thr Gly Ala
        115                 120                 125

Leu Lys Thr Phe Ile Thr Gln Gln Gly Ile Lys Ser Gln His Gln Thr
    130                 135                 140

Lys Glu Glu Gln Ser Gln Ile Thr Ser Gln Val Thr Gly Gln Ile Gly
145                 150                 155                 160

Trp Arg Arg Glu Gly Ile Lys Tyr Arg Arg Asn Glu Leu Phe Leu Asp
                165                 170                 175

Val Leu Glu Ser Val Asn Leu Leu Met Ser Pro Gln Gly Gln Val Leu
            180                 185                 190

Ser Ala His Val Ser Gly Arg Val Val Met Lys Ser Tyr Leu Ser Gly
        195                 200                 205
```

```
Met Pro Glu Cys Lys Phe Gly Met Asn Asp Lys Ile Val Ile Glu Lys
            210                 215                 220
Gln Gly Lys Gly Thr Ala Asp Glu Thr Ser Lys Ser Gly Lys Gln Ser
225                 230                 235                 240
Ile Ala Ile Asp Asp Cys Thr Phe His Gln Cys Val Arg Leu Ser Lys
                245                 250                 255
Phe Asp Ser Glu Arg Ser Ile Ser Phe Ile Pro Pro Asp Gly Glu Phe
            260                 265                 270
Glu Leu Met Arg Tyr Arg Thr Thr Lys Asp Ile Ile Leu Pro Phe Arg
            275                 280                 285
Val Ile Pro Leu Val Arg Glu Val Gly Arg Thr Lys Leu Glu Val Lys
        290                 295                 300
Val Val Ile Lys Ser Asn Phe Lys Pro Ser Leu Leu Ala Gln Lys Ile
305                 310                 315                 320
Glu Val Arg Ile Pro Thr Pro Leu Asn Thr Ser Gly Val Gln Val Ile
                325                 330                 335
Cys Met Lys Gly Lys Ala Lys Tyr Lys Ala Ser Glu Asn Ala Ile Val
            340                 345                 350
Trp Lys Ile Lys Arg Met Ala Gly Met Lys Glu Ser Gln Ile Ser Ala
            355                 360                 365
Glu Ile Glu Leu Leu Pro Thr Asn Asp Lys Lys Lys Trp Ala Arg Pro
370                 375                 380
Pro Ile Ser Met Asn Phe Glu Val Pro Phe Ala Pro Ser Gly Leu Lys
385                 390                 395                 400
Val Arg Tyr Leu Lys Val Phe Glu Pro Lys Leu Asn Tyr Ser Asp His
                405                 410                 415
Asp Val Ile Lys Trp Val Arg Tyr Ile Gly Arg Ser Gly Ile Tyr Glu
            420                 425                 430
Thr Arg Cys
        435
```

<210> SEQ ID NO 13
<211> LENGTH: 1764
<212> TYPE: DNA
<213> ORGANISM: Human

<400> SEQUENCE: 13

| | | | | | |
|---|---|---|---|---|---|
| cacggggagg | cggaggcagc | ggcggcggcg | gcggcggcgg | cggcggcggc | ggagcagatc | 60 |
| ttctggtgac | cccacttctc | gctgctcatg | ccgctgggac | tggggcgccg | gaaaaaggcg | 120 |
| ccccctctag | tggaaaatga | ggaggctgag | ccaggccgtg | gagggctggg | cgtgggggag | 180 |
| ccagggcctt | tggcggagg | tgggtcgggg | ggccccaaa | tgggcttgcc | ccccctccc | 240 |
| ccagccctgc | ggccccgcct | tgtgttccac | acccagctgg | cccatggcag | tcccactggc | 300 |
| cgcatcgagg | ggttcaccaa | cgtcaaggag | ctgtatggca | agattgccga | ggccttccgc | 360 |
| ctgccaactg | ccgaggtgat | gttttgcacc | ctgaacaccc | acaaagtgga | catgacaag | 420 |
| ctcctggggg | gccaaatcgg | gctggaggac | ttcatcttcg | cccacgtgaa | ggggcagcgc | 480 |
| aaggaggtgg | aggtgttcaa | gtcggaggat | gcactcgggc | tcaccatcac | ggacaacggg | 540 |
| gctggctacg | ccttcatcaa | gcgcatcaag | gagggcagcg | tgatcgacca | catccacctc | 600 |
| atcagcgtgg | gcgacatgat | cgaggccatt | aacgggcaga | gcctgctggg | ctgccggcac | 660 |
| tacgaagtgg | cccggctgct | caaggaactg | ccccgaggcc | gtaccttcac | gctgaagctc | 720 |
| acggagcctc | gcaaggcctt | cgacatgatc | agccagcgtt | cagcgggtgg | ccgccctggc | 780 |

```
tctggcccac aactgggcac tggccgaggg acctgcggct ccgatcccgg ggccccgcca    840
cggtggagga tctgccctct gcctttgaag agaaggccat tgagaaggtg gatgacctgc    900
tggagagtta catgggtatc agggacacgg agctggcggc caccatggtg gagctgggaa    960
aggacaaaag gaacccggat gagctggccg aggccctgga cgaacggctg ggtgactttg   1020
ccttccctga cgagttcgtc tttgacgtct ggggcgccat tggggacgcc aaggtcggcc   1080
gctactagga ctgcccccgg accctgcgat gatgacccgg cgcaacctg gtggggccc    1140
ccagcaggga cactgacgtc aggacccgag cctccaagcc tgagcctagc tcagcagccc   1200
aaggacgatg gtgaggggag gtggggccag gcccccgcc ccgctccaat cggtaccatc    1260
ccctcccgg ttcccagtct ggccgggtc cccggcccc ctgtgccctg ttcccacccc      1320
tacctcagct ggggtcaggc acagggaagg ggagggatca gccaaatttg gcggccacc   1380
cccgcctcca ccactttcca ccatcagctg ccaaactggt ccctctgtct ccctggggcc   1440
ttgggttctg tttgggggtc atgaccttcc tagtttcctg acgcagggaa tacaggggag   1500
agggttgtcc ttcccccag caaatgcaat aatgccctca ccctcctga gggagcccc    1560
ctccctgtgg agcctgttac ctccgcattt gacacgagtt gctgtgaacc ccgcaacctc   1620
ctccccacct cccatctctc cttccaggcc catccctggc ccagagcagg agggagggag   1680
ggacgatggc ggtgggtttt tgtatctgaa tttgctgtct tgaacataaa gaatctatct   1740
gctgttaaaa aaaaaaaaaa aaaa                                          1764

<210> SEQ ID NO 14
<211> LENGTH: 333
<212> TYPE: PRT
<213> ORGANISM: Human

<400> SEQUENCE: 14

Met Pro Leu Gly Leu Gly Arg Arg Lys Lys Ala Pro Pro Leu Val Glu
1               5                   10                  15

Asn Glu Glu Ala Glu Pro Gly Arg Gly Gly Leu Gly Val Gly Glu Pro
            20                  25                  30

Gly Pro Leu Gly Gly Gly Ser Gly Gly Pro Gln Met Gly Leu Pro
        35                  40                  45

Pro Pro Pro Pro Ala Leu Arg Pro Arg Leu Val Phe His Thr Gln Leu
    50                  55                  60

Ala His Gly Ser Pro Thr Gly Arg Ile Glu Gly Phe Thr Asn Val Lys
65                  70                  75                  80

Glu Leu Tyr Gly Lys Ile Ala Glu Ala Phe Arg Leu Pro Thr Ala Glu
                85                  90                  95

Val Met Phe Cys Thr Leu Asn Thr His Lys Val Asp Met Asp Lys Leu
            100                 105                 110

Leu Gly Gly Gln Ile Gly Leu Glu Asp Phe Ile Phe Ala His Val Lys
        115                 120                 125

Gly Gln Arg Lys Glu Val Glu Val Phe Lys Ser Glu Asp Ala Leu Gly
    130                 135                 140

Leu Thr Ile Thr Asp Asn Gly Ala Gly Tyr Ala Phe Ile Lys Arg Ile
145                 150                 155                 160

Lys Glu Gly Ser Val Ile Asp His Ile His Leu Ile Ser Val Gly Asp
                165                 170                 175

Met Ile Glu Ala Ile Asn Gly Gln Ser Leu Leu Gly Cys Arg His Tyr
            180                 185                 190
```

```
Glu Val Ala Arg Leu Leu Lys Glu Leu Pro Arg Gly Arg Thr Phe Thr
        195                 200                 205

Leu Lys Leu Thr Glu Pro Arg Lys Ala Phe Asp Met Ile Ser Gln Arg
    210                 215                 220

Ser Ala Gly Gly Arg Pro Gly Ser Gly Pro Gln Leu Gly Thr Gly Arg
225                 230                 235                 240

Gly Thr Leu Arg Leu Arg Ser Arg Gly Pro Ala Thr Val Glu Asp Leu
                245                 250                 255

Pro Ser Ala Phe Glu Glu Lys Ala Ile Glu Lys Val Asp Asp Leu Leu
            260                 265                 270

Glu Ser Tyr Met Gly Ile Arg Asp Thr Glu Leu Ala Ala Thr Met Val
        275                 280                 285

Glu Leu Gly Lys Asp Lys Arg Asn Pro Asp Leu Ala Glu Ala Leu
    290                 295                 300

Asp Glu Arg Leu Gly Asp Phe Ala Phe Pro Asp Glu Phe Val Phe Asp
305                 310                 315                 320

Val Trp Gly Ala Ile Gly Asp Ala Lys Val Gly Arg Tyr
                325                 330
```

```
<210> SEQ ID NO 15
<211> LENGTH: 1318
<212> TYPE: DNA
<213> ORGANISM: Human
<220> FEATURE:
<221> NAME/KEY: misc_feature
<222> LOCATION: (23)..(23)
<223> OTHER INFORMATION: Where n = unknown
<220> FEATURE:
<221> NAME/KEY: misc_feature
<222> LOCATION: (42)..(42)
<223> OTHER INFORMATION: Where n = unknown
<220> FEATURE:
<221> NAME/KEY: misc_feature
<222> LOCATION: (48)..(48)
<223> OTHER INFORMATION: Where n = unknown
<220> FEATURE:
<221> NAME/KEY: misc_feature
<222> LOCATION: (1105)..(1105)
<223> OTHER INFORMATION: Where n = unknown

<400> SEQUENCE: 15
ggccgcccgg cgcccccagc agnccgagcc ggggcgcaca gncggggngc agaccgcgcc    60
ccccgccgcg attgacatga tgtttccaca aagcaggcat tcgggctcct cgcacctacc   120
ccagcaactc aaattcacca cctcggactc ctgcgaccgc atcaaagacg aatttcagct   180
actgcaagct cagtaccaca gcctcaagct cgaatgtgac aagttggcca gtgagaagtc   240
agagatgcag cgtcactatg tgatgtacta cgagatgtcc tacggcttga acatcgagat   300
gcacaaacag gctgagatcg tcaaaaggct gaacgggatt tgtgcccagg tcctgcccta   360
cctctcccaa gagcaccagc agcaggtctt gggagccatt gagagggcca agcaggtcac   420
cgctcccgag ctgaactcta tcatccgaca gcagctccaa gcccaccagc tgtcccagct   480
gcaggccctg gccctgccct tgaccccact acccgtgggg ctgcagccgc cttcgctgcc   540
ggcggtcagc gcaggcaccg gcctcctctc gctgtccgcg ctgggttccc agggcccacc   600
tctccaagga agacaagaac gggcacgatg gtgacaccca ccaggaggat gatggcgaga   660
agtcggatta gcaggggggcc gggacgggga ggttgggagg ggggacagag gggagacaga   720
ggcacggaga gaaaggaatg tttagcacaa gacacagcgg agctcgggat gggctaaact   780
cccatagtat ttatggtggc cgccggcggg ggccccagcc cagcttgcag gccacctcta   840
```

```
gctttcttcc ctaccccatt cccggcttcc ctcctcctcc ctgcagcctg gttaggtgga      900
tacctgccct gacatgtgag gcaagctaag gcctggaggg acagctggga gaccaggtcc      960
caagggagca agacctcgcg aagcgcagca gacccggccc tttccccgtt ttaggcatgt     1020
gtaaccgaca gtctgcctgg gccacagccc tctcaacctg gtactgcatg cacgcaatgc     1080
tagctgcccc tttcccgtcc tgggnacccc gagtctcccc cgaccccggg tcccaggtat     1140
gctcccacct ccacctgccc cactcaccac ctctgctagt tccagacacc tccacgccca     1200
cctggtcctc tcctaccgca cacaaaaggg ggggaacgag ggacgagctt agctgagctg     1260
ggaggagcag ggtgagggtg ggcgacccag gattccccct cccccttccca aataaccc     1318
```

<210> SEQ ID NO 16
<211> LENGTH: 196
<212> TYPE: PRT
<213> ORGANISM: Human

<400> SEQUENCE: 16

```
Met Phe Pro Gln Ser Arg His Ser Gly Ser Ser His Leu Pro Gln Gln
1               5                   10                  15

Leu Lys Phe Thr Thr Ser Asp Ser Cys Asp Arg Ile Lys Asp Glu Phe
            20                  25                  30

Gln Leu Leu Gln Ala Gln Tyr His Ser Leu Lys Leu Glu Cys Asp Lys
        35                  40                  45

Leu Ala Ser Glu Lys Ser Glu Met Gln Arg His Tyr Val Met Tyr Tyr
    50                  55                  60

Glu Met Ser Tyr Gly Leu Asn Ile Glu Met His Lys Gln Ala Glu Ile
65                  70                  75                  80

Val Lys Arg Leu Asn Gly Ile Cys Ala Gln Val Leu Pro Tyr Leu Ser
                85                  90                  95

Gln Glu His Gln Gln Val Leu Gly Ala Ile Glu Arg Ala Lys Gln
            100                 105                 110

Val Thr Ala Pro Glu Leu Asn Ser Ile Ile Arg Gln Gln Leu Gln Ala
        115                 120                 125

His Gln Leu Ser Gln Leu Gln Ala Leu Ala Leu Pro Leu Thr Pro Leu
    130                 135                 140

Pro Val Gly Leu Gln Pro Pro Ser Leu Pro Ala Val Ser Ala Gly Thr
145                 150                 155                 160

Gly Leu Leu Ser Leu Ser Ala Leu Gly Ser Gln Ala His Leu Ser Lys
                165                 170                 175

Glu Asp Lys Asn Gly His Asp Gly Asp Thr His Gln Gly Asp Asp Gly
            180                 185                 190

Glu Lys Ser Asp
        195
```

<210> SEQ ID NO 17
<211> LENGTH: 1324
<212> TYPE: DNA
<213> ORGANISM: Human
<220> FEATURE:
<221> NAME/KEY: misc_feature
<222> LOCATION: (23)..(23)
<223> OTHER INFORMATION: Where n = unknown
<220> FEATURE:
<221> NAME/KEY: misc_feature
<222> LOCATION: (42)..(42)
<223> OTHER INFORMATION: Where n = unknown

<400> SEQUENCE: 17

```
ggccgcccgg cgcccccagc agnccgagcc ggggcgcaca gncggggcgc agcccgcgcc      60
ccccgccgcg attgacatga tgtttccaca aagcaggcat tcgggctcct cgcacctacc     120
ccagcaactc aaattcacca cctcggactc ctgcgaccgc atcaaagacg aatttcagct     180
actgcaagct cagtaccaca gcctcaagct cgaatgtgac aagttggcca gtgagaagtc     240
agagatgcag cgtcactatg tgatgtacta cgagatgtcc tacggcttga acatcgagat     300
gcacaaacag gctgagatcg tcaaaaggct gaacgggatt tgtgcccagg tcctgcccta     360
cctctcccaa gagcaccagc agcaggtctt gggagccatt gagagggcca agcaggtcac     420
cgctcccgag ctgaactcta tcatccgaca gcagctccaa gcccaccagc tgtcccagct     480
gcaggccctg gccctgccct tgaccccact acccgtgggg ctgcagccgc cttcgctgcc     540
ggcggtcagc gcaggcaccg gcctcctctc gctgtccgcg ctgggttccc aggcccacct     600
ctccaaggaa gacaagaacg ggcacgatgg tgacacccac caggaggatg atggcgagaa     660
gtcggattag caggggggccg ggacagggag gttgggaggg gggacagagg ggagacagag     720
gcacggagag aaaggaatgt ttagcacaag acacagcgga gctcgggatt ggctaatctc     780
ccatagtatt tatggtggcg ccggcggggc cccagcccag cttgcaggcc acctctagct     840
ttcttcctac cccattccgg cttccctcct cctcccctgc agcctggtta ggtggatacc     900
tgccctgaca tgtgaggcaa gctaaggcct ggagggtcag atgggagacc aggtcccaag     960
ggagcaagac ctgcgaagcg cagcagcccc ggcccttccc ccgttttgaa catgtgtaac    1020
cgacagtctg ccctgggcca cagccctctc accctggtac tgcatgcacg caatgctagc    1080
tgccccttc ccgtcctggg caccccgagt ctccccgac cccgggtccc aggtatgctc    1140
ccacctccac ctgcccccact caccacctct gctagttcca cacacctcca cgcccacctg    1200
gtcctctccc atcgcccaca aaagggggggg cacgagggac gagcttagct gagctgggag    1260
gagcagggtg agggtgggcg acccaggatt ccccctcccc ttcccaaata aagatgaggg    1320
tact                                                                  1324
```

<210> SEQ ID NO 18
<211> LENGTH: 197
<212> TYPE: PRT
<213> ORGANISM: Human

<400> SEQUENCE: 18

```
Met Met Phe Pro Gln Ser Arg His Ser Gly Ser Ser His Leu Pro Gln
1               5                   10                  15

Gln Leu Lys Phe Thr Thr Ser Asp Ser Cys Asp Arg Ile Lys Asp Glu
            20                  25                  30

Phe Gln Leu Leu Gln Ala Gln Tyr His Ser Leu Lys Leu Glu Cys Asp
        35                  40                  45

Lys Leu Ala Ser Glu Lys Ser Glu Met Gln Arg His Tyr Val Met Tyr
    50                  55                  60

Tyr Glu Met Ser Tyr Gly Leu Asn Ile Glu Met His Lys Gln Ala Glu
65                  70                  75                  80

Ile Val Lys Arg Leu Asn Gly Ile Cys Ala Gln Val Leu Pro Tyr Leu
                85                  90                  95

Ser Gln Glu His Gln Gln Val Leu Gly Ala Ile Glu Arg Ala Lys
            100                 105                 110

Gln Val Thr Ala Pro Glu Leu Asn Ser Ile Ile Arg Gln Gln Leu Gln
        115                 120                 125
```

```
Ala His Gln Leu Ser Gln Leu Gln Ala Leu Ala Leu Pro Leu Thr Pro
    130                 135                 140

Leu Pro Val Gly Leu Gln Pro Pro Ser Leu Pro Ala Val Ser Ala Gly
145                 150                 155                 160

Thr Gly Leu Leu Ser Leu Ser Ala Leu Gly Ser Gln Ala His Leu Ser
                165                 170                 175

Lys Glu Asp Lys Asn Gly His Asp Gly Asp Thr His Gln Glu Asp Asp
                180                 185                 190

Gly Glu Lys Ser Asp
        195

<210> SEQ ID NO 19
<211> LENGTH: 1809
<212> TYPE: DNA
<213> ORGANISM: Human

<400> SEQUENCE: 19
cctgctccaa ggtccagaga gctttctggt ctttgcagca ggcctgccgc cttcatgtcc      60
actctcctca tcaatcagcc ccagtatgcg tggctgaaag agctggggct ccgcgaggaa     120
aacgagggcg tgtataatgg aagctgggga ggccggggag aggttattac gacctattgc     180
cccgctaaca acgagccaat agcaagagtc cgacaggcca gtgtggcaga ctatgaagaa     240
actgtaaaga aagcaagaga agcatggaaa atctgggcag atattcctgc tccaaaacga     300
ggagaaatag taagacagat tggcgatgcc ttgcgggaga agatccaagt actaggaagc     360
ttggtgtctt tggagatggg gaaaatctta gtggaaggtg tgggtgaagt tcaggagtat     420
gtggatatct gtgactatgc tgttggttta tcaaggatga ttggaggacc tatcttgcct     480
tctgaaagat ctggccatgc actgattgag cagtggaatc ccgtaggcct ggttggaatc     540
atcacggcat tcaatttccc tgtggcagtg tatggttgga caacgccat cgccatgatc     600 tgtggaaatg tctgcctctg aaaggagct ccaaccactt ccctcattag tgtggctgtc     660
acaaagataa tagccaaggt tctggaggac aacaagctgc ctggtgcaat tgttccttg      720 acttgtggtg agcagatat tggcacagca atggccaaag atgaacgagt gaacctgctg     780
tccttcactg ggagcactca ggtgggaaaa caggtgggcc tgatggtgca ggagaggttt     840
gggagaagtc tgttggaact tggaggaaac aatgccatta ttgcctttga agatgcagac     900
ctcagcttag ttgttccatc agctctcttc gctgctgtgg aacagctgg ccagaggtgt     960 accactgcga ggcgactgtt tatacatgaa agcatccatg atgaggttgt aaacagactt    1020
aaaaaggcct atgcacagat ccgagttggg aacccatggg accctaatgt tctctatggg    1080
ccactccaca ccaagcaggc agtgagcatg tttcttggag cagtggaaga agcaaagaaa    1140
gaaggtggca cagtggtcta tggggcaag gttatggatc gccctggaaa ttatgtagaa    1200
ccgacaattg tgacaggtct tggccacgat gcgtccattg cacacacaga gactttcgct    1260
ccgattctct atgtctttaa attcaagaat gaagaagagg tctttgcatg gaataatgaa    1320
gtaaaacagg gactttcaag tagcatcttt accaaagatc tgggcagaat ctttcgctgg    1380
cttggaccta aggatcaga ctgtggcatt gtaaatgtca acattccaac aagtggggct    1440
gagattggag gtgcctttgg aggagaaaag cacactggtg gtgcagggga gtctggcagt    1500
gatgcctgga acagtacat gagaaggtct acttgtacta tcaactacag taaagacctt    1560
cctctggccc aaggaatcaa gtttcagtaa aggtgtttta gatgaacatc ccttaatttg    1620
aggtgttcca gcagctgttt ttggagaaga caaagaagat taaagttttc cctgaataaa    1680
```

```
tgcattatta tgactgtgac agtgactaat cccctatga ccccaaagcc ctgattaaat    1740
caagagattc ctttttaaa aatcaaaata aaattgttac aacatagcca tagttactaa    1800
aaaaaaaaa                                                          1809
```

<210> SEQ ID NO 20
<211> LENGTH: 511
<212> TYPE: PRT
<213> ORGANISM: Human

<400> SEQUENCE: 20

```
Met Ser Thr Leu Leu Ile Asn Gln Pro Gln Tyr Ala Trp Leu Lys Glu
1               5                   10                  15

Leu Gly Leu Arg Glu Glu Asn Glu Gly Val Tyr Asn Gly Ser Trp Gly
                20                  25                  30

Gly Arg Gly Glu Val Ile Thr Thr Tyr Cys Pro Ala Asn Asn Glu Pro
            35                  40                  45

Ile Ala Arg Val Arg Gln Ala Ser Val Ala Asp Tyr Glu Glu Thr Val
        50                  55                  60

Lys Lys Ala Arg Glu Ala Trp Lys Ile Trp Ala Asp Ile Pro Ala Pro
65                  70                  75                  80

Lys Arg Gly Glu Ile Val Arg Gln Ile Gly Asp Ala Leu Arg Glu Lys
                85                  90                  95

Ile Gln Val Leu Gly Ser Leu Val Ser Leu Glu Met Gly Lys Ile Leu
            100                 105                 110

Val Glu Gly Val Gly Glu Val Gln Glu Tyr Val Asp Ile Cys Asp Tyr
        115                 120                 125

Ala Val Gly Leu Ser Arg Met Ile Gly Gly Pro Ile Leu Pro Ser Glu
    130                 135                 140

Arg Ser Gly His Ala Leu Ile Glu Gln Trp Asn Pro Val Gly Leu Val
145                 150                 155                 160

Gly Ile Ile Thr Ala Phe Asn Phe Pro Val Ala Val Tyr Gly Trp Asn
                165                 170                 175

Asn Ala Ile Ala Met Ile Cys Gly Asn Val Cys Leu Trp Lys Gly Ala
            180                 185                 190

Pro Thr Thr Ser Leu Ile Ser Val Ala Val Thr Lys Ile Ile Ala Lys
        195                 200                 205

Val Leu Glu Asp Asn Lys Leu Pro Gly Ala Ile Cys Ser Leu Thr Cys
    210                 215                 220

Gly Gly Ala Asp Ile Gly Thr Ala Met Ala Lys Asp Glu Arg Val Asn
225                 230                 235                 240

Leu Leu Ser Phe Thr Gly Ser Thr Gln Val Gly Lys Gln Val Gly Leu
                245                 250                 255

Met Val Gln Glu Arg Phe Gly Arg Ser Leu Leu Glu Leu Gly Gly Asn
            260                 265                 270

Asn Ala Ile Ile Ala Phe Glu Asp Ala Asp Leu Ser Leu Val Val Pro
        275                 280                 285

Ser Ala Leu Phe Ala Ala Val Gly Thr Ala Gly Gln Arg Cys Thr Thr
    290                 295                 300

Ala Arg Arg Leu Phe Ile His Glu Ser Ile His Asp Glu Val Val Asn
305                 310                 315                 320

Arg Leu Lys Lys Ala Tyr Ala Gln Ile Arg Val Gly Asn Pro Trp Asp
                325                 330                 335

Pro Asn Val Leu Tyr Gly Pro Leu His Thr Lys Gln Ala Val Ser Met
            340                 345                 350
```

```
Phe Leu Gly Ala Val Glu Glu Ala Lys Lys Glu Gly Gly Thr Val Val
            355                 360                 365
Tyr Gly Gly Lys Val Met Asp Arg Pro Gly Asn Tyr Val Glu Pro Thr
        370                 375                 380
Ile Val Thr Gly Leu Gly His Asp Ala Ser Ile Ala His Thr Glu Thr
385                 390                 395                 400
Phe Ala Pro Ile Leu Tyr Val Phe Lys Phe Lys Asn Glu Glu Glu Val
                405                 410                 415
Phe Ala Trp Asn Asn Glu Val Lys Gln Gly Leu Ser Ser Ser Ile Phe
            420                 425                 430
Thr Lys Asp Leu Gly Arg Ile Phe Arg Trp Leu Gly Pro Lys Gly Ser
        435                 440                 445
Asp Cys Gly Ile Val Asn Val Asn Ile Pro Thr Ser Gly Ala Glu Ile
    450                 455                 460
Gly Gly Ala Phe Gly Gly Glu Lys His Thr Gly Gly Gly Arg Glu Ser
465                 470                 475                 480
Gly Ser Asp Ala Trp Lys Gln Tyr Met Arg Arg Ser Thr Cys Thr Ile
                485                 490                 495
Asn Tyr Ser Lys Asp Leu Pro Leu Ala Gln Gly Ile Lys Phe Gln
            500                 505                 510

<210> SEQ ID NO 21
<211> LENGTH: 1428
<212> TYPE: DNA
<213> ORGANISM: Human

<400> SEQUENCE: 21
ggcacgaggg agcccagagc cggttcggcg cgtcgactgc ccagagtccg cggccggggc      60
gcgggaggag ccaagccgcc atggcctacc acagcttcct ggtggagccc atcagctgcc     120
acgcctggaa caaggaccgc acccagattg ccatctgccc caacaaccat gaggtgcata     180
tctatgaaaa gagcggtgcc aaatggacca aggtgcacga gctcaaggag cacaacgggc     240
aggtgacagg catcgactgg gccccccgaga gtaaccgtat tgtgacctgc ggcacagacc     300
gcaacgccta cgtgtggacg ctgaagggcc gcacatggaa cccacgctg tcatcctgc      360 ggatcaaccg gctgcccgc tgcgtgcgct gggcccccaa cgagaacaag tttgctgtgg     420
gcagcggctc tcgtgtgatc tccatctgtt atttcgagca ggagaatgac tggtgggttt     480
gcaagcacat caagaagccc atccgctcca ccgtcctcag cctggactgg caccccaaca     540
atgtgctgct ggctgccggc tcctgtgact tcaagtgtcg gatcttttca gcctacatca     600
aggaggtgga ggaacggccg gcacccaccc cgtgggctc caagatgcc tttggggaac      660 tgatgttcga atccagcagt agctgcgct gggtacatgg cgtctgtttc tcagccagcg     720
ggagccgcgt ggcctggta agccacgaca gcaccgtctg cctggctgat gccgaccaga     780
agatggccgt cgcgactctg gcctctgaaa cactaccact gctggcgctg accttcatca     840
cagacaacag cctggtggca gcgggccacg actgcttccc ggtgctgttc acctatgacg     900
ccgccgcggg gatgctgagc ttcgcgggc ggctggacgt tcctaagcag agctcgcagc     960
gtggcttgac ggcccgcgag cgcttccaga acctggacaa gaaggcgagc tccgagggtg    1020
gcacggctgc gggcgcgggc ctagactcgc tgcacaagaa cagcgtcagc cagatctcgg    1080
tgctcagcgg cggcaaggcc aagtgctcgc agttctgcac cactggcatg gatggcggca    1140
tgagtatctg ggatgtgaag agcttggagt cagccttgaa ggacctcaag atcaaatgac    1200
ctgtgaggaa tatgttgcct tcatcctaac tgctggggaa gcggggagag gggtcaggga    1260
```

```
ggctaatggt tgctttgctg aatgtttctg gggtaccaat acgagttccc atagggctg    1320 ctccctcaaa aagggagggg acagatgggg agcttttctt acctattcaa ggaatacgtg   1380 ccttttctt aaatgctttc atttattgaa aaaaaaaaaa aaaaaaaa                 1428
```

<210> SEQ ID NO 22
<211> LENGTH: 372
<212> TYPE: PRT
<213> ORGANISM: Human

<400> SEQUENCE: 22

```
Met Ala Tyr His Ser Phe Leu Val Glu Pro Ile Ser Cys His Ala Trp
1               5                   10                  15

Asn Lys Asp Arg Thr Gln Ile Ala Ile Cys Pro Asn Asn His Glu Val
            20                  25                  30

His Ile Tyr Glu Lys Ser Gly Ala Lys Trp Thr Lys Val His Glu Leu
        35                  40                  45

Lys Glu His Asn Gly Gln Val Thr Gly Ile Asp Trp Ala Pro Glu Ser
    50                  55                  60

Asn Arg Ile Val Thr Cys Gly Thr Asp Arg Asn Ala Tyr Val Trp Thr
65                  70                  75                  80

Leu Lys Gly Arg Thr Trp Lys Pro Thr Leu Val Ile Leu Arg Ile Asn
                85                  90                  95

Arg Ala Ala Arg Cys Val Arg Trp Ala Pro Asn Glu Asn Lys Phe Ala
            100                 105                 110

Val Gly Ser Gly Ser Arg Val Ile Ser Ile Cys Tyr Phe Glu Gln Glu
        115                 120                 125

Asn Asp Trp Trp Val Cys Lys His Ile Lys Lys Pro Ile Arg Ser Thr
    130                 135                 140

Val Leu Ser Leu Asp Trp His Pro Asn Asn Val Leu Leu Ala Ala Gly
145                 150                 155                 160

Ser Cys Asp Phe Lys Cys Arg Ile Phe Ser Ala Tyr Ile Lys Glu Val
                165                 170                 175

Glu Glu Arg Pro Ala Pro Thr Pro Trp Gly Ser Lys Met Pro Phe Gly
            180                 185                 190

Glu Leu Met Phe Glu Ser Ser Ser Cys Gly Trp Val His Gly Val
        195                 200                 205

Cys Phe Ser Ala Ser Gly Ser Arg Val Ala Trp Val Ser His Asp Ser
    210                 215                 220

Thr Val Cys Leu Ala Asp Ala Asp Lys Lys Met Ala Val Ala Thr Leu
225                 230                 235                 240

Ala Ser Glu Thr Leu Pro Leu Leu Ala Leu Thr Phe Ile Thr Asp Asn
                245                 250                 255

Ser Leu Val Ala Ala Gly His Asp Cys Phe Pro Val Leu Phe Thr Tyr
            260                 265                 270

Asp Ala Ala Ala Gly Met Leu Ser Phe Gly Gly Arg Leu Asp Val Pro
        275                 280                 285

Lys Gln Ser Ser Gln Arg Gly Leu Thr Ala Arg Glu Arg Phe Gln Asn
    290                 295                 300

Leu Asp Lys Lys Ala Ser Ser Glu Gly Gly Thr Ala Ala Gly Ala Gly
305                 310                 315                 320

Leu Asp Ser Leu His Lys Asn Ser Val Ser Gln Ile Ser Val Leu Ser
                325                 330                 335

Gly Gly Lys Ala Lys Cys Ser Gln Phe Cys Thr Gly Met Asp Gly
            340                 345                 350
```

Gly Met Ser Ile Trp Asp Val Lys Ser Leu Glu Ser Ala Leu Lys Asp
        355                 360                 365

Leu Lys Ile Lys
    370

<210> SEQ ID NO 23
<211> LENGTH: 1435
<212> TYPE: DNA
<213> ORGANISM: Human

<400> SEQUENCE: 23

| | | | | | |
|---|---|---|---|---|---|
| gagcgcgggt | ttctcgcggc | ccctggccgc | ccccggcgtc | atgtacggct | cgcagaaggg | 60 |
| caccacgttc | accaagatct | tcgtgggcgg | cctgccgtac | cacactaccg | acgcctcgct | 120 |
| caggaagtac | ttcgagggct | tcggcgacat | cgaggaggcc | gtggtcatca | ccgaccgcca | 180 |
| gacgggcaag | tcccgcggct | acggcttcgt | gaccatggcc | gaccgggcgg | cagctgagag | 240 |
| ggcttgcaaa | gaccctaacc | ccatcatcga | cggccgcaag | gccaacgtga | acctggcata | 300 |
| tctgggcgcc | aagccttggt | gtctccagac | gggctttgcc | attggcgtgc | agcagctgca | 360 |
| ccccaccttg | atccagcgga | cttacgggct | gaccccgcac | tacatctacc | accagccat | 420 |
| cgtgcagcca | agcgtggtga | tcccagccgc | ccctgtcccg | tcgctgtcct | cgccctacat | 480 |
| tgagtacacg | ccggccagcc | cggtctacgc | ccagtaccca | ccggccacct | atgaccagta | 540 |
| cccatacgcc | gcctcgcctg | ccacggctga | cagcttcgtg | ggctacagct | accctgccgc | 600 |
| cgtgcaccag | gccctctcag | ccgcagcacc | cgcgggcacc | actttcgtgc | agtaccaggc | 660 |
| gccgcagctg | cagcctgaca | ggatgcagtg | agggcgttc | ctgccccgag | gactgtggca | 720 |
| ttgtcacctt | cacagcagac | agagctgcca | ggcatgatg | ggctggcgac | agcccggctg | 780 |
| agcttcagtg | aggtgccacc | agcacccgtg | cctccgaaga | ccgctcgggc | attccgcctg | 840 |
| cgccctggga | cagcggagag | acggcttctc | tttaatctag | gtcccattgt | gtcttgaggg | 900 |
| aggactttta | agaatgactg | agaactattt | aaagacgcaa | tcccaggttc | cttgcacacc | 960 |
| atggcagcct | ctccttgcac | cttctcctgc | ctctccacac | tccaggttcc | ctcaggcttg | 1020 |
| tgtcccact | gctgcatcgt | ggcggggtgt | cacagaccct | ctgcagcccc | tggctgccct | 1080 |
| ggactgtgca | gagatgcctg | actccaggga | aacctgaaag | caagaagtta | atggactgtt | 1140 |
| tattgtaact | tgatcctccc | gagctgtgag | cgcagtctga | ggtctgagga | cacggcctcc | 1200 |
| tgttggagtc | ccattttctc | catcagggca | cgtgggcggc | ttcctcaagc | ccggaggagc | 1260 |
| tcccaggcgc | acaggggccg | ccggtaacag | gggccgccgg | ccaaaggccc | ctttccagtc | 1320 |
| atagcactga | agttgcaact | ttttcttgt | aattgttttg | ctactaagat | aatttcagaa | 1380 |
| gttcagtcta | tttttcagc | ggatactgcc | gccaccaaga | tccaaacct | aggaa | 1435 |

<210> SEQ ID NO 24
<211> LENGTH: 230
<212> TYPE: PRT
<213> ORGANISM: Human

<400> SEQUENCE: 24

Ser Ala Gly Phe Ser Arg Pro Leu Ala Ala Pro Gly Val Met Tyr Gly
1               5                   10                  15

Ser Gln Lys Gly Thr Thr Phe Thr Lys Ile Phe Val Gly Gly Leu Pro
            20                  25                  30

Tyr His Thr Thr Asp Ala Ser Leu Arg Lys Tyr Phe Glu Gly Phe Gly
        35                  40                  45

```
Asp Ile Glu Glu Ala Val Val Ile Thr Asp Arg Gln Thr Gly Lys Ser
 50                  55                  60
Arg Gly Tyr Gly Phe Val Thr Met Ala Asp Arg Ala Ala Ala Glu Arg
 65                  70                  75                  80
Ala Cys Lys Asp Pro Asn Pro Ile Ile Asp Gly Arg Lys Ala Asn Val
                 85                  90                  95
Asn Leu Ala Tyr Leu Gly Ala Lys Pro Trp Cys Leu Gln Thr Gly Phe
                100                 105                 110
Ala Ile Gly Val Gln Gln Leu His Pro Thr Leu Ile Gln Arg Thr Tyr
                115                 120                 125
Gly Leu Thr Pro His Tyr Ile Tyr Pro Pro Ala Ile Val Gln Pro Ser
    130                 135                 140
Val Val Ile Pro Ala Ala Ala Pro Val Pro Ser Leu Ser Ser Pro Tyr
145                 150                 155                 160
Ile Glu Tyr Thr Pro Ala Ser Pro Val Tyr Ala Gln Tyr Pro Pro Ala
                165                 170                 175
Thr Tyr Asp Gln Tyr Pro Tyr Ala Ala Ser Pro Ala Thr Ala Asp Ser
                180                 185                 190
Phe Val Gly Tyr Ser Tyr Pro Ala Ala Val His Gln Ala Leu Ser Ala
                195                 200                 205
Ala Ala Pro Ala Gly Thr Thr Phe Val Gln Tyr Gln Ala Pro Gln Leu
    210                 215                 220
Gln Pro Asp Arg Met Gln
225                 230
```

<210> SEQ ID NO 25
<211> LENGTH: 1439
<212> TYPE: DNA
<213> ORGANISM: Human

<400> SEQUENCE: 25

```
gcggcggatg cagtacaacc ggcgctttgt caacgttgtg cccacctttg caagaagaa        60
gggcaccacg ttcaccaaga tcttcgtggg cggcctgccg taccacacta ccgacgcctc       120
gctcaggaag tacttcgagg gcttcggcga catcgaggag gccgtggtca tcaccgaccg       180
ccagacgggc aagtcccgcg gctacggctt cgtgaccatg gccgaccggg cggcagctga       240
gagggcttgc aaagaccct aacccccatca tcgacggccg caaggccaac gtgaacctgg       300
catatctggg cgccaagcct tggtgtctcc agacgggctt tgccattggc gtgcagcagc       360
tgcaccccac cttgatccag cggacttacg gctgaccccc gcactacatc tacccaccag       420
ccatcgtgca gccagcgtg gtgatccag ccgcccctgt cccgtcgctg tcctcgccct         480
acattgagta cacgccggcc agcccggtct acgcccagta cccaccggcc acctatgacc       540
agtaccccata cgccgcctcg cctgccacgg ctgacagctt cgtgggctac agctaccctg       600
ccgccgtgca ccaggccctc tcagccgcag caccgcgggg caccactttc gtgcagtacc       660
aggcgccgca gctgcagcct gacaggatgc agtgaggggc gttcctgccc cgaggactgt       720
ggcattgtca ccttcacagc agacagagct gccaggccat gatgggctgg cgacagcccg       780
gctgagcttc agtgaggtgc caccagcacc cgtgcctccg aagaccgctc gggcattccg       840
cctgcgccct gggacagcgg agagacggct tctcttttaat ctaggtccca ttgtgtcttg       900
agggaggact tttaagaatg actgagaact atttggggac gcaatcccag gttccttgca       960
caccatggca gcctctcctt gcaccttctc ctgcctctcc acactccagg ttccctcagg      1020
cttgtgtccc cactgctgca tcgtggcggg gtgtcacaga ccctctgcag ccctggctg       1080
```

| | | | |
|---|---|---|---|
| ccctggactg tgcagagatg cctgactcca gggaaacctg aaagcaagaa gttaatggac | | | 1140 |
| tgtttattgt aacttgatcc tcccgagctg tgagcgcagt ctgaggtctg aggacacggc | | | 1200 |
| ctcctgttgg agtcccattt tctccatcag ggcacgtggg cggcttcctc aagcccggag | | | 1260 |
| gagctcccag gcgcacaggg gccgccggta acaggggccg ccggcaaag gccccttcc | | | 1320 |
| agtcatagca ctgaagttgc aactttttc ttgtaattgt tttgctacta agataatttc | | | 1380 |
| agaagttcag tctatttttt cagcggatac tgccgccacc aagaatccaa acctaggaa | | | 1439 |

```
<210> SEQ ID NO 26
<211> LENGTH: 230
<212> TYPE: PRT
<213> ORGANISM: Human

<400> SEQUENCE: 26
```

Arg Arg Met Gln Tyr Asn Arg Arg Phe Val Asn Val Pro Thr Phe
 1               5                   10                  15

Gly Lys Lys Lys Gly Thr Thr Phe Thr Lys Ile Phe Val Gly Gly Leu
             20                  25                  30

Pro Tyr His Thr Thr Asp Ala Ser Leu Arg Lys Tyr Phe Glu Gly Phe
             35                  40                  45

Gly Asp Ile Glu Glu Ala Val Val Ile Thr Asp Arg Gln Thr Gly Lys
         50                  55                  60

Ser Arg Gly Tyr Gly Phe Val Thr Met Ala Asp Arg Ala Ala Ala Glu
 65                  70                  75                  80

Arg Ala Cys Lys Asp Pro Asn Pro Ile Ile Asp Gly Arg Lys Ala Asn
                 85                  90                  95

Val Asn Leu Ala Tyr Leu Gly Ala Lys Pro Trp Cys Leu Gln Thr Gly
            100                 105                 110

Phe Ala Ile Gly Val Gln Gln Leu His Pro Thr Leu Ile Gln Arg Thr
            115                 120                 125

Tyr Gly Leu Thr Pro His Tyr Ile Tyr Pro Pro Ala Ile Val Gln Pro
        130                 135                 140

Ser Val Val Ile Pro Ala Ala Pro Val Pro Ser Leu Ser Ser Pro Tyr
145                 150                 155                 160

Ile Glu Tyr Thr Pro Ala Ser Pro Val Tyr Ala Gln Tyr Pro Pro Ala
                165                 170                 175

Thr Tyr Asp Gln Tyr Pro Tyr Ala Ala Ser Pro Ala Thr Ala Asp Ser
            180                 185                 190

Phe Val Gly Tyr Ser Tyr Pro Ala Ala Val His Gln Ala Leu Ser Ala
        195                 200                 205

Ala Ala Pro Ala Gly Thr Thr Phe Val Gln Tyr Gln Ala Pro Gln Leu
    210                 215                 220

Gln Pro Asp Arg Met Gln
225                 230

```
<210> SEQ ID NO 27
<211> LENGTH: 2029
<212> TYPE: DNA
<213> ORGANISM: 27

<400> SEQUENCE: 27
```

| | | | |
|---|---|---|---|
| actcagtgtt cgcgggagcc gcacctacac cagccaaccc agatcccgag gtccgacagc | | | 60 |
| gcccggccca gatccccacg cctgccagga gcaagccgag agccagccgg ccggcgcact | | | 120 |
| ccgactccga gcagtctctg tccttcgacc cgagccccgc gcccttccg ggacccctgc | | | 180 |

-continued

```
cccgcgggca gcgctgccaa cctgccggcc atggagaccc cgtcccagcg gcgcgccacc      240
cgcagcgggg cgcaggccag ctccactccg ctgtcgccca cccgcatcac ccggctgcag      300
gagaaggagg acctgcagga gctcaatgat cgcttggcgg tctacatcga ccgtgtgcgc      360
tcgctggaaa cggagaacgc agggctgcgc cttcgcatca ccgagtctga agaggtggtc      420
agccgcgagg tgtccggcat caaggccgcc tacgaggccg agctcgggga tgcccgcaag      480
acccttgact cagtagccaa ggagcgcgcc cgcctgcagc tggagctgag caaagtgcgt      540
gaggagttta aggagctgaa agcgcgcaat accaagaagg agggtgacct gatagctgct      600
caggctcggc tgaaggacct ggaggctctg ctgaactcca aggaggccgc actgagcact      660
gctctcagtg agaagcgcac gctggagggc gagctgcatg atctgcgggg ccaggtggcc      720
aagcttgagg cagccctagg tgaggccaag aagcaacttc aggatgagat gctgcggcgg      780
gtggatgctg agaacaggct gcagaccatg aaggaggaac tggacttcca gaagaacatc      840
tacagtgagg agctgcgtga gaccaagcgc cgtcatgaga cccgactggt ggagattgac      900
aatgggaagc agcgtgagtt tgagagccgg ctggcggatg cgctgcagga actgcgggcc      960
cagcatgagg accaggtgga gcagtataag aaggagctgg agaagactta ttctgccaag     1020
ctggacattg ccaggcagtc tgctgagagg aacagcaacc tggtgggggc tgcccacgag     1080
gagctgcagc agtcgcgcat ccgcatcgac agcctctctg cccagctcag ccagctccag     1140
aagcagctgg cagccaagga ggcgaagcct cgagacctgg aggactcact ggcccgtgag     1200
cgggacacca gccggcggct gctggcggaa aaggagcggg agatggccga gatgcgggca     1260
aggatgcagc agcagctgga cgagtaccag gagcttctgg acatcaagct ggccctggac     1320
atggagatcc acgcctaccg caagctcttg gagggcgagg aggagaggct acgcctgtcc     1380
cccagcccta cctcgcagcg cagccgtggc cgtgcttcct ctcactcatc ccagacacag     1440
ggtgggggca gcgtcaccaa aaagcgcaaa ctggagtcca ctgagagccg cagcagcttc     1500
tcacagcacg cacgcactag cgggcgcgtg gccgtggagg aggtggatga ggagggcaag     1560
tttgtccggc tgcgcaacaa gtccaatgag gaccagtcca tgggcaattg gcagatcaag     1620
cgccagaatg gagatgatcc cttgctgact taccggttcc caccaaagtt caccctgaag     1680
gctgggcagg tggtgacgat ctgggctgca ggagctgggg ccacccacag ccccccctacc     1740 gacctggtgt ggaaggcaca gaacacctgg ggctgcggga cagcctgcg tacggctctc     1800 atcaactcca ctggggaaga agtggccatg cgcaagctgg tgcgctcagt gactgtggtt     1860
gaggacgacg aggatgagga tggagatgac ctgctccatc accaccatgt gagtggtagc     1920
cgccgctgag gccgagcctg cactggggcc acccagccag gcctggggc agcctctccc     1980 cagcctcccc gtgccaaaaa tcttttcatt aaagaatgtt tggaacttt               2029
```

<210> SEQ ID NO 28
<211> LENGTH: 572
<212> TYPE: PRT
<213> ORGANISM: Human

<400> SEQUENCE: 28

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

-continued

```
Val Arg Ser Leu Glu Thr Glu Asn Ala Gly Leu Arg Leu Arg Ile Thr
 50                  55                  60

Glu Ser Glu Glu Val Val Ser Arg Glu Val Ser Gly Ile Lys Ala Ala
 65                  70                  75                  80

Tyr Glu Ala Glu Leu Gly Asp Ala Arg Lys Thr Leu Asp Ser Val Ala
                 85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
            115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
            195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
            275                 280                 285

His Glu Glu Leu Gln Gln Ser Arg Ile Arg Ile Asp Ser Leu Ser Ala
290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
            355                 360                 365

Leu Asp Met Glu Ile His Ala Tyr Arg Lys Leu Leu Glu Gly Glu Glu
370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
            435                 440                 445

Gly Lys Phe Val Arg Leu Arg Asn Lys Ser Asn Glu Asp Gln Ser Met
450                 455                 460
```

```
Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Thr Asp Leu
            500                 505                 510

Val Trp Lys Ala Gln Asn Thr Trp Gly Cys Gly Asn Ser Leu Arg Thr
            515                 520                 525

Ala Leu Ile Asn Ser Thr Gly Glu Glu Val Ala Met Arg Lys Leu Val
            530                 535                 540

Arg Ser Val Thr Val Val Glu Asp Asp Glu Glu Asp Gly Asp Asp
545                 550                 555                 560

Leu Leu His His His His Val Ser Gly Ser Arg Arg
                565                 570
```

<210> SEQ ID NO 29
<211> LENGTH: 10
<212> TYPE: PRT
<213> ORGANISM: Human

<400> SEQUENCE: 29

```
Asn Leu Leu Glu Lys Asp Tyr Phe Gly Leu
1               5                   10
```

<210> SEQ ID NO 30
<211> LENGTH: 10
<212> TYPE: PRT
<213> ORGANISM: Human

<400> SEQUENCE: 30

```
Val Leu Phe Asp Leu Val Cys Glu His Leu
1               5                   10
```

<210> SEQ ID NO 31
<211> LENGTH: 9
<212> TYPE: PRT
<213> ORGANISM: Human

<400> SEQUENCE: 31

```
Lys Leu Gln His Pro Asp Met Leu Val
1               5
```

<210> SEQ ID NO 32
<211> LENGTH: 9
<212> TYPE: PRT
<213> ORGANISM: Human

<400> SEQUENCE: 32

```
Lys Met Leu Asp Ala Glu Asp Ile Val
1               5
```

<210> SEQ ID NO 33
<211> LENGTH: 10
<212> TYPE: PRT
<213> ORGANISM: Human

<400> SEQUENCE: 33

```
Lys Met Thr Leu Gly Met Ile Trp Thr Ile
1               5                   10
```

```
<210> SEQ ID NO 34
<211> LENGTH: 9
<212> TYPE: PRT
<213> ORGANISM: Human

<400> SEQUENCE: 34

Phe Met Pro Ser Glu Gly Lys Met Val
1               5

<210> SEQ ID NO 35
<211> LENGTH: 10
<212> TYPE: PRT
<213> ORGANISM: Human

<400> SEQUENCE: 35

Lys Leu Ala Ser Asp Leu Leu Glu Trp Ile
1               5                   10

<210> SEQ ID NO 36
<211> LENGTH: 9
<212> TYPE: PRT
<213> ORGANISM: Human

<400> SEQUENCE: 36

Gly Leu Val Thr Phe Gln Ala Phe Ile
1               5

<210> SEQ ID NO 37
<211> LENGTH: 10
<212> TYPE: PRT
<213> ORGANISM: Human

<400> SEQUENCE: 37

Cys Gln Leu Glu Ile Asn Phe Asn Ser Val
1               5                   10

<210> SEQ ID NO 38
<211> LENGTH: 10
<212> TYPE: PRT
<213> ORGANISM: Human

<400> SEQUENCE: 38

Trp Leu Ala Ala Val Thr Lys Gln Asn Val
1               5                   10

<210> SEQ ID NO 39
<211> LENGTH: 10
<212> TYPE: PRT
<213> ORGANISM: Human

<400> SEQUENCE: 39

Ile Leu Pro Phe Arg Val Ile Pro Leu Val
1               5                   10

<210> SEQ ID NO 40
<211> LENGTH: 9
<212> TYPE: PRT
<213> ORGANISM: Human

<400> SEQUENCE: 40

Ser Leu Leu Ala Gln Lys Ile Glu Val
1               5
```

```
<210> SEQ ID NO 41
<211> LENGTH: 9
<212> TYPE: PRT
<213> ORGANISM: Human

<400> SEQUENCE: 41

Lys Leu Asn Tyr Ser Asp His Asp Val
1               5

<210> SEQ ID NO 42
<211> LENGTH: 9
<212> TYPE: PRT
<213> ORGANISM: Human

<400> SEQUENCE: 42

Lys Leu Leu Gly Gly Gln Ile Gly Leu
1               5

<210> SEQ ID NO 43
<211> LENGTH: 10
<212> TYPE: PRT
<213> ORGANISM: Human

<400> SEQUENCE: 43

Ser Leu Leu Gly Cys Arg His Tyr Glu Val
1               5                   10

<210> SEQ ID NO 44
<211> LENGTH: 10
<212> TYPE: PRT
<213> ORGANISM: Human

<400> SEQUENCE: 44

Tyr Leu Ser Gln Glu His Gln Gln Gln Val
1               5                   10

<210> SEQ ID NO 45
<211> LENGTH: 10
<212> TYPE: PRT
<213> ORGANISM: Human

<400> SEQUENCE: 45

Lys Val Met Asp Arg Pro Gly Asn Tyr Val
1               5                   10

<210> SEQ ID NO 46
<211> LENGTH: 9
<212> TYPE: PRT
<213> ORGANISM: Human

<400> SEQUENCE: 46

Ala Leu Ile Glu Gln Trp Asn Pro Val
1               5

<210> SEQ ID NO 47
<211> LENGTH: 9
<212> TYPE: PRT
<213> ORGANISM: Human

<400> SEQUENCE: 47

Ile Ile Thr Ala Phe Asn Phe Pro Val
1               5
```

```
<210> SEQ ID NO 48
<211> LENGTH: 9
<212> TYPE: PRT
<213> ORGANISM: Human

<400> SEQUENCE: 48

Phe Gln Gln Glu Asn Asp Trp Trp Val
1               5

<210> SEQ ID NO 49
<211> LENGTH: 9
<212> TYPE: PRT
<213> ORGANISM: Human

<400> SEQUENCE: 49

Tyr Leu Gly Ala Lys Pro Trp Cys Leu
1               5

<210> SEQ ID NO 50
<211> LENGTH: 10
<212> TYPE: PRT
<213> ORGANISM: Human

<400> SEQUENCE: 50

Cys Leu Gln Thr Gly Phe Ala Ile Gly Val
1               5                   10

<210> SEQ ID NO 51
<211> LENGTH: 10
<212> TYPE: PRT
<213> ORGANISM: Human

<400> SEQUENCE: 51

Lys Leu Leu Glu Gly Glu Glu Glu Arg Leu
1               5                   10

<210> SEQ ID NO 52
<211> LENGTH: 9
<212> TYPE: PRT
<213> ORGANISM: Human

<400> SEQUENCE: 52

Lys Leu Val Arg Ser Val Thr Val Val
1               5

<210> SEQ ID NO 53
<211> LENGTH: 9
<212> TYPE: PRT
<213> ORGANISM: Human

<400> SEQUENCE: 53

Arg Leu Ala Asp Ala Leu Gln Glu Leu
1               5
```

TUMOR-ASSOCIATED MARKER

This application is a continuation of U.S. Ser. No. 09/664,958, filed Sep. 18, 2000, now U.S. Pat. No. 7,060,802, issued Jun. 13, 2006, the contents of which are hereby incorporated by reference.

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art.

BACKGROUND OF THE INVENTION

The seminal discovery by Kohler and Milstein (Kohler, G. and Milstein, C., 1975) of mouse "hybridomas" capable of secreting specific monoclonal antibodies (mAbs) against predefined antigens ushered in a new era in experimental immunology. Many problems associated with antisera were circumvented. Clonal selection and immortality of hybridoma cell lines assured monoclonality and permanent availability of antibody products. At the clinical level, however, the use of such antibodies is clearly limited by the fact that they are foreign proteins and act as antigens in humans.

Since the report of Kohler and Milstein (Kohler, G. and Milstein, C., 1975), the production of mouse monoclonal antibodies has become routine. However, the application of xenogenic monoclonal antibodies for in vivo diagnostics and therapy is often associated with undesirable effects such as a human anti-mouse immunoglobulin response. In addition, monoclonal antibodies have great potential as tools for imaging. Moreover, therapeutic treatment has motivated the search for means for the production of human monoclonal antibodies (humAbs) (Levy, R., and Miller R A., 1983).

However, progress in this area has been hampered by the absence of human myelomas suitable as fusion partners with characteristics similar to those of mouse myeloma cells (Posner M R, et al., 1983). The use of Epstein-Barr virus (EBV) has proved to be quite efficient for human lymphocyte immortalization (Kozbor D, and Roder J., 1981; Casual O, 1986), but has certain limitations such as low antibody secretion rate, poor clonogenicity of antibody-secreting lines, and chromosomal instability requiring frequent subcloning. Undifferentiated human lymphoblastoid cell lines appear more attractive. In contrast to differentiated myeloma cells, these cell lines are readily adapted to culture conditions, though the problems of low yield and unstable secretion remain unresolved (Glassy M C, 1983; Ollson L, et al., 1983). The best potential fusion partners are syngenic myeloma cells with well-developed protein synthesis machinery (Nilsson K. and Ponten J., 1975). However, due to culturing difficulties few lines have been conditioned for in vitro growth and capability to produce viable hybrids (Goldman-Leikin R E, 1989). Existing myelomas have low fusion yield and slow hybrid growth, although monoclonal antibody production is relatively stable (Brodin T, 1983). Genetic instability is a major disadvantage of interspecies hybrids. This is the case, for example, when a mouse myeloma is used as the immortalizing partner. Production of mouse-human cell hybrids is not difficult, and these cells have growth characteristics In vitro similar to those of conventional mouse-mouse hybridomas (Teng N N H, 1983). However, spontaneous elimination of human chromosomes considerably reduces the probability of stable mAb secretion (Weiss M C, and Green H., 1967). In order to improve growth characteristics and stability of human monoclonal antibody production, heterohybrids between mouse myeloma cells and human lymphocyte (Oestberg L, and Pursch E., 1983) as well as heteromyelomas (Kozbor D, et. al., 1984) are used as fusion partners.

The role of humoral immunity in cancer is poorly understood. Numerous data demonstrate the presence of tumor specific, anti-tumor antibodies in cancer patients. Such antibodies can participate in potential protective anti-tumor responses that can eliminate tumor cells through any of several physiological mechanisms. Anti-tumor antibodies developed in the laboratory through immunization of animals bearing malignant tissues offer great promise in diagnostics and imaging, but have serious shortcomings in clinical application because such antibodies themselves can provoke strong immune reactions and lack important biological functions. Until recently, fully human antibodies directed to tumor-associated antigens have not been available because the human fusion partner cell lines necessary to construct human hybridomas capable of making human antibodies in large quantities were not adequate.

The general idea of developing fully human monoclonal antibodies using B-lymphocytes directly from cancer patients was discussed a few years ago. However the implementation of this idea became possible only recently when the appropriate fusion partner cell line was developed. It is now possible to capture specific B-lymphocytes producing such antibodies and maintain them in culture, harvesting the antibodies of interest.

The present invention comprises a unique fusion partner cell line that fuses with human lymphocytes derived from lymph nodes, spleen, tonsils, or peripheral blood. The cell line allows for immortalization of cancer-specific B-cells through hybridoma technique. The resulting hybrids have proved to be stable producers of human immune substances called immunoglobulins and represent a reliable source of human antibodies for immunotherapy. Using a proprietary fusion partner cell line, which was designated as MFP-2, a few human antibody-producing hybridomas with specificity towards human breast and prostate cancer were established, and thereby several monoclonal antibodies with specific immunoreactivity towards human breast and prostate cancer were developed. These antibodies reacted both with the human cancer cell lines and with primary tumor tissues. These fully human antibodies have specificity to human cancer cell lines as well as primary cancer tissues. Antigen targets were identified for some of these antibodies. Also developed was a hybridoma fusion system, which allows for capturing human lymph node or peripheral blood lymphocytes secreting specific antibodies to cancer antigens. These fully human antibodies may be used to help identify novel tumor-associated antigens, or may be employed for in vivo diagnostic and immunotherapeutic treatment of cancer.

Potential advantages of human monoclonal antibodies include the possibility of identifying the molecular target of the antibody. Such a target could turn out to be a novel molecule altogether or a known molecule whose association with cancer is novel itself. A few years ago scientists at the Ludwig Institute for Cancer Research developed the SEREX method, which allows the identification of novel tumor-associated antigens through the spontaneous antibodies present in cancer patients' blood. Their task was focused specifically on the identification of novel tumor markers. The present invention focused initially on the development of human monoclonal antibodies capable of differentiating cancerous from normal tissue. The identity of a molecular target was secondary to this mission.

In the present invention, molecular targets for some of the antibodies were identified and shown to be specific only for cancer cells. One of the targets which appeared is the PDZ domain containing protein localized both in cytosol and cell membrane of human breast cancer cells. This protein, called GIPC or TIP-2 (Tax interacting protein clone 2) is involved in vesicle trafficking and formation of protein networks. It has several properties, such as the ability to bind to RGS-Ga interacting protein, C domain, binding to HTLV-1 oncogene tax and binding both to a-actinin and glucose transporter 1. The precise physiological role of this protein is not known, while it shows a consistent overexpression in breast cancer cells, with negligible if any expression in prostate cancer cells and none in human fibroblasts. Although this protein was described previously (2), its association with cancer was not known. It was also not known that a spontaneous antibody response to this marker occurs in breast cancer patients.

One advantage of the present invention is that establishing the association of TIP-2 with malignant transformation allows application of this antigen/protein as a diagnostic marker, both in vitro and in vivo, for immunohistopathology analysis as well as for immunochemical testing; This protein may be found in the circulation in cancer patients. This protein could also serve as a molecular target for therapeutic purposes given its specific expression in primary tumors. This protein can also be used as a soluble tumor marker for cancer diagnostic, cancer progression and monitoring of cancer treatment in breast and prostate cancer patients. Since this protein is expressed on the surface of cancer cells, it can be used as a target for the specific antibody-driven delivery of liposomes loaded with drugs, or antibody-conjugated drugs, prodrugs, toxins or inhibitors of cell growth. Proving the relevance of TIP-2 for cell survival, this novel marker can be considered as a candidate for vaccine development for immunotherapy of cancer.

Antibodies to TIP-2 derived from breast cancer patient's lymphocytes can be used as a vector for in vivo diagnostic (imaging) and immunotherapy (e.g., for delivery of drug-loaded liposomes, or radioimmune- or immunotoxic conjugates to the tumor site). Fully human monoclonal antibodies to TIP-2 can and will be used to isolate preparative quantities of TIP-2 from breast cancer cells or primary tumors and to develop high affinity mouse antibodies for the purpose of diagnostic and therapeutic use had their biological value been proven. The present invention also provides a basis for the possible development of specific immunoassays or an immunohistochemistry kit for the detection and measurement of this novel tumor marker.

An advantage of the present invention is that human antibodies directed to TIP-2 can be used as an immunosorbent tool for isolation and further characterization of this protein's chemical structure (amino acid composition, protein sequence, modification).

Another advantage of the present invention is an immunosorbent prepared on the basis of human anti-TIP-2 monoclonal antibodies allows isolation of this antigen and its use for developing mouse monoclonal antibodies of high affinity and specificity which can be used to develop better tools for TIP-2 immunoassay.

Another advantage of the present invention is that, knowing the DNA sequence for TIP-2 and its association with cancer, it becomes possible to screen different tissues, normal as well as cancerous, for the expression of this marker.

Another advantage of the present invention is, since human monoclonal antibodies to TIP-2 are available and there is a strong potential to develop non-human antibodies which are even more efficient for certain diagnostic and therapeutic purposes, it is highly likely that TIP-2 can be used as a potential target for immunotherapy and for in vivo diagnostic (imaging).

Another advantage is that since TIP-2 was identified through naturally developed antibodies in breast cancer patients, its existence supports the hypothesis that this antigen can be immunogenic in humans and hence can be considered as a starting candidate for the development of an anti-cancer vaccine.

SUMMARY OF THE INVENTION

The present invention provides a heteromyeloma cell which does not produce any antibody and is capable of producing a trioma cell which does not produce any antibody when fused with a human lymphoid cell; wherein the trioma cell so produced is capable of producing a tetroma cell which produces a monoclonal antibody having specific binding affinity for an antigen when fused with a second human lymphoid cell and such second human lymphoid cell produces an antibody having specific binding affinity for the antigen, with the proviso that the heteromyeloma cell is not B6B11 (ATCC accession number HB-12481).

The present invention further provides a trioma cell which does not produce any antibody obtained by fusing a heteromyeloma cell with a human lymphoid cell.

The present invention also provides a tetroma cell capable of producing a monoclonal antibody having specific binding affinity for an antigen, obtained by fusing the above-described trioma cell which does not produce any antibody with a human lymphoid cell capable of producing an antibody having specific binding affinity for the antigen.

The present invention additionally provides a monoclonal antibody produced by the above-described tetroma.

The present invention further provides a method of generating the above-described trioma cell comprising: (a) fusing a heteromyeloma cell which does not produce any antibody with a human lymphoid cell thereby forming trioma cells; (b) incubating the trioma cells formed in step (a) under conditions permissive for the production of antibody by the trioma cells; and (c) selecting a trioma cell that does not produce any antibody.

Still further, the present invention provides a method of generating tetroma cells comprising: (a) fusing the described trioma cell with a human lymphoid cell, thereby forming tetroma cells; (b) incubating the tetroma cells formed in step (a) under conditions permissive for the production of antibody by the tetroma cells; and (c) selecting a tetroma cell capable of producing a monoclonal antibody.

The present invention also provides a method of producing a monoclonal antibody comprising (a) fusing a lymphoid cell capable of producing antibody with the above-described trioma cell, thereby forming tetroma cells; and (b) incubating the tetroma cell formed in step (a) under conditions permissive for the production of antibody by the tetroma cells; (c) selecting a tetroma cell capable of producing the monoclonal antibody; and (d) culturing the tetroma cell of step (c) so as to produce the monoclonal antibody.

Also, the present invention provides a method of producing a monoclonal antibody specific for an antigen associated with a given condition in a subject comprising: (a) fusing a lymphoid cell capable of producing antibody with the above-described trioma cell, thereby forming tetroma cells; (b) incubating the tetroma cell formed in step (a) under conditions permissive for the production of antibody by the tetroma cells; (c) selecting a tetroma cell producing a monoclonal antibody; (d) contacting the monoclonal antibody of step (c)

with (1) a sample from a subject with the given condition or (2) a sample from a subject without the given condition, so as to form a complex between the monoclonal antibody and the sample; (e) detecting any complex formed between the monoclonal antibody and the sample; (f) determining the amount of complex formed in step and (e); and (g) comparing the amount of complex determined in step (f) for the sample from the subject with the given condition with amount determined in step (f) for the sample from the subject without the given condition, a greater amount of complex formation for the sample from the subject with the given condition indicating that a monoclonal antibody specific for an antigen specific for the condition has been produced.

Additionally, the present invention provides a method of identifying an antigen associated with a given condition in a sample comprising: (a) contacting the monoclonal antibody produced by the above-described method with the sample, under conditions permissive for the formation of a complex between the monoclonal antibody and the sample; (b) detecting any complex formed in step (a); and (c) isolating any complex detected in step (b), so as to thereby identify the antigen associated with the condition in the sample.

The present invention additionally provides a method of diagnosing a given condition in a subject comprising: (a) contacting a sample from the subject with a monoclonal antibody produced by the above-described method under conditions permissive for the formation of a complex between the monoclonal antibody and the sample; and (b) detecting the formation of any complex formed between the monoclonal antibody and the sample, detection of complex so formed indicating the presence of an antigen specific for the given condition in the sample, and thus providing a diagnosis of the given condition in the subject.

The present invention further provides a composition comprising a monoclonal antibody described by the method described herein and a suitable carrier.

Further, the present invention also provides a therapeutic composition comprising a therapeutically effective amount of a monoclonal antibody of this invention and a pharmaceutically acceptable carrier.

Also, the present invention further provides a method of treating a given condition in a subject comprising administering to the subject an amount of the above-described therapeutic composition effective to treat the condition in the subject.

The present invention also provides a method of preventing a given condition in a subject comprising administering to the subject an amount of the above-described therapeutic composition effective to prevent the condition in the subject.

The present invention provides a monoclonal antibody which specifically binds and forms a complex with TIP-2 antigen located on the surface of human cancer cells, the TIP-2 antigen being an antigen to which monoclonal antibody 27.B1 specifically binds.

The present invention provides the monoclonal antibody 27.B1 produced by the hybridoma having ATCC Accession No. PTA-1599 deposited Mar. 29, 2000 under the Budapest Treaty with the American Type Culture Collection, 10801 University Blvd, Manassas, Va. 20110-2209, USA.

The present invention provides a hybridoma cell producing the monoclonal antibody of this invention.

The present invention provides a pharmaceutical composition comprising the monoclonal antibody of this invention and a pharmaceutically acceptable carrier.

The present invention provides a vaccine comprising the monoclonal antibody of this invention and a pharmaceutically acceptable carrier.

The present invention provides a monoclonal antibody which specifically binds and forms a complex with TIP-2 antigen located on the surface of human cancer cells, the TIP-2 antigen being an antigen to which monoclonal antibody 27.F7 specifically binds.

The present invention provides the monoclonal antibody 27.F7 produced by the hybridoma having ATCC Accession No. PTA-1598 deposited Mar. 29, 2000 under the Budapest Treaty with the American Type Culture Collection, 10801 University Blvd, Manassas, Va. 20110-2209, U.S.A.

The present invention provides a hybridoma cell producing the monoclonal antibody of this invention.

The present invention provides a pharmaceutical composition comprising the monoclonal antibody of this invention and a pharmaceutically acceptable carrier.

The present invention provides a vaccine comprising the monoclonal antibody of this invention and a pharmaceutically acceptable carrier.

The present invention provides a method of detecting TIP-2 antigen bearing cancer cells in a sample comprising: (a) contacting the sample with an antibody directed to an epitope on TIP-2 antigen, or an Fab fragment of an antibody directed to an epitope on TIP-2 antigen, which epitope is recognized by the antibody or the Fab fragment, said antibody or Fab fragment being detectably labeled, under appropriate conditions to produce an antibody/Fab fragment-antigen complex comprising the detectably labeled antibody or Fab fragment bound to any TIP-2 antigen on the surface of cells in the sample; (b) removing any labeled antibody/Fab fragment not bound in the antibody/Fab fragment-antigen complex formed in step (a); and (b) determining presence of the antibody/Fab fragment-antigen complex by detecting the label of the detectably labeled antibody, presence of antibody/Fab fragment-antigen complex indicating TIP-2 antigen-bearing cancer cells in the sample.

The present invention provides a method of detecting TIP-2 antigen bearing cancer cells in a sample comprising: (a) contacting the sample with an antibody directed to an epitope on TIP-2 antigen, or an Fab fragment of an antibody directed to an epitope on TIP-2 antigen, which epitope is recognized by the antibody or the Fab fragment under appropriate conditions to produce an antibody/Fab fragment-antigen complex comprising the antibody or Fab fragment bound to any TIP-2 antigen on the surface of cells in the sample; (b) removing any antibody/Fab fragment not bound in the antibody/Fab fragment-antigen complex formed in step (a); (c) contacting the antibody/Fab fragment-antigen complex of step (b) with a second antibody which specifically binds to the antibody/Fab fragment-antigen complex, said second antibody being detectably labeled, under appropriate conditions to permit the second labeled antibody to bind to the antibody/Fab fragment-antigen complex; (d) removing any second labeled antibody not bound to the antibody/Fab fragment-antigen complex product in (c); and (e) determining presence of the antibody/Fab fragment-antigen complex bound to the second labeled antibody by detecting the label of second antibody, presence of antibody/Fab fragment-antigen complex indicating TIP-2 antigen-bearing human cancer cells in the sample.

The present invention provides a method of detecting TIP-2 antigen on the surface of cancer cells in a sample comprising: (a) contacting the sample with a antibody directed to an epitope on TIP-2 antigen or an Fab fragment thereof, which epitope is recognized by monoclonal antibody 27.F7 produced by the hybridoma designated ATCC Accession No. PTA-1598, said antibody or Fab fragment thereof being detectably labeled, under appropriate conditions to produce an antibody 27.F7/Fab fragment-TIP-2 antigen complex comprising the detectably labeled antibody bound to any TIP-2 antigen on the surface of cells in the sample; b) removing any labeled antibody/Fab fragment not bound in the antibody 27.F7/Fab fragment-TIP-2 antigen complex formed in step (a); and (c) determining presence of the antibody 27.F7/Fab fragment-TIP-2 antigen complex by detecting the label of the detectably labeled antibody, presence of antibody 27.F7/Fab fragment-TIP-2 antigen complex indicating TIP-2 antigen-bearing human cancer cells in the sample.

The present invention provides a method of detecting TIP-2 antigen on the surface of cancer cells in a sample comprising: (a) contacting the sample with an antibody directed to an epitope on TIP-2 antigen which epitope is recognized by monoclonal antibody 27.F7 produced by the hybridoma designated ATCC Accession No. PTA-1598 or Fab fragment thereof, under appropriate conditions to produce an antibody 27.F7/Fab fragment-TIP-2 antigen complex comprising the antibody bound to any TIP-2 antigen on the surface of cells in the sample; (b) removing any antibody or Fab fragment thereof not bound in the antibody 27.F7/Fab fragment-TIP-2 antigen complex formed in step (a); (c) contacting the antibody 27.F7/Fab fragment-TIP-2 antigen complex of step (b) with a second antibody which specifically binds to the antibody 27.F7/Fab fragment-TIP-2 antigen complex, said second antibody being detectably labeled, under appropriate conditions to permit the second labeled antibody to bind to the antibody 27.F7/Fab fragment-TIP-2 antigen complex; (d) removing any second labeled antibody not bound to the antibody 27.F7/Fab fragment-TIP-2 antigen complex product in (c); and (e) determining presence of the antibody 27.F7/Fab fragment-TIP-2 antigen complex bound to the second labeled antibody by detecting the label of second antibody, presence of antibody 27.F7/Fab fragment-TIP-2 antigen complex indicating TIP-2 antigen-bearing human cancer cells in the sample.

The present invention provides a method of detecting TIP-2 antigen on the surface of cancer cells in a sample comprising: (a) contacting the sample with a antibody directed to an epitope on TIP-2 antigen or an Fab fragment thereof, which epitope is recognized by monoclonal antibody 27.B1 produced by the hybridoma designated ATCC Accession No. PTA-1599 or Fab fragment thereof, said antibody or Fab fragment thereof being detectably labeled, under appropriate conditions to produce an antibody 27.B1/Fab fragment-TIP-2 antigen complex comprising the detectably labeled antibody bound to any TIP-2 antigen on the surface of cells in the sample; (b) removing any labeled antibody not bound in the antibody 27.B1-TIP-2 antigen complex formed in step (a); and (c) determining presence of the antibody 27.B1/Fab fragment-TIP-2 antigen complex by detecting the label of the detectably labeled antibody, presence of antibody 27.B1/Fab fragment-TIP-2 antigen complex indicating TIP-2 antigen-bearing human cancer cells in the sample.

The present invention provides a method of detecting TIP-2 antigen on the surface of cancer cells in a sample comprising: (a) contacting the sample with an antibody directed to an epitope on TIP-2 antigen or an Fab fragment thereof, which epitope is recognized by monoclonal antibody 27.B1 produced by the hybridoma designated ATCC Accession No. PTA-1599, or Fab fragment thereof under appropriate conditions to produce an antibody 27.B1/Fab fragment-TIP-2 antigen complex comprising the antibody bound to any TIP-2 antigen on the surface of cells in the sample; (b) removing any antibody/Fab fragment thereof not bound in the antibody 27.B1/Fab fragment-TIP-2 antigen complex formed in step (a); (c) contacting the antibody 27.B1/Fab fragment-TIP-2 antigen complex of step (b) with a second antibody which specifically binds to the antibody 27.B1/Fab fragment-TIP-2 antigen complex, said second antibody being detectably labeled, under appropriate conditions to permit the second labeled antibody to bind to the antibody 27.B1/Fab fragment-TIP-2 antigen complex; (d) removing any second labeled antibody not bound to the antibody 27.B1/Fab fragment-TIP-2 antigen complex product in (c); and (e) determining presence of the antibody 27.B1/Fab fragment-TIP-2 antigen complex bound to the second labeled antibody by detecting the label of second antibody, presence of antibody 27.B1/Fab fragment-TIP-2 antigen complex indicating TIP-2 antigen-bearing human cancer cells in the sample.

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or an Fab fragment thereof, which epitope is recognized by monoclonal antibody 27.F7 produced by the hybridoma designated ATCC Accession No. PTA-1598 or an Fab fragment thereof, said antibody being detectably labeled, under appropriate conditions to produce an antibody 27.F7/Fab fragment-TIP-2 antigen complex comprising the detectably labeled antibody bound to any TIP-2 antigen on the surface of cells in the sample; (c) removing any labeled antibody/Fab fragment not bound in the antibody 27.F7/Fab fragment-TIP-2 antigen complex formed in step (b); and (d) determining presence of the antibody 27.F7/Fab fragment-TIP-2 antigen complex by detecting the label of the detectably labeled antibody, presence of antibody 27.F7/Fab fragment-TIP-2 antigen complex indicating diagnosis of cancer in the subject.

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or Fab fragment thereof, which epitope is recognized by monoclonal antibody 27.F7 produced by the hybridoma designated ATCC Accession No. PTA-1598 or Fab fragment thereof, under appropriate conditions to produce an antibody 27.F7/Fab fragment-TIP-2 antigen complex comprising the antibody bound to any TIP-2 antigen on the surface of cells in the sample; (c) removing any antibody/Fab fragment not bound in the antibody 27.F7/Fab fragment-TIP-2 antigen complex formed in step (b); (d) contacting the antibody 27.F7/Fab fragment-TIP-2 antigen complex of step (c) with a second antibody which specifically binds to the antibody 27.F7/Fab fragment-TIP-2 antigen complex, said second antibody being detectably labeled, under appropriate conditions to permit the second labeled antibody to bind to the antibody 27.F7/Fab fragment-TIP-2 antigen complex; (e) removing any second labeled antibody not bound to the antibody 27.F7/Fab fragment-TIP-2 antigen complex product in (d); and (f) determining presence of the antibody 27.F7/Fab fragment-TIP-2 antigen complex bound to the second labeled antibody by detecting the label of second antibody, presence of antibody 27.F7/Fab fragment-TIP-2 antigen complex indicating diagnosis of cancer in the subject.

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or Fab fragment thereof, which epitope is recognized by monoclonal antibody 27.B1 produced by the hybridoma designated ATCC Accession No. PTA-1599, said antibody being detectably labeled, under appropriate conditions to produce an antibody 27.B1/Fab fragment-TIP-2 antigen complex comprising the detectably labeled antibody bound to any TIP-2 antigen on the surface of cells in the sample; (c) removing any labeled antibody/Fab fragment not bound in the antibody 27.B1/Fab fragment-TIP-2 antigen complex formed in step (b); and (d) determining presence of the antibody 27.B1/Fab fragment-TIP-2 antigen complex by detecting the label of the detectably labeled antibody, presence of antibody 27.B1/Fab fragment-TIP-2 antigen complex indicating diagnosis of cancer in the subject.

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or Fab fragment thereof, which epitope is recognized by monoclonal antibody 27.B1/Fab fragment produced by the hybridoma designated ATCC Accession No. PTA-1599 or Fab fragment thereof, under appropriate conditions to produce an antibody 27.B1/Fab fragment-TIP-2 antigen complex comprising the antibody bound to any TIP-2 antigen on the surface of cells in the sample; (c) removing any antibody/Fab fragment not bound in the antibody 27.B1/Fab fragment-TIP-2 antigen complex formed in step (b); (d) contacting the antibody 27.B1/Fab fragment-TIP-2 antigen complex of step (c) with a second antibody which specifically binds to the antibody 27.B1/Fab fragment-TIP-2 antigen complex, said second antibody being detectably labeled, under appropriate conditions to permit the second labeled antibody to bind to the antibody 27.B1/Fab fragment-TIP-2 antigen complex; (e) removing any second labeled antibody not bound to the antibody 27.B1/Fab fragment-TIP-2 antigen complex product in (d); and (f) determining presence of the antibody 27.B1/Fab fragment-TIP-2 antigen complex bound to the second labeled antibody by detecting the label of second antibody, presence of antibody 27.B1/Fab fragment-TIP-2 antigen complex indicating diagnosis of cancer in the subject.

The present invention provides an in vivo method for diagnosing cancer in a subject by detecting TIP-2 antigen-bearing cancer cells which comprises: (a) administering to the subject an antibody directed to an epitope on TIP-2 antigen or Fab fragment thereof, which epitope is recognized by monoclonal antibody 27.F7 produced by the hybridoma designated ATCC Accession No. PTA-1598, said antibody being detectably labeled, under appropriate conditions to bind the antibody to TIP-2 antigen on the surface of any cells in the subject; and (b) determining presence of the detectably labeled antibody 27.F7 bound to the surface of cells in the subject, presence of detectably labeled antibody 27.F7 bound to cells indicating diagnosis of cancer in the subject.

The present invention provides an in vivo method for diagnosing cancer in a subject by detecting TIP-2 antigen-bearing cancer cells which comprises: (a) administering to the subject an antibody directed to an epitope on TIP-2 antigen or Fab fragment thereof, which epitope is recognized by monoclonal antibody 27.B1 produced by the hybridoma designated ATCC Accession No. PTA-1599, said antibody/Fab fragment being detectably labeled, under appropriate conditions to bind the antibody to TIP-2 antigen on the surface of any cells in the subject; and (b) determining presence of the detectably labeled antibody/Fab fragment 27.B1 bound to the surface of cells in the subject, presence of detectably labeled antibody 27.F7/Fab fragment bound to cells indicating diagnosis of cancer in the subject.

The present invention provides a method for delivering exogenous material to TIP-2 antigen-bearing cancer cells of a human subject comprising administering to the subject a liposome carrying a conjugate of the exogenous material, wherein antibody 27.B1 or an Fab fragment of 27.B1 is coupled to the outer surface of the liposome to target delivery to the cancer cells.

The present invention provides a method for delivering exogenous material to TIP-2 antigen-bearing cancer cells of a human subject comprising administering to the subject a liposome carrying a conjugate of the exogenous material, wherein an antibody 27.F7 or an Fab fragment of 27.F7 is coupled to the outer surface of the liposome to target delivery to the cancer cells.

The present invention provides a method for treating cancer in a human subject by evoking a specific immune response which comprises administering to the subject a whole TIP-2 antigen protein or a peptide fragment of TIP-2 to the subject.

The present invention provides a method for treating cancer in a human subject by inducing apoptosis of cancer cells which comprises administering to the subject a whole TIP-2 antigen protein or a peptide fragment of TIP-2 to the subject.

The present invention provides a method for treating cancer in a human subject by evoking a specific immune response which comprises: (a) removing dendritic cells from said subject; (b) contacting the dendritic cells of step (a) with a whole TIP2 antigen protein or a peptide fragment of TIP-2; and (c) reintroducing the dendritic cells of step (b) into said subject.

The present invention provides a method for treating cancer in a human subject by inducing apoptosis of cancer cells which comprises administering a whole TIP-2 antigen protein or a peptide fragment of TIP-2 to the subject.

The present invention provides a method for treating cancer in a human subject by passive immunization which comprises administering an antibody directed to an epitope on TIP-2 antigen or a peptide fragment thereof.

The present invention provides an isolated peptide having the amino acid sequence Lys Leu Leu Gly Gly Gln Ile Gly Leu (SEQ ID NO:3).

The present invention provides an isolated peptide having the amino acid sequence Ser Leu Leu Gly Cys Arg H is Tyr Glu Val (SEQ ID NO:4).

The present invention provides a method for immunohistochemical screening of a tissue section from a tumor sample for the presence of TIP-2 antigen bearing cancer cells which comprises: (a) contacting the tissue section from the tumor sample with a detectably labeled antibody directed to an epitope on TIP-2 antigen or Fab fragment thereof, which epitope is recognized by monoclonal antibody 27.F7 produced by the hybridoma designated ATCC Accession No. PTA-1598, said antibody/Fab fragment being detectably labeled, under appropriate conditions to produce an antibody 27.F7/Fab fragment-TIP-2 antigen complex comprising the detectably labeled antibody bound to any TIP-2 antigen on the surface of cells in the tissue section; (a) removing any labeled antibody/Fab fragment not bound in the antibody 27.F7/Fab fragment-TIP-2 antigen complex formed in step (a); and (b) determining presence of the antibody 27.F7/Fab fragment-TIP-2 antigen complex by detecting the label of the detectably labeled antibody, presence of antibody 27.F7/Fab fragment-TIP-2 antigen complex indicating TIP-2 antigen-bearing human cancer cells in the sample.

The present invention provides a kit for detecting the presence of TIP-2 antigen-bearing cancer cells in a sample comprising: (a) solid support having a plurality of covalently linked probes which may be the same or different, each probe of which comprises a monoclonal antibody directed to an epitope on TIP-2 antigen or Fab fragment thereof; and (b) a means for determining the presence of monoclonal antibody/Fab fragment-TIP-2 antigen complex.

The present invention provides a method for detecting the presence of TIP-2 antigen in biological fluid comprising: (a) contacting a sample of the biological fluid with a antibody directed to an epitope on TIP-2 antigen or Fab fragment thereof, which epitope is recognized by monoclonal antibody 27.F7 produced by the hybridoma designated ATCC Accession No. PTA-1598, said antibody being detectably labeled, under appropriate conditions to produce an antibody 27.F7/Fab fragment-TIP-2 antigen complex comprising the detectably labeled antibody bound to any TIP-2 antigen on the surface of cells in the sample; (c) removing any labeled antibody not bound in the antibody 27.F7/Fab fragment-TIP-2 antigen complex formed in step (a); and (d) determining presence of the antibody 27.F7/Fab fragment-TIP-2 antigen complex by detecting the label of the detectably labeled antibody, presence of antibody 27.F7/Fab fragment-TIP-2 antigen complex indicating TIP-2 antigen-bearing human cancer cells in the biological fluid.

The present invention provides a method for detecting the presence of TIP-2 antigen in biological fluid comprising: (a) contacting a sample of the biological fluid with a antibody directed to an epitope on TIP-2 antigen or Fab fragment thereof, which epitope is recognized by monoclonal antibody 27.B1 produced by the hybridoma designated ATCC Accession No. PTA-1599, said antibody being detectably labeled, under appropriate conditions to produce an antibody 27.B1/Fab fragment-TIP-2 antigen complex comprising the detectably labeled antibody bound to any TIP-2 antigen on the surface of cells in the sample; (c) removing any labeled antibody not bound in the antibody 27.B1/Fab fragment-TIP-2 antigen complex formed in step (a); and (d) determining presence of the antibody 27.B1/Fab fragment-TIP-2 antigen complex by detecting the label of the detectably labeled antibody, presence of antibody 27.B1/Fab fragment-TIP-2 antigen complex indicating TIP-2 antigen-bearing human cancer cells in the biological fluid.

The present invention provides a method for immunohistochemical screening of tissue sections from a tumor sample for the presence of TIP-2 antigen-bearing cancer cells which comprises: (a) contacting the tissue section from the tumor sample with a detectably labeled antibody/Fab fragment directed to an epitope on TIP-2 antigen or Fab fragment thereof, which epitope is recognized by monoclonal antibody 27.B1 produced by the hybridoma designated ATCC Accession No. PTA-1599, said antibody being detectably labeled, under appropriate conditions to bind the antibody to TIP-2 antigen on the surface of any cells in the sample; and (b) removing any labeled antibody not bound to the cells in the sample; (c) determining presence of antibody 27.B1 bound to the cells in the sample, presence of antibody 27.B1 bound to cells indicating TIP-2 antigen-bearing cancer cells in the tumor sample.

The present invention provides a method for monitoring progression of cancer, wherein cancer cells are TIP-2 antigen-bearing cancer cells, in a subject comprising: (a) administering to a subject diagnosed with cancer an antibody directed to an epitope on TIP-2 antigen or Fab fragment thereof, which epitope is recognized by monoclonal antibody 27.F7 produced by the hybridoma designated ATCC Accession No. PTA-1598, said antibody being detectably labeled, under appropriate conditions to bind the antibody to TIP-2 antigen on the surface of any cells in the subject; (b) determining presence of detectably labeled antibody 27.F7/Fab fragment bound to the surface of cells in the subject according to the above-described method of detecting TIP-2 antigen on the surface of cancer cells in a sample; (c) comparing the presence of detectably labeled antibody/Fab fragment 27.F7 bound to cells in step (b) with the presence of detectably labeled antibody 27.F7 bound to cells at (i) diagnosis time or (ii) after treatment, wherein a greater presence of detectably labeled antibody 27.F7/Fab fragment bound to cells in step (b) than at (i) diagnosis time or (ii) after treatment, indicates progression of the cancer in the subject and a lesser presence of detectably labeled antibody 27.F7/Fab fragment bound to cells in step (b) than at (i) diagnosis time or (ii) after treatment indicates regression of the cancer in the subject.

The present invention provides a method for monitoring progression of cancer, wherein cancer cells are TIP-2 antigen-bearing cancer cells, in a subject comprising: (a) administering to a subject diagnosed with cancer an antibody directed to an epitope on TIP-2 antigen or Fab fragment thereof, which epitope is recognized by monoclonal antibody 27.B1 produced by the hybridoma designated ATCC Accession No. PTA-1599, said antibody/Fab fragment being detectably labeled, under appropriate conditions to bind the antibody to TIP-2 antigen on the surface of any cells in the subject; (b) determining presence of detectably labeled antibody 27.B1/Fab fragment bound to the surface of cells in the subject according to the above-described method for detecting TIP-2 antigen on the surface of cancer cells in a sample; (c) comparing the presence of detectably labeled antibody/Fab fragment 27.B1 bound to cells in step (b) with the presence of detectably labeled antibody 27.B1/Fab fragment bound to cells at (i) diagnosis time or (ii) after treatment, wherein a greater presence of detectably labeled antibody 27.B1/Fab fragment bound to cells in step (b) than at (i) diagnosis time or (ii) after treatment, indicates progression of the cancer in the subject and a lesser presence of detectably labeled antibody 27.B1/Fab fragment bound to cells in step (b) than at (i) diagnosis time or (ii) after treatment indicates regression of the cancer in the subject.

The present invention provides a method for monitoring progression of cancer, wherein cancer cells are TIP-2 antigen-bearing cancer cells, in a subject comprising: (a) administering to a subject diagnosed with cancer an antibody directed to an epitope on TIP-2 antigen or an Fab fragment thereof, which epitope is recognized by monoclonal antibody 27.F7 produced by the hybridoma designated ATCC Accession No. PTA-1598, said antibody/Fab fragment being detectably labeled, under appropriate conditions to bind the antibody to TIP-2 antigen on the surface of any cells in the subject; (b) determining quantity of detectably labeled antibody 27.F7/Fab fragment bound to the surface of cells in the subject according to the above-described method for detecting TIP-2 antigen on the surface of cancer cells in a sample; (c) comparing the quantity of detectably labeled antibody 27.F7/Fab fragment bound to cells in step (b) with the presence of detectably labeled antibody 27.F7/Fab fragment bound to cells at (i) diagnosis time or (ii) after treatment, wherein a greater quantity of detectably labeled antibody 27.F7/Fab fragment bound to cells in step (b) than at (i) diagnosis time or (ii) after treatment, indicates progression of the cancer in the subject and a lesser quantity of detectably labeled antibody 27.F7/Fab fragment bound to cells in step (b) than at (i) diagnosis time or (ii) after treatment indicates regression of the cancer in the subject.

The present invention provides a method for monitoring progression of cancer, wherein cancer cells are TIP-2 antigen-bearing cancer cells, in a subject comprising: (a) administering to a subject diagnosed with the cancer an antibody directed to an epitope on TIP-2 antigen or an Fab fragment thereof, which epitope is recognized by monoclonal antibody 27.B1 produced by the hybridoma designated ATCC Accession No. PTA-1599, said antibody/Fab fragment being detectably labeled, under appropriate conditions to bind the antibody to TIP-2 antigen on the surface of any cells in the subject; (b) determining quantity of detectably labeled antibody 27.B1/Fab fragment bound to the surface of cells in the subject according to the above-described method of (c) comparing the quantity of detectably labeled antibody 27.B1/Fab fragment bound to cells in step (b) with the presence of detectably labeled antibody 27.B1 bound to cells at (i) diagnosis time or (ii) after treatment, wherein a greater quantity of detectably labeled antibody 27.B1/Fab fragment bound to cells in step (b) than at (i) diagnosis time or (ii) after treatment, indicates progression of the cancer in the subject and a lesser quantity of detectably labeled antibody 27.B1/Fab fragment bound to cells in step (b) than at (i) diagnosis time or (ii) after treatment indicates regression of the cancer in the subject.

The present invention provides a method for diagnosing cancer associated with the expression of TIP-2 antigen in a human subject which comprises: (a) obtaining mRNA from a sample of the subject's peripheral blood; (b) preparing cDNA from the mRNA from step (a); (c) amplifying DNA encoding TIP-2 antigen present in the cDNA prepared in step (b) by a polymerase chain reaction utilizing at least two oligonucleotide primers, wherein each of the primers specifically hybridizes with DNA encoding TIP-2 antigen, wherein the primers comprise oligonucleotides having a sequence included within the sequence of SEQ ID NO:2; and (d) detecting the presence of any resulting amplified DNA, the presence of such amplified DNA being diagnostic for cancer associated with the expression of TIP-2 antigen.

The present invention provides a method for diagnosing cancer associated with the expression of TIP-2 antigen in a human subject which comprises: (a) obtaining mRNA from a sample of the subject's peripheral blood; (b) preparing cDNA from the mRNA from step (a); (c) amplifying DNA encoding TIP-2 antigen present in the cDNA prepared in step (b) by a polymerase chain reaction utilizing at least two oligonucleotide primers, wherein each of the primers specifically hybridizes with DNA encoding TIP-2 antigen, wherein the primers comprise oligonucleotides having a sequence included within the sequence of SEQ ID NO:2; and (d) determining the amount of any resulting amplified DNA; and (e) comparing the amount of amplified DNA determined in step (d) with previously determined standard amounts of amplified DNA, each standard amount being indicative of a particular stage of cancer associated with the expression of TIP-2 antigen.

The present invention further provides a vaccine comprising a monoclonal antibody produced by the method described herein and a suitable carrier.

The present invention also provides a vaccine comprising an effective amount of a monoclonal antibody of this invention and a pharmaceutically acceptable carrier.

The present invention further provides a method of treating a condition in a subject comprising administering to the subject an amount of the above-described vaccine effective to bind the antigen associated with the condition, thereby treating the condition in the subject.

Finally, the present invention provides a method of preventing a condition in a subject comprising administering to the subject an amount of the above-described vaccine effective to bind the antigen associated with the condition, thereby preventing the condition in the subject.

BRIEF DESCRIPTION OF THE FIGURES

FIGS. 1A-1C

Distribution of cells according to the number of chromosomes. The X-axis indicates the amount of chromosomes. The Y-axis indicates the percentage of cells with appropriate number of chromosomes. The data represent the average ones based on the analysis of more than 50 metaphase plates for each line: P3.X63.Ag8.653 FIG. 1A, RPMI 8226 FIG. 1B, B6B11 FIG. 1C.

FIG. 2

Fragment of G-banded karyotype of B6B11 line. The arrows indicate genetic material presumably of human origin; 3p portion of chromosome 3 and chromosome 19.

FIG. 3

B6B11 fusion efficiency with fresh isolated and cultured splenocytes. SPL were isolated in LSM, immediately after a portion of the cells were fused with B6B11 cells and the remaining SPL were cultivated in vitro for 7-9 days in RPMI-C containing 15% FCS in the presence of ConA, LPS, PHA, PWM or without mitogens, then these cells were also fused with B6B11. PWM in the concentration of 5 µg/ml influenced effectively the fusion efficiency.

FIGS. 4A-4D

Figure 4A:
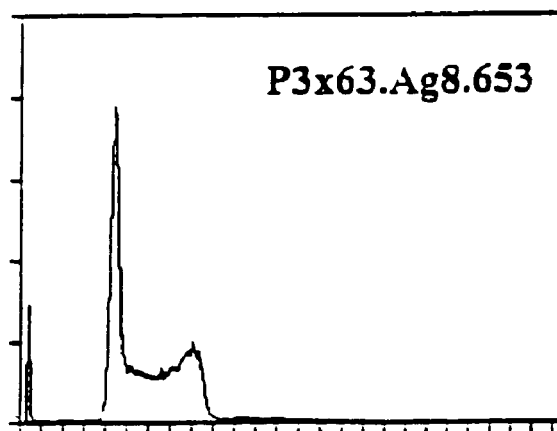
Figure 4B:
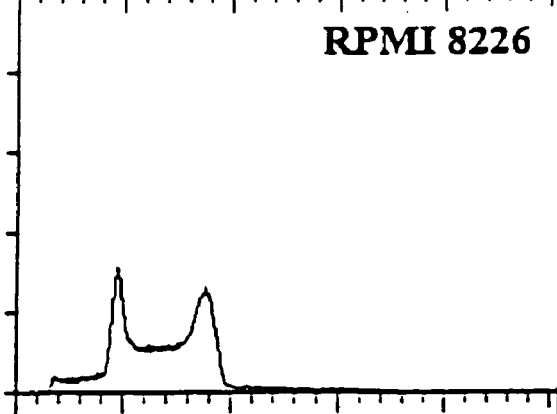
Figure 4C:
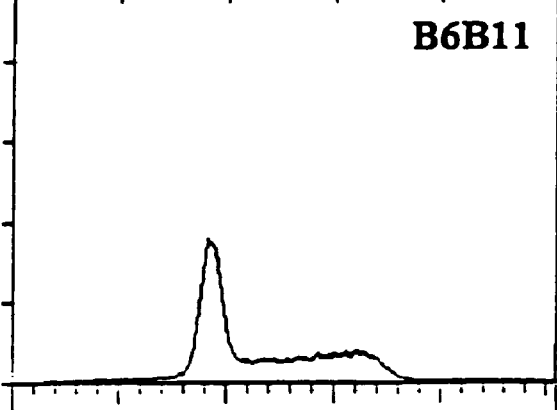
Figure 4D:
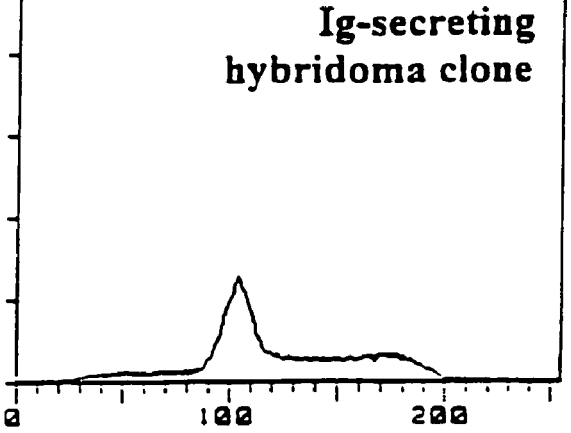

DNA histograms of parental cells 653 (FIG. 4A) and 8226 (FIG. 4B), heteromyeloma B6B11 (FIG. 4C) and B6B11-splenocyte hybrid (FIG. 4D). The amount of B6B11 DNA constitutes about 100% of the total amount of 653 DNA plus 8226 DNA. The DNA content of B6B11-SPL hybrid is greater than that of B6B11.

FIGS. 5A-5B

Figure 5B:
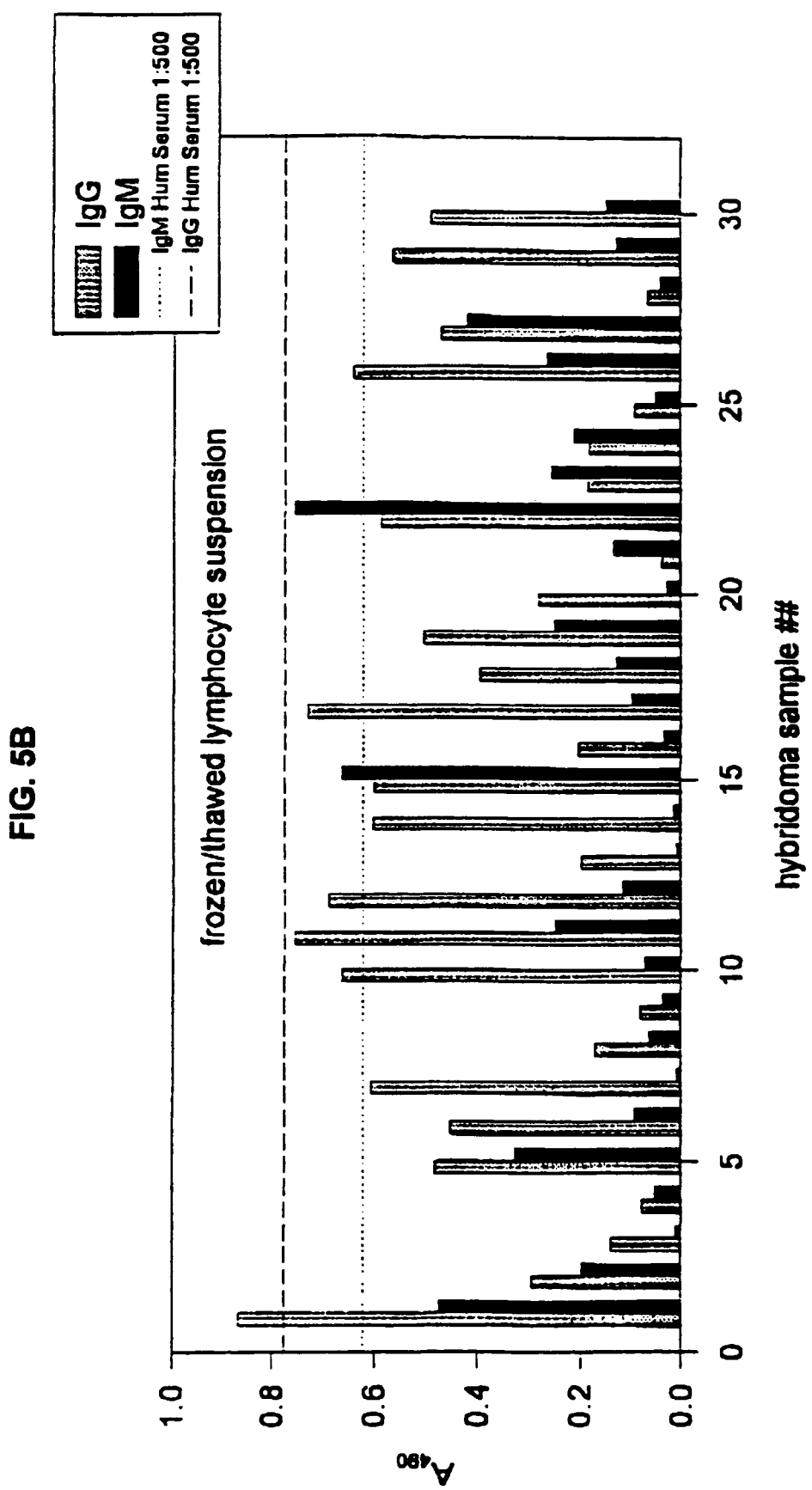

Immunoglobulin production by hybridomas (tetromas) derived from the fusion of PBLs with MFP-2. FIG. 5A shows results of fusing fresh lymphocyte suspensions with MFP-2. FIG. 5B shows results of fusing frozen/thawed lymphocyte suspensions with MFP-2. The dark rectangles indicate IgM production. The gray rectangles indicate IgG production. The Y-axis indicates optical density at $A_{490}$ for different hybridoma samples (tetromas) generated from fusion with the MFP-2 trioma line (X-axis). The dotted line indicates the optical density at $A_{490}$ for a 1:500 dilution of IgM antibody. The dashed line indicates the optical density at $A_{490}$ for a 1:500 dilution of IgG antibody.

FIG. 6

Anti-thyroglobulin antibody production by thyroid cancer lymph node lymphocytes fused to fusion partner MFP-2 cells. The Y-axis indicates optical density at $A_{405}$ ($OD_{405}$) for different hybridoma samples (tetromas) generated from fusion with the MFP-2 trioma line (X-axis). Thirty-three tetromas produced antibody which reacted positively against thyroglobulin; eight were particularly strongly reactive.

FIG. 7

Flow cytometry analysis of fixed and live cells treated with anti-TIP-2 fhMAbs. Green=control; Red=cells treated with antibodies.

FIG. 8

Western blot analysis of breast and prostate cancer cell lysates for the presence of TIP-2. Two non-transformed human fibroblasts cell lines were used as a negative control. Human monoclonal anti-TIP-2 antibodies 27.B1 and 27.F7 were used as a tag. 7 mg of total cell lysate protein was applied to each line. The strong TIP-2 expression can be observed in breast cancer cells.

FIG. 9

Immunofluorescence staining of formalin-fixed human cells with human monoclonal anti-TIP-2 antibodies 27.B1 and 27.F7. Size bars represent 20 µm. On this and other figures with immunofluorescence staining red is a propidium iodide counterstaining of cell nuclei and green is FITC-labeled antibody staining. Confocal microscopy was done for SK-BR-3 breast cancer cells.

FIG. 10

Immunofluorescence staining of normal and cancerous human breast tissues using human anti-TIP-2 monoclonal antibody 27.B1. Upper panel—different cases of invasive ductal adenocarcinoma; lower panel—normal breast tissue. Size bars represent 20 μm.

FIG. 11

Immunofluorescence staining of human prostate tissues using human anti-TIP-2 monoclonal antibody 27.B1. Upper panel—different cases of prostate adenocarcinoma; lower panel—benign prostate hypertrophy as negative control. Size bars represent 20 μm.

FIG. 12

Same as FIG. 4, but with fhMAb 27.F7.

FIG. 13

Same as FIG. 5, but with fhMAb 27.F7.

FIG. 14

Immunofluorescence staining of lymph nodes with breast cancer metastatic spread. Human monoclonal anti-TIP-2 antibodies 27.B1 and 27.F7 were used in this experiment. Size bars represent 20 μm.

FIG. 15

Formalin fixed and freshly frozen sections of breast adenocarcinoma using two anti-TIP-2 antibodies 27.B1 and 27.F7. Size bars represent 20 μm.

FIG. 16

Immunofluorescence staining of male breast intraductal carcinoma and seminoma using fhMAbs 27.F7 and 27.B1. Size bars represent 20 μm.

FIG. 17

Immunofluorescence staining of breast cancer and other cancerous and normal tissues using fhMAbs 27.F7 and 27.B1. Size bars represent 20 mm.

FIG. 18

Schematic view of G-protein signaling system.

FIG. 19

Regulators of G-signaling system and PDZ domain-containing proteins.

FIG. 20

Principle of SEREX technology.

FIG. 21

Immunization of mice to TIP-2 using immunoprecipitation with human anti-TIP-2 antibody and Western blotting.

FIG. 22

Immunoreactivity of polyclonal mouse anti-TIP-2 antiserum with TIP-2 from SK-BR-3 cell lysate. Human antibody 27.F7 was used a positive control.

FIG. 23

Immunohistochemical staining of breast adenocarcinoma using immune serum from mouse immunized with TIP-2. Size bars represent 20 μm.

FIG. 24

Analysis of $K_a$ for anti-TIP-2 antibody 27.F7 and calculation of number of copies of TIP-2 present on SK-BR-3 cells.

FIG. 25

Expression of TIP-2 in normal and cancerous breast epithelia.

FIG. 26

Coupling of anti-TIP-2 antibody 27.F7 to liposomes.

FIG. 27

Alcohol precipitation of TIP-2 from human blood serum spiked with SK-BR-3 cell lysate.

FIG. 28

The release of TIP-2 antigen into cell culture media of SK-BR-3 cells treated with different concentration of Taxol. The lines are as follows (from left to right): 1) SK-BR-3 cell lysate prepared form approximately 70,000 cells; 2) empty lane; 3) Taxol, 88 uM added to 35 mm tissue plate containing approximately 250,000 cells; 4) same with Taxol, 44 uM; 5) same with Taxol, 22 uM; 7) same with Taxol, 11 uM; 8) same with Taxol, 5.5 uM; 9) cell lysate prepared from cells which were not treated with Taxol; 10) lysate prepared from the residual dead cells' remnants after treatment with Taxol, 88 uM.

FIG. 29

The amino acid sequence (SEQ ID NO:1) of GIPC/TIP-2 protein. In italics, the amino acid sequence of TIP-2 only. Underlined are two peptides identified as high HLA-*A0201 binders (theoretical calculation).

FIG. 30

The mRNA sequence (SEQ ID NO:2) of GIPC. The part of the sequence corresponding to TIP-2 is underlined.

FIG. 31

Protein Antigens Identified by Natural Human Monoclonal Antibodies Developed form Breast and Prostate Cancer Patients' B-Cells. The unique peptide sequence shown correspond to SEQ ID NOs. as follows: NLLEKDYFGL (SEQ ID NO:29), VLFDLVCEHL (SEQ ID NO:30), KLQHPDMLV (SEQ ID NO:31), KMLDAEDIV (SEQ ID NO:32), KMTLGMIWTI (SEQ ID NO:33), EMPSEGKMV (SEQ ID NO:34), KLASDLLEWI (SEQ ID NO:35), GLVTFQAFI (SEQ ID NO:36), CQLEINFNSV (SEQ ID NO:37), WLAAVTKQNV (SEQ ID NO:38), ILPFRVIPLV (SEQ ID NO:39), SLLAQKIEV (SEQ ID NO:40), KLNYSDHDV (SEQ ID NO:41), KLLGGQIGL (SEQ ID NO:42), SLLGC-RHYEV (SEQ ID NO:43), YLSQEHQQQV (SEQ ID NO:44), KVMDRPGNYV (SEQ ID NO:45), ALIEQWNPV (SEQ ID NO:46), IITAFNFPV (SEQ ID NO:47), FEQEND-WWV (SEQ ID NO:48), YLGAKPWCL (SEQ ID NO:49), CLQTGFAIGV (SEQ ID NO:50), KLLEGEEERL (SEQ ID NO:51), KLVRSVTVV (SEQ ID NO:52), and RLAD-ALQEL (SEQ ID NO:53).

FIG. 32

Human mRNA sequence for KIAA0338 gene, partial cds (SEQ ID NO:5). F Sequence of translation product (SEQ ID NO:6).

FIG. 33

Human non-muscle alpha-actinin mRNA sequence, complete cds (SEQ ID NO:7)—the second non-muscle alpha-actinin isoform designated ACTN4 (actinin-4). D. Sequence of translation product (SEQ ID NO:8).

FIG. 34

*Homo sapiens* actinin, alpha 4 (ACTN4) mRNA sequence (SEQ ID NO:9). C. Sequence of translation product (SEQ ID NO:10).

FIG. 35

Clathrin coat assembly protein AP50 mRNA sequence (SEQ ID NO:11). C Sequence of translation product (SEQ ID NO:12).

FIG. 36

*Homo sapiens* GLUT1 C-terminal Binding protein (GLUT1CBP) mRNA sequence (SEQ ID NO:13). C. Sequence of translation product (SEQ ID NO:14).

FIG. 37 gp130 associated protein GAM sequence (SEQ ID NO:15) and sequence of translation product (SEQ ID NO:16).

FIG. 38

*Homo sapiens* amino-terminal enhancer of split (AES) mRNA sequence (SEQ ID NO:17) and sequence of translation product (SEQ ID NO:18).

FIG. 39

Antiquitin 1 (antiquitin=26 g turgor protein homolog), mRNA sequence (SEQ ID NO:19). C. Sequence of translation product (SEQ ID NO:20).

FIG. 40

ARP2/3 protein complex 41 KD subunit (P41-ARC), mRNA sequence (SEQ ID NO:21) and sequence of translation product (SEQ ID NO:22).

FIG. 41a

*H. sapiens* seb4D mRNA sequence (SEQ ID NO:23) and sequence of translation product (SEQ ID NO:24).

FIG. 41b

*H. sapiens* seb4B mRNA sequence (SEQ ID NO:25) and sequence of translation product (SEQ ID NO:26).

FIG. 42

*Homo sapiens* lamin A/C (LMNA) mRNA sequence (SEQ ID NO:27). C. Sequence of translation product (SEQ ID NO:28).

DETAILED DESCRIPTION OF THE INVENTION

The present invention provides a heteromyeloma cell which does not produce any antibody and is capable of producing a trioma cell which does not produce any antibody when fused with a human lymphoid cell; wherein the trioma cell so produced is capable of producing a tetroma cell which produces a monoclonal antibody having specific binding affinity for an antigen when fused with a second human lymphoid cell and such second human lymphoid cell of produces an antibody having specific binding affinity for the antigen, with the proviso that the heteromyeloma cell is not B6B11 (ATCC accession number HB-12481).

The present invention also provides a trioma cell which does not produce any antibody obtained by fusing a heteromyeloma cell with a human lymphoid cell. In one embodiment of this invention, the heteromyeloma cell is the cell designated B6B11 (ATCC accession number HB-12481). In another embodiment, the trioma is a B6B11-like cell. For purposes of this invention a B6B11-like cell includes a cell which is substantially identical to the B6B11 cell at the genetic level and a functionally equivalent thereto. B6B11-like cells thus specifically include clones or other cells derived from B6B11 including mutants of the B6B11 and of clones thereof. In certain embodiments of this invention, the human lymphoid cell is a myeloma cell. In other embodiments of this invention, the human lymphoid cell is a splenocyte or a lymph node cell (lymphocyte). According to certain embodiments of the present invention, the trioma cell is the cell designated MFP-2 (ATCC accession number 12482).

The present invention also provides a tetroma cell capable of producing a monoclonal antibody having specific binding affinity for an antigen, obtained by fusing the above-described trioma cell which does not produce any antibody with a human lymphoid cell capable of producing antibody having specific binding affinity for the antigen. The human lymphoid cell may be a peripheral blood lymphocyte, a splenocyte, a lymph node cell, a B cell, a T cell, a tonsil gland lymphocyte, a monocyte, a macrophage, an erythroblastoid cell or a Peyer's patch cell. In one embodiment of this invention, the trioma cell is the cell designated MFP-2 (ATCC accession number HB-12482).

According to certain embodiments of this invention, the antigen is a tumor-associated antigen, a cell-specific antigen, a tissue-specific antigen, an enzyme, a nucleic acid, an immunoglobulin, a toxin, a viral antigen, a bacterial antigen or a eukaryotic antigen. In one embodiment, the antigen is a mammalian, insect, fungal, *E. coli* or *Klebsiella* antigen.

The present invention provides a monoclonal antibody produced by the above-described tetroma. The present invention also provides an isolated nucleic acid encoding the monoclonal antibody produced by the described tetroma. The nucleic acid may include, but is not limited to DNA, RNA, cDNA, oligonucleotide analogs, vectors, expression vectors or probes. Additionally, the present invention contemplates the expression of the nucleic acid encoding the monoclonal antibody introduced into a host cell capable of expression the monoclonal antibody or portions thereof.

The present invention also provides isolated nucleic acids including all or a portion of the antibody binding regions of such monoclonal antibodies and the use of such nucleic acid to express portions of such antibodies, for example, single chain antibodies per se or phage-displayed single chain antibodies (sFv-a antibody).

Moreover, nucleic acids encoding all or a portion of such nucleic acids may be used to transfect mammalian cells such as mouse myeloma or CHO cells to permit increased production of such monoclonal antibody or portion thereof.

The present invention further provides a method of generating the described trioma cell comprising: (a) fusing a heteromyeloma cell which does not produce any antibody with a human lymphoid cell thereby forming trioma cells; (b) incubating the trioma cells formed in step (a) under conditions permissive for the production of antibody by the trioma cells; and (c) selecting a trioma cell that does not produce any antibody.

According to one embodiment of this invention, the heteromyeloma cell of step (a) is designated B6B11 (ATCC accession number HB-12481). According to other embodiments of this invention, the human lymphoid cell is a lymph node lymphocyte or a splenocyte. According to certain embodiments of the present invention, the method further comprises selecting a trioma cell capable of growth in serum-free media. Other embodiments comprise selecting a trioma cell that is capable of fusing with a peripheral blood lymphocyte or lymph node lymphocyte. The present invention further provides a trioma cell generated by the above-described method.

Still further, the present invention provides a method of generating a tetroma cell comprising: (a) fusing the above-described trioma cell with a human lymphoid cell thereby forming tetroma cells; (b) incubating the tetroma cell formed in step (a) under conditions permissive to the production of antibody by the tetroma cells; and (c) selecting a tetroma cell capable of producing a monoclonal antibody. According to one embodiment of this invention, the trioma cell of step (a) the cell is designated MFP-2 (ATCC accession number HB-12482). According to an embodiment of this invention, the human lymphoid cell is a peripheral blood lymphocyte, a splenocyte, a lymph node cell, a B cell, a T cell, a tonsil gland lymphocyte, a monocyte, a macrophage, an erythroblastoid cell or a Peyer's patch cell. In some embodiments of this invention, the human lymphoid cell produces antibodies having specific binding affinity for an antigen and the tetroma cell produces a monoclonal antibody having specific binding affinity for such antigen. According to certain embodiments of this invention, the antigen is a tumor-associated antigen, a cell-specific antigen, a tissue-specific antigen, an enzyme, a nucleic acid, an immunoglobulin, a toxin, a viral antigen, a bacterial antigen, or a eukaryotic antigen. In some embodiments of this invention, the antigen is a mammalian, insect, *E.*

*coli* or *Klebsiella* antigen. The present invention further provides a tetroma cell generated by the above-described method.

This invention also provides human hybridoma fusion partner cell line heteromyeloma BGB11, and human hybridoma fusion partner cell line trioma MFP-2. These hybridoma cell lines were deposited on Mar. 17, 1998 with the American Type Culture Collection (ATCC), 10801 University Blvd, Manassas, Va. 20110-2209, USA under the provision of the Budapest Treaty for the International Recognition of the Deposit of Microorganism for the Purposes of Patent Procedure. These hybridoma have been accorded with ATCC Accession Nos. HB-12481 and HB-12482 respectively.

The present invention also provides a method of producing a monoclonal antibody comprising (a) fusing a lymphoid cell capable of producing antibody with the described trioma cell, thereby forming a tetroma cell; and (b) incubating the tetroma cell formed in step (a) under conditions permissive for the production of antibody by the tetroma cell so as to thereby produce the monoclonal antibody.

Also, the present invention provides a method of producing a monoclonal antibody specific for an antigen associated with a given condition in a subject comprising: (a) fusing a lymphoid cell capable of producing antibody with the above-described trioma cell, thereby forming tetroma cells; (b) incubating the tetroma cell formed in step (a) under conditions permissive for the production of antibody by the tetroma cells; (c) selecting a tetroma cell producing a monoclonal antibody; (d) contacting the monoclonal antibody of step (c) with (1) a sample from a subject with the given condition or (2) a sample from a subject without the given condition under conditions permissive to the formation of a complex between the monoclonal antibody and the sample; (e) detecting the complex formed between the monoclonal antibody and the sample; (f) determining the amount of complex formed in step (e); and (g) comparing the amount of complex determined in step (f) for the sample from the subject with the condition with amount determined in step (f) for the sample from the subject without the condition, a greater amount of complex formation for the sample from the subject with the condition indicating that a monoclonal antibody specific for the antigen specific for the condition has been produced.

In one embodiment of the present invention, step (a) further comprises freezing the lymphoid cell. According to one embodiment of the present invention, step (c) further comprises incubating the selected tetroma cell under conditions permissive for cell replication. According to certain embodiments of this invention, the tetroma replication is effected in vitro or in vivo. According to one embodiment of this invention, the trioma cell is the cell designated MFP-2 (ATCC Accession No. HB-12482). The present invention provides a monoclonal antibody specific for an antigen associated with a condition, identified by the described method. The present invention also provides an isolated nucleic acid encoding the described monoclonal antibody. The nucleic acid may include, but is not limited to DNA, RNA, cDNA, oligonucleotide analogs, vectors, expression vectors or probes. Additionally, the present invention contemplates the expression of the nucleic acid encoding the monoclonal antibody introduced into a host cell capable of expression the monoclonal antibody or portions thereof.

The present invention also provides isolated nucleic acids including all or a portion of the antibody binding regions of such monoclonal antibodies and the use of such nucleic acid to express portions of such antibodies, for example, single chain antibodies per se or phage-displayed single chain antibodies (sFv-a antibody).

Moreover, nucleic acids encoding all or a portion of such nucleic acids may be used to transfect mammalian cells such as mouse myeloma or CHO cells to permit increased production of such monoclonal antibody or portion thereof.

According to an embodiment of this invention, the given condition as is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally, the condition may be any other abnormality, including that resulting from infection, cancer, autoimmune dysfunction, cardiovascular disease, or transplantation. In an embodiment of this invention, the given condition is septicemia, sepsis, septic shock, viremia, bacteremia or fungemia. In certain embodiments of this invention, the cancer may be, but is not limited to lung cancer, liver cancer, leukemia, lymphoma, neuroblastoma, glioma, meningioma, bone cancer, thyroid cancer, ovarian cancer, bladder cancer, pancreatic cancer, breast cancer, or prostate cancer. According to certain embodiments of this invention, the infectious agent may be, but is not limited to Hanta virus, HTLV I, HTLV II, HIV, herpes virus, influenza virus, Ebola virus, human papilloma virus, *Staphlococcus, Streptococcus, Klebsiella, E. coli*, anthrax, or *cryptococcus*. According to certain embodiments of this invention, the toxin is tetanus, anthrax, botulinum snake venom or spider venom. In one embodiment of this invention, the tumor is benign. In another embodiment, the enzyme dysfunction is hyperactivity or overproduction of the enzyme. In still another embodiment, the hormone dysfunction is hyperactivity or overproduction of the hormone. In yet other embodiments of this invention, the immune dysfunction is CD3 or CD4 mediated. In still other embodiments of this invention, the autoimmune disease is lupus, thyroidosis, graft versus host disease, transplantation rejection, or rheumatoid arthritis. In still other embodiments of the invention, the condition is any abnormality. In still other embodiments, the condition is the normal condition.

Additionally, the present invention provides a method of identifying an antigen associated with a given condition in a sample comprising: (a) contacting the monoclonal antibody produced by the above-described method with the sample under conditions permissive for the formation of a complex between the monoclonal antibody and the sample; (b) detecting any complex formed in step (a); and (c) isolating the complex detected in step (b), thereby identifying the antigen associated with the condition in the sample.

In one embodiment of the above-described method, the condition is a tumor.

In another embodiment of the above-identified method, the antigen is not previously known.

This invention also provides a tumor antigen identified by the above-described method where the antigen is not previously known.

This invention also provides a method for diagnosing a tumor in a sample comprising detecting the presence of the tumor antigen identified by the above-described method wherein the condition is a tumor, the presence of said antigen indicating the presence of tumor in the subject.

This invention also provides the above-described method, wherein the detecting comprises: (a) obtaining an appropriate sample which contains the tumor antigen from the subject; (b) contacting the sample with an antibody which is capable of specifically binding to the tumor antigen under conditions permitting the formation of a complex between the antibody and the antigen; and (c) detecting the complex formed, thereby detecting the presence of the tumor antigen.

In certain embodiments of this invention, the method further comprises separating the monoclonal antibody from the monoclonal antibody-antigen complex. In some embodiments the separation is by size fractionation, e.g. the size fractionation effected by polyacrylamide or agarose gel electrophoresis.

According to certain embodiments of this invention, the given condition is associated with, a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally, the condition may be any other abnormality, including one resulting from infection, cancer, autoimmune dysfunction, cardiovascular disease, or transplantation. In an embodiment of this invention, the condition is septicemia, sepsis, septic shock, viremia, bacteremia or fungemia. In some embodiments of this invention, the cancer may be but is not limited to lung cancer, liver cancer, leukemia, lymphoma, neuroblastoma, glioma, meningioma, bone cancer, thyroid cancer, colon cancer, ovarian cancer, bladder cancer, pancreatic cancer, breast cancer or prostate cancer. According to some embodiments of this invention, the infectious agent may be but is not limited to Hanta virus, HTLV I, HTLV II, HIV, herpes virus, influenza virus, Ebola virus, human papilloma virus, *Staphlococcus, Streptococcus, Kiebsiella, E. coli*, anthrax or *cryptococcus*. According to some embodiments of this invention, the toxin is tetanus, anthrax, botulinum, snake venom or spider venom. In one embodiment of this invention, the tumor is benign. In other embodiments, the enzyme dysfunction is hyperactivity or overproduction of the enzyme. In still other embodiments, the hormone dysfunction is hyperactivity or overproduction of the hormone. In yet other embodiments of this invention, the immune dysfunction is CD3 or CD4 mediated. In still other embodiments of this invention, the autoimmune disease is lupus, thyroidosis, graft versus host disease, transplantation rejection or rheumatoid arthritis. In still other embodiments of the invention, the condition is any abnormality. In still other embodiments, the condition is the normal condition.

The present invention additionally provides a method of diagnosing a condition in a subject comprising: (a) contacting a sample from the subject with a monoclonal antibody produced by the above-described method under conditions permissive for the formation of a complex between the monoclonal antibody and the sample; and (b) detecting the formation of any complex formed between the monoclonal antibody and the sample, positive detection of such complex indicating the presence of an antigen specific for the condition in the sample which correlates with diagnosing the condition in the subject.

According to an embodiment of this invention, the monoclonal antibody is coupled to a detectable marker. In an embodiment of this invention, the detectable marker is a radiolabel, a fluorofor, or fluorescent molecule, an enzyme, a ligand, a colorimetric marker, or a magnetic bead.

According to some embodiments of this invention, the given condition is or is associated with, a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally the condition may be any other abnormality, including one resulting from infection, cancer, autoimmune dysfunction, cardiovascular disease, or transplantation. In certain embodiments of this invention, the condition is septicemia, sepsis, septic shock, viremia, bacteremia or fungemia. In some embodiments of this invention, the cancer may be, but is not limited to lung cancer, liver cancer, leukemia, lymphoma, neuroblastoma, glioma, meningioma, bone cancer, thyroid cancer, ovarian cancer, bladder cancer, pancreatic cancer, breast cancer or prostate cancer. According to other embodiments of this invention, the infectious agent may be, but os not limited to Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*. According to some embodiments of this invention, the toxin is tetanus, anthrax, botulinum, snake venom or spider venom. In one embodiment of this invention, the tumor is benign. In other embodiments, the enzyme dysfunction is hyperactivity or overproduction of the enzyme. In still other embodiments, the hormone dysfunction is hyperactivity or overproduction of the hormone. In yet other embodiments of this invention, the immune dysfunction is CD3 or CD4 mediated. In still other embodiments of this invention, the autoimmune disease is lupus, thyroidosis, graft versus host disease, transplantation rejection or rheumatoid arthritis. In still other embodiments of the invention, the condition is any abnormality. In still other embodiments, the condition is the normal condition.

The present invention further provides a composition comprising a monoclonal antibody produced by the method described herein and a suitable carrier.

Further, the present invention also provides a therapeutic composition comprising a therapeutically effective amount of a monoclonal antibody of this invention and a pharmaceutically acceptable carrier.

According to certain embodiments of this invention, the condition is cancer and the amount of monoclonal antibody is sufficient to inhibit the growth of or eliminate the cancer. According to certain embodiments, the condition is an infection and the amount of monoclonal antibody is sufficient to inhibit the growth of or kill the infectious agent. According to certain embodiments of this invention, the condition is associate with a toxin and the amount of monoclonal antibody is sufficient to reduce the amount of or destroy the toxin. In still other embodiments, the condition is an autoimmune disease and the amount of monoclonal antibody is sufficient to reduce the amount of or destroy the offending antibody or subunit(s) thereof. In still other embodiments, the condition is a cardiovascular disease and the amount of monoclonal antibody is sufficient to reduce the condition. In yet other embodiments, the condition is a transplantation rejection, and the amount of monoclonal antibody is sufficient to reduce the condition.

According to certain embodiments of this invention, the monoclonal antibody is coupled to an effector compound. In certain embodiments of this invention, the effector compound is a cytotoxic agent, drug, enzyme, dye, or radioisotope. In certain embodiments of this invention, the monoclonal antibody is coupled to a carrier. According to other embodiments of this invention, the carrier is a liposome.

Also, the present invention further provides a method of treating a given condition in a subject comprising administering to the subject an amount of the above-described therapeutic composition effective to treat the condition in the subject. According to one embodiment of this invention, the therapeutic composition is administered to a second subject.

According to an embodiment of this invention, the given condition is or is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally, the condition may be any other abnormality, including that resulting from infection, cancer, autoimmune dysfunction, cardiovascular disease, or transplantation. In an embodiment of this invention, the given condition is septicemia, sepsis, septic shock, viremia, bacteremia or fungemia. In certain embodiments of this invention, the cancer may be but is not limited to lung cancer, liver cancer, leukemia, lymphoma, neuroblastoma, glioma, meningioma, bone cancer, thyroid cancer, colon cancer, ovarian cancer, bladder cancer, pancreatic cancer, breast cancer or prostate cancer. According to an embodiment of this invention, the infectious agent may be, but is not limited to Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*. According to certain embodiments of this invention, the toxin is tetanus, anthrax, botulinum, snake venom or spider venom. In one embodiment of this invention, the tumor is benign. In another embodiment, the enzyme dysfunction is hyperactivity or overproduction of the enzyme. In still another embodiment, the hormone dysfunction is hyperactivity or overproduction of the hormone. In yet other embodiments of this invention, the immune dysfunction is CD3 or CD4 mediated. In still other embodiments of this invention, the autoimmune disease is lupus, thyroidosis, graft versus host disease, transplantation rejection or rheumatoid arthritis. In still other embodiments of the invention, the condition is any abnormality. In still other embodiments, the condition is the normal condition.

Finally, the present invention provides a method of preventing a given condition in a subject comprising administering to the subject an amount of the above-described therapeutic composition effective to prevent the condition in the subject. In one embodiment of this invention, the subject previously exhibited the condition. According to one embodiment of this invention, the therapeutic composition is administered to a second subject.

According to certain embodiments of this invention, the condition is or is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally, the condition may be any other abnormality, including one resulting from infection, cancer, autoimmune dysfunction, cardiovascular disease, or transplantation. In certain embodiments of this invention, the condition is septicemia, sepsis, septic shock, viremia, bacteremia or fungemia. In some embodiments of this invention, the cancer may be but is not limited to lung cancer, liver cancer, leukemia, lymphoma, neuroblastoma, glioma, meningioma, bone cancer, thyroid cancer, colon cancer, ovarian cancer, bladder cancer, pancreatic cancer, breast cancer or prostate cancer. According to an embodiment of this invention, the infectious agent may be but is not limited to Hanta virus, HTLV I, HTLV II, HIV, herpes virus, influenza virus, Ebola virus, human papilloma virus, Staphlococcus, *Streptococcus, Klebsiella, E. coli*, anthrax or *cryptococcus*. According to some embodiments of this invention, the toxin is tetanus, anthrax, botulinum, snake venom or spider venom. In one embodiment of this invention, the tumor is benign. In other embodiments, the enzyme dysfunction is hyperactivity or overproduction of the enzyme. In still other embodiments, the hormone dysfunction is hyperactivity or overproduction of the hormone. In yet other embodiments of this invention, the immune dysfunction is CD3 or CD4 mediated. In still other embodiments of this invention, the autoimmune disease is lupus, thyroidosis, graft versus host disease, transplantation rejection or rheumatoid arthritis. In still other embodiments of the invention, the condition is any abnormality. In still other embodiments, the condition is the normal condition.

The present invention also provides the production of antibodies for antigens which are not associated with a given condition, but more properly constitute a component of the entire repertoire of antibodies in a human immune system.

In addition, the present invention provides identification of novel antigens relevant to a given condition in a subject and the use thereof for diagnosis and treatment of the given condition in the subject. The invention also provides identification of the repertoire of naturally occurring antibodies in normal subjects and subjects having a pathological condition. In one embodiment, the condition may be venom detoxicification (neutralization). For example, the condition may result from scorpion, spider, rattle snake or poison toad bites or venom exposure. The present invention provides antibodies to act as antidote for such conditions.

The trioma cell of the present invention may also be fused with macrophages, monocytes, T-lymphocytes, and erythroblastoid cells. Hybridoma cells resulting from such fusions may produce growth factors, cytokines, enzymes, hemoglobin.

As used herein, a human-murine hybridoma (the "immortalizing hybridoma") is an immortal cell line which results from the fusion of a murine myeloma or other murine tumor cell with a human lymphoid cell derived from a normal subject. As described herein below, by careful selection and mutation, an immortalizing hybridoma which provides improved chromosomal stability, has human characteristics, and which does not secrete immunoglobulin may be obtained. The antibody secreting capability of such a resulting trioma may be provided by the third cell fusion which is typically derived either from B cells of an immunized human individual, or with B cells which have been immortalized.

As used herein, a "B6B11" cell is a hybrid cell produced by the fusion of mouse myeloma 653 and human myeloma RPMI 8226.

As used herein, a "B6B11-like" cell is a hybrid cell produced by the fusion of mouse myeloma 653-related cell and human myeloma RPMI 8226-related cell.

As used herein, a "MFP" cell is a hybrid cell produced by the fusion of a B6B11 cell and a human lymphocyte. B6B11-like cells share function properties and characteristics with B6B11 heteromyeloma cells.

As used herein, a "MFP-like" cell is a hybrid cell produced by the fusion of a B6B11-like cell and a human lymphocyte. MFP-like cells share function properties and characteristics with MFP trioma cells.

As used herein, "non-secreting" or "non-producing" hybridoma refers to a hybridoma which is capable of continuous reproduction and, therefore, is immortal, and which does not produce immunoglobulin.

As used herein, a hybridoma "having human characteristics" refers to a hybridoma which retains detectable human-derived chromosomes such as those producing human HLA antigen which may be expressed on the cell surface.

As used herein, lymphoid cells "immunized against a predefined determinant" refers to lymphoid cells derived from an subject who has been exposed to an antigen having the determinant. For example, a subject can be induced to produce (from its lymphoid B cells) antibodies against the antigenic determinants of various blood types, by exposure, through transfusions or previous pregnancy, or against the antigenic determinants of specific viruses or of bacteria by virus of exposure through past infections or vaccinations.

As used herein, "cell line" refers to various embodiments including but not limited to individual cells, harvested cells and cultures containing cells so long as these are derived from cells of the cell line referred to may not be precisely identical to the ancestral cells or cultures and any cell line referred to include such variants.

As used herein, "trioma" refers to a cell line which contains generic components originating in three originally separate cell linages. These triomas are stable, immortalized cells which result from the fusion of a human-murine hybridoma with a human lymphoid cell.

As used herein, "tetroma" refers to a cell line which contains generic components originating in four originally separate cell lineages. These tetromas are stable, immortalized antibody producing cells which result from the fusion of a trioma with a human lymphoid cell which is capable of producing antibody.

As used herein, "autologously" refers to a situation where the same subject is both the source of cell immunoglobulin and the target for cells, or immunoglobulin or therapeutic composition.

As used herein, "heterologously" refers to a situation where one subject is the source of cells or immunoglobulin and another subject is the target for the cell, immunoglobulin or therapeutic composition.

In the practice of any of the methods of the invention or preparation of any of the pharmaceutical compositions a "therapeutically effective amount" is an amount which is capable of binding to an antigen associated with the condition. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, liposomes, tablets, coated tablets, capsules and RBC shadows. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions capable of binding to an antigen associated with the condition together with suitable diluents, preservatives, solubilizers, emulsifiers, adjuvants and/or carriers. Such compositions are liquids or lyophilized or otherwise dried formulations and include diluents of various buffer content (e.g., Tris-HCl., acetate, phosphate), pH and ionic strength; additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987) Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The carrier includes a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

The present invention describes the production of human monoclonal antibodies directed to tumor-associated antigens, tumor cells, infectious agents, infection-specific antigens, and self antigens using a modified cell fusion partner, trioma cell line and human lymphocytes derived from lymph nodes, spleen, Peyer's patches, or any other lymph tissue or peripheral blood of the human subjects.

Antibodies are selected using cultured cells, purified antigens, primary human cells and tissues and combinatorial libraries relevant to the antibody screening including cells and tissues obtained from autologous donor of lymphoid cells.

The present invention provides a monoclonal antibody which specifically binds and forms a complex with TIP-2 antigen located on the surface of human cancer cells, the TIP-2 antigen being an antigen to which monoclonal antibody 27.B1 specifically binds. According to certain embodiments of the present invention, the monoclonal antibody of the invention is a murine monoclonal antibody, a chimaeric monoclonal antibody, a humanized monoclonal antibody, or a human monoclonal antibody. In an embodiment of the present invention, the monoclonal antibody of the invention is capable of binding to the epitope which is specifically recognized by monoclonal antibody 27.B1 produced by the hybridoma having ATCC Accession No. PTA-1599.

The present invention provides the monoclonal antibody 27.B1 produced by the hybridoma having ATCC Accession No. PTA-1599.

The present invention provides a hybridoma cell producing the monoclonal antibody of this invention. In an embodiment of the invention, the hybridoma cell has ATCC Accession No. PTA-1599.

Hybridoma 27.B1 was deposited on Mar. 29, 2000 with the American Type Culture Collection (ATCC), 10801 University Boulevard, Manassas, Va., U.S.A. under the provisions of the Budapest Treaty for the International Recognition of the Deposit of Microorganism for the Purposes of Patent Procedure. 27.B1 was accorded ATCC Accession Number PTA-1599.

In an embodiment of this invention, a monoclonal antibody of the invention is labelled with a detectable marker. In another embodiment of the invention, the detectable marker is a radioactive isotope, enzyme, dye, biotin, fluorescent label or chemiluminescent label. In another embodiment of the invention, the monoclonal antibody is conjugated to a therapeutic agent. In another embodiment of the invention, the therapeutic agent is a radioisotope, toxin, toxoid or chemotherapeutic agent. In another embodiment of the invention, the monoclonal antibody is conjugated to an imaging agent. In yet another embodiment of the invention, the imaging agent is a radioisotope.

The present invention provides a pharmaceutical composition comprising the monoclonal antibody of this invention and a pharmaceutically acceptable carrier.

The present invention provides a vaccine comprising the monoclonal antibody of this invention and a pharmaceutically acceptable carrier.

The present invention provides a monoclonal antibody which specifically binds and forms a complex with TIP-2 antigen located on the surface of human cancer cells, the TIP-2 antigen being an antigen to which monoclonal antibody 27.F7 specifically binds. According to certain embodiments of the present invention, the monoclonal antibody of the invention is a murine monoclonal antibody, a chimaeric monoclonal antibody, a humanized monoclonal antibody, or a human monoclonal antibody. In an embodiment of the present invention, the monoclonal antibody of the invention is capable of binding to the epitope which is specifically recognized by monoclonal antibody 27.F7 produced by the hybridoma having ATCC Accession No. PTA-1598.

The present invention provides the monoclonal antibody 27.F7 produced by the hybridoma having ATCC Accession No. PTA-1598.

The present invention provides a hybridoma cell producing the monoclonal antibody of this invention. In an embodiment of the invention, the hybridoma cell has ATCC Accession No. PTA-1598.

Hybridoma 27.F7 was deposited on Mar. 29, 2000 with the American Type Culture Collection (ATCC), 10801 University Boulevard, Manassas, Va., U.S.A. under the provisions of the Budapest Treaty for the International Recognition of the Deposit of Microorganism for the Purposes of Patent Procedure. 27.F7 was accorded ATCC Accession Number PTA-1598.

In an embodiment of this invention, a monoclonal antibody of the invention is labelled with a detectable marker. In another embodiment of the invention, the detectable marker is a radioactive isotope, enzyme, dye, biotin, fluorescent label or chemiluminescent label. In another embodiment of the invention, the monoclonal antibody is conjugated to a therapeutic agent. In another embodiment of the invention, the therapeutic agent is a radioisotope, toxin, toxoid or chemotherapeutic agent. In another embodiment of the invention, the monoclonal antibody is conjugated to an imaging agent. In yet another embodiment of the invention, the imaging agent is a radioisotope.

The present invention provides a pharmaceutical composition comprising the monoclonal antibody of this invention and a pharmaceutically acceptable carrier.

The present invention provides a vaccine comprising the monoclonal antibody of this invention and a pharmaceutically acceptable carrier.

The present invention provides a method of detecting TIP-2 antigen bearing cancer cells in a sample comprising: (a) contacting the sample with an antibody directed to an epitope on TIP-2 antigen, or an Fab fragment of an antibody directed to an epitope on TIP-2 antigen, which epitope is recognized by the antibody or the Fab fragment, said antibody or Fab fragment being detectably labeled, under appropriate conditions to produce an antibody/Fab fragment-antigen complex comprising the detectably labeled antibody or Fab fragment bound to any TIP-2 antigen on the surface of cells in the sample; (b) removing any labeled antibody/Fab fragment not bound in the antibody/Fab fragment-antigen complex formed in step (a); and (c) determining presence of the antibody/Fab fragment-antigen complex by detecting the label of the detectably labeled antibody, presence of antibody/Fab fragment-antigen complex indicating TIP-2 antigen-bearing cancer cells in the sample.

As used herein, "antibody/Fab fragment" means antibody or Fab fragment of the antibodies.

In the practice of any of the methods of the invention, the unbound antibody or its fragment are usually removed by thorough washing of the sample under testing.

In the practice of any of the methods of the invention, it is more economical to first prepare the fragment and then label it with the label of interest.

In an embodiment of this invention the detectable label is selected from the group consisting of a radioactive isotope, enzyme, dye, biotin, fluorescent label or chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

In an embodiment of this invention the sample is culture media.

The present invention provides a method of detecting TIP-2 antigen bearing cancer cells in a sample comprising: (a) contacting the sample with an antibody directed to an epitope on TIP-2 antigen, or an Fab fragment of an antibody directed to an epitope on TIP-2 antigen, which epitope is recognized by the antibody or the Fab fragment under appropriate conditions to produce an antibody/Fab fragment-antigen complex comprising the antibody or Fab fragment bound to any TIP-2 antigen on the surface of cells in the sample; (b) removing any antibody/Fab fragment not bound in the antibody/Fab fragment-antigen complex formed in step (a); (c) contacting the antibody/Fab fragment-antigen complex of step (b) with a second antibody which specifically binds to the antibody/Fab fragment-antigen complex, said second antibody being detectably labeled, under appropriate conditions to permit the second labeled antibody to bind to the antibody/Fab fragment-antigen complex; (d) removing any second labeled antibody not bound to the antibody/Fab fragment-antigen complex product in (c); and (e) determining presence of the antibody/Fab fragment-antigen complex bound to the second labeled antibody by detecting the label of second antibody, presence of antibody/Fab fragment-antigen complex indicating TIP-2 antigen-bearing human cancer cells in the sample.

In an embodiment of this invention the detectable label is a radioactive isotope, enzyme, dye, biotin, fluorescent label or chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method of detecting TIP-2 antigen on the surface of cancer cells in a sample comprising: (a) contacting the sample with a antibody directed to an epitope on TIP-2 antigen or an Fab fragment thereof, which epitope is recognized by monoclonal antibody 27.F7 produced by the hybridoma designated PTA-1598, said antibody or Fab fragment thereof being detectably labeled, under appropriate conditions to produce an antibody 27.F7/Fab fragment-TIP-2 antigen complex comprising the detectably labeled antibody bound to any TIP-2 antigen on the surface of cells in the sample; b) removing any labeled antibody/Fab fragment not bound in the antibody 27.F7/Fab fragment-TIP-2 antigen complex formed in step (a); and (c) determining presence of the antibody 27.F7/Fab fragment-TIP-2 antigen complex by detecting the label of the detectably labeled antibody, presence of antibody 27.F7/Fab fragment-TIP-2 antigen complex indicating TIP-2 antigen-bearing human cancer cells in the sample.

In an embodiment of this invention the detectable label is selected from the group consisting of a radioactive isotope, enzyme, dye, biotin, fluorescent label or chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method of detecting TIP-2 antigen on the surface of cancer cells in a sample comprising: (a) contacting the sample with an antibody directed to an epitope on TIP-2 antigen which epitope is recognized by monoclonal antibody 27.F7 produced by the hybridoma designated PTA-1598 or Fab fragment thereof, under appropriate conditions to produce an antibody 27.F7/Fab fragment-TIP-2 antigen complex comprising the antibody bound to any TIP-2 antigen on the surface of cells in the sample; (b) removing any antibody or Fab fragment thereof not bound in the antibody 27.F7/Fab fragment-TIP-2 antigen complex formed in step (a); (c) contacting the antibody 27.F7/Fab fragment-TIP-2 antigen complex of step (b) with a second antibody which specifically binds to the antibody 27.F7/Fab fragment-TIP-2 antigen complex, said second antibody being detectably labeled, under appropriate conditions to permit the second labeled antibody to bind to the antibody 27.F7/Fab fragment-TIP-2 antigen complex; (d) removing any second labeled antibody not bound to the antibody 27.F7/Fab fragment-TIP-2 antigen complex product in (c); and (e) determining presence of the antibody 27.F7/Fab fragment-TIP-2 antigen complex bound to the second labeled antibody by detecting the label of second antibody, presence of antibody 27.F7/Fab fragment-TIP-2 antigen complex indicating TIP-2 antigen-bearing human cancer cells in the sample.

In an embodiment of this invention the detectable label is a radioactive isotope, enzyme, dye, biotin, fluorescent label or chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method of detecting TIP-2 antigen on the surface of cancer cells in a sample comprising: (a) contacting the sample with a antibody directed to an epitope on TIP-2 antigen or an Fab fragment thereof, which epitope is recognized by monoclonal antibody 27.B1 produced by the hybridoma designated PTA-1599 or Fab fragment thereof, said antibody or Fab fragment thereof being detectably labeled, under appropriate conditions to produce an antibody 27.B1/Fab fragment-TIP-2 antigen complex comprising the detectably labeled antibody bound to any TIP-2 antigen on the surface of cells in the sample; (b) removing any labeled antibody not bound in the antibody 27.B1-TIP-2 antigen complex formed in step (a); and (c) determining presence of the antibody 27.B1/Fab fragment-TIP-2 antigen complex by detecting the label of the detectably labeled antibody, presence of antibody 27.B1/Fab fragment-TIP-2 antigen complex indicating TIP-2 antigen-bearing human cancer cells in the sample.

In an embodiment of this invention the detectable label is selected from the group consisting of a radioactive isotope, enzyme, dye, biotin, fluorescent label or chemiluminescent label.

In an embodiment of this invention TIP-2 antigen-bearing cancer cells are human cancer cells.

In an embodiment of this invention the cancer cells are selected from a group consisting of human melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method of detecting TIP-2 antigen on the surface of cancer cells in a sample comprising: (a) contacting the sample with an antibody directed to an epitope on TIP-2 antigen or an Fab fragment thereof, which epitope is recognized by monoclonal antibody 27.B1 produced by the hybridoma designated PTA-1599, or Fab fragment thereof under appropriate conditions to produce an antibody 27.B1/Fab fragment-TIP-2 antigen complex comprising the antibody bound to any TIP-2 antigen on the surface of cells in the sample; (b) removing any antibody/Fab fragment thereof not bound in the antibody 27.B1/Fab fragment-TIP-2 antigen complex formed in step (a); (c) contacting the antibody 27.B1/Fab fragment-TIP-2 antigen complex of step (b) with a second antibody which specifically binds to the antibody 27.B1/Fab fragment-TIP-2 antigen complex, said second antibody being detectably labeled, under appropriate conditions to permit the second labeled antibody to bind to the antibody 27.B1/Fab fragment-TIP-2 antigen complex; (d) removing any second labeled antibody not bound to the antibody 27.B1/Fab fragment-TIP-2 antigen complex product in (c); and (e) determining presence of the antibody 27.B1/Fab fragment-TIP-2 antigen complex bound to the second labeled antibody by detecting the label of second antibody, presence of antibody 27.B1/Fab fragment-TIP-2 antigen complex indicating TIP-2 antigen-bearing human cancer cells in the sample.

In an embodiment of this invention the detectable label is a radioactive isotope, enzyme, dye, biotin, fluorescent label or chemiluminescent label.

In an embodiment of this invention the TIP-2 antigen-bearing cancer cells are human cancer cells.

In an embodiment of this invention the cancer cells are selected from a group consisting of human melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or an Fab fragment thereof, which epitope is recognized by monoclonal antibody 27.F7 produced by the hybridoma designated PTA-1598 or an Fab fragment thereof, said antibody being detectably labeled, under appropriate conditions to produce an antibody 27.F7/Fab fragment-TIP-2 antigen complex comprising the detectably labeled antibody bound to any TIP-2 antigen on the surface of cells in the sample; (c) removing any labeled antibody/Fab fragment not bound in the antibody 27.F7/Fab fragment-TIP-2 antigen complex formed in step (b); and (d) determining presence of the antibody 27.F7/Fab fragment-TIP-2 antigen complex by detecting the label of the detectably labeled antibody, presence of antibody 27.F7/Fab fragment-TIP-2 antigen complex indicating diagnosis of cancer in the subject.

In an embodiment of this invention the detectable label is a radioactive isotope, enzyme, dye, biotin, fluorescent label or chemiluminescent label.

In an embodiment of this invention the subject is human.

In an embodiment of this invention the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or Fab fragment thereof, which epitope is recognized by monoclonal antibody 27.F7 produced by the hybridoma designated PTA-1598 or Fab fragment thereof, under appropriate conditions to produce an antibody 27.F7/Fab fragment-TIP-2 antigen complex comprising the antibody bound to any TIP-2 antigen on the surface of cells in the sample; (c) removing any antibody/Fab fragment not bound in the antibody 27.F7/Fab fragment-TIP-2 antigen complex formed in step (b); (d) contacting the antibody 27.F7/Fab fragment-TIP-2 antigen complex of step (c) with a second antibody which specifically binds to the antibody 27.F7/Fab fragment-TIP-2 antigen complex, said second antibody being detectably labeled, under appropriate conditions to permit the second labeled antibody to bind to the antibody 27.F7/Fab fragment-TIP-2 antigen complex; (e) removing any second labeled antibody not bound to the antibody 27.F7/Fab fragment-TIP-2 antigen complex product in (d); and (f) determining presence of the antibody 27.F7/Fab fragment-TIP-2 antigen complex bound to the second labeled antibody by detecting the label of second antibody, presence of antibody 27.F7/Fab fragment-TIP-2 antigen complex indicating diagnosis of cancer in the subject.

In an embodiment of this invention the detectable label is a radioactive isotope, enzyme, dye, biotin, fluorescent label or chemiluminescent label.

In an embodiment of this invention the subject is human.

In an embodiment of this invention the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or an Fab fragment thereof, which epitope is recognized by monoclonal antibody 27.B1 produced by the hybridoma designated PTA-1599, said antibody being detectably labeled, under appropriate conditions to produce an antibody 27.B1/Fab fragment-TIP-2 antigen complex comprising the detectably labeled antibody bound to any TIP-2 antigen on the surface of cells in the sample; (c) removing any labeled antibody/Fab fragment not bound in the antibody 27.B1/Fab fragment-TIP-2 antigen complex formed in step (b); and (d) determining presence of the antibody 27.B1/Fab fragment-TIP-2 antigen complex by detecting the label of the detectably labeled antibody, presence of antibody 27.B1/Fab fragment-TIP-2 antigen complex indicating diagnosis of cancer in the subject.

In an embodiment of this invention the detectable label is a radioactive isotope, enzyme, dye, biotin, fluorescent label or chemiluminescent label.

In an embodiment of this invention the subject is human.

In an embodiment of this invention the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides a method for diagnosing cancer in a subject by detecting TIP-2 antigen-bearing cancer cells which comprises: (a) obtaining a sample of the subject's peripheral blood; (b) contacting the sample with an antibody directed to an epitope on TIP-2 antigen or Fab fragment thereof, which epitope is recognized by monoclonal antibody 27.B1/Fab fragment produced by the hybridoma designated PTA-1599 or Fab fragment thereof, under appropriate conditions to produce an antibody 27.B1/Fab fragment-TIP-2 antigen complex comprising the antibody bound to any TIP-2 antigen on the surface of cells in the sample; (c) removing any antibody/Fab fragment not bound in the antibody 27.B1/Fab fragment-TIP-2 antigen complex formed in step (b); (d) contacting the antibody 27.B1/Fab fragment-TIP-2 antigen complex of step (c) with a second antibody which specifically binds to the antibody 27.B1/Fab fragment-TIP-2 antigen complex, said second antibody being detectably labeled, under appropriate conditions to permit the second labeled antibody to bind to the antibody 27.B1/Fab fragment-TIP-2 antigen complex; (e) removing any second labeled antibody not bound to the antibody 27.B1/Fab fragment-TIP-2 antigen complex product in (d); and (f) determining presence of the antibody 27.B1/Fab fragment-TIP-2 antigen complex bound to the second labeled antibody by detecting the label of second antibody, presence of antibody 27.B1/Fab fragment-TIP-2 antigen complex indicating diagnosis of cancer in the subject.

In an embodiment of this invention the detectable label is a radioactive isotope, enzyme, dye, biotin, fluorescent label or chemiluminescent label.

In an embodiment of this invention the subject is human.

In an embodiment of this invention the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention TIP-2 is concentrated from the sample by alcohol precipitation prior to step (a).

The present invention provides an in vivo method for diagnosing cancer in a subject by detecting TIP-2 antigen-bearing cancer cells which comprises: (a) administering to the subject an antibody directed to an epitope on TIP-2 antigen or Fab fragment thereof, which epitope is recognized by monoclonal antibody 27.F7 produced by the hybridoma designated PTA-1598, said antibody being detectably labeled, under appropriate conditions to bind the antibody to TIP-2 antigen on the surface of any cells in the subject; and (b) determining presence of the detectably labeled antibody 27.F7 bound to the surface of cells in the subject, presence of detectably labeled antibody 27.F7 bound to cells indicating diagnosis of cancer in the subject.

In an embodiment of this invention the detectable label is a radioactive isotope, enzyme, dye, biotin, fluorescent label or chemiluminescent label.

In an embodiment of this invention the subject is human.

In an embodiment of this invention the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of this invention the antibody is a monoclonal antibody.

In an embodiment of this invention the antibody is a human monoclonal antibody or a murine monoclonal antibody.

In an embodiment of this invention in step (b) presence of the antibody 27.F7 or Fab fragment thereof bound to the surface of cells in the subject is detected wherein means for detecting the detectable label is an imaging device.

In an embodiment of this invention the imaging device is magnetic resonance imaging device.

In an embodiment of this invention the imaging device is X-ray immunoscintigraphy-imaging device.

The present invention provides an in vivo method for diagnosing cancer in a subject by detecting TIP-2 antigen-bearing cancer cells which comprises: (a) administering to the subject an antibody directed to an epitope on TIP-2 antigen or Fab fragment thereof, which epitope is recognized by monoclonal antibody 27.B1 produced by the hybridoma designated PTA-1599, said antibody/Fab fragment being detectably labeled, under appropriate conditions to bind the antibody to TIP-2 antigen on the surface of any cells in the subject; and (b) determining presence of the detectably labeled antibody/Fab fragment 27.B1 bound to the surface of cells in the subject, presence of detectably labeled antibody 27.F7/Fab fragment bound to cells indicating diagnosis of cancer in the subject.

In an embodiment of this invention the detectable label is a radioactive isotope, enzyme, dye, biotin, fluorescent label or chemiluminescent label.

In an embodiment of this invention the subject is human.

In an embodiment of this invention the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of this invention the antibody is a monoclonal antibody.

In an embodiment of this invention the antibody is a human monoclonal antibody or a murine monoclonal antibody.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention in step (b) presence of the antibody 27.B1 or fragment thereof bound to the surface of cells in the subject is detected by means for detecting the detectable label is an imaging device.

In an embodiment of this invention the imaging device is magnetic resonance imaging device.

In an embodiment of this invention the imaging device is X-ray immunoscintigraphy-imaging device.

The present invention provides a method for delivering exogenous material to TIP-2 antigen-bearing cancer cells of a human subject comprising administering to the subject a liposome carrying a conjugate of the exogenous material, wherein antibody 27.B1 or an Fab fragment of 27.B1 is coupled to the outer surface of the liposome to target delivery to the cancer cells.

In an embodiment of this invention the exogenous material is selected from the group consisting of anti-cancer drugs, radioisotopes, toxins, antibiotics, prodrugs, enzymes, and chemotherapeutic compounds.

In an embodiment of this invention the TIP-2 antigen-bearing cancer cells are human melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

The present invention provides a method for delivering exogenous material to TIP-2 antigen-bearing cancer cells of a human subject comprising administering to the subject a liposome carrying a conjugate of the exogenous material, wherein an antibody 27.F7 or an Fab fragment of 27.F7 is coupled to the outer surface of the liposome to target delivery to the cancer cells.

In an embodiment of this invention the exogenous material is selected from the group consisting of anti-cancer drugs, radioisotopes, toxins, antibiotics, prodrugs, enzymes, and chemotherapeutic compounds.

In an embodiment of this invention the TIP-2 antigen-bearing cancer cells are human melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

The present invention provides a method for treating cancer in a human subject by evoking a specific immune response which comprises administering to the subject a whole TIP-2 antigen protein or a peptide fragment of TIP-2 to the subject.

In the above-described method, the whole TIP-2 or TIP-2 derived peptides can be either (1) injected directly or (2) coupled to a carrier protein or (3) in a mixture with adjuvant or (4) otherwise modified (such as by coupling to tetanus toxoid) to boost the immune response directed to all TIP-2 bearing cells.

In an embodiment of this invention the specific immune response is complement-dependent cytolysis of TIP-2 antigen-bearing cancer cells.

In an embodiment of this invention the specific immune response is activation of natural killer cells towards TIP-2 antigen-bearing cancer cells.

In an embodiment of this invention the peptide fragment of TIP-2 antigen comprises the amino acid sequence Lys Leu Leu Gly Gly Gln Ile Gly Leu (SEQ ID NO:3).

In an embodiment of this invention the peptide fragment of TIP-2 antigen comprises the amino acid sequence Ser Leu Leu Gly Cys Arg His Tyr Glu Val (SEQ ID NO:4).

The present invention provides a method for treating cancer in a human subject by inducing apoptosis of cancer cells which comprises administering to the subject a whole TIP-2 antigen protein or a peptide fragment of TIP-2 to the subject.

The present invention provides a method for treating cancer in a human subject by evoking a specific immune response which comprises: (a) removing dendritic cells from said subject; (b) contacting the dendritic cells of step (a) with a whole TIP-2 antigen protein or a peptide fragment of TIP-2; and (c) reintroducing the dendritic cells of step (b) into said subject.

In the above-described method, the dendritic cells will present the antigen to the autologous immune system and thereby induce antibodies in the subject.

In an embodiment of this invention the peptide fragment of TIP-2 antigen comprises the amino acid sequence Lys Leu Leu Gly Gly Gln Ile Gly Leu (SEQ ID NO:3).

In an embodiment of this invention the peptide fragment of TIP-2 antigen comprises the amino acid sequence Ser Leu Leu Gly Cys Arg His Tyr Glu Val (SEQ ID NO:4).

In an embodiment of this invention the specific immune response is complement-dependent cytolysis of TIP-2 antigen-bearing cancer cells.

In an embodiment of this invention the specific immune response is activation of natural killer cells towards TIP-2 antigen-bearing cancer cells.

In an embodiment of this invention the specific immune response is the production of antibodies in the subject against the whole TIP-2 antigen protein or the peptide fragment of TIP-2.

In the above-described method, antibodies injected into the patient in order to evoke immune response to cancer can be either fully human, humanized, or fragments thereof, either directly or indirectly coupled to a toxin, a drug or a prodrug, an enzyme, a radionuclide, or to liposomes carrying the payload of a drug, toxin, prodrug, enzyme or radionuclide. Such antibodies can evoke the immune response by activating effector cells (natural killer cells and macrophages), causing ADCC; can activate complement, causing CDC, or can act directly through apoptosis. Such antibodies can also induce the cascade of anti-idiotypic antibodies, where Ab2 (mimetics of the antigen, in this case TIP-2) will cause even stronger anti-TIP-2 immune response by inducing Ab3 (mimetics of original anti-TIP-2 Ab1).

The present invention provides a method for treating cancer in a human subject by inducing apoptosis of cancer cells which comprises administering a whole TIP-2 antigen protein or a peptide fragment of TIP-2 to the subject.

The present invention provides a method for treating cancer in a human subject by passive immunization which comprises administering an antibody directed to an epitope on TIP-2 antigen or a peptide fragment thereof.

In an embodiment of this invention the antibody induces apoptosis of TIP-2 antigen bearing cells.

The present invention provides an isolated peptide having the amino acid sequence Lys Leu Leu Gly Gly Gln Ile Gly Leu (SEQ ID NO:3).

The present invention provides an isolated peptide having the amino acid sequence Ser Leu Leu Gly Cys Arg His Tyr Glu Val (SEQ ID NO:4).

The present invention provides a method for immunohistochemical screening of a tissue section from a tumor sample for the presence of TIP-2 antigen bearing cancer cells which comprises: (a) contacting the tissue section from the tumor sample with an antibody directed to an epitope on TIP-2 antigen or Fab fragment thereof, which epitope is recognized by monoclonal antibody 27.F7 produced by the hybridoma designated ATCC Accession No. PTA-1598, said antibody/Fab fragment being detectably labeled, under appropriate conditions to produce an antibody 27.F7/Fab fragment-TIP-2 antigen complex comprising the detectably labeled antibody bound to any TIP-2 antigen on the surface of cells in the tissue section; (a) removing any labeled antibody/Fab fragment not bound in the antibody 27.F7/Fab fragment-TIP-2 antigen complex formed in step (a); and (b) determining presence of the antibody 27.F7/Fab fragment-TIP-2 antigen complex by detecting the label of the detectably labeled antibody, presence of antibody 27.F7/Fab fragment-TIP-2 antigen complex indicating TIP-2 antigen-bearing human cancer cells in the sample.

In an embodiment of this invention the tissue section is preserved freshly frozen tissue or formalin-fixed tissue.

In an embodiment of this invention the detectable label is a radioactive isotope, enzyme, dye, biotin, fluorescent label or a chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells. The antibody is a monoclonal antibody.

In an embodiment of this invention the antibody is a human monoclonal antibody.

The present invention provides a kit for detecting the presence of TIP-2 antigen-bearing cancer cells in a sample comprising: (a) solid support having a plurality of covalently linked probes which may be the same or different, each probe of which comprises a monoclonal antibody directed to an epitope on TIP-2 antigen or Fab fragment thereof; and (b) a means for determining the presence of monoclonal antibody/Fab fragment-TIP-2 antigen complex.

In an embodiment of this invention the means for determining the presence of the monoclonal antibody/Fab fragment-TIP-2 antigen complex is a detectably labeled second antibody which specifically binds to the monoclonal antibody directed to the epitope on TIP-2 antigen.

In an embodiment of this invention the monoclonal antibody directed to the epitope on TIP-2 antigen is human monoclonal antibody 27.F7 directed to an epitope on TIP-2 antigen, which epitope is recognized by monoclonal antibody 27.F7 produced by the hybridoma designated ATCC Accession No. PTA-1598.

In an embodiment of this invention the monoclonal antibody directed to the epitope on TIP-2 antigen is human monoclonal antibody 27.B1 directed to an epitope on TIP-2 antigen, which epitope is recognized by monoclonal antibody 27.B1 produced by the hybridoma designated ATCC Accession No. PTA-1599.

In an embodiment of this invention the monoclonal antibody directed to the epitope of TIP-2 antigen is murine monoclonal antibody directed to an epitope on TIP-2 antigen, which epitope is recognized by monoclonal antibody produced by the hybridoma designated ATCC Accession No. PTA-1599.

In an embodiment of this invention the detectable label is a radioactive isotope, enzyme, dye, biotin, fluorescent label or a chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of this invention the sample is culture media.

In an embodiment of this invention the sample is a tumor sample.

The present invention provides a method for detecting the presence of TIP-2 antigen in biological fluid comprising: (a) contacting a sample of the biological fluid with a antibody directed to an epitope on TIP-2 antigen or Fab fragment thereof, which epitope is recognized by monoclonal antibody 27.F7 produced by the hybridoma designated ATCC Accession No. PTA-1598, said antibody being detectably labeled, under appropriate conditions to produce an antibody 27.F7/Fab fragment-TIP-2 antigen complex comprising the detectably labeled antibody bound to any TIP-2 antigen on the surface of cells in the sample; (c) removing any labeled antibody not bound in the antibody 27.F7/Fab fragment-TIP-2 antigen complex formed in step (a); and (d) determining presence of the antibody 27.F7/Fab fragment-TIP-2 antigen complex by detecting the label of the detectably labeled antibody, presence of antibody 27.F7/Fab fragment-TIP-2 antigen complex indicating TIP-2 antigen-bearing human cancer cells in the biological fluid.

In an embodiment of this invention the detectable label is a radioactive isotope, enzyme, dye, biotin, fluorescent label or a chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the biological fluid is selected from the group consisting of serum, plasma, saliva, tears, mucosal discharge, urine, peritoneal fluid, cerebrospinal fluid, and lymphatic fluid.

In an embodiment of this invention TIP-2 is concentrated from the sample by alcohol precipitation prior to step (a).

In an embodiment of this invention the biological fluid is culture media.

In an embodiment of this invention the monoclonal antibody directed to the epitope on TIP-2 antigen is human monoclonal antibody 27.F7 directed to an epitope on TIP-2 antigen, which epitope is recognized by monoclonal antibody 27.F7 produced by the hybridoma designated ATCC Accession No. PTA-1598.

In an embodiment of this invention the monoclonal antibody directed to the epitope on TIP-2 antigen is human monoclonal antibody 27.B1 directed to an epitope on TIP-2 antigen, which epitope is recognized by monoclonal antibody 27.B1 produced by the hybridoma designated ATCC Accession No. PTA-1599.

In an embodiment of this invention the monoclonal antibody directed to the epitope of TIP-2 antigen is a murine monoclonal antibody directed to an epitope on TIP-2 antigen.

In an embodiment of this invention the TIP-2 antigen is present on TIP-2 antigen-bearing cancer cells in the biological fluid.

The present invention provides a method for immunohistochemical screening of tissue sections from a tumor sample for the presence of TIP-2 antigen-bearing cancer cells which comprises: (a) contacting the tissue section from the tumor sample with a detectably labeled antibody directed to an epitope on TIP-2 antigen or Fab fragment thereof, which epitope is recognized by monoclonal antibody 27.B1 produced by the hybridoma designated ATCC Accession No. PTA-1599, said antibody being detectably labeled, under appropriate conditions to bind the antibody to TIP-2 antigen on the surface of any cells in the sample; and (b) removing any labeled antibody not bound to the cells in the sample; (c) determining presence of antibody 27.B1 bound to the cells in the sample, presence of antibody 27.B1 bound to cells indicating TIP-2 antigen-bearing cancer cells in the tumor sample.

In an embodiment of this invention tissue section is preserved freshly frozen tissue or formalin-fixed tissue.

In an embodiment of this invention the detectable label is a radioactive isotope, enzyme, dye, biotin, fluorescent label or a chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention the antibody is a monoclonal antibody.

In an embodiment of this invention the monoclonal antibody is a human monoclonal antibody or a murine monoclonal antibody.

The present invention provides a method for monitoring progression of cancer, wherein cancer cells are TIP-2 antigen-bearing cancer cells, in a subject comprising: (a) administering to a subject diagnosed with cancer an antibody directed to an epitope on TIP-2 antigen or Fab fragment thereof, which epitope is recognized by monoclonal antibody 27.F7 produced by the hybridoma designated ATCC Accession No. PTA-1598, said antibody being detectably labeled, under appropriate conditions to bind the antibody to TIP-2 antigen on the surface of any cells in the subject; (b) determining presence of detectably labeled antibody 27.F7/Fab fragment bound to the surface of cells in the subject according to the according to the method of claim 20; (c) comparing the presence of detectably labeled antibody/Fab fragment 27.F7 bound to cells in step (b) with the presence of detectably labeled antibody 27.F7 bound to cells at (i) diagnosis time or (ii) after treatment, wherein a greater presence of detectably labeled antibody 27.F7/Fab fragment bound to cells in step (b) than at (i) diagnosis time or (ii) after treatment, indicates progression of the cancer in the subject and a lesser presence of detectably labeled antibody 27.F7/Fab fragment bound to cells in step (b) than at (i) diagnosis time or (ii) after treatment indicates regression of the cancer in the subject.

In an embodiment of this invention the detectable label a radioactive isotope, enzyme, dye, biotin, fluorescent label or chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention in step (b) presence of the detectably labeled antibody 27.F7/Fab fragment bound to the surface of cells in the subject is detected by means for detecting the detectable label is an imaging device.

In an embodiment of this invention the imaging device is magnetic resonance imaging device.

In an embodiment of this invention the imaging device is X-ray immunoscintigraphy-imaging device.

The present invention provides a method for monitoring progression of cancer, wherein cancer cells are TIP-2 antigen-bearing cancer cells, in a subject comprising: (a) administering to a subject diagnosed with cancer an antibody directed to an epitope on TIP-2 antigen or Fab fragment thereof, which epitope is recognized by monoclonal antibody 27.B1 produced by the hybridoma designated ATCC Accession No. PTA-1599, said antibody/Fab fragment being detectably labeled, under appropriate conditions to bind the antibody to TIP-2 antigen on the surface of any cells in the subject; (b) determining presence of detectably labeled antibody 27.B1/Fab fragment bound to the surface of cells in the subject according to the according to the method of claim 20; (c) comparing the presence of detectably labeled antibody/Fab fragment 27.B1 bound to cells in step (b) with the presence of detectably labeled antibody 27.B1/Fab fragment bound to cells at (i) diagnosis time or (ii) after treatment, wherein a greater presence of detectably labeled antibody 27.B1/Fab fragment bound to cells in step (b) than at (i) diagnosis time or (ii) after treatment, indicates progression of the cancer in the subject and a lesser presence of detectably labeled antibody 27.B1/Fab fragment bound to cells in step (b) than at (i) diagnosis time or (ii) after treatment indicates regression of the cancer in the subject.

In an embodiment of this invention the detectable label a radioactive isotope, enzyme, dye, biotin, fluorescent label or chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention in step (b) presence of the antibody 27.B1 bound to the surface of cells in the subject is detected by means for detecting the detectable label is an imaging device.

In an embodiment of this invention the imaging device is magnetic resonance imaging device.

In an embodiment of this invention the imaging device is X-ray immunoscintigraphy-imaging device.

The present invention provides a method for monitoring progression of cancer, wherein cancer cells are TIP-2 antigen-bearing cancer cells, in a subject comprising: (a) administering to a subject diagnosed with cancer an antibody directed to an epitope on TIP-2 antigen or an Fab fragment thereof, which epitope is recognized by monoclonal antibody 27.F7 produced by the hybridoma designated ATCC Accession No. PTA-1598, said antibody/Fab fragment being detectably labeled, under appropriate conditions to bind the antibody to TIP-2 antigen on the surface of any cells in the subject; (b) determining quantity of detectably labeled antibody 27.F7/Fab fragment bound to the surface of cells in the subject according to the according to the method of claim 20; (c) comparing the quantity of detectably labeled antibody 27.F7/Fab fragment bound to cells in step (b) with the presence of detectably labeled antibody 27.F7/Fab fragment bound to cells at (i) diagnosis time or (ii) after treatment, wherein a greater quantity of detectably labeled antibody 27.F7/Fab fragment bound to cells in step (b) than at (i) diagnosis time or (ii) after treatment, indicates progression of the cancer in the subject and a lesser quantity of detectably labeled antibody 27.F7/Fab fragment bound to cells in step (b) than at (i) diagnosis time or (ii) after treatment indicates regression of the cancer in the subject.

In the above described method, given the high heterogenicity of tumor cells, some cells may carry more of the antigen, some less.

The quantity of the antigen may determine different stages of the disease, i.e. it may differentiate between a pre-cancerous lesions and a cancerous one.

In an embodiment of this invention the detectable label a radioactive isotope, enzyme, dye, biotin, fluorescent label or a chemiluminescent label.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of this invention in step (b) quantity of the antibody 27.F7 bound to the surface of cells in the subject is detected by means for detecting the detectable label is an imaging device.

In the above-described embodiment of the invention, an estimate of accumulated quantity of the radionuclide-labeled antibody can be made by using an imaging device. Formulas assist in concluding whether the accumulation is specific or not.

In an embodiment of this invention the imaging device is magnetic resonance imaging device.

In an embodiment of this invention the imaging device is X-ray immunoscintigraphy-imaging device.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

The present invention provides a method for monitoring progression of cancer, wherein cancer cells are TIP-2 antigen-bearing cancer cells, in a subject comprising: (a) administering to a subject diagnosed with the cancer an antibody directed to an epitope on TIP-2 antigen or an Fab fragment thereof, which epitope is recognized by monoclonal antibody 27.B1 produced by the hybridoma designated ATCC Accession No. PTA-1599, said antibody/Fab fragment being detectably labeled, under appropriate conditions to bind the antibody to TIP-2 antigen on the surface of any cells in the subject; (b) determining quantity of detectably labeled antibody 27.B1/Fab fragment bound to the surface of cells in the subject according to the according to the method of claim 20; (c) comparing the quantity of detectably labeled antibody 27.B1/Fab fragment bound to cells in step (b) with the presence of detectably labeled antibody 27.B1 bound to cells at (i) diagnosis time or (ii) after treatment, wherein a greater quantity of detectably labeled antibody 27.B1/Fab fragment bound to cells in step (b) than at (i) diagnosis time or (ii) after treatment, indicates progression of the cancer in the subject and a lesser quantity of detectably labeled antibody 27.B1/Fab fragment bound to cells in step (b) than at (i) diagnosis time or (ii) after treatment indicates regression of the cancer in the subject.

In an embodiment of this invention the detectable label a radioactive isotope, enzyme, dye, biotin, fluorescent label or chemiluminescent label.

In an embodiment of this invention in step (b) quantity of the antibody 27.B1/Fab fragment bound to the surface of cells in the subject is detected by means for detecting the detectable label is an imaging device.

In an embodiment of this invention the imaging device is magnetic resonance imaging device.

In an embodiment of this invention the imaging device is X-ray immunoscintigraphy-imaging device.

In an embodiment of this invention the TIP-2 antigen-bearing cancer cells are human cancer cells.

In an embodiment of this invention the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

The present invention provides a method for diagnosing cancer associated with the expression of TIP-2 antigen in a human subject which comprises: (a) obtaining mRNA from a sample of the subject's peripheral blood; (b) preparing cDNA from the mRNA from step (a); (c) amplifying DNA encoding TIP-2 antigen present in the cDNA prepared in step (b) by a polymerase chain reaction utilizing at least two oligonucleotide primers, wherein each of the primers specifically hybridizes with DNA encoding TIP-2 antigen, wherein the primers comprise oligonucleotides having a sequence included within the sequence of SEQ ID NO:2; and (d) detecting the presence of any resulting amplified DNA, the presence of such amplified DNA being diagnostic for cancer associated with the expression of TIP-2 antigen.

In the above described method, since the nucleic acid structure of TIP-2 is known, one of skill in the art may measure the expression of TIP-2 mRNA by Northern Blot since the full mRNA sequence is known and the full size cDNA can therefore be made. Another way to measure the expression is by quantitative PCR using 18-21 mer primers on the basis of the known mRNA sequence. One of skill in the art may also synthesize specific primers or make the full size cDNA. The full mRNA sequence of GIPC (GAIP Interacting Protein, C terminus) is shown in FIG. 30, with the part corresponding to TIP-2 sequence underlined.

In an embodiment of this invention the presence of any amplified DNA in step (d) is detected using a labeled oligonucleotide probe which specifically hybridizes with the amplified DNA.

In an embodiment of this invention the labeled probe is radiolabeled with $^{32}$P or $^{33}$P.

The present invention provides a method for diagnosing cancer associated with the expression of TIP-2 antigen in a human subject which comprises: (a) obtaining mRNA from a sample of the subject's peripheral blood; (b) preparing cDNA from the mRNA from step (a); (c) amplifying DNA encoding TIP-2 antigen present in the cDNA prepared in step (b); (d) determining the amount of any resulting amplified DNA; and (e) comparing the amount of amplified DNA determined in step (d) with previously determined standard amounts of amplified DNA, each standard amount being indicative of a particular stage of cancer associated with the expression of TIP-2 antigen.

In an embodiment of this invention the stage is precancerous cancer or benign dysplasia.

In an embodiment of this invention the cancer is selected from the group consisting of a tumor, cancer in the lymph nodes, and metastatic cancer.

The most widely used cancer staging system is the one based on the so-called TNM system (T, tumor; N, nodes; and M, metastases) Stage 0 amounts to Paget disease without a tumor or carcinom in situ with no lymph nodes involved and no metastases. Stage 1 is a tumor not larger that 2 cm without metastases or lymph nodes involved. Stage 11 is a tumor larger than 5 cm with auxillary lymph node(s) involvement, no distant metastases. Stage III is the same as Stage 11 with a string of the involved lymph nodes fixed to one another or to other structures and in the advance cases lymph nodes in mammary gland. Stage 1V is the most advanced disease with a tumor of any size, massive involvement of lymph nodes and any distant metastases.

As used herein, "whole TIP-2 antigen protein" comprises the amino acid sequence shown in FIG. 29 (SEQ ID NO:1).

The present invention further provides a vaccine comprising a monoclonal antibody produced by the method described herein and a suitable carrier.

The present invention also provides a vaccine comprising an effective amount of a monoclonal antibody of this invention and a pharmaceutically acceptable carrier.

According to certain embodiments of this invention, the condition is cancer and the amount of monoclonal antibody is sufficient to inhibit the growth of or eliminate the cancer. According to certain embodiments, the cancer is breast cancer, thyroid cancer or prostate cancer. According to certain embodiments, the condition is an infection and the amount of monoclonal antibody is sufficient to inhibit the growth of or kill the infectious agent.

According to certain embodiments, the infectious agent is Hanta virus, HTLV I, HTLV II, HIV, herpes virus, influenza virus, Ebola virus, human papilloma virus, *Staphylococcus, Streptococcus, Kiebsiella, E. coli*, anthrax or *cryptococcus*. According to certain embodiments, the condition is associated with a toxin and the amount of monoclonal antibody is sufficient to reduce the amount of or destroy the toxin. According to certain embodiments, the toxin is tetanus, anthrax, botulinum, snake venom or spider venom. According to certain embodiments, the condition is an autoimmune disease and the amount of monoclonal antibody is sufficient to reduce the amount of or destroy the offending antibody. In certain embodiments of this invention, the autoimmune disease is lupus, thyroiditis, graft versus host disease, transplantation rejection or rheumatoid arthritis.

According to certain embodiments of this invention, the monoclonal antibody is coupled to an effector molecule. According to another embodiment of this invention, the effector molecule is a cytotoxic agent, drug, enzyme, dye, or radioisotope. In another embodiment of this invention, the monoclonal antibody is coupled to a carrier. According to another embodiment of this invention, the carrier is a liposome.

The present invention further provides a method of treating a condition in a subject comprising administering to the subject an amount of the above-described vaccine effective to bind the antigen associated with the condition, thereby treating the condition in the subject.

The present invention further provides a method of preventing a condition in a subject comprising administering to the subject an amount of the above-described vaccine effective to bind the antigen associated with the condition, thereby preventing the condition in the subject. In an embodiment of the invention, the subject previously exhibited the condition. In another embodiment of the invention, the vaccine is administered to a second subject.

According to an embodiment of the invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, or rejection of a transplanted tissue. In another embodiment of the invention, the condition is septicemia, sepsis, septic shock, viremia, bacteremia or fungemia.

According to another embodiment of the invention, the cancer is thyroid cancer, breast cancer or prostate cancer. In another embodiment of the invention, the infectious agent is Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*. According to another embodiment of the invention, the toxin is tetanus, anthrax, botulinum, snake venom or spider venom. In a further embodiment of the invention, the tumor is benign.

In yet another embodiment of the invention, the enzyme dysfunction is hyperactivity or overproduction of the enzyme. According to a further embodiment of the invention, the hormone dysfunction is hyperactivity or overproduction of the hormone. In another embodiment of the invention, the immune dysfunction is CD3 or CD4 mediated. In a further embodiment of the invention, the autoimmune disease is lupus, thyroiditis, graft versus host disease, transplantation rejection or rheumatoid arthritis.

The present invention further provides a vaccine comprising a whole TIP-2 antigen protein or a peptide form of TIP-2 and a suitable carrier.

The present invention also provides a vaccine comprising an effective amount of a whole TIP-2 antigen protein or a peptide form of TIP-2 and a pharmaceutically acceptable carrier.

According to certain embodiments of this invention, the condition is cancer and the amount of whole TIP-2 antigen protein or a peptide form of TIP-2 is sufficient to inhibit the growth of or eliminate the cancer. According to certain embodiments, the cancer is breast cancer, thyroid cancer or prostate cancer. According to certain embodiments, the condition is an infection and the amount of monoclonal antibody is sufficient to inhibit the growth of or kill the infectious agent. According to certain embodiments, the infectious agent is Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*. According to certain embodiments, the condition is associated with a toxin and the amount of monoclonal antibody is sufficient to reduce the amount of or destroy the toxin. According to certain embodiments, the toxin is tetanus, anthrax, botulinum, snake venom or spider venom. According to certain embodiments, the condition is an autoimmune disease and the amount of monoclonal antibody is sufficient to reduce the amount of or destroy the offending antibody. In certain embodiments of this invention, the autoimmune disease is lupus, thyroiditis, graft versus host disease, transplantation rejection or rheumatoid arthritis.

According to certain embodiments of this invention, the whole TIP-2 antigen protein or peptide form of TIP2 is coupled to an effector molecule. According to another embodiment of this invention, the effector molecule is a cytotoxic agent, drug, enzyme, dye, or radioisotope. In another embodiment of this invention, the monoclonal antibody is coupled to a carrier. According to another embodiment of this invention, the carrier is a liposome.

The present invention further provides a method of treating a condition in a subject comprising administering to the subject an amount of the above-described vaccine effective to bind the antigen associated with the condition, thereby treating the condition in the subject.

The present invention further provides a method of preventing a condition in a subject comprising administering to the subject an amount of the above-described vaccine effective to bind the antigen associated with the condition, thereby preventing the condition in the subject. In an embodiment of the invention, the subject previously exhibited the condition. In another embodiment of the invention, the vaccine is administered to a second subject.

According to an embodiment of the invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, or rejection of a transplanted tissue. In another embodiment of the invention, the condition is septicemia, sepsis, septic shock, viremia, bacteremia or fungemia.

According to another embodiment of the invention, the cancer is thyroid cancer, breast cancer or prostate cancer. In another embodiment of the invention, the infectious agent is Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*. According to another embodiment of the invention, the toxin is tetanus, anthrax, botulinum, snake venom or spider venom. In a further embodiment of the invention, the tumor is benign. In yet another embodiment of the invention, the enzyme dysfunction is hyperactivity or overproduction of the enzyme. According to a further embodiment of the invention, the hormone dysfunction is hyperactivity or overproduction of the hormone. In another embodiment of the invention, the immune dysfunction is CD3 or CD4 mediated. In a further embodiment of the invention, the autoimmune disease is lupus, thyroiditis, graft versus host disease, transplantation rejection or rheumatoid arthritis.

The present invention further provides a vaccine comprising dendritic cells which have been removed from a patient and contacted with a whole TIP-2 antigen protein or a peptide form of TIP-2 and a suitable carrier.

The present invention also provides a vaccine comprising an effective amount of dendritic cells which have been removed from a patient and contacted with a whole TIP-2 antigen protein or a peptide form of TIP-2 and a pharmaceutically acceptable carrier.

According to certain embodiments of this invention, the condition is cancer and the amount of dendritic cells which have been removed from a patient and contacted with whole TIP-2 antigen protein or a peptide form of TIP-2 is sufficient to inhibit the growth of or eliminate the cancer. According to certain embodiments, the cancer is breast cancer, thyroid cancer or prostate cancer. According to certain embodiments, the condition is an infection and the amount of monoclonal antibody is sufficient to inhibit the growth of or kill the infectious agent. According to certain embodiments, the infectious agent is Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*. According to certain embodiments, the condition is associated with a toxin and the amount of monoclonal antibody is sufficient to reduce the amount of or destroy the toxin. According to certain embodiments, the toxin is tetanus, anthrax, botulinum, snake venom or spider venom. According to certain embodiments, the condition is an autoimmune disease and the amount of monoclonal antibody is sufficient to reduce the amount of or destroy the offending antibody. In certain embodiments of this invention, the autoimmune disease is lupus, thyroiditis, graft versus host disease, transplantation rejection or rheumatoid arthritis.

According to certain embodiments of this invention, the dendritic cells which have been removed from a patient and contacted with whole TIP-2 antigen protein or peptide form of TIP-2 is coupled to an effector molecule. According to another embodiment of this invention, the effector molecule is a cytotoxic agent, drug, enzyme, dye, or radioisotope. In another embodiment of this invention, the monoclonal antibody is coupled to a carrier. According to another embodiment of this invention, the carrier is a liposome.

The present invention further provides a method of treating a condition in a subject comprising administering to the subject an amount of the above-described vaccine effective to bind the antigen associated with the condition, thereby treating the condition in the subject.

The present invention further provides a method of preventing a condition in a subject comprising administering to the subject an amount of the above-described vaccine effective to bind the antigen associated with the condition, thereby preventing the condition in the subject. In an embodiment of the invention, the subject previously exhibited the condition. In another embodiment of the invention, the vaccine is administered to a second subject.

According to an embodiment of the invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, or rejection of a transplanted tissue. In another embodiment of the invention, the condition is septicemia, sepsis, septic shock, viremia, bacteremia or fungemia.

According to another embodiment of the invention, the cancer is thyroid cancer, breast cancer or prostate cancer. In another embodiment of the invention, the infectious agent is Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*. According to another embodiment of the invention, the toxin is tetanus, anthrax, botulinum, snake venom or spider venom. In a further embodiment of the invention, the tumor is benign. In yet another embodiment of the invention, the enzyme dysfunction is hyperactivity or overproduction of the enzyme. According to a further embodiment of the invention, the hormone dysfunction is hyperactivity or overproduction of the hormone. In another embodiment of the invention, the immune dysfunction is CD3 or CD4 mediated. In a further embodiment of the invention, the autoimmune disease is lupus, thyroiditis, graft versus host disease, transplantation rejection or rheumatoid arthritis.

A monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598).

A murine monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598).

A chimeric monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598).

A humanized monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598

A human monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598).

In one embodiment of the invention, the monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598) binds to the same epitope as monoclonal antibody 27.B1.

The monoclonal antibody 27.B1 produced by hybridoma 27.B1 (ATCC Designation No. PTA-1599).

A hybridoma cell producing a monoclonal antibody of which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598).

The hybridoma cell designated 27.B1 (ATCC Accession No. PTA-1599).

A monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598) labeled with a detectable marker.

A monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1596) labeled with a detectable marker, wherein the detectable marker is a radioactive isotope, enzyme, dye, biotin, fluorescent label or chemiluminescent label.

A monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598) conjugated to a therapeutic agent.

A monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598) conjugated to a therapeutic agent, wherein the therapeutic agent is a radioisotope, toxin, toxoid or chemotherapeutic agent.

A monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598) conjugated to an imaging agent.

A monoclonal antibody which specifically binds and forms a complex with TIP-2 antigen located on the surface of human cancer cells, wherein the monoclonal antibody binds to the same antigen as monoclonal antibody 27.B1 produced by hybridoma 27.B1 (ATCC Designation No. PTA-1599) or monoclonal antibody 27.F7 produced by hybridoma 27.F7 (ATCC Designation No. PTA-1598) conjugated to an imaging agent, wherein the imaging agent is a radioisotope.

A monoclonal antibody which specifically binds and forms a complex with TIP-2 antigen located on the surface of human cancer cells, wherein the monoclonal antibody binds to the same epitope as monoclonal antibody 27.F7.

The monoclonal antibody 27.F7 produced by hybridoma 27.F7 (ATCC Designation No. 1598).

A hybridoma designated 27.F7 (ATCC Designation No. 1598).

A method of detecting TIP-2 antigen bearing cancer cells in a sample comprising:
  a) contacting the sample with an antibody directed to an epitope on TIP-2 antigen, or an Fab fragment of an antibody directed to an epitope on TIP-2 antigen, which epitope is recognized by the antibody or the Fab fragment, said antibody or Fab fragment being detectably labeled, under appropriate conditions to produce an antibody/Fab fragment-antigen complex comprising the detectably labeled antibody or Fab fragment bound to any TIP-2 antigen on the surface of cells in the sample;
  b) removing any labeled antibody/Fab fragment not bound in the antibody/Fab fragment-antigen complex formed in step (a); and
  c) determining presence of the antibody/Fab fragment-antigen complex by detecting the label of the detectably labeled antibody, presence of antibody/Fab fragment-antigen complex indicating TIP-2 antigen-bearing cancer cells in the sample.

In an embodiment of the instant method of the detectable label is selected from the group consisting of a radioactive isotope, enzyme, dye, biotin, fluorescent label or chemiluminescent label.

In an embodiment of the instant method, the TIP-2 antigen-bearing cancer cells are human cancer cells.

In an embodiment of the instant method the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of the instant method the antibody is a monoclonal antibody.

In an embodiment of the instant method of the invention the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the monoclonal antibody is a human monoclonal antibody or a murine monoclonal antibody.

In an embodiment of the instant method the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of the instant method TIP-2 is concentrated from the sample by alcohol precipitation prior to step (a).

In an embodiment of the instant method the sample is culture media.

A method of detecting TIP-2 antigen bearing cancer cells in a sample comprising:
  a) contacting the sample with an antibody directed to an epitope on TIP-2 antigen, or an Fab fragment of an antibody directed to an epitope on TIP-2 antigen, which epitope is recognized by the antibody or the Fab fragment under appropriate conditions to produce an antibody/Fab fragment-antigen complex comprising the antibody or Fab fragment bound to any TIP-2 antigen on the surface of cells in the sample;
  b) removing any antibody/Fab fragment not bound in the antibody/Fab fragment-antigen complex formed in step (a);
  c) contacting the antibody/Fab fragment-antigen complex of step (b) with a second antibody which specifically binds to the antibody/Fab fragment-antigen complex, said second antibody being detectably labeled, under appropriate conditions to permit the second labeled antibody to bind to the antibody/Fab fragment-antigen complex;
  d) removing any second labeled antibody not bound to the antibody/Fab fragment-antigen complex product in (c); and
  e) determining presence of the antibody/Fab fragment-antigen complex bound to the second labeled antibody by detecting the label of second antibody, presence of antibody/Fab fragment-antigen complex indicating TIP-2 antigen-bearing human cancer cells in the sample.

In an embodiment of the instant method the detectable label is a radioactive isotope, enzyme, dye, biotin, fluorescent label or chemiluminescent label.

In an embodiment of the instant method the TIP-2 antigen-bearing cancer cells are human cancer cells.

In an embodiment of the instant method the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of the instant method the antibody is a monoclonal antibody.

In an embodiment of the instant method the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the monoclonal antibody is a human monoclonal antibody or a murine monoclonal antibody.

In an embodiment of the instant method the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of the instant method TIP-2 is concentrated from the sample by alcohol precipitation prior to step (a).

A method for diagnosing cancer in a subject by detecting TIP-2 antigen-bearing cancer cells which comprises:
  (a) obtaining a sample of the subject's peripheral blood;
  (b) contacting the sample with an antibody directed to an epitope on TIP-2 antigen or an Fab fragment thereof, which epitope is recognized by the antibody or an Fab fragment thereof, said antibody being detectably labeled, under appropriate conditions to produce an antibody/Fab fragment-TIP-2 antigen complex comprising the detectably labeled antibody bound to any TIP-2 antigen on the surface of cells in the sample;
  (c) removing any labeled antibody/Fab fragment not bound in the antibody/Fab fragment-TIP-2 antigen complex formed in step (b); and
  (d) determining presence of the antibody/Fab fragment-TIP-2 antigen complex by detecting the label of the detectably labeled antibody, presence of antibody/Fab fragment-TIP-2 antigen complex indicating diagnosis of cancer in the subject.

In an embodiment of the instant method the detectable label is a radioactive isotope, enzyme, dye, biotin, fluorescent label or chemiluminescent label.

In an embodiment of the instant method the subject is human.

In an embodiment of the instant method the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of the instant method the antibody is a monoclonal antibody.

In an embodiment of the instant method the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the antibody is a human monoclonal antibody or a murine monoclonal antibody.

In an embodiment of the instant method the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of the instant method TIP-2 is concentrated from the sample by alcohol precipitation prior to step (a).

A method for diagnosing cancer in a subject by detecting TIP-2 antigen-bearing cancer cells which comprises:
  a) obtaining a sample of the subject's peripheral blood;
  b) contacting the sample with an antibody directed to an epitope on TIP-2 antigen or Fab fragment thereof, which epitope is recognized by monoclonal antibody/Fab fragment or Fab fragment thereof, under appropriate conditions to produce an antibody/Fab fragment-TIP-2 antigen complex comprising the antibody bound to any TIP-2 antigen on the surface of cells in the sample;
  c) removing any antibody/Fab fragment not bound in the antibody/Fab fragment-TIP-2 antigen complex formed in step (b);
  d) contacting the antibody/Fab fragment-TIP-2 antigen complex of step (c) with a second antibody which specifically binds to the antibody/Fab fragment-TIP-2 antigen complex, said second antibody being detectably labeled, under appropriate conditions to permit the second labeled antibody to bind to the antibody/Fab fragment-TIP-2 antigen complex;
  e) removing any second labeled antibody not bound to the antibody/Fab fragment-TIP-2 antigen complex product in (d); and
  f) determining presence of the antibody/Fab fragment-TIP-2 antigen complex bound to the second labeled antibody by detecting the label of second antibody, presence of antibody/Fab fragment-TIP-2 antigen complex indicating diagnosis of cancer in the subject.

In an embodiment of the instant method the detectable label is a radioactive isotope, enzyme, dye, biotin, fluorescent label or chemiluminescent label.

In an embodiment of the instant method the subject is human.

In an embodiment of the instant method the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of the instant method the antibody is a monoclonal antibody.

In an embodiment of the instant method the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the antibody is a human monoclonal antibody or a murine monoclonal antibody.

In an embodiment of the instant method the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of the instant method TIP-2 is concentrated from the sample by alcohol precipitation prior to step (a).

An in vivo method for diagnosing cancer in a subject by detecting TIP-2 antigen-bearing cancer cells which comprises:
  a) administering to the subject an antibody directed to an epitope on TIP-2 antigen or Fab fragment thereof, which epitope is recognized by the antibody or the Fab fragment, said antibody being detectably labeled, under appropriate conditions to bind the antibody to TIP-2 antigen on the surface of any cells in the subject; and b) determining presence of the detectably labeled antibody bound to the surface of cells in the subject, presence of detectably labeled antibody bound to cells indicating diagnosis of cancer in the subject.

In an embodiment of the instant method the detectable label is a radioactive isotope, enzyme, dye, biotin, fluorescent label or chemiluminescent label.

In an embodiment of the instant method the subject is human.

In an embodiment of the instant method the cancer is human melanoma, basal cell carcinoma, squamous cell carcinoma, neuroblastoma, glioblastoma multiforme, myeloid leukemia, breast carcinoma, colon carcinoma, endometrial carcinoma, lung carcinoma, ovarian carcinoma, prostate carcinoma, cervical carcinoma, osteosarcoma, testicular carcinoma and lymphoma.

In an embodiment of the instant method the antibody is a monoclonal antibody.

In an embodiment of the instant method the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the antibody is a human monoclonal antibody or a murine monoclonal antibody.

In an embodiment of the instant method in step (b) presence of the antibody or Fab fragment thereof bound to the surface of cells in the subject is detected, wherein the means for detecting the detectable label is an imaging device.

In an embodiment of the instant method the imaging device is a magnetic resonance imaging device.

In an embodiment of the instant method the imaging device is an X-ray immunoscintigraphy imaging device.

A method for delivering exogenous material to TIP-2 antigen-bearing cancer cells of a human subject comprising administering to the subject a liposome carrying a conjugate of the exogenous material, wherein an antibody or Fab fragment of the antibody is coupled to the outer surface of the liposome to target delivery to the cancer cells.

In an embodiment of the instant method the exogenous material is selected from the group consisting of anti-cancer drugs, radioisotopes, toxins, antibiotics, prodrugs, enzymes, and chemotherapeutic compounds.

In an embodiment of the instant method the TIP-2 antigen-bearing cancer cells are human melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

A method for treating cancer in a human subject by evoking a specific immune response which comprises administering to the subject a whole TIP-2 antigen protein or a peptide fragment of TIP-2 to the subject.

In an embodiment of the instant method the specific immune response is complement-dependent cytolysis of TIP-2 antigen-bearing cancer cells.

In an embodiment of the instant method the specific immune response is activation of natural killer cells towards TIP-2 antigen-bearing cancer cells.

In an embodiment of the instant method the peptide fragment of TIP-2 antigen comprises the amino acid sequence Lys Leu Leu Gly Gly Gln Ile Gly Leu (SEQ ID NO:3).

In an embodiment of the instant method the peptide fragment of TIP-2 antigen comprises the amino acid sequence Ser Leu Leu Gly Cys Arg His Tyr Glu Val (SEQ ID NO:4).

A method for treating cancer in a human subject by inducing apoptosis of cancer cells which comprises administering to the subject a whole TIP-2 antigen protein or a peptide fragment of TIP-2 to the subject.

A method for treating cancer in a human subject by evoking a specific immune response which comprises:
  a) removing dendritic cells from said subject;
  b) contacting the dendritic cells of step (a) with a whole TIP-2 antigen protein or a peptide fragment of TIP-2; and
  c) reintroducing the dendritic cells of step (b) into said subject.

In an embodiment of the instant method the peptide fragment of TIP-2 antigen comprises the amino acid sequence Lys Leu Leu Gly Gly Gln Ile Gly Leu (SEQ ID NO:3).

In an embodiment of the instant method the peptide fragment of TIP-2 antigen comprises the amino acid sequence Ser Leu Leu Gly Cys Arg His Tyr Giu Val (SEQ ID NO:4).

In an embodiment of the instant method the specific immune response is complement-dependent cytolysis of TIP-2 antigen-bearing cancer cells.

In an embodiment of the instant method the specific immune response is activation of natural killer cells or macrophages towards TIP-2 antigen-bearing cancer cells.

In an embodiment of the instant method the specific immune response is the production of antibodies in the subject against the whole TIP-2 antigen protein or the peptide fragment of TIP-2.

A method for treating cancer in a human subject by inducing apoptosis of cancer cells which comprises administering a whole TIP-2 antigen protein or a peptide fragment of TIP-2 to the subject.

A method for treating cancer in a human subject by passive immunization which comprises administering an antibody directed to an epitope on TIP-2 antigen or a peptide fragment thereof.

In an embodiment of the instant method the antibody induces apoptosis of TIP-2 antigen bearing cells.

An isolated peptide having the amino acid sequence Lys Leu Leu Gly Gly Gln Ile Gly Leu (SEQ ID NO:3).

An isolated peptide having the amino acid sequence Ser Leu Leu Gly Cys Arg His Tyr Glu Val (SEQ ID NO:4).

A method for immunohistochemical screening of a tissue section from a tumor sample for the presence of TIP-2 antigen bearing cancer cells which comprises:
  a) contacting the tissue section from the tumor sample with an antibody directed to an epitope on TIP-2 antigen or Fab fragment thereof, which epitope is recognized by the antibody or Fab fragment said antibody/Fab fragment being detectably labeled, under appropriate conditions to produce an antibody/Fab fragment-TIP-2 antigen complex comprising the detectably labeled antibody bound to any TIP-2 antigen on the surface of cells in the tissue section;
  b) removing any labeled antibody/Fab fragment not bound in the antibody/Fab fragment-TIP-2 antigen complex formed in step (a); and c) determining presence of the antibody/Fab fragment-TIP-2 antigen complex by detecting the label of the detectably labeled antibody, presence of antibody/Fab fragment-TIP-2 antigen complex indicating TIP-2 antigen-bearing human cancer cells in the sample.

In an embodiment of the instant method the tissue section is preserved freshly frozen tissue or formalin-fixed tissue.

In an embodiment of the instant method the detectable label is a radioactive isotope, enzyme, dye, biotin, fluorescent label or chemiluminescent label.

In an embodiment of the instant method the TIP-2 antigen-bearing cancer cells are human cancer cells.

In an embodiment of the instant method the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of the instant method the antibody is a monoclonal antibody.

In an embodiment of the instant method the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the antibody is a human monoclonal antibody or a murine monoclonal antibody.

A kit for detecting the presence of TIP-2 antigen-bearing cancer cells in a sample comprising:
  a) a solid support having a plurality of covalently linked probes which may be the same or different, each probe of which comprises a monoclonal antibody directed to an epitope on TIP-2 antigen or Fab fragment thereof; and
  b) a means for determining the presence of monoclonal antibody/Fab fragment-TIP-2 antigen complex.

In an embodiment of the instant kit the means for determining the presence of the monoclonal antibody/Fab fragment-TIP-2 antigen complex is a detectably labeled second antibody which specifically binds to the monoclonal antibody directed to the epitope on TIP-2 antigen.

In an embodiment of the instant kit the monoclonal antibody directed to the epitope on TIP-2 antigen is human monoclonal antibody 27.F7 directed to an epitope on TIP-2 antigen, which epitope is recognized by monoclonal antibody 27.F7 produced by the hybridoma designated 27.F7 (ATCC Designation No. PTA-1598).

In an embodiment of the instant kit the monoclonal antibody directed to the epitope on TIP-2 antigen is human monoclonal antibody 27.B1 directed to an epitope on TIP-2 antigen, which epitope is recognized by monoclonal antibody 27.B1 produced by the hybridoma designated 27.B1 (ATCC Designation No. PTA-1599).

In an embodiment of the instant kit the detectable label is a radioactive isotope, enzyme, dye, biotin, fluorescent label or chemiluminescent label.

In an embodiment of the instant kit the TIP-2 antigen-bearing cancer cells are human cancer cells.

In an embodiment of the instant kit the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of the instant kit the antibody is a monoclonal antibody.

In an embodiment of the instant kit the antibody is a human monoclonal antibody or a murine monoclonal antibody.

In an embodiment of the instant kit the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, culture media, and other tumors where TIP-2 can be an associated antigen.

In an embodiment of the instant kit the sample is culture media.

In an embodiment of the instant kit the sample is a tumor sample.

A method for detecting the presence of TIP-2 antigen in biological fluid comprising:
  a) contacting a sample of the biological fluid with a antibody directed to an epitope on TIP-2 antigen or Fab fragment thereof, which epitope is recognized by the antibody or Fab fragment thereof, said antibody being detectably labeled, under appropriate conditions to produce an antibody/Fab fragment-TIP-2 antigen complex comprising the detectably labeled antibody bound to any TIP-2 antigen on the surface of cells in the sample;
  b) removing any labeled antibody not bound in the antibody/Fab fragment-TIP-2 antigen complex formed in step (a); and
  c) determining presence of the antibody/Fab fragment-TIP-2 antigen complex by detecting the label of the detectably labeled antibody, presence of antibody/Fab fragment-TIP-2 antigen complex indicating TIP-2 antigen-bearing human cancer cells in the biological fluid.

In an embodiment of the instant method the detectable label is a radioactive isotope, enzyme, dye, biotin, fluorescent label or chemiluminescent label.

In an embodiment of the instant method the TIP-2 antigen-bearing cancer cells are human cancer cells.

In an embodiment of the instant method the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of the instant method the antibody is a monoclonal antibody.

In an embodiment of the instant method the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the antibody is a human monoclonal antibody or a murine monoclonal antibody.

In an embodiment of the instant method the biological fluid is selected from the group consisting of serum, plasma, saliva, tears, mucosal discharge, urine, peritoneal fluid, cerebrospinal fluid, and lymphatic fluid.

In an embodiment of the instant method TIP-2 is concentrated from the sample by alcohol precipitation prior to step (a).

In an embodiment of the instant method the biological fluid is culture media.

In an embodiment of the instant method the monoclonal antibody directed to the epitope on TIP-2 antigen is human monoclonal antibody 27.F7 directed to an epitope on TIP-2 antigen, which epitope is recognized by monoclonal antibody 27.F7 produced by the hybridoma designated ATCC Accession No. PTA-1598.

In an embodiment of the instant method the monoclonal antibody directed to the epitope of TIP-2 antigen is a murine monoclonal antibody directed to an epitope on TIP-2 antigen.

In an embodiment of the instant method the TIP-2 antigen is present on TIP-2 antigen-bearing cancer cells in the biological fluid.

A method for monitoring progression of cancer wherein cancer cells are TIP-2 antigen-bearing cancer cells, in a subject comprising:
  a) administering to a subject diagnosed with cancer an antibody directed to an epitope on TIP-2 antigen or Fab fragment thereof, which epitope is recognized the antibody or Fab fragment thereof, said antibody being detectably labeled, under appropriate conditions to bind the antibody to TIP-2 antigen on the surface of any cells in the subject;
  b) determining presence of detectably labeled antibody/Fab fragment bound to the surface of cells in the subject;
  c) comparing the presence of detectably labeled antibody/Fab fragment bound to cells in step (b) with the presence of detectably labeled antibody bound to cells at (i) diagnosis time or (ii) after treatment, wherein a greater presence of detectably labeled antibody/Fab fragment bound to cells in step (b) than at (i) diagnosis time or (ii) after treatment, indicates progression of the cancer in the subject and a lesser presence of detectably labeled antibody/Fab fragment bound to cells in step (b) than at (i) diagnosis time or (ii) after treatment indicates regression of the cancer in the subject.

In an embodiment of the instant method the detectable label is a radioactive isotope, enzyme, dye, biotin, fluorescent label or chemiluminescent label.

In an embodiment of the instant method the TIP-2 antigen-bearing cancer cells are human cancer cells.

In an embodiment of the instant method the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells, testicular carcinoma cells and lymphoma cells.

In an embodiment of the instant method the antibody is a monoclonal antibody.

In an embodiment of the instant method the epitope is recognized by monoclonal antibody 27.F7 produced by the hybridoma designated 27.F7 (ATCC Designation No. PTA-1598).

In an embodiment of the instant method the epitope is recognized by monoclonal antibody 27.B1 produced by the hybridoma designated 27.B1 (ATCC Designation No. PTA-1599).

In an embodiment of the instant method the antibody is a human monoclonal antibody or a murine monoclonal antibody.

In an embodiment of the instant method in step (b) presence of the detectably labeled antibody/Fab fragment bound to the surface of cells in the subject is detected by means for detecting the detectable label, is an imaging device.

In an embodiment of the instant method the imaging device is magnetic resonance imaging device.

In an embodiment of the instant method the imaging device is an X-ray immunoscintigraphy-imaging device.

A method for diagnosing cancer associated with the expression of TIP-2 antigen in a human subject which comprises:
  (a) obtaining mRNA from a sample of the subject's peripheral blood;
  (b) preparing cDNA from the mRNA from step (a);
  (c) amplifying DNA encoding TIP-2 antigen present in the cDNA prepared in step (b) by a polymerase chain reaction utilizing at least two oligonucleotide primers, wherein each of the primers specifically hybridizes with DNA encoding TIP-2 antigen, wherein the primers comprise oligonucleotides having a sequence included within the sequence of SEQ ID NO:2; and
  (d) detecting the presence of any resulting amplified DNA, the presence of such amplified DNA being diagnostic for cancer associated with the expression of TIP-2 antigen.

In an embodiment of the instant method the presence of any amplified DNA in step (d) is detected using a labeled oligonucleotide probe which specifically hybridizes with the amplified DNA.

In an embodiment of the instant method the labeled probe is radiolabeled with $^{32}P$ or $^{33}P$.

A method for diagnosing cancer associated with the expression of TIP-2 antigen in a human subject which comprises:
  (a) obtaining mRNA from a sample of the subject's peripheral blood;
  (b) preparing cDNA from the mRNA from step (a);
  (c) amplifying DNA encoding TIP-2 antigen present in the cDNA prepared in step (b);
  (d) determining the amount of any resulting amplified DNA; and
  (e) comparing the amount of amplified DNA determined in step (d) with previously determined standard amounts of amplified DNA, each standard amount being indicative of a particular stage of cancer associated with the expression of TIP-2 antigen.

In an embodiment of the instant method the stage is precancerous cancer or benign dysplasia.

In an embodiment of the instant method the cancer is a tumor, cancer in the lymph nodes, or metastatic cancer.

A composition which comprises a suitable carrier and an effective amount of a monoclonal antibody, which monoclonal antibody is produced by a method comprising:
  (a) fusing a lymphoid cell capable of producing antibody with a trioma cell which does not produce any antibody and is obtained by fusing a heteromyeloma cell which does not produce any antibody with a human lymphoid cell so as to thereby form tetroma cells;

(b) incubating the tetroma cells formed in step (a) under conditions permissive for the production of antibody by the tetroma cells, so as to thereby produce the monoclonal antibody; and (c) recovering the monoclonal antibody so produced.

In an embodiment of the instant composition the monoclonal antibody is specific for an antigen associated with a condition in a subject.

In an embodiment of the instant composition, which comprises a suitable carrier and an effective amount of a monoclonal antibody, wherein the monoclonal antibody is specific for an antigen associated with a condition in a subject, the condition is cancer and the amount of monoclonal antibody is sufficient to inhibit the growth of or eliminate the cancer.

In an embodiment of the instant composition, which comprises a suitable carrier and an effective amount of a monoclonal antibody, wherein the monoclonal antibody is specific for an antigen associated with a condition in a subject, and wherein the condition is cancer and the amount of monoclonal antibody is sufficient to inhibit the growth of or eliminate the cancer, the cancer is breast cancer, thyroid cancer or prostate cancer.

In an embodiment of the instant composition which comprises a suitable carrier and an effective amount of a monoclonal antibody, wherein the monoclonal antibody is specific for an antigen associated with a condition in a subject, the condition is an infection and the amount of monoclonal antibody is sufficient to inhibit the growth of or kill the infectious agent.

In an embodiment of the instant composition, which comprises a suitable carrier and an effective amount of a monoclonal antibody, wherein the monoclonal antibody is specific for an antigen associated with a condition in a subject, and wherein the condition is an infection and the amount of monoclonal antibody is sufficient to inhibit the growth of or kill the infectious agent, the infectious agent is Hanta virus, HTLV I, HTLV II, HIV, herpes virus, influenza virus, Ebola virus, human papilloma virus, *Staphlococcus, Streptococcus, Klebsiella, E. coli*, anthrax or *cryptococcus*.

In an embodiment of the instant composition, which comprises a suitable carrier and an effective amount of a monoclonal antibody, wherein the monoclonal antibody is specific for an antigen associated with a condition in a subject, the condition is associated with a toxin and the amount of monoclonal antibody is sufficient to reduce the amount of or destroy the toxin.

In an embodiment of the instant composition, which comprises a suitable carrier and an effective amount of a monoclonal antibody, wherein the monoclonal antibody is specific for an antigen associated with a condition in a subject, and wherein the condition is associated with a toxin and the amount of monoclonal antibody is sufficient to reduce the amount of or destroy the toxin, the toxin is tetanus, anthrax, botulinum, snake venom or spider venom.

In an embodiment of the instant composition, which comprises a suitable carrier and an effective amount of a monoclonal antibody, wherein the monoclonal antibody is specific for an antigen associated with a condition in a subject, the condition is an autoimmune disease and the amount of monoclonal antibody is sufficient to reduce the amount of or destroy the offending antibody.

In an embodiment of the instant composition, which comprises a suitable carrier and an effective amount of a monoclonal antibody, wherein the monoclonal antibody is specific for an antigen associated with a condition in a subject, and wherein the condition is an autoimmune disease and the amount of monoclonal antibody is sufficient to reduce the amount of or destroy the offending antibody, the autoimmune disease is lupus, thyroiditis, graft versus host disease, transplantation rejection or rheumatoid arthritis.

In an embodiment of the instant composition which comprises a suitable carrier and an effective amount of a monoclonal antibody, wherein the monoclonal antibody is specific for an antigen associated with a condition in a subject, the monoclonal antibody is coupled to an effector molecule.

In an embodiment of the instant composition which comprises a suitable carrier and an effective amount of a monoclonal antibody, wherein the monoclonal antibody is specific for an antigen associated with a condition in a subject, wherein the monoclonal antibody is coupled to an effector molecule, the effector molecule is a cytotoxic agent, drug, enzyme, dye, or radioisotope.

In an embodiment of the instant composition which comprises a suitable carrier and an effective amount of a monoclonal antibody, wherein the monoclonal antibody is specific for an antigen associated with a condition in a subject, the monoclonal antibody is coupled to a carrier.

In an embodiment of the instant composition which comprises a suitable carrier and an effective amount of a monoclonal antibody, wherein the monoclonal antibody is specific for an antigen associated with a condition in a subject, wherein the monoclonal antibody is coupled to a carrier, the carrier is a liposome.

A method of treating a condition in a subject comprising administering to the subject an amount of the instant composition which comprises a suitable carrier and an effective amount of a monoclonal antibody, wherein the monoclonal antibody is specific for an antigen associated with a condition in a subject, effective to bind the antigen associated with the condition so as to treat the condition in the subject.

A method of preventing a condition in a subject comprising administering to the subject an amount of the instant composition which comprises a suitable carrier and an effective amount of a monoclonal antibody, wherein the monoclonal antibody is specific for an antigen associated with a condition in a subject, effective to bind the antigen associated with the condition so as to treat the condition in the subject.

In an embodiment of the instant method of preventing a condition in a subject comprising administering to the subject an amount of the instant composition the subject previously exhibited the condition.

In an embodiment of the instant method of the invention for treating or preventing a condition in a subject comprising administering to the subject an amount of the instant composition effective to bind the antigen associated with the condition so as to treat or prevent the condition in the subject, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, or rejection of a transplanted tissue.

In an embodiment of the instant method of the invention for treating or preventing a condition in a subject comprising administering to the subject an amount of the composition effective to bind the antigen associated with the condition so as to treat or prevent the condition in the subject, wherein the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, or rejection of a transplanted tissue, the condition is septicemia, sepsis, septic shock, viremia, bacteremia or fungemia.

In an embodiment of the instant method of the invention for treating or preventing a condition in a subject comprising administering to the subject an amount of the composition effective to bind the antigen associated with the condition so as to treat or prevent the condition in the subject the condition is associated with a cancer, the cancer is thyroid cancer, breast cancer or prostate cancer.

In an embodiment of the instant method of the invention for treating or preventing a condition in a subject comprising administering to the subject an amount of the composition effective to bind the antigen associated with the condition so as to treat or prevent the condition in the subject, wherein the condition is associated with an infectious agent, the infectious agent is Hanta virus, HTLV I, HTLV II, HIV, herpes virus, influenza virus, Ebola virus, human papilloma virus, *Staphylococcus, Streptococcus, Klebsiella, E. coli*, anthrax or *cryptococcus*.

In an embodiment of the instant method of the invention for treating or preventing a condition in a subject comprising administering to the subject an amount of the composition effective to bind the antigen associated with the condition so as to treat or prevent the condition in the subject, wherein the condition is associated with a toxin, and wherein the toxin is tetanus, anthrax, botulinum, snake venom or spider venom.

In an embodiment of the instant method of the invention for treating or preventing a condition in a subject comprising administering to the subject an amount of the composition effective to bind the antigen associated with the condition so as to treat or prevent the condition in the subject, wherein the condition is associated with a tumor, the tumor is benign.

In an embodiment of the instant method of the invention for treating or preventing a condition in a subject comprising administering to the subject an amount of the composition effective to bind the antigen associated with the condition so as to treat or prevent the condition in the subject, wherein the condition is associated with an enzyme dysfunction, the enzyme dysfunction is hyperactivity or overproduction of the enzyme.

In an embodiment of the instant method of the invention for treating or preventing a condition in a subject comprising administering to the subject an amount of the composition effective to bind the antigen associated with the condition so as to treat or prevent the condition in the subject, wherein the condition is associated with a hormone dysfunction, the hormone dysfunction is hyperactivity or overproduction of the hormone.

In an embodiment of the instant method of the invention for treating or preventing a condition in a subject comprising administering to the subject an amount of the composition effective to bind the antigen associated with the condition so as to treat or prevent the condition in the subject, wherein the condition is associated with an immune dysfunction, the immune dysfunction is CD3 or CD4 mediated.

In an embodiment of the instant method of the invention for treating or preventing a condition in a subject comprising administering to the subject an amount of the composition effective to bind the antigen associated with the condition so as to treat or prevent the condition in the subject, wherein the condition is associated with an autoimmune disease, and wherein the autoimmune disease is lupus, thyroiditis, graft versus host disease, transplantation rejection or rheumatoid arthritis.

In an embodiment of the instant composition, the heteromyeloma cell is the cell designated B6B11 (ATCC accession number HB-12481).

In an embodiment of the instant composition, the heteromylema cell is a B6B11-like cell.

In an embodiment of the instant composition, the human lymphoid cell is a myeloma cell.

In an embodiment of the instant composition, the human lymphoid cell is splenocyte or a lymph node cell.

In an embodiment of the instant composition, the trioma cell is the cell designated MFP-2 (ATCC accession number HB-12482).

This invention will be better understood from the Experimental Details which follow. However, one skilled in the art will readily appreciate that the specific methods and results discussed are merely illustrative of the invention as described more fully in the claims which follow thereafter.

Experimental Details:

FIRST SERIES OF EXPERIMENTS

Example 1

Construction of Mouse-Human Heteromyeloma for the Production of Human Monoclonal Antibodies Introduction B6B11 or B6B11-like cells may be produced by the fusion of mouse myeloma cells with human myeloma cells selected for non-secretion of antibody. The specific generation and application of heteromyeloma B6B11, is described herein below. B6B11 was obtained by fusing the mouse HAT-sensitive and G-418 resistant myeloma X63.Ag8.653 with the subclone of human myeloma RPMI 8226 selected for non secretion of lambda light chains. Fusion of human splenocytes and B6B11 cells resulted in a fusion frequency of 30-50 hybrids per $10^7$ cells. This is similar to the frequency of murine hybridoma formation. The hybrids are readily cloned by limiting dilution, produce antibodies for at least 10 month and grow in serum-free media. Two clones were obtained which secreted human IgM reactive against lipopolysaccharide (LPS) of Gram-negative bacteria. These clones were obtained by fusing in vitro immunized human splenocytes with the B6B11 cells. Anti-lipid A murine mAb is known to prevent development of septic shock (Shnyra A A, et al., 1990). Human mAbs have important clinical applications.

Results

Heteromyeloma B6B11. Heteromyeloma, B6B11, was generated by PEG-fusion of mouse myeloma 653 (HAT-sensitive, G-418) with human RPMI 8226, which was selected for non-secretion of lambda chains. Hybrids were selected in the presence of HAT and G-418. Selection for 8-Ag resistance was done by gradually increasing the 8-Ag concentration from 2 ug/ml to 20 ug/ml for 2.5-3 weeks. The HAT-sensitive hybrid population 653×8226 was twice cloned. Clones were tested for the ability to produce hybrids with human lymphocytes. One clone, designated as B6B11, was selected. B6B11 cells died in medium containing aminopterine, during a period of 5-6 days; no revertants were detected for more than 18 months. In RPMI 1640 supplemented with 10% fetal calf serum (FCS), the line had the doubling time of about 25-30 hours, the maximal density in 75 $cm^2$ flasks was approximately 1.5×$10^6$ cells/ml (in a volume of 30 ml). B6B11 culture medium was tested for the presence of human immunoglobulin by enzyme linked immunoassay (ELISA) using rabbit anti-human immunoglobulin. B6B11 exhibited secretion of IgG, IgM or IgA. Staining the cell preparations with MAH-L,H by PAP-technique detected no traces of cytoplasmic light and heavy chain human immunoglobulin.

Karyotyping. FIG. 1 illustrates the distribution of parental and B6B11 cells by chromosomal content. Chromosomal analysis of the heteromyeloma cells indicated that chromosomal number varies from 60 to 82.

Figure 2:

FIG. 2 shows a fragment of the G-banded karyotype of B6B11 cells. Normal mouse chromosomes constitute about 84% of the karyotype. There are several rearranged chromosomes. There are some markers for mouse myeloma chromosomes as well as rearranged heteromyeloma (human-mouse chimeric) chromosomes. One large telocentric chromosome was represented in all B6B11 metaphase plates examined. This suggested that the proximal portion of this chromosome contains mouse and the distal portion contains human genetic material of chromosome 3 (3p21.1-3p ter) Localization of human material was performed as described (33). In some of analyzed B6B11, cells human chromosome 19 and human chromosome 7 was deleted.

Fusion Of B6B11 Cells With Human Lymphocytes. Fusion of B6B11 cells with freshly isolated peripheral blood lymphocytes (PBL) and splenic lymphocytes (SPL) was performed as described herein below in the Experimental Procedures Section. Fusion of peripheral blood lymphocytes (PBL) and pokeweed mitogen (PWM) treated peripheral blood lymphocytes (PBL) resulted in low hybridoma yield (1-5 hybrids per $10^7$ lymphocytes), while fusion with splenic lymphocytes (SPL) and pokeweed mitogen (PWM) treated splenic lymphocytes (SPL) yielded 30-60 hybrids per $10^7$ cells (see Table 1). After the fusion, cells were seeded at a density of $1.5 \times 10^5$ cells per well. Variations in the cell ratios of 1:1 to 1:2 (heteromyeloma:lymphocyte) had no effect on the fusion efficiency for PBL or SPL. However, fusion efficiency was dramatically reduced at B6B11: lymphocyte ratios of 1:4 to 1:8.

TABLE 1

Fusion of human lymphocytes with B6B11 cells.

| | LYMPHOCYTES | | | |
|---|---|---|---|---|
| | PBL | PBL-PWM | SPL | SPL-PWM |
| Number of fusion | 4 | 6 | 10 | 8 |
| Number of wells | 1536 | 2304 | 4800 | 3072 |
| Growth[2], % | 4 | 6,9 | 55 | 72 |
| Hybrid populations[3] per $10^7$ lymphocytes | 1-3 | 3-5 | 30-50 | 40-60 |
| Wells with Ig secretion[4], % | 95 | 92 | 84 | 82 |

[1]Fresh isolated peripheral blood lymphocytes (PBL) and splenocytes (SPL) were activated with PWM (5 ug/ml) for 7-9 days in complete RPMI 1640 supplemented with 15% FCS.
[2]Wells with hybrids (% of the total well number)
[3]After fusion cells were seeded at a density of $15 \times 10^4$ cells/well
[4]Total Ig production was determined by ELISA with mouse monoclonal antibodies to H- and L-chains of human Ig The effects of splenocyte stimulation with various mitogens on the fusion efficiency are illustrated in FIG. 3. PWM treatment significantly increased the efficiency of SPL hybridization compared with ConA-treatment, PHA-treatment, LPS-treatment or untreated SPL. Fusion efficiency was dependent on the timing of the HAT addition. When HAT was added immediately following fusion, the yield decreased to 10-15 hybrids per $10^7$ lymphocytes (for SPL).

Cloning of hybrids with SPL and PBL (stimulated and non-stimulated) indicated that PBL could not be used for hybridoma formation. Cloning was performed 4-6 weeks after fusion in 50% epithelial conditioned media (ECM) (preincubated for 24 hours at 37° C. in 96-well plates) and 50% RPMI 1640 containing 15% FCS. Results were determined at in 2-2.5 weeks. Cloning efficiency (1.5-2 cells per well) was 50-80% for SPL and 10-30% for PBL. ELISA using rabbit anti-human immunoglobulin and MAH-L,H indicated that the total immunoglobulin production was present in 90-95% of growing hybrids with PBL and 80-85% with SPL hybridomas. Based on SPL was selected for PWM stimulation and in vitro immunization.

In order to increase the efficiency of hybridization, splenocytes were treated with 2.5 mM Leu-Ome and fused with B6B11 cells at ratio of 1:1 or 1:2 (B6B11: SPL) (see Table 2). The effect on this treatment was apparent after 18-24 hours of cultivation with PWM; SPL without Leu-Ome treatment exhibited blasts only after three days. The efficiency of hybridization of Leu-Ome-treated SPL was somewhat higher (80%) compared with non-treated SPL (72%). This treatment considerably increased (93%) the number of Ig-secreting hybrids.

TABLE 2

Effect of Leu-Ome treatment of splenocytes on the efficiency of their hybridization with B6B11 cells (data from 3 spleens)

| Lymphocytes | Number of wells | Wells with hybrid populations, (%) | Wells2 with Ig secretion, (%) |
|---|---|---|---|
| SPL | 1440 | 1034 (72) | 825 (80) |
| SPL-Leu-Ome | 864 | 691 (80) | 642 (93) |

[1]Splenocytes were isolated in LSM. One portion was treated with Leu-Ome (2.5 mM, 40 minutes in serum-free RPMI 1640), the other served as a control. Prior to fusion both portions were cultured for 7 days in complete RPMI 1640 supplemented with 15% FCS in the presence of 5 μg/ml PWM.
[2]Ig production was determined by ELISA with mouse monoclonal antibodies to H- and L-chains of human Ig.

The heteromyeloma cells were fused with Leu-Ome-treated splenocytes immunized with *Salmonella minnesota* Re595 (Re595) in the presence of PWM and mouse thymocyte conditioned media (TCM) (Table 3). The hybridoma culture supernatants were tested for anti-bacterial antibodies at different stages of hybrid growth: (1) after transferring responding populations to 24-well plates and (2) after cloning and subsequent clonal expansion. Two independent clones producing anti-bacterial antibodies were selected. ELISA using immobilized lipoplysaccharide (LPS) or immobilized Re595 and LPS in solution determined that the antibodies produced by both clones reacted with LPS.

ELISA using immobilized Re595 monoclonal mouse anti-human isotypes and goat anti-mouse peroxidase conjugate absorbed with human immunoglobulin, determined that the antibody isotype was IgM-kappa. Both clones were adapted to serum free media (SFM) by gradual replacing of the growth medium containing 10% FCS. The maximal density upon culturing in SFM was approximately $1.2 \times 10^6$ cells/ml. SFM-adapted cells were cloned as described above. The efficiency and cloning time were similar to those of the cells cultured in serum-supplemented RPMI 1640 medium.

TABLE 3

Fusion of in vitro immunized splenocytes[1] with B6B11 cells.

| | Number of fusion | | |
|---|---|---|---|
| | 1 | 2 | 3 |
| Number of wells | 288 | 864 | 576 |
| Wells with hybrid populations, (%) | 193 (69) | 734 (85) | 472 (82) |
| Wells with ig secretion, (%) | 173 (90) | 675 (92) | 420 (89) |
| Primary response[2] to Re595, number of wells | 9 (4.5) | — | 17 (3.6) |

TABLE 3-continued

Fusion of in vitro immunized splenocytes[1] with B6B11 cells.

| | Number of fusion | | |
|---|---|---|---|
| | 1 | 2 | 3 |
| Secondary response[3], number of wells | 2 | — | 16 |
| Number of responding populations after cloning | — | — | 2 |

[1]Splenocytes after treatment with Leu-Ome (2.5 mM, 40 min) were in vitro immunized with *S. minnesota* Re595 ($10^7$-$10^{10}$ cells/ml) in the presence of PWM (5 ug/ml) and TCM for 7-9 days. Fusions with B6B11 cells were done at ratios 1:1 and 1:2
[2]ELISA of hybridoma culture supernatants from 96-well plates (rabbit anti-human Ig).
[3]ELISA of hybridoma culture supernatants after transferring in 24-well plates (rabbit anti-human Ig).

DNA analysis. FIG. 4 illustrates the distribution of the DNA content by parental lines, B6B11 heteromyeloma and B6B11-splenocyte hybrid. The DNA of heteromyeloma cells consists of 78.7% of the total parental DNA. The DNA content of B6B11-splenocyte hybrid cells is 3% greater than that of B6B11 cells.

Discussion

A partner cell line for production of human monoclonal antibodies was generated by somatic hybridization of mouse X63.Ag8.653 and human RPMI 1640 myeloma cells. Adaptation to medium with 8-Ag, subsequent cloning and selection by hybridization efficiency led to a heterohybrid clone which was designated B6B11. Fusion between heterohybrid lines and lymphocytes gives essentially stable productive hybrids (Raison R L, et al., 1982). The mechanisms underlying this phenomenon are unknown. It is suggested that human chromosomes or their fragments retained in the partner line after the first fusion modify the intracellular environment in such a way that the human lymphocyte chromosomes or fragments after the second fusion are stabilized (Oestberg L, and Pursch E., 1983). The large number of chromosomes, the presence of hybrid marker chromosomes and increased DNA content observed in the experiments described herein, confirmed the hybrid nature of B6B11 cells. The DNA content of B6B11-SPL hybrid cells was also increased. Immunocytochemical testing for intracellular heavy and light chains and ELISA testing for immunoglobulin secretion demonstrated that B6B11 cells produce neither immunoglobulins nor heavy and light chains. Fusion of B6B11 with SPL resulted in more hybrids than fusion with PBL (30-50 per $10^7$ SPL compound to 1-5 per $10^7$ PBL). Cloning efficiency with SPL was 50-80% as compared to 10-30% with PBL. Thus SPL were the more preferable partner for fusion. The culture media was conditioned by endothelial cells; which was deemed crucial for viability and clonogeneity of the hybrids. In the case of B6B11-PBL hybrids, immunoglobulin secretion was detected in up to 95% of the hybrids. To increase the yield of immunoglobulin-secreting hybrids after fusion with SPL (up to 93%) Leu-Ome was used. Almost all hybrids secreted antibodies of unknown specificity. The antibody production by B6B11 hybrids was stable for at least 10 months. The hybrids were readily adapted to serum-free media, thereby facilitating a ex-vivo antibody production.

Two antibody-producing clones (with probably similar specificity to LPS of *S. minnesota* Re595) were obtained after fusion of immunized SPL with B6B11 cells. As demonstrated herein, human-mouse heteromyeloma, B6B11, is useful for producing human monoclonal antibodies to various antigens. Proper in vitro sensitization of lymphocytes is also of critical importance for generating human antibodies.

Experimental Procedures

Cell Culture. 8-Azaguanine (8-Ag) resistant mouse myeloma X63.Ag8.653 (653) cells were transfected with plasmid pBgl-neoR (Dr. A. Ibragimov) as described below. The myeloma cells were maintained in DMEM medium supplemented with 10% fetal calf serum (FCS), 4 mM L-glutamine, 1 mM Sodium pyruvate, non-essential amino acids and vitamins (Flow Laboratories). Prior to fusion the cells were passaged 3 times in the presence of 20 µg/ml 8-Ag (Sigma) and 500 µg/ml G-418 (Gibco).

Human myeloma cell line RPMI 8226 (8226) was cultured in RPMI 1640 medium with above-mentioned supplements (regular RPMI 1640). The hybrid heteromyeloma B6B11 was cultured either in regular RPMI 1640 with 10% FCS or in serum-free media which represented 1:1 mixture of Iscove's modification of Dulbecco medium (IMDM) and HAM F-12 (Flow Laboratories) supplemented with bovine serum albumin fraction #5, 2 mg/ml, (BSA) (Sigma), bovine insulin, 5 µg/ml (Serva), human transferrin, 5 µg/ml (Sigma), progesterone, 6 ng/ml (Gibco), hydrocortisone, 60 ng/ml (Gibco). Hybridomas were adapted to this serum free medium (SFM) by gradual replacement of the growth medium containing 10% FCS. All cells were cultured in a humidified atmosphere of 5.5% $CO_2$/94.5% air at 37° C.

Human peripheral blood lymphocytes (PBL) were isolated using lymphocytes separation medium (LSM) (Flow Laboratories) as per manufacturer instructions. Spleens collected at autopsy not later than 2 hours after death (males aged 50-60 years old) were homogenized and splenocytes (SPL) were isolated in LSM.

Production of Geneticin (G-418) Resistant 653 Myeloma Cells. Cells were washed in sterile phosphate buffered saline (PBS) without $Ca^{++}$ or $Mg^{++}$. pBgl-neoR Plasmid DNA linearized by BamH1 (constructed by P. Chumakov, Institute of Molecular Biology of the Academy of Sciences of the USSR, Moscow, USSR) was added to the cell suspension. Prior to adding the DNA to the cell suspension, the DNA was twice phenol extracted using phenol-ether at 4° C., 96% ethanol precipitated and dried under sterile conditions.

Transfection was performed by electroporation at 4° C. using a unit constructed by L. Chernomordik (Institute of Electrical Chemistry of the Academy of Sciences of the USSR, Moscow, USSR). Approximately $4×10^6$ 653 myeloma cells and 3.5 µg of plasmid DNA were combined in an 80 µl electroporation chamber. The final concentration of DNA was 44 µg/ml). An electrical current impulse of 1.7 Kv/cm was pulsed through the chamber for 100 µsec. After resting for 10 minutes the cells were transferred to 0.5 ml complete media in 16 $mm^2$ wells at $5×10^3$ and $2×10^4$ cells/well. After 36 hours, 0.5 ml of media containing 1 mg/ml of Geneticin (G-418) was added to a final concentration of 0.5 mg/ml. Subsequently, 50% of the media volume was changed every 2 days for 12 days.

Production of heteromyeloma. G-418-resistant 653 cells were mixed with 8226 cells at a 1:1 ratio and pelleted. 50% (v/v) polyethylenglycol (PEG) 3350 (Sigma) was added (200-300 µl per $4-5×10^7$ cells) for 1 min with constant stirring. Several portions of serum-free RPMI 1640 (RPMI-S⁻) were added for 5 minutes (first 10 ml), 1 minute (10 ml), and 1 minute (30 ml). Cells were pelletted resuspended in regular RPMI 1640 with 20% FCS, hypoxanthine ($1×10^4$ M), aminopterine ($4×10^7$ M), thymidine ($1.6×10^5$ M) (HAT, Flow Laboratories) and 500 µg/ml G-418 and seeded in 96-well plates (Linbro) at a density of $10^5$ cells per well. At two weeks the medium (½ volume) was replaced with medium containing hypoxanthine ($2\times10^4$ M), thymidine ($3.2\times10^5$M) (HT, Flow laboratories) and G-418 (500 µg/ml). The procedure was repeated after two weeks.

Production of human monoclonal antibodies. Fusion of B6B11 cells with human lymphocytes was accomplished by the above-described method with following modifications. Lymphocytes were mixed with B6B11 at a 1:1 or a 1:2 ratio, pelleted, washed with RPMI 1640-S- and incubated with PEG (600 µl per $10^5$ cells) for 3 minutes with constant stirring. The portions of added RPMI-S- were as follows: 10 ml/10 minutes, 10 ml/10 5 minutes, 10 ml/1 minute. Cells were pelleted, re-suspended in regular RPMI supplemented with 15% FCS and seeded in 96-well plates ($1.5\times10^5$ cells per well). HAT-medium was added after 24 hours. The growth medium (½ volume) was replaced with fresh HAT in 7-9 days. HAT-medium was replaced with HT-medium at 15-18 days.

Cloning. Parent heteromyeloma and hybridoma cells were cloned by the limiting dilution method in medium conditioned by human umbilical or aortic endothelial cells (Antonov A S, et al., 1986) (gift from Dr. A. Antonov) (ECM). 100 µl/well was incubated in 96-well plates at 37° C. overnight. Cells were planted at approximately 1 to 2 cells per well. The culture medium was tested for antibodies at 2.5-3 weeks.

Immunization in vitro. Freshly isolated lymphocytes were resuspended in RPMI-S- containing 2.5 mM L-leucine methyl ester (Leu-OMe) (Borrebaeck, C A K, et al., 1987) to a final concentration of 1 cells per ml. After 40 minutes of incubation at room temperature, cells were washed 3 times with RPMI-S- and resuspended in regular RPMI 1640 supplemented with 15% FCS. Medium conditioned by mouse thymocytes (TCM) was used as a source of lymphokines (Reading C L., 1982). Pokeweed mitogen (PWM) (Flow laboratories) to a final concentration 5 µg/ml, TCM (25%) and antigen in different concentrations were added to the cell suspension. The cell suspension ($4-6\times10^6$ cell/ml) was transferred to flasks (30 ml/75 cm² flask). Fusion was performed after 7-9 days of cultivation. Concanavalin A (ConA) (Flow 5-10 µg/ml), Phytohemagglutinin (PHA) (Flow, 5-10 µg/ml) and lipopolysaccharide (LPS) (SIGMA, 10-15 µg/ml) were used instead of PWM. S. minnesota Re595 (gift of Dr. O. Luderitz, Max Plank Institute fur Immunologie, Feiburg, Germany) was used as an antigen. The bacteria were grown in medium containing 16 g/l tryptic soy broth (TSB), Difco), 16 g/l brain-heart infusion (BHI) (Difco) and 4 g/l yeast extract (YE) (DIFCO) for 18 hours at 37° C. with constant stirring and then heat inactivated. The antigen concentration varied from $10^7$-$10^{10}$ cells/ml.

Determination of antibodies and non-specific Ig production. Enzyme linked immunoassay (ELISA) was used to test hybridoma supernatants for the presence of antibodies against Salmonella minnesota Re595 and LPS.

Screening for mAbs reactive against bacteria. 96-well plates were covered with glutaraldehyde (1%, 100 µl per well) for 2 hours at room temperature. The plates were washed with distilled water 3 times. Bacteria were resuspended in 50 mM ammonium carbonate buffer (pH 9.6) and transferred to plates ($5\times10^7$ cells in 100 µl per well), centrifuged at 780×g for 30 minutes and washed with distilled water 4 times. The supernatants tested (100 µl) were supplemented with 0.1% Tween 20 (Fluka), put into bacteria-containing wells and incubated for 1 hour at room temperature. The media was then removed and the wells were washed with distilled water. Affinity purified rabbit anti-human immunoglobulin conjugated to alkaline phosphatase (RAH-AP), diluted in tris-buffered solution (TBS, 50 mM, pH 7.4), containing 0.1% Tween 20 was added to 1 µg in 100 µl per well. After 1 hour of incubation at room temperature and 6 washes with distilled water 100 µl of 4-nitrophenyl-phosphate (1 mg/ml, Sigma) in diethanolamine buffer (10% diethanolamine, 0.5 mM $MgCl_2$, pH 9.8) was added. After 1 hour, the results were read using a Multiscan (Flow Laboratories) at 405 nm. The negative control was culture medium RPMI 1640 supplemented with 15% FCS.

Screening for mAbs reactive against lipopolysaccharide. LPS was purified from Salmonella minnesota Re595 as described (Galanos G, et al., 1969). The LPS preparation was sonicated and transferred to the plates at 2.5 µg per well in 5 mM ammonium carbonate buffer (pH 9.6). After overnight incubation at room temperature, the above described procedures for determining mAb reactive against bacteria were performed.

Screening for non-specific production of mAbs. Non-specific production of immunoglobulin and separate chains was assessed after the addition of 100 µl of rabbit anti-human immunoglobulin (10 µg/ml in phosphate buffer, PBS, pH 7.2) or 100 µl/well (10 ng/ml in PBS) of mouse monoclonal antibodies to light and heavy chains of human immunoglobulin (MAH-L, H) (Rokhlin O V, 1989) (gift of O. Rochlin, CRC, Moscow). Subsequent procedures were performed as described above.

Determination of the isotype of secreted antibodies. The isotype of human antibodies was determined by ELISA using murine anti-human light and heavy chains (MAH-L, H) and goat anti-mouse immunoglobulin (25 ug/ml) conjugated to peroxidase and absorbed with human immunoglobulin.

Determination of cytoplasmic light or heavy chains production. Production of cytoplasmic light and/or heavy chains in hybridomas, B6B11 and the parental cell lines was estimated immunocytochemically using the peroxidase-anti-peroxidase system (PAP). Cell smears were air-dried, fixed for 45 seconds with 10% formaldehyde (v/v) and 45% acetone (v/v) in phosphate buffered saline (PBS, 10 mM $NaH_2PO_4$, pH 6.6) and incubated with MAH-L,H (200 µl, 5-10 mg/ml). Then 1 ml rabbit anti-mouse immunoglobulin (38 mg/ml in PBS) was added. All incubations were 30 minutes. Washings were performed using PBS for 10 minutes.

Chromosomal analysis. Preparations of metaphase chromosomes were obtained by the following technique. Colchicine was added to cells during exponential growth (1.5-2 hours to parental lines and B6B11 cells). Cells were then trypsinized and stained for G-banding as described (Seabright S., 1971) (10-15 plates from each line). To count chromosome number, at least 50 metaphase figures were analyzed for each cell line.

DNA analysis by flow cytometry. To estimate the DNA content the cells ($1\times10^6$) were fixed with 1 ml 70% ethanol, washed, incubated for 2-3 hours with 0.3 mg/ml Ribonuclease A (Serva) in Hank's solution (pH 7.4) and stained for 2 hours with propidium iodide (0.05 mg/ml, Sigma) in Hank's solution. The DNA content was measured in a FACS-II cytofluorometer (Becton Dickinson). Fluorescence was excited by an argon ion laser at 488 nm (164-05 Model, Spectra-Physics) at a power of 400 mW and registered behind a 600 nm long pass interference filter (Ditric Optica).

Parental lines. The myeloma line 653 was maintained in DMEM supplemented with 10 FCS, 20 ng/ml 8-Azaguanine and 500 µg/ml G-418. The myeloma line 8226 producing lambda chains of human Ig was cultured in RPMI-C containing 10% FCS. In order to create a heteromyeloma, a non-producing clone of 8226 line was selected by cloning in ECM (2 cells per well). Lambda chain production was estimated at 2-2.5 weeks using MAH-L, H. The frequency of non-secreting clones was $1 \times 10^{-3}$.

Example 2

Trioma MFP-2, a Fusion Partner for Generating Human Monoclonal Antibodies

Introduction

A precursor hybridoma cell line was obtained by hybridization of the commercially available human myeloma cell line RPMI 8226 and mouse myeloma X63.Ag8.653 resistant to both 8-Azaguanine (8-Ag) and Geneticin 418 (G-418). One of the resulting clones, B6B11, was selected in the presence of G-418. B6B11 was grown in the presence of increased concentrations of 8-Ag and is resistant to both G-418 and 8-Ag (See Example 1).

Although B6B11 can be used to make human hybridomas by fusing with human lymph node-derived lymphocytes or spleen-derived lymphocytes, B6B11 was not capable of fusing with human peripheral blood lymphocytes (PBL) or resulted in a very low yield of hybrids (see example 1).

In order to overcome this problem, B6B11 was fused with human lymph node lymphocytes and several hybrids were obtained. The resulting cells were analyzed for human immunoglobulin production or production of separate immunoglobulin chains. Those clones, which did not synthesize immunoglobulin or immunoglobulin chains were selected for further evaluation in terms of fusion capability and antibody secretion potential. These hybrids were determined to be quite stable. These fusion products were designated "modified fusion partner" (MFP) cells. These MFP cells as the product of the fusion of the B6B11 hybridoma and lymphocytes are referred to herein as "trioma" cells because they are, in essence, the product of a three fused cells. One of the clones, MFP-2, exhibited a very high efficiency for fusing with peripheral blood lymphocytes as well as for fusing with human lymphocytes of any varied origin (i.e. lymph nodes, spleen, Peyer's patches etc). MFP-2 was selected on the basis of its superior characteristics and stability as a fusion partner and was used in the experiments described herein below.

The products of fusions between the MFP trioma cells and lymphocytes are referred to herein as "tetroma" cells becase they are, in essence, the product of four fused cells.

Results

Immunoglobulin Production. In order to demonstrate that human hybrioma (trioma) fusion partner cell line, MFP-2, is capable of fusing with human lymphocytes and producing high yields of hybrids with stable immunoglobulin production, experiments were performed using human lymphocytes from different sources.

The heteromyeloma cell line, B6B11 (precursor to MFP-2), can be fused with high efficiency with lymph node and spleen lymphocytes. (See, Example 1). Up to 90% of the resulting hybrids produced IgG or IgM. However, B6B11 was incapable of fusing to lymphocytes derived from peripheral blood (PBLs). The trioma cell line, MFP-2, (resulting from a fusion between B6B11 and human lymph node lymphocytes) overcame this problem and exhibited high fusion efficiency with PBL, yielding a high rate of immunoglobulin production by the resulting tetroma hybrids. The capability of MFP-2 to fuse with PBL was tested in two ways: (1) by fusion with freshly isolated lymphocytes in suspension, and (2) by fusion with thawed lymphocytes which had been stored frozen for various periods of time. (See Experimental Procedures). The results of these experiments are shown in FIG. 5.

The fusion efficiency was $10^5$ (1 hybrid per $10^5$ lymphmphocytes). Thirty primary hybridoma (tetroma) populations were obtained and analyzed for capacity to secrete immunoglobulin. (A primary hybridoma population is likely to be a mixture of two or more individual clones). Twenty-seven populations (90%) produced IgM at a level 5-fold greater than background. Twenty-four populations (80%) secreted IgE at a level 5-fold greater than background. The fusion of MFP-2 with lymphocyte suspensions which had been frozen and thawed also resulted in immunoglobulin-producing hybrids. Nineteen percent and 11% of these hybridoma populations produced human IgM and IgG respectively. The efficiency of fusion, itself, was not effected by the freeze-thaw procedure. These results demonstrate that both freshly isolated as well as frozen PBLs can be used to generate human hybridomas capable of producing antibody.

Identification of tumor-associated antigens and production of specific antibodies using the MFP-2 fusion partner: Human monoclonal antibodies against thyroglobulin. In this experiment, human anti-thyroglobulin antibodies were generated by MFP-2 fusion using lymph nodes from patients diagnosed with thyroid adenocarcinoma. A periclavicular lymph node was excised during lymphadenectomy surgery from a female thyroid cancer patient and lymphocytes were isolated and fused with MFP-2, generating tetroma cells.

Figure 6:
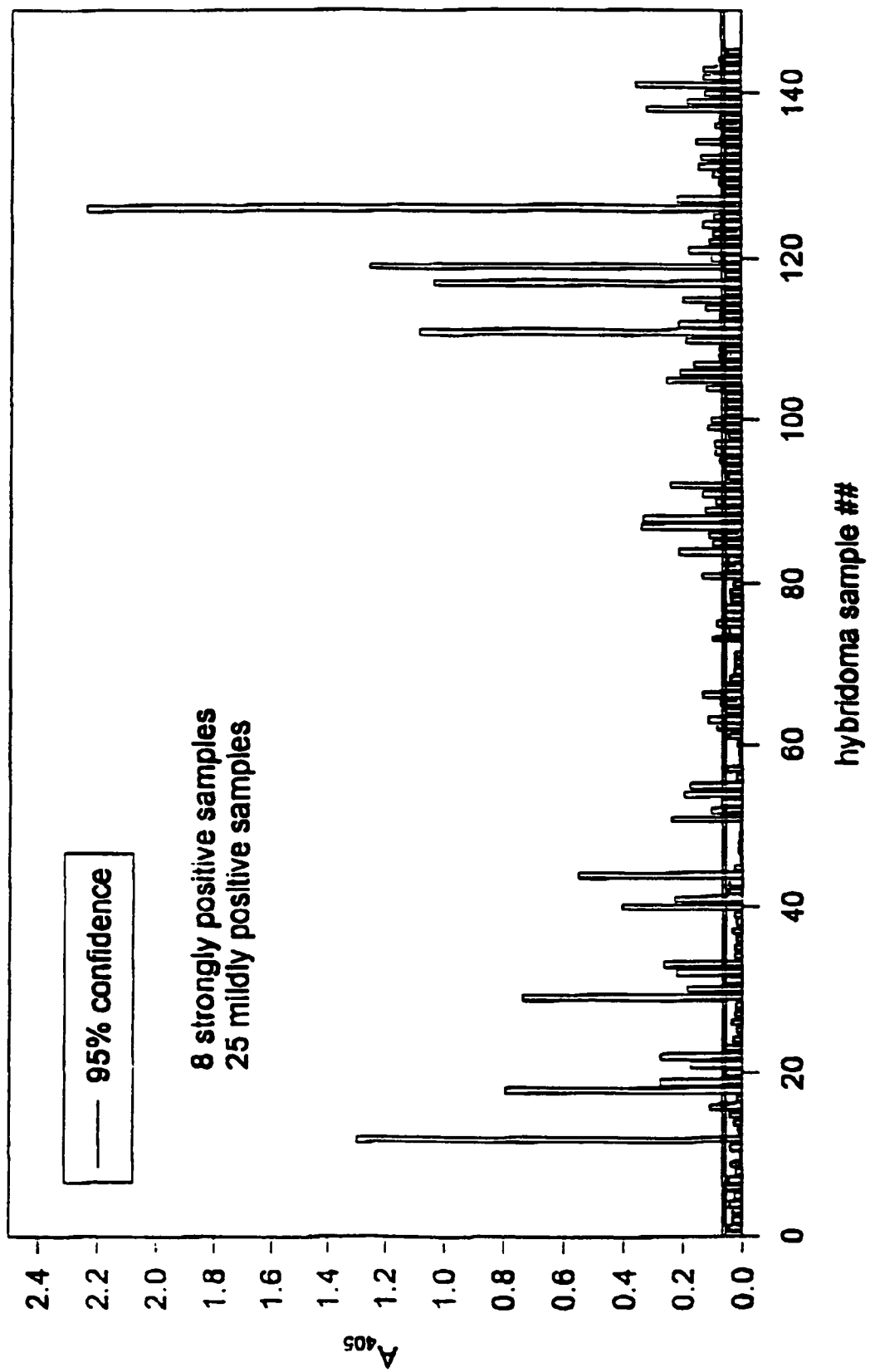

The resulting hybridomas (tetromas) were tested for production of human antibodies reactive against thyroglobulin using an enzyme linked immunoassay (ELISA) procedure. Purified human thyroglobulin was used to coat a microtitre plate. Results are shown in FIG. 6. Thirty-three of 144 tetromas exhibited a response against the thyroglobulin antigen. Eight of these were particularly strong. (See FIG. 6). Thus, lymph node-derived tetromas from this thyroid cancer patient were producing anti-thyroglobulin antibodies. This was an unexpected and surprising result because the patient had no known history of autoimmune (i.e. anti-thyroid antibodies) disease. This suggests that the antibodies produced in this patient to thyroglobulin were induced by the presence of cancerous thyroid adenocarcinoma cells. Cancerous thyroid adenocarcinoma cells are known to secrete thyroglobulin. This experiment demonstrates that tumor cells can induce a humoral immune response to tumor-associated antigens and that the antibody-producing cells can be identified and immortalized through the techniques described herein using the MFP-2 fusion partner in order to produce human anti-tumor monoclonal antibodies.

Production of human monoclonal antibodies against breast cancer associated antigens. In another experiment, human monoclonal antibodies were produced against cancer associated antigens using lymph node and peripheral blood lymphocytes from breast cancer patients. Axillary lymph nodes were excised from breast cancer patients who underwent mastectomy or lumpectomy. Lymphocytes isolated from these lymph nodes were fused to MFP-2 and the resulting tetromas were screened against breast cancer cell lines MCF7, SK-BR-3, ZR-75-1. Nearly all the tetromas were producing IgG or IgM (approximately 85% and 10% respectively). Surprisingly, nearly 15% of the tetromas assayed against breast cancer cell lines produced antibodies specifically directed against cancer cells. The tetroma supernatants were tested in two ways: (1) on a live cells in the CELISA (cellular ELISA) assay and (2) by Western blotting using cell lysates. The molecular weight range of the specific antigens recognized by human monoclonal antibodies was 25 to 160 kDA. In order to delineate the nature of the antigenic target, immunoprecipitation followed by microsequencing is performed. In addition, random peptide combinatorial libraries are used to identify the molecular targets of the cancer-specific antibodies.

In one patient with Stage IV breast cancer, lymph nodes were not available so PBLs were fused to MFP-2 and 156 tetromas were obtained. The tetromas were analyzed for immunoglobulin production as well as for cancer-specific antibody production. IgM was produced by 28 tetromas; 87 tetromas produced IgG. Four of the IgM antibodies and seven of the IgG antibodies were identified as reactive against cellular antigens; three IgM anti-bodies and four IgG antibodies were specific for breast cancer cells. The rest of the tetromas exhibited immunoreactivity against other cell types including human prostate cancer cell lines, human diploid fibroblasts and human skin fibroblasts. These latter antibodies were probably directed to common antigens (common for normal and cancerous cells).

The PBLs were isolated from the blood of a patient who received 77 cycles of chemotherapy which would reasonably be expected to have a depressing effect on the patient's immune system. None-the-less, this patient still produced anti-cancer antibodies suitable for fusing with MFP-2.

Human tetromas generated from fusing MFP-2 and prostate cancer lymphocytes are tested for the presence of PSA-specific antibodies as well as antibodies directed to prostate cancer cell lines LNCaP, DU-145, and PC-3.

Production of human antibodies against infectious disease-associated antigens. Infectious diseases are commonly accompanied by a well-developed humoral and cellular immune response. Patients with certain infections often contain large numbers of specific antibody producing cells. One important application of the antibody immunotherapy described by the present invention, is the production of human monoclonal antibodies to proinflammatory cytokines which are involved in septic shock. Among these targets are cytokines such as tumor necrosis factor α (TNF-α) and interleukin-1a (IL-1a). Additional targets include other cytokines and lymphokines, infectious agents and their toxins, including tetanus toxin, anthrax toxin, botulinum toxin, and lipid A. The peripheral blood of patients infected with bacteria, fungi, protozoa or viruses typically contains circulating antibody-producing cells which can be isolated and used as a source for fusion with MFP-2. For example, PBLs from patients with septic shock, Hanta virus infection, HIV, HTLV-I, HTLV-II, influenza, hepatitis, or herpes virus can be fused with MFP-2 and the resulting tetroma cells can be screened against the respective antigens. In AIDS, in particular, patient lymphocytes can be immortalized using the techniques described herein in order to generate bulk quantities of anti-HIV antibodies for use in passive immunotherapy in an autologous or heterologous manner.

Production of human antibodies against autoimmune disease. A general consideration for the use of human monoclonal antibodies in autoimmune disease is to block autoantibodies, or to block $CD4^+$ T cells which are involved in autoimmune cellular cytotoxicity. In one approach, human monoclonal antibodies against $CD4^+$ cells are generated following fusion with the MFP-2 trioma cell. Resulting tetroma cells which produce anti-CD4 antibodies are used to reduce or deplete $CD4^+$ T cells, thereby relieving autoimmune cellular attack. In another approach MFP-2 is used to generate tetroma cells capable of producing anti-idiotypic antibodies directed to specific autoantibodies. For example, autoimmune thyroiditis is an autoimmune dysfunction in which there is a high titer of anti-thyroglobulin antibodies in a patient's plasma. PBL-derived lymphocytes are isolated from such patients for fusion with MFP-2. The resultant tetroma cells are screened for those capable of producing antibodies with a substantial anti-idiotypic immune response directed against the autoantibodies reactive with thyroglobulin. These anti-idiotypic antibodies are then used to modulate the autoimmune disease by reducing or depleting the anti-thyroglobulin antibodies. Such an approach may be used autologously or heterologously. In an autologous approach, the anti-idiotypic antibody-producing cells are identified in peripheral blood of the patient to be treated, then isolated and fused with MFP-2 and following selection for specific anti-anti-thyroglobulin antibodies, passively administered to the original patient. In a heterologous approach, the anti-anti-thyroglobulin antibodies are administered to a different patient.

Other Applications: Preventing rejection of transplanted organs, blood clotting. Among other applications of human monoclonal antibodies, is prevention of organ transplant rejection by blocking T cells through the OKT-3 (anti-CD3) marker. Antibodies to adhesion molecules (anti-integrin antibodies) also prevent migration of immune cells, which is important, for example in rheumatoid arthritis. Blood clotting may be modulated, for example, in acute cardiac ischemia following coronary angioplasty, using human monoclonal antibodies against GPIIb/IIIa of platelet. Intravenous infusion of immunoglobulins helps to neutralize the Fc-receptor mediated cell aggregation of platelet or other blood cells (e.g. thrombobytopenic purpura).

In addition, this approach may be used to detoxify or neutralize toxin or venom exposure. Such exposures include, but are not limited to snake, spider or poison toad bites or yellow jacket or scorpion stings. The horse anti-serum currently used to neutralize rattle snake venom causes serum sickness disease in 30% of cases.

There is a shortage of natural human immunoglobulin required for these kinds of treatments. The human monoclonal antibody production system described herein facilitates production, in vitro, of unlimited quantities of human immunoglobulins which can be selected to fit particular need. For example, in the case of immunoglobulin which blocks Fc receptors, instead of treating the patient with the pooled preparation of immunoglobulins where only a small fraction of molecules possess the required qualities, the immunoglobulin preparation of the molecules with the required properties can be produced using the fusion partner described herein.

Discussion

There has long been a need for human monoclonal antibodies for diagnosis, treatment, and monitoring of cancer. Attempts to employ xenoantibodies in clinical trials have not produced promising results. Non-human antibodies from mice, for example, cause development of a human anti-mouse immune response, sensitization to foreign protein which may eventually result in anaphylactic reaction, and lack of biological effect since the effector properties of the xenoantibodies may mismatch the components of the human immune system. Human monoclonal antibodies have numerous advantages. One is that human monoclonal antibodies can identify those tumor-associated antigens (TAA) which are immunogenic only in humans, while xenoantibodies in most cases recognize those antigens and antigenic epitopes which express immunodominance in a host and are often the tissue specific epitopes. Another advantage is the well-developed interaction of human monoclonal antibodies with the effector components (such as complement) of the host immune system. In addition, allergic and/or anaphylactic reaction to the injectible human monoclonal antibodies is less of a concern since human monoclonal antibodies are syngenic in human subjects. Alternative attempts have been made to develop antibodies such as chimeric antibodies (partially human, partially murine), where the Fc part of the murine immunoglobulin was substituted with the human IgG-Fc. Humanized antibodies, are human immunoglobulins grafted with the CDR regions of the specific murine antibodies. Single chain (Fc) human antibodies have been developed in phage using phage display libraries. A downside of these approaches is that the resulting antibodies are not natural; they have not emerged as part of a natural immune response to cancer or infectious agent.

Use of the hybridoma techniques described herein and the availability of the MFP-2 trioma fusion partner cell line described herein, facilitates identification, immortalization, and ex-vivo expansion of antibody-producing cells which emerge in vivo as a result of natural humoral immune responses to an antigen. Since such cells are a part of the natural immune system response, the antibodies produced by these cells dovetail with the other components of the immune system and are able to provide an effective and specific biological response.

A number of breast cancer specific antigens have been described which are potential targets for the immunotherapy of cancer, including HER2/neu, Mucin 1 and Mucin 2, p53, c-myc, blood antigens T, Tn and sialyl-Tn, tuncated form of EGF, Lewis-Y antigen and others. The presence of circulating antibodies to these antigens have also been described in cancer patients. (G. Moller, 1995). Lymph nodes are important sites of such antibody-producing cells. By isolating lymph node (or peripheral blood) lymphocytes and immortalizing them by fusing them with human hybridoma fusion partner MFP-2, hybrids (tetromas), which produce antibodies directed against cancer-associated antigens may be obtained. As described above, specific monoclonal antibody producing cells are identified and may be produced in unrestricted fashion, ex-vivo (using bioreactors, SCID mice, etc). The antibodies may be used therapuetically as passive immunotherapy either autologously in the same subject or heterologously in a different subject. Even another cancer may be treated, provided there is an overlapping tumor antigen.

Syngenic or allogenic use of human monoclonal antibody can be highly effective since such an antibody can be infused many times without the risk or threat of developing an anti-xenogenic immune response. The infused antibodies, depending on their effector functions, can initialize complement dependent cytolysis of the target tumor cells, or antibody-dependent cellular cytotoxicity antibody dependent cellular cytotoxicity (ADCC) (by NK or CTL cells), or provide direct cytotoxic effect through apoptosis.

Summary

A unique fusion partner cell line, MFP, was obtained which can be used to generate specific human monoclonal antibodies. These monoclonal antibodies may be in vivo based on a natural immune response to infectious agents, cancer cells or an autoimmune dysfunction, or can be in vitro based by immunization of human lymphoid cells in vitro.

The methods described herein for generating specific monoclonal antibodies may be used to provide adoptive humoral immunotherapy either as an autologous procedure or as a heterologous procedure. Lymphocytes isolated from a patient with a cancer or infectious disease are immortalized by fusion with MFP-2. The resulting tetromas, producing antibodies directed to the respective antigens, are selected in vitro. Following selection, these antibody-producing cells are expanded and antibodies may be produced using a bioreactor or immune-deficient mice (e.g., nude mice or SCID mice). Such antibodies may then be used for the treatment of the original donor as an autologous adoptive immunotherapy procedure or for the treatment of a different subject as a heterologous, adoptive immunology procedure.

The developed antibodies may also be applied both to invasive diagnostics (imaging, immunoscintigraphy) or therapy (drug targeting, radioimmunotherapy, complement-dependent cytolysis, ADCC, apoptotic cytolysis etc.)

This approach also provides a method for identification of novel tumor markers or novel infectious agent antigens. The immune system responds to cancer cells or infectious agents by producing antibodies directed to different components of the foreign formation and can recognize different neo-epitopes. Fusing tumor reactive or infectious agent antigen reactive immunoglobulin with MFP-2 can be used to identify novel tumor markers or infectious antigens. Such antibodies are important in treatment against specific cancers or infectious agents, and in the generation of specific imaging and diagnostic techniques. Previous attempts to generate human anti-tumor or anti-infectious antibodies required forced or artificial immunization of a subject with purified or isolated antigen. In the present invention, the antigen may be unknown; the starting material for developing antibodies is the pool of immunocompetent lymphocytes which evolved as a part of natural immune response to the foreign antigens presented in their natural form and in natural environment in vivo. In an autologous application, selection can be conducted using an autologous tissue of interest (e.g. tumor biopsies) which will increase the chances to select the right antibody. Also, autologous blood plasma and white blood cells can be used to select for cytotoxic antibodies from the same donor.

Thus, the MFP fusion partner (1) allows fusion with peripheral blood lymphocytes yielding high levels of hybrids; (2) allows consideration of an adoptive humoral immunotherapy on an individual basis (selection of the antibodies against tumor cells or infectious agents derived from the same donor the lymphocytes were obtained from and the autologous treatment of the patient); (3) fusion with the donor's lymphocytes undergoing immunization in vitro; (4) allows use of frozen lymphocytes or lymphocytes derived from plasmapheresis as a source of antibody-producing cells.

Experimental Procedures

Hybridoma fusion partner MFP-2 was developed as a trioma cell line by fusing non-producing heteromyeloma B6B11 with human lymphocytes isolated from the paraclavicular lymph node.

Isolation of lymphocytes. Paraclavicular lymph nodes from a patient diagnosed with metastatic thyroid cancer were excised during the surgery and placed into sterile conservation media RPMI1640 supplemented with L-glutamine (4 mM), non essential amino acids (100× stock), vitamins (100× stock), sodium pyruvate (1 mM) and Gentamicin (2× concentration). Lymph node tissue was transferred to a 100 mm tissue culture TC dish in the same media and gently disrupted with forceps and scissors. The disrupted tissue was passed through a metal sieve (50 mesh) using a glass pestle. The suspension was transferred into 15 ml sterile conical tubes containing lymphocyte separation media (Histopaque 1.077 Sigma) as an underlying layer at a ratio of 2:1 (lymphocytes suspension: Histopaque). Following centrifugation at 400×g for 20 minutes, an opaque ring formed at the border between layers. Red blood cells (RBC) were present as a pellet at the bottom of the tube. If RBC are not present in the starting lymphocyte suspension (which is a quite normal situation for lymph nodes) the separation step can be skipped. The opaque ring containing lymphocytes was carefully collected using a Pasteur pipette and was diluted 10-fold diluted with regular serum-free RPMI 1640. Cells were spun at 300×g for 10 minutes and washed twice with media.

The final lymphocyte suspension was diluted with media and cells were counted using 0.05% Trypan Blue. Cell viability after isolation was usually 95%. Total yield was approximately $4 \times 10^7$ cells.

Preparation of B6B11. Heteromyeloma B6B11 was grown in RPMI 1640 with 10% cosmic calf serum (Hyclone), standard set of supplements (L-Glu, 4 mM non-essential amino acids, vitamins, Sodium Pyruvate) without antibiotics. Before fusion, cells were cultured in the presence of 8-Ag (20 μg/ml) to avoid reversion of HAT-sensitive cells to wildtype. Cells were grown to a density of 10% in logarithmic growth phase.

Cell fusion. Both B6B11 cells and lymph node lymphocytes were washed 3 times by centrifugation at 300×g for 5 minutes in order to remove any residential protein in the media. Cells were mixed at a ratio of 5:1 (lymphocyte: myeloma) and spun at 300×g for 10 minutes. The supernatant was carefully and completely removed the pellet was "puffed" gently and 100 μl of PEG/DMSO solution warmed to room temperature was added to the cell mixture which was gently tapped for 3 minutes. Then 15 ml of Hank's Balanced Salt Solution (HBSS) and PBS (1:1) (from a 10× stock, Cellgro) were added as follows: 10 ml slowly in 10 minutes, then 5 ml over 5 minutes, then 10 ml of complete media (media for cell culturing) over 5 minutes and finally 5 ml over 1 minute. The total volume was 30 ml. Then 600 μl of HT solution (of 10× stock) and 1 drop (about 20-30 μl) of DMSO were added to the tube. The cell suspension was mixed in a tube, transferred to Petri dish (100×15) and incubated in a 37° C. $CO_2$ incubator overnight. The cells were then harvested, pelleted at 300×g for 10 minutes and resuspended in complete media supplemented with HAT-solution and HT-solution (both from 50× stock) and then plated into 96-well plates in a 200 μl volume at about 250,000 cells per well. Twice a week, 50% of the media was replaced with fresh media. Cells were cultured in the presence of HAT and HT for 14-20 days before screening for antibody production.

ELISA screening for nonspecific immunoglobulin. ELISA plates were coated with polyclonal goat-anti-human IgG (Fc-specific) (Sigma), goat-anti-human IgM (μ-specific) (Sigma) or goat-anti-human Ig(G+M+A) H-chains (Sigma) in 100 μl of plating buffer (0.1 M Sodium Carbonate, pH 9.0) at 100 ng per well. The plates were sealed with Parafilm or sealing covers and incubated overnight at 4° C. The antigen was washed out with distilled water twice. Residual drops of water were removed and 200 μl of blocking solution (0.4% dry non-fat milk in PBS) was added to the wells. Complete cell culture media served as a negative control. Human serum (1:2000) was used as a positive control. Plates were incubated for 2 hours at room temperature or overnight at 4° C. The plates were washed 4 times with distilled water and secondary antibodies (same as capture antibodies but conjugated to HRP) diluted in 0.4% milk/PBS at 1:2000 were added to the wells. After 1 hour incubation at room temperature the wells were washed 4 times with $H_2O$ and peroxidase substrate (or-tophenylendiamine in phosphate-citrate buffer with peroxide) was added to the plates. The color reaction was stopped by adding 20 μl of 10% sulfuric acid. Colorimetric reading was performed on a Multiscan reader at $A_{492}$. Samples which exhibited at least a 3-fold increase over background were considered to be immunoglobulin-producing cells.

Assay for the intracellular (non-secreted) presence of immunoglobulins or their individual chains. Cells which did not secrete immunoglobulin in the supernatant culture media were tested for the presence of intracellular immunoglobulin-immunoreactive material. ELISA plates were coated with goat-anti-human kappa chain (Sigma), goat-anti-human lambda chain (Sigma) and goat-anti-human IgH (G,M,A) as described above. Cells were grown in 75 cm² flasks to the density $10^6$ cells per ml, harvested and washed 3 times with HBSS. Cells were resuspended in PBS and disrupted by sonication (8×15 seconds at 25 MHz on ice). The suspension was spun for 15 minutes at 10,000×g and the supernatant was used for immunoglobulin testing. An equivalent of $2 \times 10^6$ cells was used. As a negative control mouse fibroblasts 3T3 were used at the same protein amount equivalent. The rest of the protocol was the same as described above for the hybridoma supernatant testing. Clones which showed the signal equal to the control cells or lower were chosen as potential candidates for fusion with human peripheral blood lymphocytes. These trioma clones were designated as modified fusion partner series (MFP-S) and numbered sequentially (MFP-1, MFP-2, MFP-3, etc.) Six non-producing, non-secreting triomas were selected for further analysis.

Selection for 8-Ag resistant MFP mutants. To use MFP trioma cells as fusion partners, the MFP cells were placed in complete media containing an increasing amounts of 8-Ag. Resistance to 8-Ag is determined by the impaired enzyme HGPRT or its absence. Selection was therefore focused on cells which survived in the presence of 8-Ag. After 5 to 10 passages at the lower concentrations of 8-Ag (5 μg/ml) the survivors were cultured in media with a higher concentration (10 μg/ml). This was repeated until a concentration of 20 μg/ml was reached. After 5-6 passages in the presence of 8-Ag (20 μg/ml) cells were tested for their viability in HAT-media. None of the cells grown on 8-Ag survived after 3 days of culture in the presence of HAT.

Fusion efficiency. The MFP clones were tested for ability to fuse with lymph node lymphocytes and PBL. MFP-2 yielded approximately 2-3 hybrids per $10^5$ lymph node lymphocytes and 0.7-1.5 hybrids per $10^5$ of PBL. The immunoglobulin secretion rate for the hybrids developed using MFP-2 ranged between 0.5 to 15 ug/ml with no decrease over 7 months.

SECOND SERIES OF EXPERIMENTS

1. The trioma cell line MFP-2 used for fusion with human peripheral blood B-lymphocytes and human lymph node B-lymphocytes can be also used for fusion with human peripheral blood and lymph node T-cells and yield stable hybrids.
2. The trioma cell line MFP-2 can be used for fusion with peripheral blood and lymph node lymphocytes from two primate species: rhesus monkey (Macaque mulatta) and baboon (Papio hamadryas) yielding monkey immunoglobulin-producing hybrids. This has a potential application for the development of monkey monoclonal antibodies to different infectious agents to test them in primate models.
3. Trioma fusion partner cell line MFP-2 was adapted to the growth in protein-free media with the growth characteristics not different from those when cultured in serum containing or serum-free (protein supplemented-media).
4. It was inferred that, since MFP-2 can be cultured in protein-free media, the deriving hybridomas would be relatively easy to adapt to the same protein-free media.
5. Four out of 6 hybridomas were successfully adapted to protein-free media without changing the growth characteristics and loosing the antibody production. This feature of MFP-2 adds to the advantage of this cell line in developing hybridomas capable of growing in protein-free media.
6. 27 human hybridomas, producing human monoclonal antibodies to breast and prostate-associated antigens have been developed using MFP-2 and peripheral blood and lymph node B-lymphocytes from breast and prostate cancer patients.
7. 23 human hybridomas derive from breast cancer patient and 4 derive from prostate cancer patients.
8. Prostate cancer-derived hybridomas:
   1. hyridoma (32-B8) produces IgM, lambda antibody which reacts specifically with 2 human prostate adenocarcinoma cell lines and with one human breast adenocarcinoma cell line and is directed to an unknown antigen most likely of a non-protein nature (western blot is negative, although it well may be that the antigen is a protein but the antigen determinant is conformational and labile)
   2. hybridoma (32-F6) also produces IgM, lambda antibody reactive with both prostate and breast adenocarcinoma cells and recognizing the proteinous antigen of 60-kDa molecular weight.
   3. hybridoma (39-A7) is also IgM, lambda antibody directed to an unknown protein target specific for both breast and prostate adenocarcinoma.
   4. hybridoma (50-1B3) produces IgM, kappa antibody directed to both breast and prostate adenocarcinoma to a molecular target of unknown nature
9. Breast cancer-associated hybridomas are the following:
   1. hybridoma (13-42), IgM, kappa recognizes protein antigen of ~42 kDa molecular weight which is present both on the surface and intracellularly of adenocarcinoma cells (breast and prostate) but not in human normal fibroblasts.
   2. hyridoma (13-74), IgM, kappa reacts with protein antigen of ~65 kDa specific for the breast adenocarcinoma cells and expressed on the cell surface as well as intracellularly
   3. hybridoma (13-82), IgM, kappa is reactive with intracellular protein antigen specific only for breast and prostate adenocarcinoma cells but not for human skin fibroblasts.
   4. hybridoma (13-2C1), IgM kappa is reactive with a protein of ~100 kDa which is present both in adenocarcinoma and normal fibroblast cells.
   5. hybridoma (22-3E9) isotype is not determined, recognizes several protein targets (which may be all related) of molecular weight 35, 45 and 250 kDa which are present on both adenocarcinoma and fibroblasts. The antigen is mostly on the surface of the cells. Reacts specifically with primary cancerous lesions
   6. hybridoma (22-6E7), IgM, lambda, the antigen is unknown, the antibody is reactive only with breast adenocarcinoma cells in culture.
   7. hybridoma (22-8D11), IgM, lambda, antigen is unknown, reacts with human breast and prostate adenocarcinoma cells in culture.
   8. hybridoma (27-F7), IgM, kappa, reacts only with breast adenocarcinoma cells in culture. The antigen is a TAX interacting protein 2 of molecular weight ~35-40 kDa
   9. hybridoma (27-B1) same as 27-F7, shows high specific reactivity with the cancerous lesions in primary tumors, no cross-reactivity with the connective tissue or with normal mammary epithelial cells
   10. hybridoma (36-G7) antibody isotype is not determined; specificity is the same as 27-B1
   11. hybridoma (27-F10), IgG, lambda, reactive with the protein approx. 200 kDa on breast adenocarcinoma cells
   12. hybridoma (33-2F10), IgM, kappa, antigen is not known, reactive with breast adenocarcinoma cells
   13. hybridoma (33-2H6), IgM, lambda, recognizes 65 kDa protein on breast and prostate adenocarcinoma cells but not on human skin fibroblasts
   14. hybridoma (59-3G7), IgM, lambda, is reactive with a 70 kDa protein lamin A or C in adenocarcinoma cells. Cross-reactivity with other cells has not been Tested
   15. hybridoma (59-2F6), IgG, lambda, reacts only with breast adenocarcinoma cells with unknown antigen
   16. hybridoma (69-C12), IgM, kappa, reactive mostly with breast adenocarcinoma cells directed to a protein, 50 kDa 17-hybridoma (76-2F6), IgM, lambda, reactive with unknown antigen only on breast adenocarcinoma cells
   18. hybridoma (83-3A6), isotype not determined, reactive only with breast adenocarcinoma cells
   19. hyridoma (85-E1), IgM, lambda, reactive only with breast adenocarcinoma cells expressing Her2/neu; antigen is not identified yet
   20. hybridoma (88-1D8), isotype is not determined yet, recognizes protein antigens on breast cancer cells; molecular weights vary –70, 90 and 100 kDa
   21. hybridoma (89) isotype is not determined, reactive only with Her2/neu-negative adenocarcinoma cells; antigen is not known
   22. hybridoma (100-1F4), IgM, kappa, only reactive with breast adenocarcinoma cells; antigen is not known
   23. hybridoma (100-2H3) similar to 100-1F4

REFERENCES FOR SECOND SERIES OF EXPERIMENTS

Kohler G, and Milstein C., Nature 1975; 256:495
Levy, R., and Miller R A. Federation Proceedings 1983; 42:2650.
Posner M R, et al., Hybridoma 1983; 2:369.
Kozbor D, and Roder J., J. Immunology 1981; 127:1275.
Casual O, Science 1986; 234:476.
Glassy M C, Proc. Natl. Acad. Sci (USA) 1983; 80:6327.
Ollson L, et al., J. Immunol. Methods 1983; 61:17
Nilsson K. and Ponten J., Int. J. Cancer 1975; 15:321
Goldman-Leikin R E, J. Lab. Clin. Med. 1989: 113:335.
Brodin T, J. Immunol. Meth. 1983; 60:1.
Teng N N H, Proc. Natl. Acad. Sci. (USA) 1983; 80:7308.
Weiss M C, and Green H. Proc. Natl. Acad. Sci. (USA) 1967; 58:1104.
Oestberg L, and Pursch E., Hybridoma 1983; 2:361
Kozbor D, et. al., J. Immunology 1984; 133:3001
Shnyra A A, et al., In: Friedman H, Klein T W, Nakano M, Nowotny A, and Eds. Advances in Exp. Medicine & Biology Endotoxin New York: Plenum, 1990; 256:681.
Antonov A S, et al., Atherosclerosis 1986; 59:1.
Borrebaeck C A K, et al., Biochem. Biophys. Res. Commun. 1987; 148:941.
Reading C L., J. Immunol. Meth. 1982; 53:261.
Galanos G, et al., Eur. J. Biochem 1969; 9:245.

Rokhlin O V, 8th Int. Congress of Immunology, Berlin. Abstracts 1989; 6.

Seabright S., Lancet 1971; 2:971.

Yunis J J., Cancer Genetics and Cytogenetics 1980; 2:221.

Raison R L, et al., J. Exp. Medicine 1982; 156:1380.

Moller, G, 1995. (editor) Immunological Reviews Vol 145: Tumor Immunology.

THIRD SERIES OF EXPERIMENTS

Example I

Development of Fully Human Monoclonal Antibodies

Introduction

The present invention comprises a unique fusion partner cell line that fuses with human lymphocytes derived from lymph nodes, spleen, tonsils, or peripheral blood. The resulting hybrids have proved to be stable producers of human immune substances called immunoglobulins and represent a reliable source of human antibodies for immunotherapy. Using this fusion partner cell line, which was designated as MFP-2, we have developed several monoclonal antibodies with specific reactivity towards human breast and prostate cancer.

Results

Hybridoma Technology

Fully human monoclonal antibodies (fhMAb) were developed through hybridoma technology using proprietary fusion partner cell line MFP-2 and human lymph node lymphocytes (LNL) isolated from the lymph node of Stage IV breast cancer female patient who underwent mastectomy and lymphadenoectomy. Fusion of MFP-2 to LNL yielded several clones producing antibodies specifically reactive with established breast cancer cell lines SK-BR-3, MCF-7 and ZR-75-1. Two of the antibodies designated as 27.F7 and 27.B1 reacted specifically with the protein target from these cells of molecular weight approximately 43 kD, as was shown by Western blotting analysis of those cells' lysates both under reduced and non-reduced conditions. The hybridoma cell lines were adapted to growth in serum free media reaching the density $1.5 \times 10^6$ cells per ml in flasks/TC dishes at the plateau phase. The cell line 27.F7 was also capable of growing in hollow-fiber Bioreactor reaching the density of $20$-$25 \times 10^6$/ml and the cell line 27.B1 was growing effectively in spinner flasks. The production of the antibodies was 17 ug/ml/$10^6$ cells/24 h for 27.F7 and 49 ug/ml/$10^6$ cells/24 h for 27.B1. Both antibodies were IgM, k. For further studies of the molecular target for these antibodies, cells were cultured in quantities using serum free media and purification was done using size-exclusion chromatography of Sephacryl™S-200 (High Resolution) were IgM appeared in a void volume.

Example II

Antibody Binding to Cancer Cell Lines

The antibodies produced reacted both with the human cancer cell lines and with primary tumor tissues. Antigen targets were identified for some of these antibodies. Two antibodies, 27.F7 and 27.B1, were directed to the same antigen, which was identified as Tax interacting protein, clone 2 (TIP-2). The antibodies 27.B1 and 27.F7 were reactive with three human breast cancer cell lines, MCF-7, SK-BR-3 and ZR-1-75, have tracer or no reactivity with human prostate cancer cell and negative with human fibroblasts.

Results

Elisa Assay

Cellular ELISA assay demonstrated the binding of 27.F7 and 27.B1 to human breast cancer cell lines in a specific manner, and no binding to human skin or trunk fibroblasts.

Flow Cytometry

Flow cytometry studies revealed that the antigen target is accessible on the surface of live cells as well as in cytosol of formaldehyde-fixed cells. However, the pattern of antibody binding to the cells was different, indicating that these antibodies probably recognize different epitopes of one and the same antigen. Antibody 27.B1 reacted with the surface of breast cancer cells SK-BR-3 and MCF-7 and did not react with live prostate cancer cells PC-3 and LNCaP and with live human fibroblasts (FIG. 7). However, when formaldehyde-fixed cells were used in flow cytometry analysis it showed that 27.B1 antibody reacted with both breast cancer cell lines and with prostate cancer cells LNCaP, although it was still negative to human fibroblasts. Antibody 27.F7 showed a different pattern of reactivity: it reacted with the fixed primary fibroblasts, apparently with some intracellular epitope. Using cell lysates prepared from three breast cancer cell lines (SK-BR-3, MCF-7 and ZR-75-1), three prostate cancer cell lines (LNCaP, PC-3 and Du-145) and two human fibroblast cell lines (Hs556.Sk and Hs143.We)

Western Blot

Figure 8:
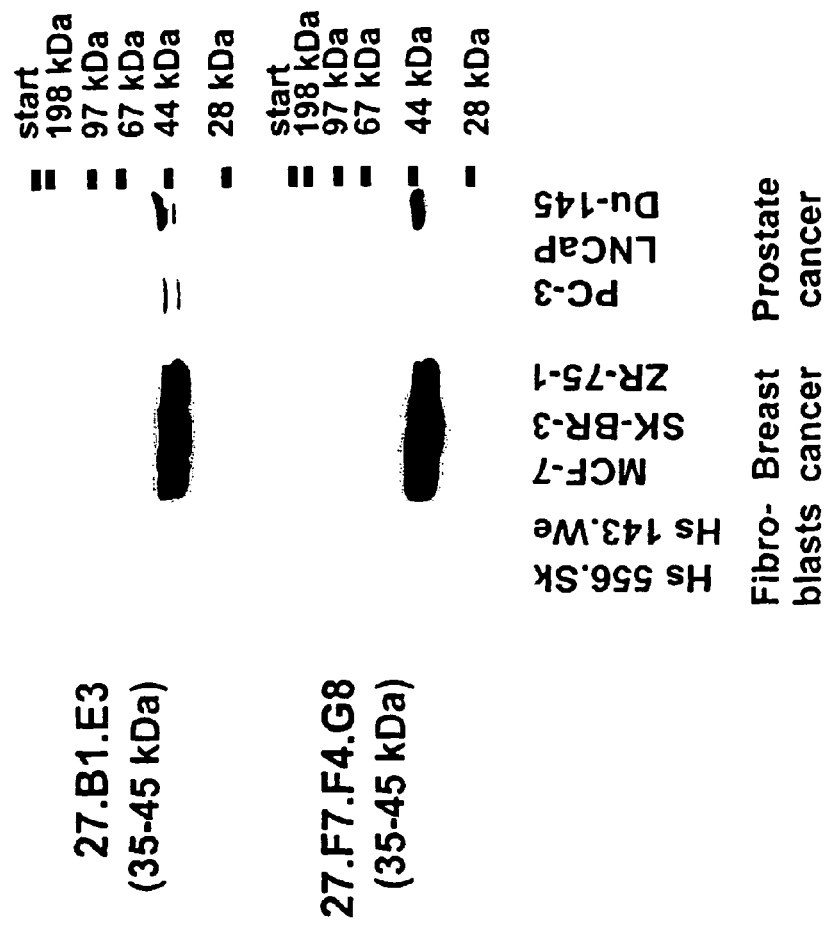
Figure 10:
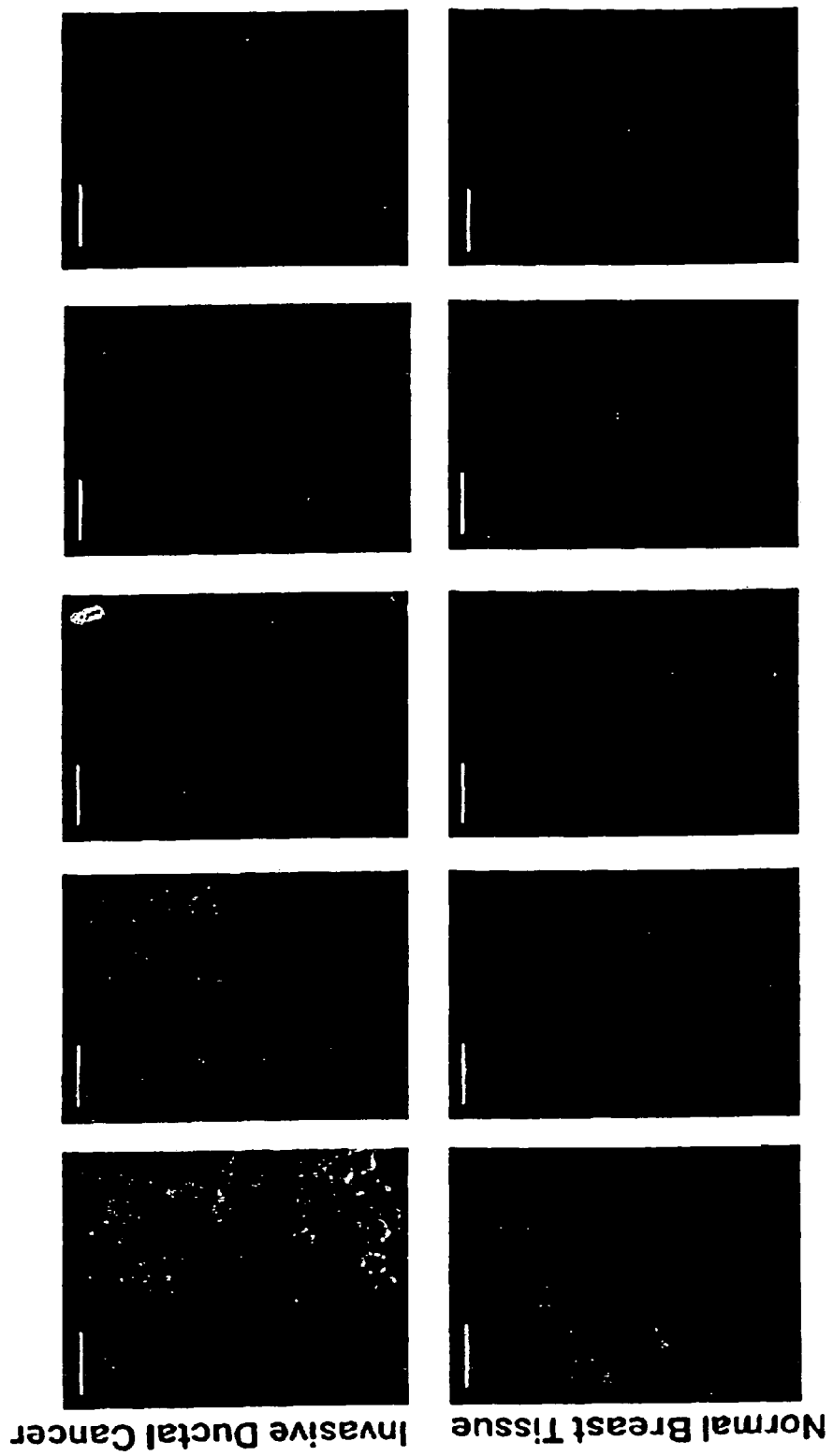
Figure 11:
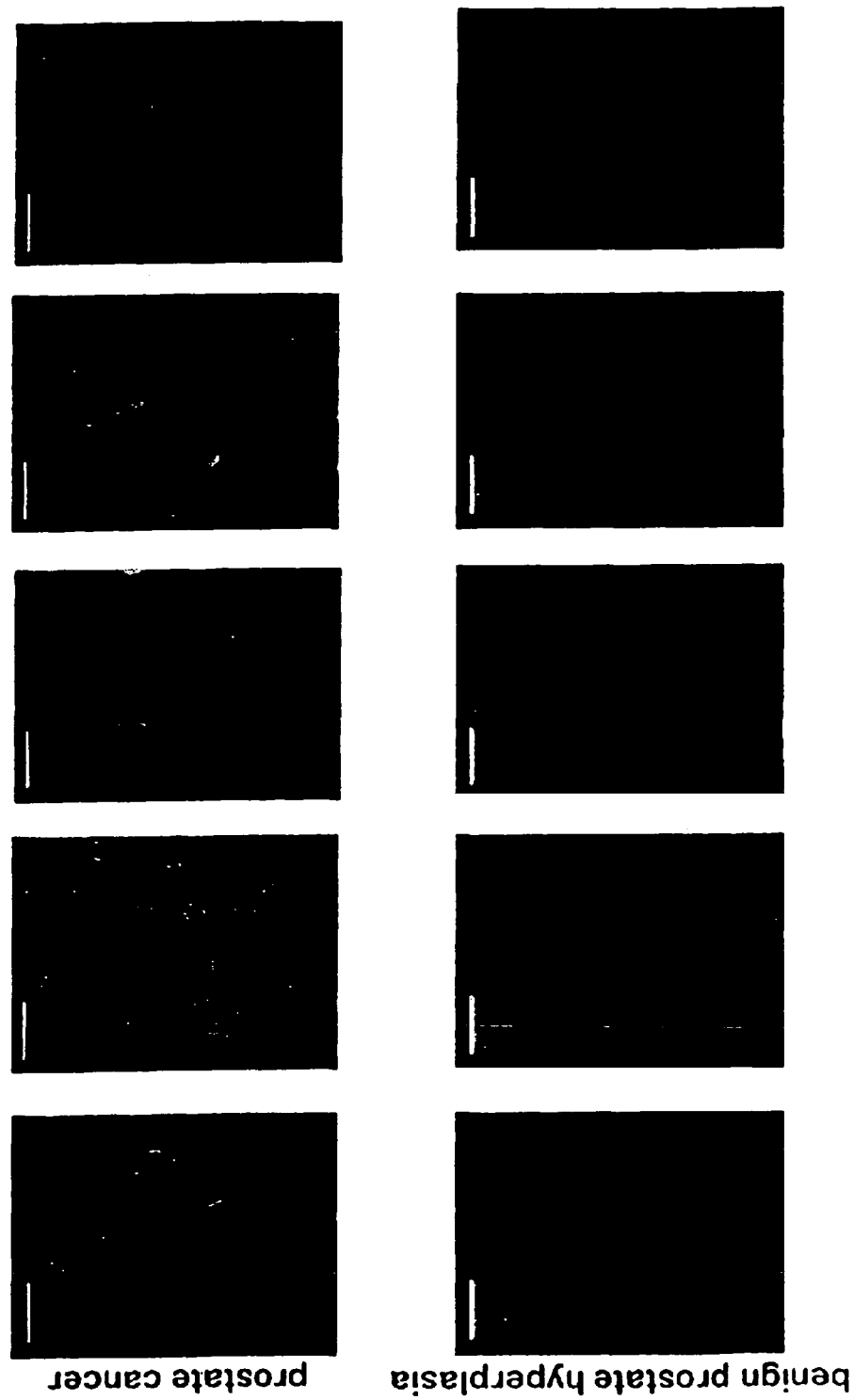
Figure 12:
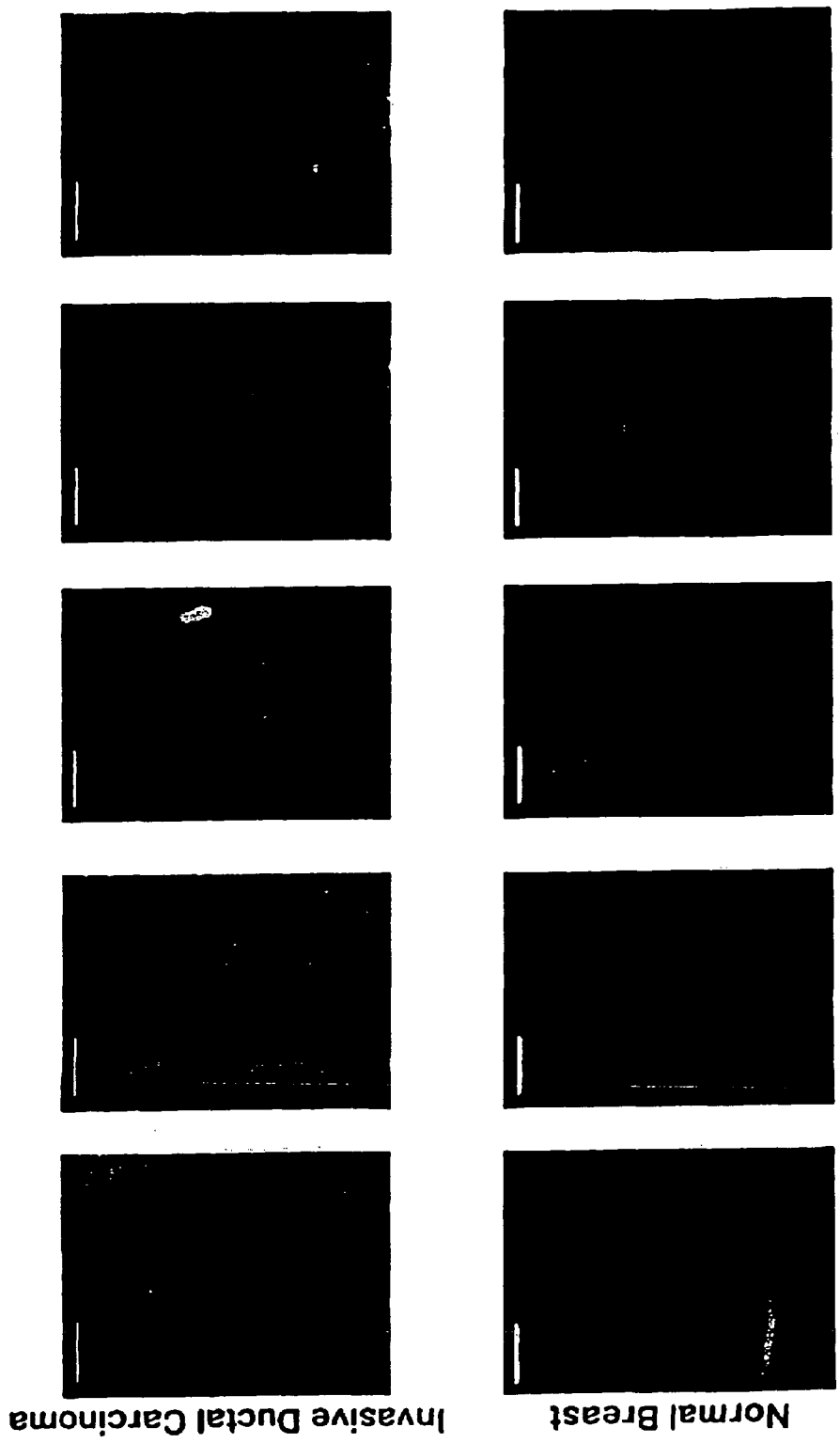
Figure 13:
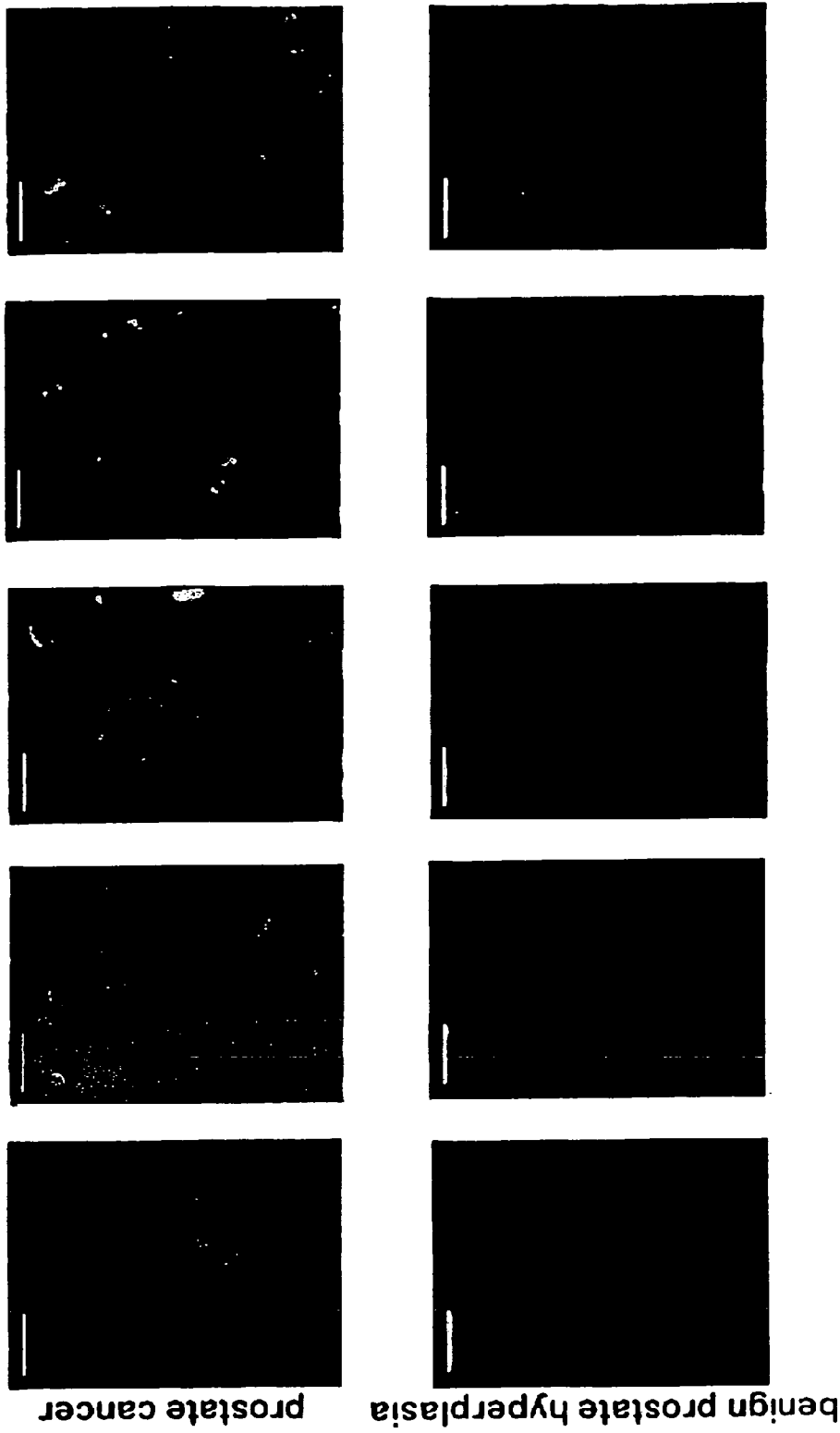

The Western blot analysis demonstrated that both antibodies 27.F7 and 27.B1 react with the protein of approximately 43 kD which appears on a blot as a double band. This protein is profoundly expressed in all three breast cancer cell lines, not expressed in two human fibroblast cell lines and very weekly in prostate cancer cells PC-3 and Du-145. LNCaP cells show expresses negligible if any level of this protein (FIG. 8).

Immunocyto- and Histochemical Studies

Figure 14:
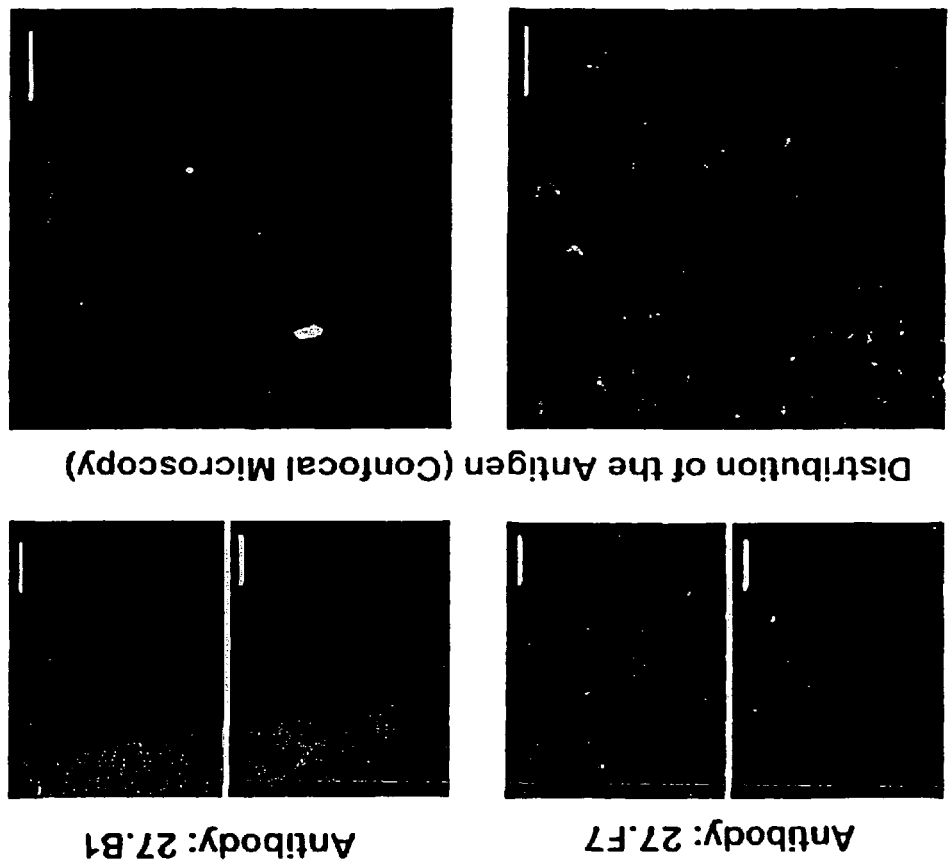
Figure 15:
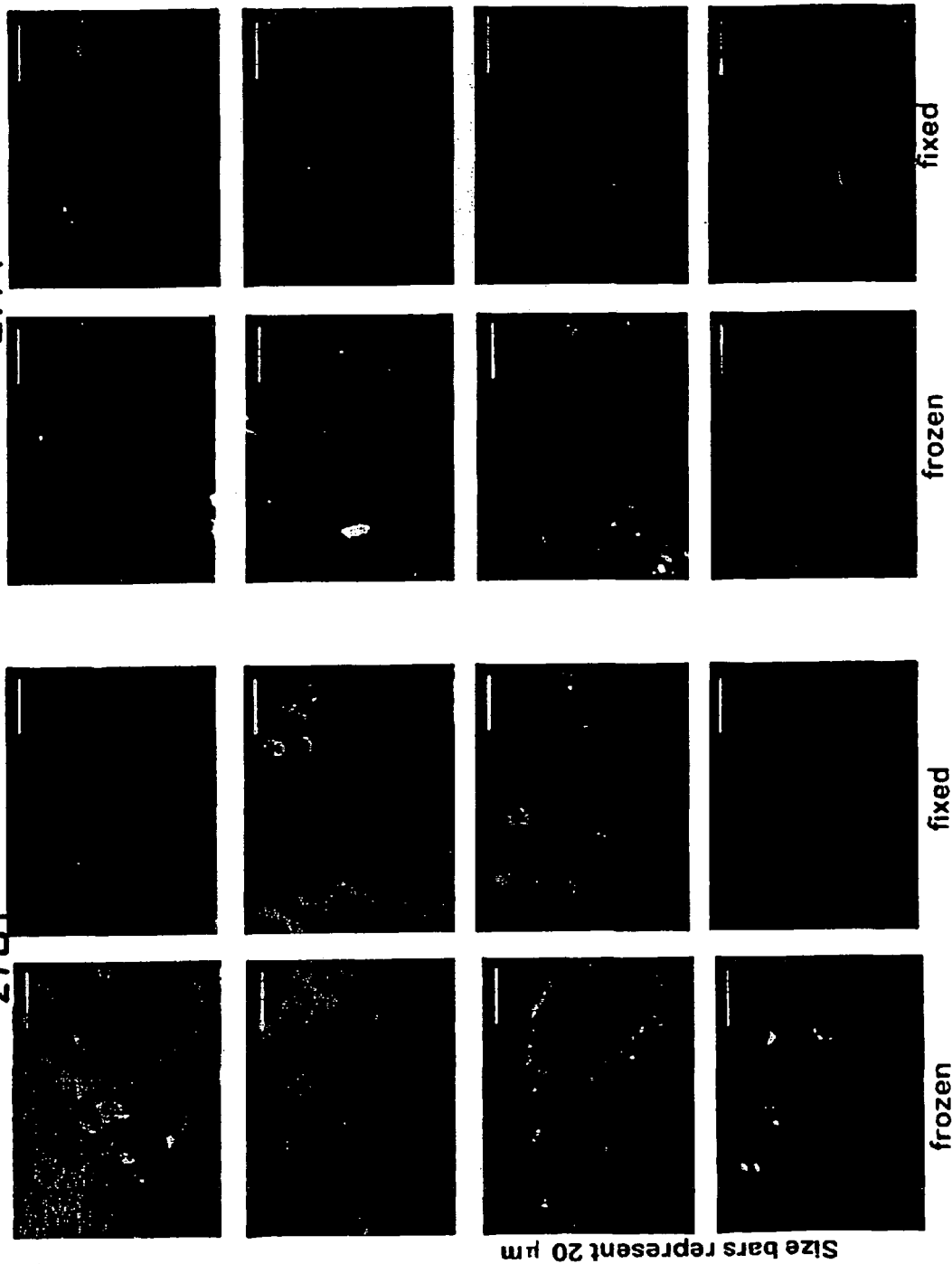
Figure 16:
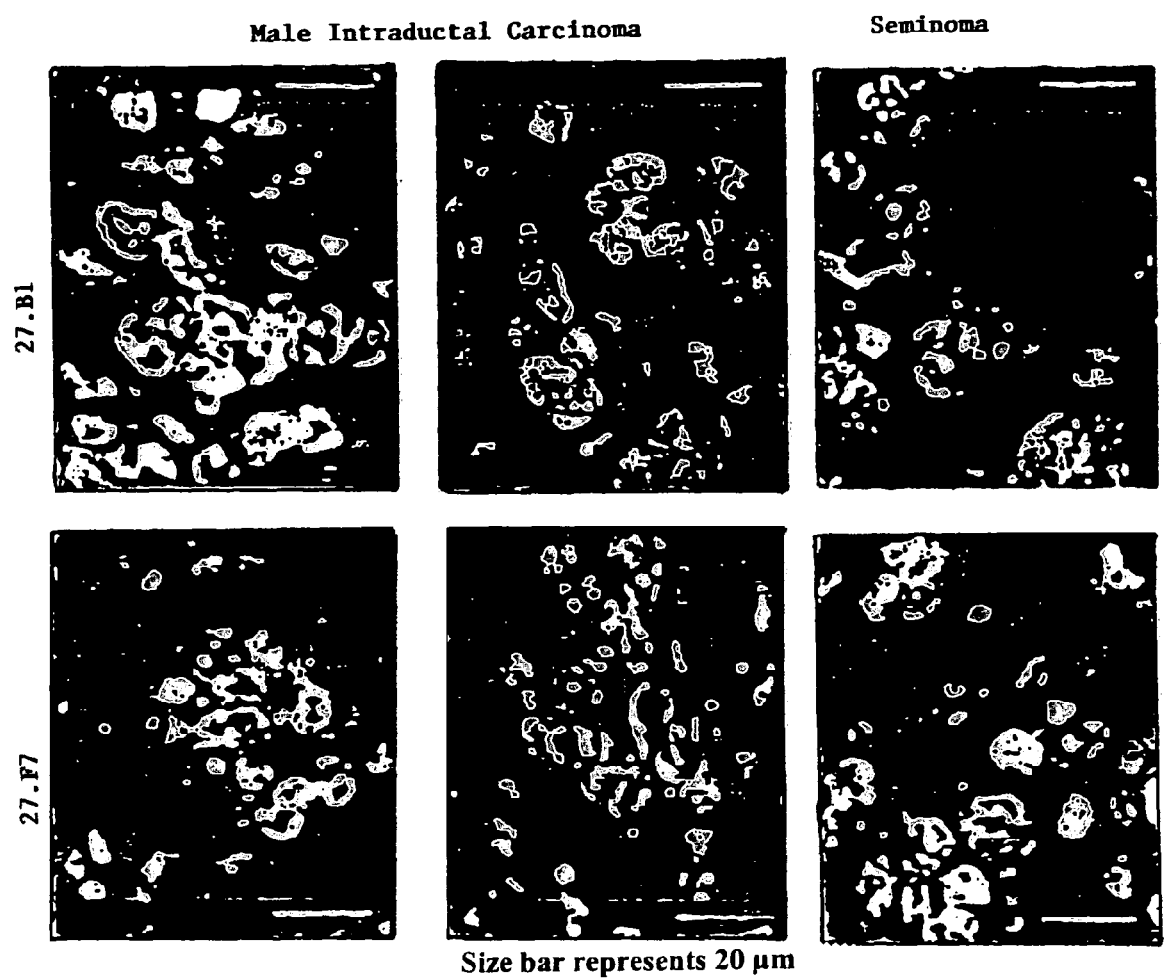

Immunocyto- and histochemistry studies using established human cell lines and primary and metastatic lesions of tumor tissues from a number of breast and prostate cancer patients showed a very specific pattern of immunostaining of breast and prostate cancer cells (FIG. 9), primary tumors (FIGS. 10, 11, 12 and 13) and metastatic lesions in the lymph nodes (FIG. 14). Both fixed and freshly frozen tumor tissues were positive when immunostained with antibodies 27.B1 and 27.F7 (FIG. 15). Out of 10 breast cancer cases tested in immunohistochemistry with fhMAb 27.B1 all 10 were positive while the matching number of normal breast epithelia samples all turned out negative. Beside these two types of cancer, also observed was positive staining of male breast cancer and seminoma (FIG. 16).

Figure 17:
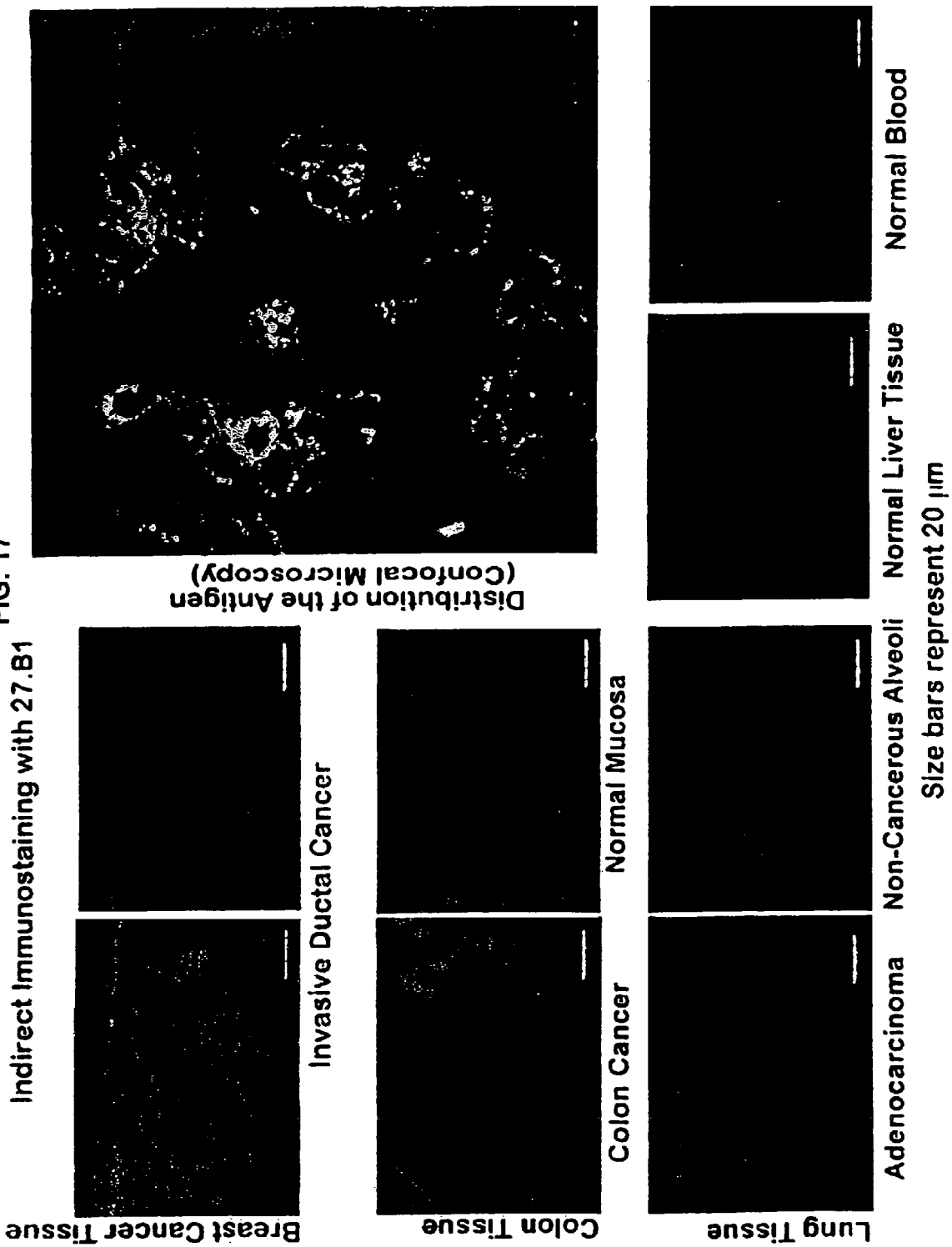

Of other tissues tested for the presence of 27.B1/27.F7 immunoreactivity, such as normal colon mucosa, colon cancer, renal cancer, normal renal glomeruli, normal liver and both normal and cancerous lung tissues—all were negative (FIG. 17). At the same time immunostaining of normal breast epithelium, unaffected lymph nodes and benign prostate hyperplasia was negative. This suggests the breast/prostate cancer specificity for these fhMAbs.

Discussion

Two of the developed antibodies, both IgM, kappa are reactive with a cancer-specific antigen called GIPC or TIP-2. GIPC stands for GAIP (Ga interacting protein, regulator of G signaling) interacting protein, C domain and TIP-2 stands for Tax interacting protein, clone 2. The presence of this protein was associated only with breast cancer cells while prostate cancer cells had trace if any amount. Human fibroblasts were negative for the presence of GIPC/TIP-2 antigen. The Scatchard analysis of the number of copies of TIP-2 antigen in SK-BR-3 cells (TIP-2—positive cells) revealed approximately 300 000 copies per cell. The immunohistochemistry studies found that both 27.F7 and 27.B1 stain positively all three major types of breast cancer: invasive lobular, invasive ductal and adenocarcinoma in situ. These antibodies also stain prostate cancer, while normal breast epithelia and benign prostate hyperplasia (BPH) were negative. The antibodies were also negative on normal and cancerous lung tissue, normal colon mucosa and colon cancer and normal and cancerous renal tissue. Therefore, GIPC/TIP-2 marker is as a valuable immunohistochemical marker for histopathology evaluation of cancer tissue specimen.

Example III

Identification of the Antigen

Figure 20:
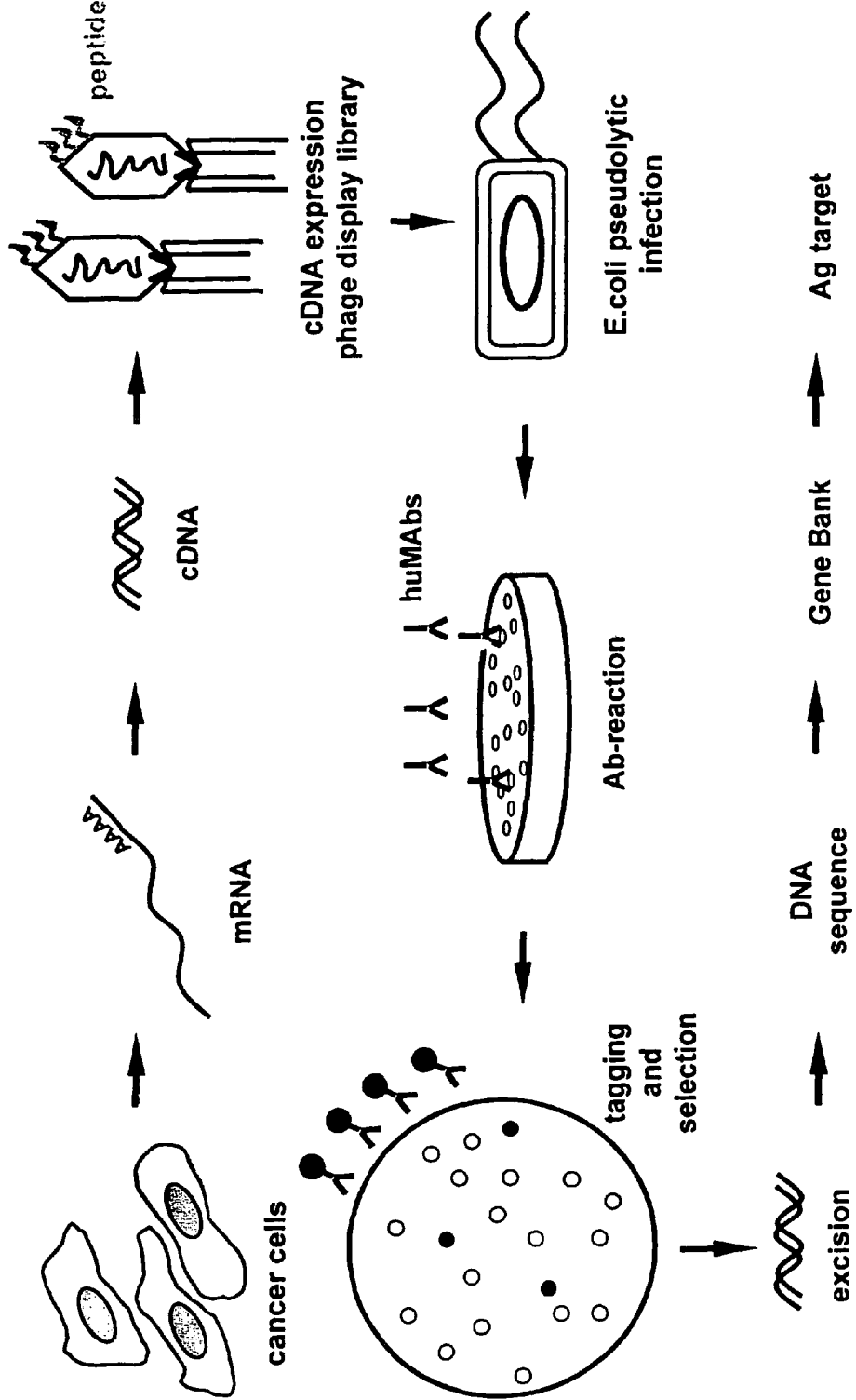

Based on the antibodies described above, a novel tumor associated antigen specific to breast and prostate adenocarcinoma has been identified as GIPC (Tax Interacting Protein 2). The method used to identify this novel tumor-associated antigen was SEREX (SErological analysis of antigens by REcombinant EXpression cloning or spontaneous antibody responses to tumor-associated antigens) (FIG. 20). This method was originally developed in the Ludwig Institute for the purpose of identifying specific protein targets for the antibodies found in plasma or serum of cancer patients (1). The invention describes a 43-kDa protein, which belongs to so-called PDZ domain containing proteins. PDZ domains are protein motifs of 80-100 aminoacids where the repeat consensus of GLGF is a distinctive characteristic. The PDZ domain (named after mammalian postsynaptic density protein PSD-95, *Drosophila* disc large protein Dlg and a mammalian tight junction protein ZO-1) is found in more than 50 proteins, which for the most part appear, unrelated to one another. These proteins are commonly involved in signaling networks, such as G protein-mediated signaling pathways. PDZ domains are found, for example, in signaling molecules such as Dlg, nitric oxide synthase (NOS), protein-tyrosine phosphatase, membrane-associated guanylate kinases (MAGUK), and so on.

Most PDZ domain-containing proteins are associated with the cytoskeleton and apparently involved with formation of multimeric protein complexes (2,3). The only PDZ domain-containing protein associated with human colon cancer was described by Scanlan et al. (4,5). This antigen, NY-Co-38/PDZ-73, was identified through IgG autoantibodies developed in colon cancer patients. The same authors also described a few tissue-specific isoforms of PDZ-73, that appear to be truncated forms containing one or two PDZ domains (the original PDZ-73 form has three domains). The function of these proteins is not known, although they bear the structural similarity with the MAGUK family of proteins. The PDZ domain, although its particular function is not clear, is believed to participate in protein-protein interaction and formation of large protein networks.

TIP-2 was recently identified by Rousset et al. (1) as one of 6 cellular proteins of unknown function that interact with the C-terminus of Tax oncoprotein through their PDZ domain. As C-terminal motif S/TXV is important for interaction with PDZ domain, it turned that Tax oncoprotein preserves interaction with TIP-2 even if the critical C-terminal valine is replaced, for example, with alanine, while all other Tax-binding PDZ domain-containing proteins lose their binding potential.

Results

TIP-2 was identified by screening breast cancer patients' B-cell-derived antibodies on a cDNA expression library prepared from human breast cancer cell line SK-BR-3. Briefly, poly(A)+ RNA was isolated from the cells, transcribed into cDNA and ligated into lambda pseudolytic phage, resulting in approximately $5 \times 10^5$ recombinants. The phage was amplified in *E. coll* Y1090 and then transferred to nitrocellulose membranes, which were treated with human antibodies. After exposure to antibodies the membranes were treated with anti-uchain rabbit polyclonal antibodies conjugated to horseradish peroxidase. Positive cDNA clones were converted into plasmid forms by excision in vivo, and the plasmid DNA was purified and submitted to sequence analysis. The resulting sequence was submitted to homology search using a Gene Bank database. Two human monoclonal antibodies (27.F7 and 27.B1) developed from breast cancer patient's lymph node B-cells were identified as antibodies reactive with TIP-2—however apparently with different epitopes.

Figure 21:
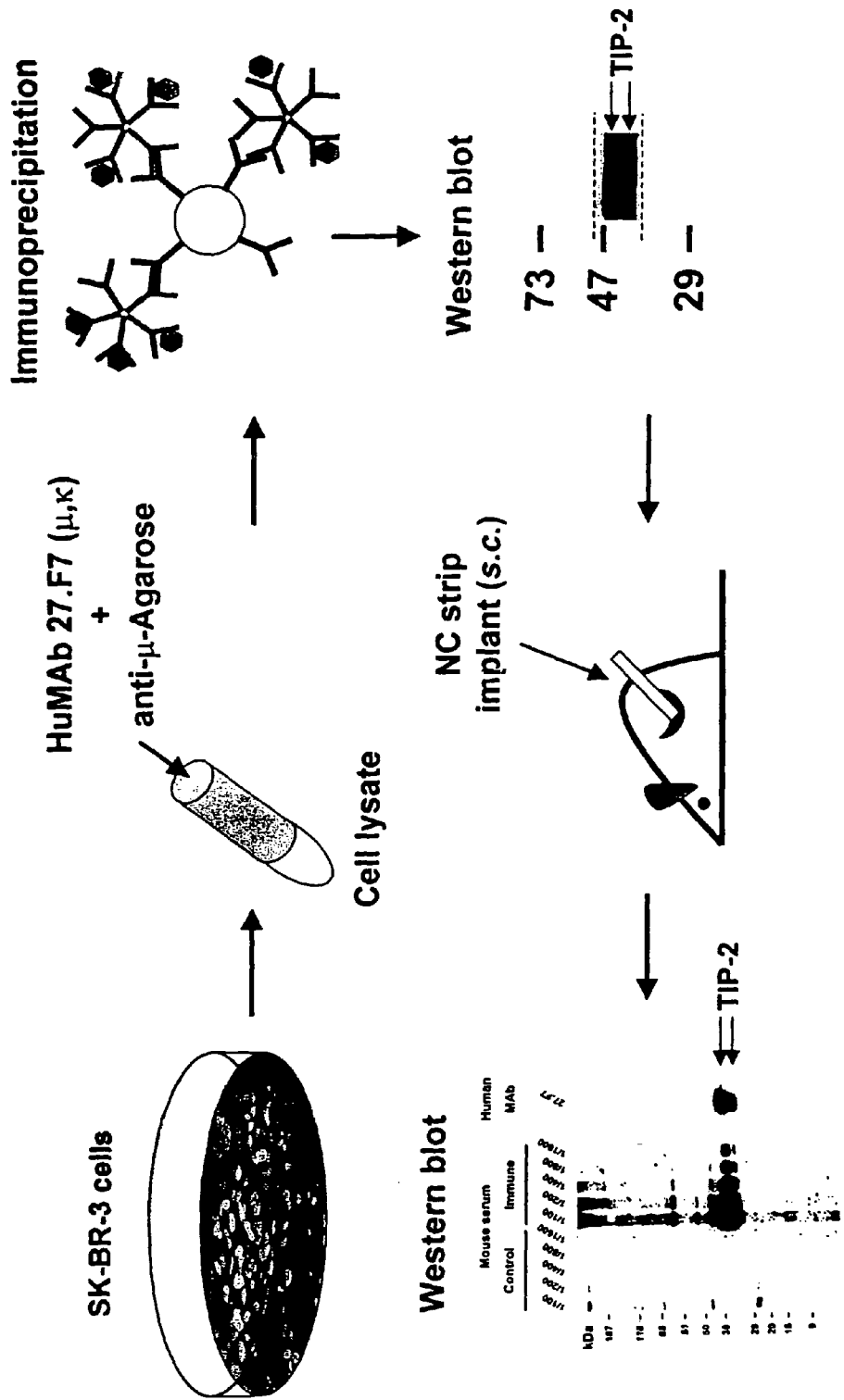
Figure 22:
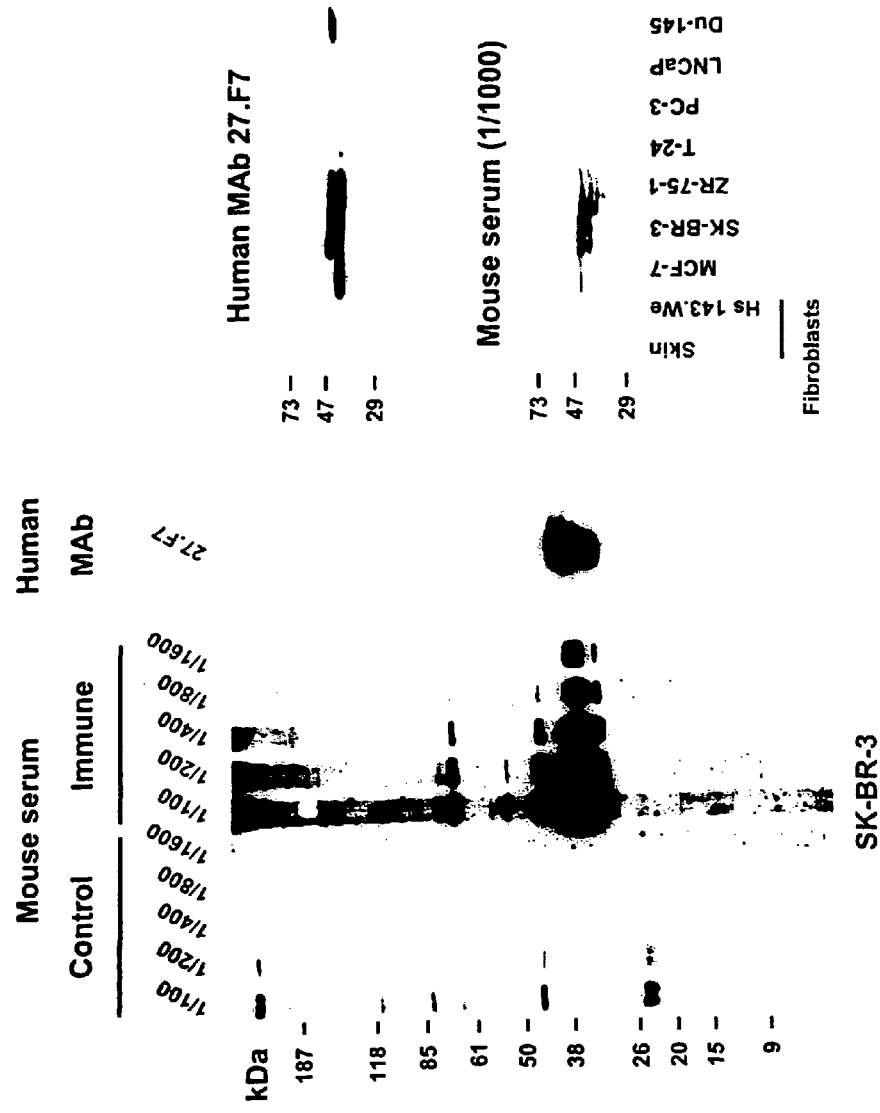
Figure 23:
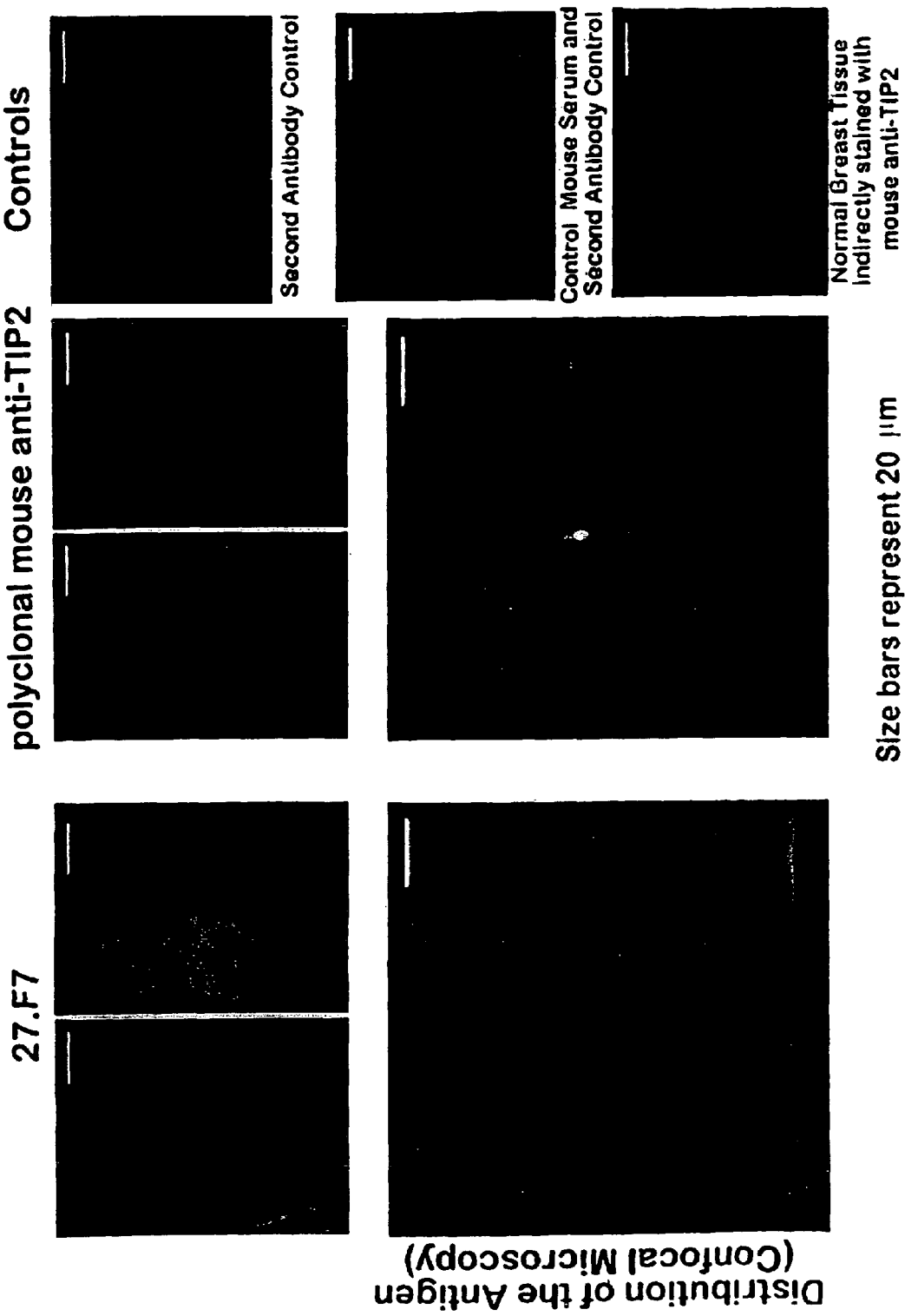
Figure 28:
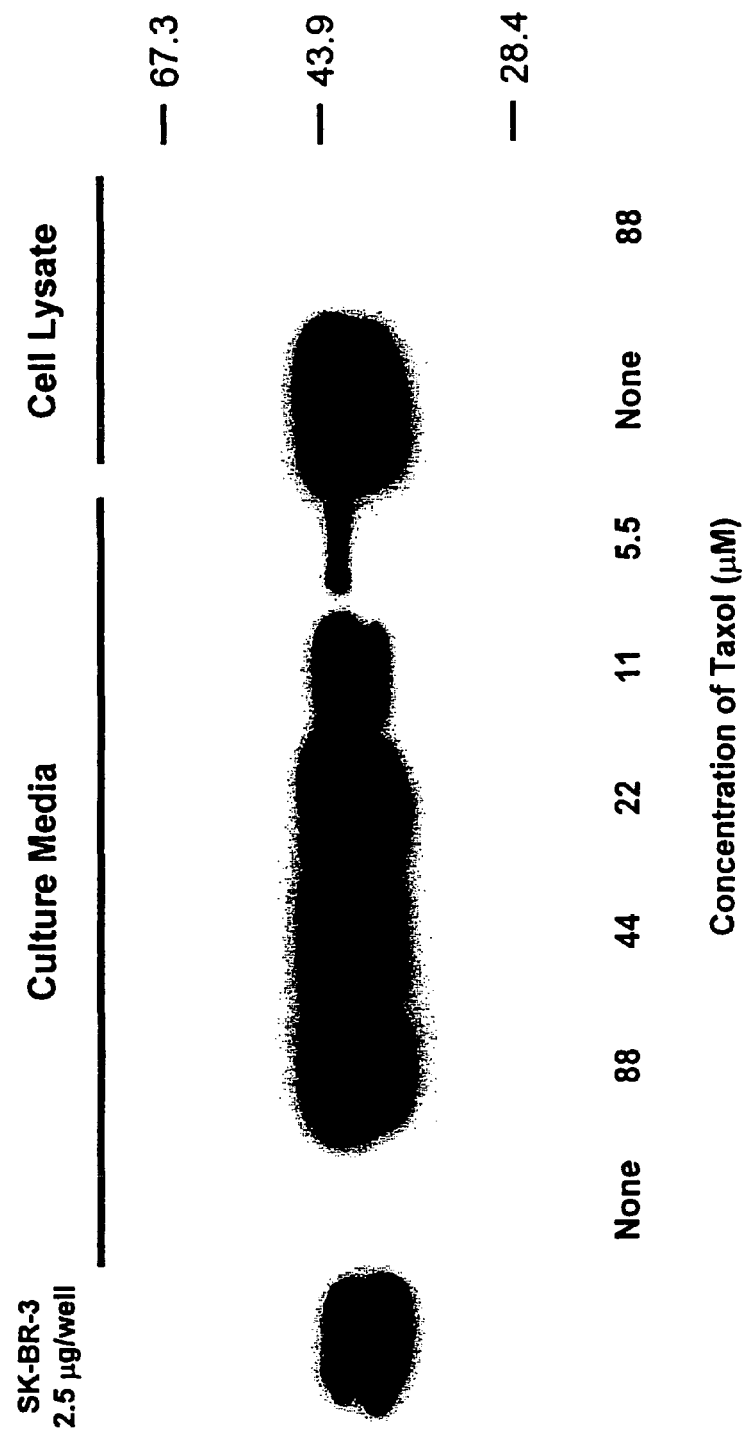

One of the antibodies, 27.F7, was produced in a Bioreactor in large quantities and used for immunoprecipitation of TIP-2 from the SK-BR-3 cell lysate. The precipitate yielded 2 bands of molecular weight characteristic of TIP-2 and corresponding to the bands recognized by anti-TIP-2 antibodies in Western blotting of cell lysates. The nitrocellulose membrane strip containing bands of TIP-2 was implanted subcutaneously into Balb/C mice in order to immunize them. After two implantations the mice developed a significant immune response to TIP-2 as proved by Western blot analysis of mice sera against SK-BR-3 cell lysates (FIGS. 21 and 28). The immune serum from these mice was positive in immunohistochemistry of actual tumor tissues (FIG. 23). These mice will be used for further development of mouse anti-TIP-2 monoclonal antibodies.

Figure 24:
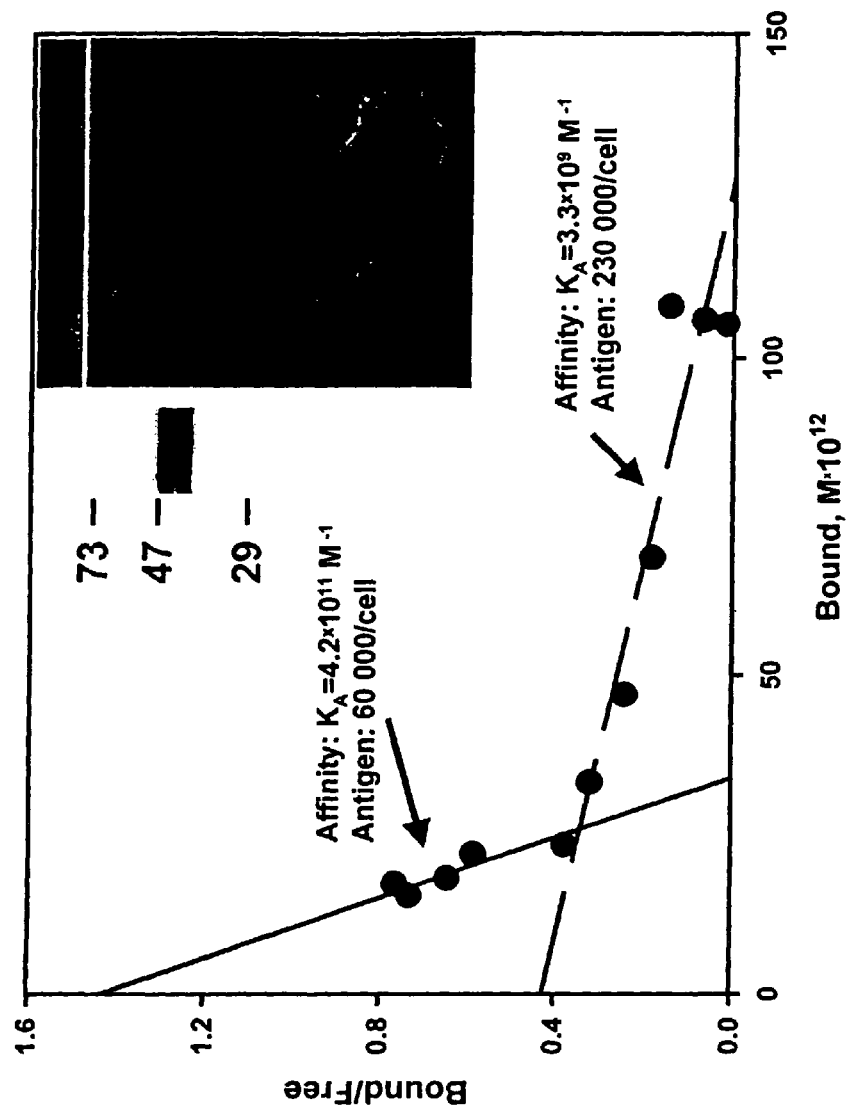
Figure 25:
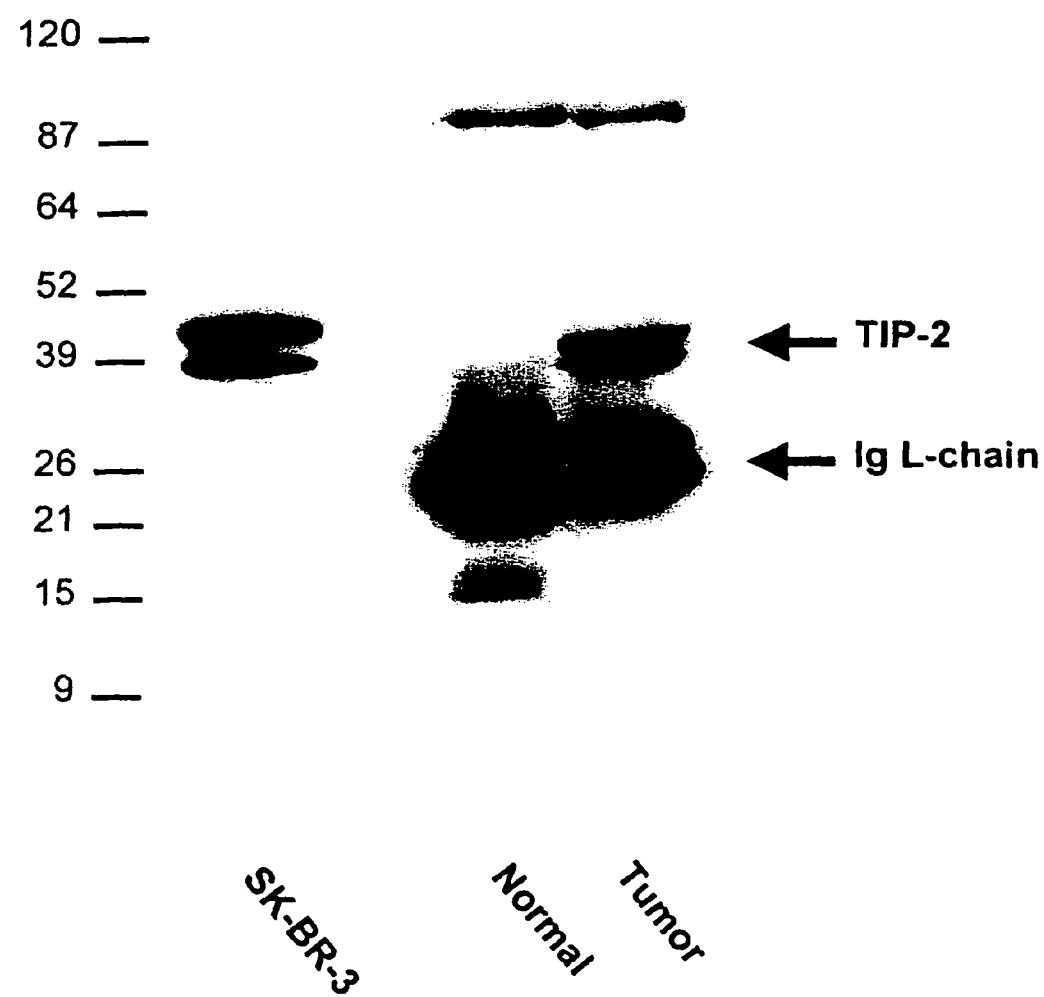

Using fhMAb 27.F7 an estimate of its affinity and also of number of TIP-2 molecules on the surface of SK-BR-3 was made. It was found that there are two subsets of TIP-2 molecules (which corresponds to Western blot data) which have different affinity to 27.F7. One subset (isoform) of TIP-2 is present at about 60 000 copies per cell and binds 27.F7 with the $K_a = 4.2 \times 10^{11} M^{-1}$ and another one is present at 230 000 copies per cell with the $K_a = 3.3 \times 10^9 M^{-1}$ (FIG. 24). Western blot analysis using human breast cancer cell lysates as well as primary tumor lysates showed a strong expression of TIP-2 in all tumor lesions and no traces of this antigen in normal unaffected breast epithelia (FIG. 25) These data were consistent with immunohistochemistry studies of the tissue section from the same clinical cases (data not shown).

Coupling 27.F7 to Liposomes

Figure 26:
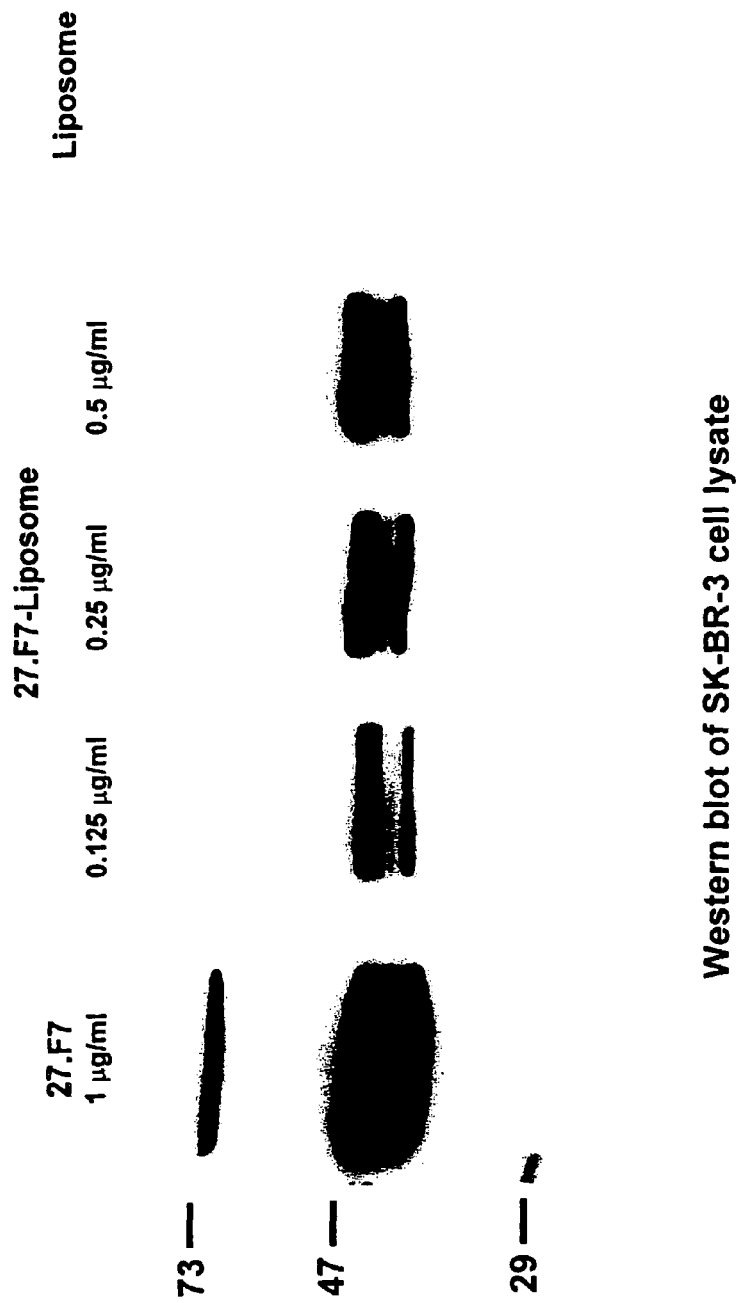

In order to explore the possibility of using anti-TIP-2 antibody as a vector for liposome delivery, a few different methods of coupling 27.F7 to liposomes were tested. Given the fact that the antibodies were of IgM, k isotype problems with the chemistry of coupling IgM to liposomes were expected. One of the protocols proved to be most effective yielding high ratio of antibody coupling to liposomes and preserving the antibody intact and reactive to TIP-2 as has been demonstrated by Western blot (FIG. 26).

TIP-2 Identification in Breast Cancer Patients

Figure 27:
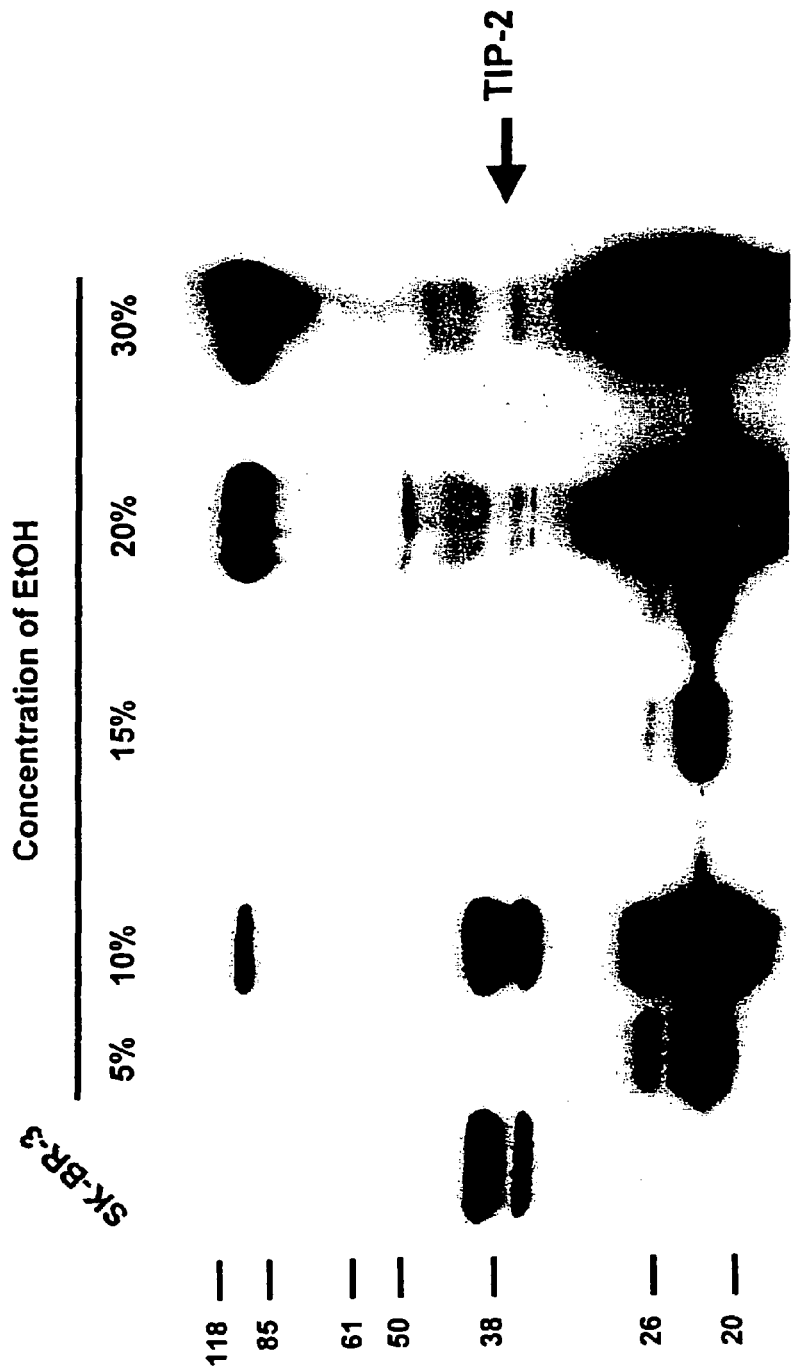

Also attempted were experiments to identify TIP-2 in serum or plasma of breast cancer patients. The rationale for such an assumption is that since TIP-2 is expressed on the surface of the cells, some part of it can be shed into circulation or even if this is not a case, then it still may appear in advanced stage disease patients' sera as a result of necrosis of the tumor or as a result of chemotherapeutic treatment. Since there is no ELISA assay for such a testing, patients' sera was tested for TIP-2 using Western blot of the whole serum sample and fhMAb 27.F7 as a tag. This method did not work because of a technical problem: The abundance of human serum albumin (HSA) in human serum masks the region on a gel where one would expect to locate TIP-2. Spiking the serum sample with the SK-BR-3 cell lysate (containing TIP-2) showed that TIP-2 could be identified both in human serum and human plasma by Western blot. In order to make the identification of TIP-2 in serum more profound a stepwise alcohol fractionation of human serum spiked with SK-BR-3 cell lysate was done to identify the alcohol concentration sufficient to precipitate TIP-2. It was shown (FIG. 27) that TIP-2 can be completely precipitated by 10% alcohol, while HSA and immunoglobulins (the major protein constituent if human serum) were still remaining in a solution. This can make the identification of TIP-2 in serum using Western blot easier. A two site immunoenzymatic assay, using high affinity mouse antibodies would provide another means of TIP-2 antigen identification.

Discussion

One of the targets which appeared is the PDZ domain containing protein localized both in cytosol and cell membrane of human breast cancer cells. This protein, called GIPC or TIP-2 (Tax interacting protein clone 2), is involved in vesicle trafficking and formation of protein networks. It has several properties, such as the ability to bind to RGS-Ga interacting protein, C domain, binding to HTLV-1 oncogene tax and bonding both to a-actinin and glucose transporter 1. While the precise physiological role of this protein is not known, it shows a consistent overexpression in breast cancer cells, with negligible if any expression in prostate cancer cells, and no expression in human fibroblasts. GIPC/TIP-2 is a 42 kDa protein which is present on a Western blot in a form of a doublet, probably because it has two open reading frames in its N-terminus. The number of copies per SK-BR-3 human breast cancer cell is quite high, approximately 300,000 copies per cell. Two fully human antibodies through which this antigen was identified belong to IgM isotype and have different epitope specificity. One of the antibodies, 27.B1 has a significant immunoreactivity with the surface of TIP-2-positive cells, while another, 27.F7 reacts only with the fixed cells, i.e. intracellularly. 27.B1 also expresses the profound internalization ability, while 27.F7 does not. Testing 27.B1 for its biological effect in the presence and absence of complement revealed that this antibody can cause the cellular cytolytic/cytostatic effect without the complement. The mechanism of this effect is most likely an apoptosis.

Figure 18:
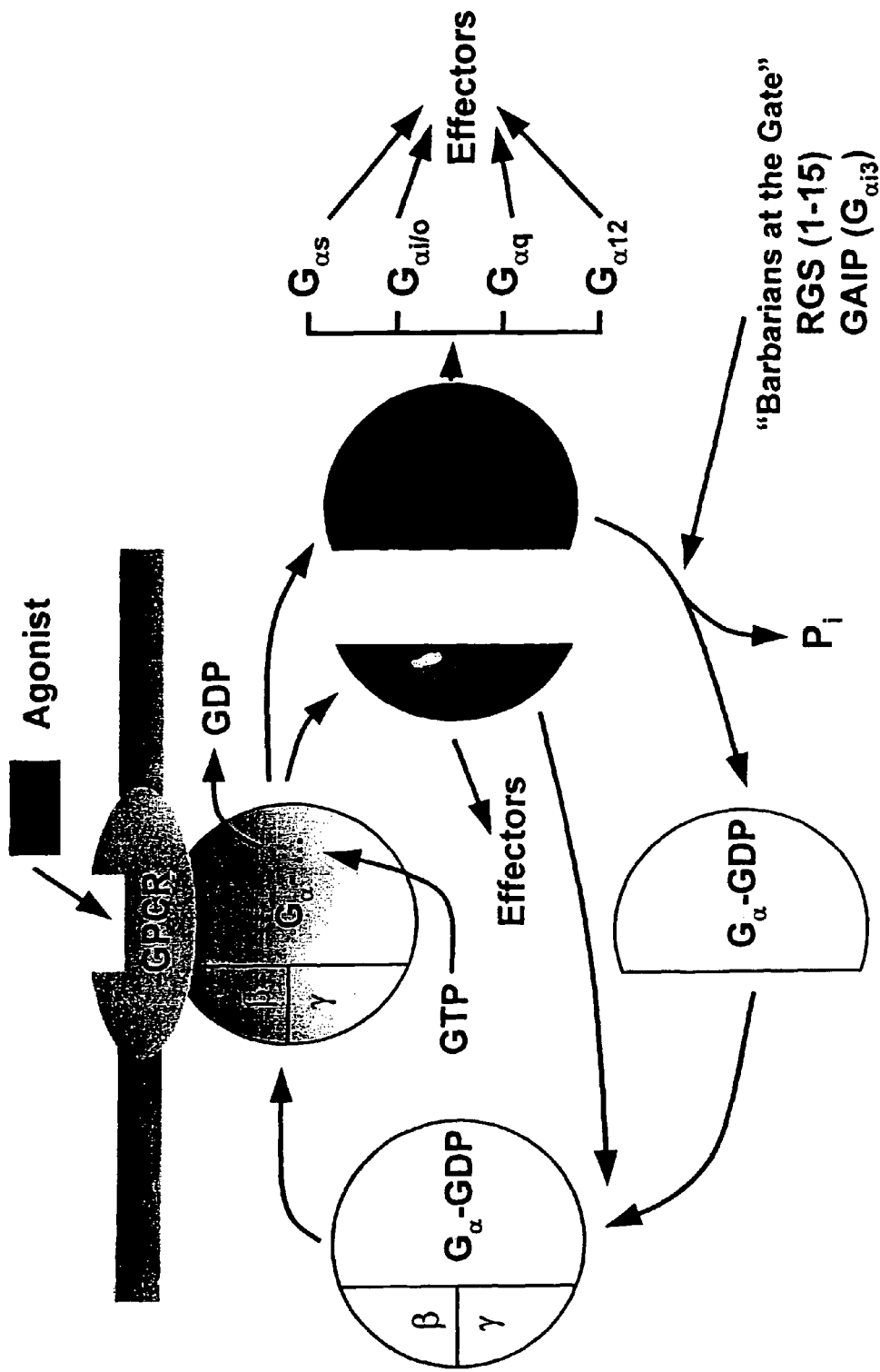

The protein identified herein was recently described as GIPC (GAIP Interacting Protein, C terminus), a protein which binds through its the PDZ domain to the C-terminal motif of the target proteins (6). In this case the target protein is GAIP ($G_{ai3}$ Interacting Protein), a membrane-anchored RGS (Regulators of G Signaling) protein, that interacts with $a_{i3}$ subunit of G protein and enhances its GTP-ase activity, facilitating deactivation of the G protein (FIG. 18, 19) (7). GIPC is the only protein described to date that binds to the C terminus of GAIP. The functional meaning of this interaction is not known. Recently, Rousset et al. (8) isolated an incomplete GIPC cDNA using Tax transactivator protein from HTLV-1 as a bait. They called this form of GIPC TIP-2 for Tax Interacting Protein clone 2 and showed that this form effectively interacts with the C-terminus of Tax oncoprotein. Tax oncoprotein is not the only oncoprotein that binds to PDZ domain through its C-terminus. E6 oncoprotein of human papilloma virus (HPV) (9) and E4 oncoprotein of D adenovirus type 9 (Ad9) also have C terminal motifs that bind to the PDZ domain (10). Such binding could be an underlying mechanism in the development of HPV-associated cancers or as in the case of E4 oncoprotein of mammary tumors (Ad9 is unique in eliciting only estrogen-dependent mammary tumors in female rats [11]). For all three oncoproteins the C terminal region is crucial for eliciting transforming potential (8,9,10). As C-terminal motif S/TXV is important for interaction with PDZ domain; it turned that Tax oncoprotein preserves interaction with TIP-2 even if the critical C-terminal valine is replaced, for example, with alanine, while all other Tax-binding PDZ domain-containing proteins lose their binding potential. TIP-2 was identified by screening breast cancer patients' B-cell-derived antibodies on a cDNA expression library prepared from human breast cancer cell line SK-BR-3. Briefly, poly(A)+ RNA was isolated from the cells, transcribed into cDNA and ligated into lambda pseudolytic phage, resulting in approximately $5 \times 10^5$ recombinants. The phage was amplified in *E. coli* Y1090 and then transferred to nitrocellulose membranes, which were treated with human antibodies. After exposure to antibodies the membranes were treated with anti-u chain rabbit polyclonal antibodies conjugated to horseradish peroxidase. Positive cDNA clones were converted into plasmid forms by excision in vivo, and the plasmid DNA was purified and submitted to sequence analysis (FIG. 8). The resulting sequence was submitted to homology search using a Gene Bank database. Two human monoclonal antibodies (27.F7 and 27.B1) developed from breast cancer patient's lymph node B-cells were identified as antibodies reactive with TIP-2—however apparently with different epitopes.

The GeneBank/Protein Database information for this protein is the following: NCBI reference—NP005707.1PGGLUT1CBP; *Homo sapiens* RGS-GAIP interacting protein GIPC mRNA, complete cds (AF0889816); *Homo sapiens* Tax interacting protein 2 mRNA, partial cds (AF028824). The subject invention demonstrates that this antigen, Tax Interacting Protein 2 (TIP-2), can serve as a distinctive and specific marker for breast and prostate adenocarcinoma.

Summary of Experiments

Using a specific fusion partner cell line MFP-2 were developed two fully human antibodies to breast and prostate cancer-associated antigens. Both antigens were reactive with a 42 kDa-protein target, which was identified through SEREX technology as Ga-interacting protein, C terminus or Tax interacting protein, clone 2. This protein is specifically overexpressed in three human breast cancer cell lines, SK-BR-3, MCF-7 and ZR-1-75, has very low if any expression level in human prostate cancer cell lines, PC-3, LNCaP and DU-145 and no expression in two human fibroblast cell lines. The TIP-2 antigen was found to be expressed in all breast cancer tissues and most of prostate cancer. Normal breast epithelia were negative for staining with anti-TIP-2 antibodies as was benign prostate hyperplasia (BPH) tissue. Two fully human monoclonal antibodies against GIPC/TIP-2 antigen were directed against different epitopes and gave a distinctive pattern of immunoreactivity with human breast cancer cells. Antibody 27.F7 was reactive both with formalin-fixed and live cancer cells SK-BR-3 and MCF-7, while antibody 27.B1 reacted with live and fixed SK-BR-3 cells and only with fixed MCF-7 cells. On the other hand antibody. 27.B1 showed a rapid internalization, while 27.F7 would not internalize. Also, when tested for cytolytic/cytostatic effect in the presence and without complement, it appeared, that 27.F7 does not cause any cytotoxic effect on the cells, while 27.B1 causes cytotoxic effect which is not dependent on complement. The Scatchard analyis of number of copies of GIPC/TIP-2 antigen per cell showed that thus antigen is present at quite high number of copies reaching somewhat 300 000 copies per cell. This includes the total number of TIP-2 molecules, both on the surface and in cytosol. Using one of the human antibodies, 27.F7 as immunoprecipitation bait, isolated was a small amount of TIP-2 and were able to raise several mouse monoclonal antibodies to this antigen. All the antibodies react in Western Blot with the protein band, which corresponds to TIP-2, and also give distinctive and specific positive straining of cancer cell and primary tumor tissues. Using human antibodies it was shown that normally GIPC/TIP-2 is not secreted or shed by cancer cells but can be found in culture media only as a result of cell destruction. The treatment of SK-BR-3 cells with the increasing amounts of Taxol, showed TIP-2 antigen released into the media in a dose dependent manner, therefore indicating that this marker is valuable for the monitoring of natural or chemotherapy-induced necrosis of tumor lesions.

REFERENCES FOR THIRD SERIES OF EXPERIMENTS

1733. Sahin U, Tureci O, Schmitt H, Cochlovius B, et al. Human neoplasms elicit multiple specific immune responses in the autologous host. Proc. Natl. Acad. Sci USA 92:11810-11813, 1995.
2. Saras J, Heldin C H. PDZ domains bind carboxy-terminal sequences of target proteins TIBS 21:455-458, 1996.
3. Kennedy M B. Origin of PDZ (DHR, GLGF) domains. Trends Biochem Sci. 20:350, 1995.
4. Scanlan M J, Chen Y-T, Williamson B, Gure A O, Stockert, J D, Gordan O, Tureci O, Sahin U, Pfreundschuh M, Old L J. Characterization of human colon cancer antigens recognized by autologous antibodies. Int. J. Cancer 76:652-658, 1998.
5. Scanlan M J, Williamson B, Jungbluth A, Stockert E, Arden K C, Viars C S, Gure A O, Gordan J D, Chen Y-T, Old L J. Isoforms of the human PDZ-73 protein exhibit differential tissue expression. Biochimica et Biophysica Acta 1445:39-52, 1999.
6. De Vries L, Lou X, Zhao G, Zheng B, Farquhar M G. GIPC, a PDZ domain containing protein, interacts specifically with the C terminus of RGS-GAIP. Proc. Natl. Acad. Sci. USA 95:12340-12345, 1998
7. Berman D M, Gilman A G. Mammalian RGS proteins: barbarians at the gate. J. Biol. Chem. 273:1269-1272, 1998
8. Rousset R, Fabre S, Desbois C, Bantignies F, Jalinot P. The C-terminus of the HTLV-1 Tax oncoprotein mediates interaction with the PDZ domain of cellular proteins. Oncogene 16:643-654, 1998.
9. Kyono T, Hiraiwa A, Fujita M, Hayashi Y, Akiyama T, Ishibasahi M. Binding of high risk papillomavirus E6 oncoproteins to the human homologue of the *Drosophila* discs large tumor suppressor protein. Proc. Natl. Acad. Sci. USA 94:11612-11616, 1997.
10. Lee S S, Weiss R S, Javier R T. Binding of human virus oncoproteins to hDlg/SAP97, a mammalian homologue of the *Drosophila* discs large tumor suppressor protein. Proc. Natl. Acad. Sci. USA 94:6670-6675, 1997.
11. Shenk T. in Fields Virology, eds. Fields B N, Knipe D M, Howley P M (Lippinscott, Philadelphia), Vol. 2. pp. 2111-2148, 1996.

FOURTH SERIES OF EXPERIMENTS

Protein Antigens Identified by Natural Human Monoclonal Antibodies Developed from Breast and Prostate Cancer Patients' B-Cells Introduction In addition to GIPC/TIP-2, the method described in the third series of experiments (above) may be used to identify other protein antigens, including those listed below.

Example I

Human mRNA for KIAA0338 gene, Partial Cds

Fully human monoclonal antibody (fhMAb) 13.42 recognizes the unknown antigen human mRNA of which is known for the gene called KIAA0338 (sequence shown in FIG. 32). The calculated molecular weight (MW) for this breast cancer-associated marker is 103.5 kDa, although on Western blot it shows the protein of molecular weight ~40 kDa. Three MHC I binding peptides were deduced from the sequence; these peptides may be considered as peptide vaccine candidates.

Example II

Human Non-Muscle Alpha-Actinin mRNA, Complete Cds: *Homo sapiens* Actinin, Alpha 4 (ACTN4) mRNA fhMAb 13.2C1 recognizes non-muscle alpha-actinin of MW 105 kDa (sequence shown in FIG. 33) which is found in many human tissues, but there are reports on the association of this marker with breast cancer. We have deduced three MHC I-restricted peptides, which can be considered as peptide vaccine candidates for breast cancer. fhMAb 13.2C1 also recognizes *homo sapiens* actinin, alpha 4 (ACTN4) mRNA (sequence shown in FIG. 34).

Example III

Human Clathrin Coat Assembly Protein 50 (AP50) mRNA fhMAb 22.8D11 is directed against breast and prostate cancer-associated marker which is human clathrin coat assembly protein 50 (AP50) of MW 50 kDa. Although its mRNA (sequence shown in FIG. 34) was reported in some human tissues including ovarian tumors, the protein product seems to be associated with breast and prostate cancer. To the best of our knowledge this marker was not reported before as being associated with these types of cancer. We have deduced four MHC I-restricted peptides for their possible significance as peptide vaccine candidates.

Example IV

*Homo sapiens* gp 130 Associated Protein GAM mRNA; *Homo sapiens* Amino-Terminal Enhancer of Split (AES) mRNA; Antiquitin 1 mRNA fhMAb 33.2H6 is directed against human gp130-associated protein GAM of MW ~22 kDa. This protein was never reported before as breast cancer-associated antigen, although its mRNA (sequence shown in FIG. 37) was found in ovarian tumors. Its homologue human amino-terminal enhancer of split (AES) mRNA (sequence shown in FIG. 38) has an unknown function but has been proposed as a candidate human cancer antigen. We have deduced one MHC I binding peptide as possible peptide vaccine candidate. The same antibody was reactive towards antiquitin 1 (MW 55 kDa)—26 g turgor protein homolog (sequence shown in FIG. 39). Partial mRNA for this antigen was found in a number of human tissues, however it was never reported before for its association with breast cancer. We have deduced three MHC I-restricted peptides from the amino acid sequence of this protein.

Example V

ARP2/3 Protein Complex 41 KD subunit (P41-ARC), mRNA fhMAb 39.A7 is directed against ARP2/3 protein complex 41 kDa subunit (P41-ARC). This protein was not known for being associated with breast cancer before. We have deduced one MHC I-restricted peptide as a candidate for peptide-based vaccine (sequence shown in FIG. 40).

Example VI

*Homo sapiens* seb4D mRNA; *Homo sapiens* seb4B mRNA fhMAb 50.1B3 recognizes the protein in breast and prostate cancer tissues which was identified as seb4B/4D antigen of MW~ s25 kDa. This protein also was not known for its specific association with breast cancer. The function is unknown, while its mRNA was found in a number of normal human tissues. We have deduced two MHC 1-restricted peptides from the primary sequence of this protein (sequences shown in FIGS. 41a and 41b.

Example VII

*Homo sapiens* Lamin A/C (LMNA) mRNA fhMAb 59.3G7 is reactive to human lamin A/C an intermediate filament protein, mRNA for which was found in many human tissues. The MW for this protein is ~65 kDa. This protein was identified earlier by different research group through the serum antibody found in cancer patients. It is considered to be overexpressed in breast adenocarcinomas as well as in some other types of cancer. We have deduced three MHC I-restricted as potential candidates for peptide-based vaccine (sequence shown in FIG. 42).

---

What is claimed is:

1. A method for diagnosing a breast cancer in a subject by detecting TIP-2 antigen-bearing cancer cells which comprises:
   (a) obtaining a sample of the subject's peripheral blood;
   (b) contacting the sample with an antibody directed to an epitope on TIP-2 antigen or a Fab fragment of such an antibody, wherein the epitope is recognized by the antibody or Fab fragment, and the antibody or Fab fragment is detectably labeled, under appropriate conditions so as to produce an antibody-TIP-2 antigen complex or a Fab fragment-TIP-2 antigen complex comprising the detectably labeled antibody or Fab fragment bound to any TIP-2 antigen bearing breast cancer cells in the sample;
   (c) removing any labeled antibody or Fab fragment not in the antibody-TIP-2 antigen complex or Fab fragment-TIP-2 antigen complex formed in step (b); and
   (d) determining the presence of any antibody-TIP-2 antigen complex or any Fab fragment-TIP-2 antigen complex by detecting the detectably labeled antibody or Fab fragment, the presence of antibody-TIP-2 antigen complex or Fab fragment-TIP-2 antigen complex being diagnostic of breast cancer so as to thereby diagnose breast cancer in the subject.

2. The method of claim 1, wherein the detectably labeled antibody or Fab fragment is labeled with a radioactive isotope, an enzyme, a dye, a biotin, a fluorescent label or a chemiluminescent label.

3. The method of claim 1, wherein the antibody is a monoclonal antibody.

4. The method of claim 1, wherein the epitope is recognized by monoclonal antibody 27.F7 produced by the hybridoma designated 27.F7 (ATCC Designation No. PTA-1598).

5. The method of claim 1, wherein the epitope is recognized by monoclonal antibody 27.B1 produced by the hybridoma designated 27.B1 (ATCC Designation No. PTA-1599).

6. The method of claim 1, wherein the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, tissues from breast metastases, or culture media.

7. A method for diagnosing a breast cancer in a subject by detecting TIP-2 antigen-bearing cancer cells which comprises:
(a) obtaining a sample of the subject's peripheral blood;
(b) contacting the sample with an antibody directed to an epitope on TIP-2 antigen or a Fab fragment of such an antibody, wherein the epitope is recognized by the antibody or Fab fragment, under appropriate conditions to produce an antibody-TIP-2 antigen complex or Fab fragment-TIP-2 antigen complex comprising the antibody or Fab fragment bound to any TIP-2 antigen bearing breast cancer cells in the sample;
(c) removing any antibody or Fab fragment not in the antibody-TIP-2 antigen complex or Fab fragment-TIP-2 antigen complex formed in step (b);
(d) contacting the antibody-TIP-2 antigen complex or Fab fragment-TIP-2 antigen complex from step (c) with a second antibody which specifically binds to the antibody-TIP-2 antigen complex or the Fab fragment-TIP-2 antigen complex, said second antibody being detectably labeled, under appropriate conditions so as to permit the labeled second antibody to bind to the antibody-TIP-2 antigen complex or the Fab fragment-TIP-2 antigen complex;
(e) removing any labeled second antibody or Fab fragment not bound to the antibody-TIP-2 antigen complex or the Fab fragment-TIP-2 antigen complex product from (d); and
(f) determining the presence of any antibody-TIP-2 antigen complex or Fab fragment-TIP-2 antigen complex bound to the labeled second antibody by detecting the label, the presence of the antibody-TIP-2 antigen complex or the Fab fragment-TIP-2 antigen complex being diagnostic of breast cancer so as to thereby diagnose breast cancer in the subject.

8. The method of claim 7, wherein the detectably labeled second antibody is labeled with a radioactive isotope, an enzyme, a dye, biotin, a fluorescent label or a chemiluminescent label.

9. The method of claim 7, wherein the antibody is a monoclonal antibody.

10. The method of claim 7, wherein the epitope is recognized by monoclonal antibody 27.F7 produced by the hybridoma designated 27.F7 (ATCC Designation No. PTA-1598).

11. The method of claim 7, wherein the epitope is recognized by monoclonal antibody 27.B1 produced by the hybridoma designated 27.B1 (ATCC Designation No. PTA-1599).

12. The method of claim 7, wherein the sample is selected from the group consisting of serum, plasma, saliva, tears, mucosal discharge, urine, peritoneal fluid, cerebrospinal fluid, lymphatic fluid, bone marrow, breast biopsy, tissue, lymph nodes, prostate tissue, tissues from breast and prostate metastases, or culture media.

13. An in vivo method for diagnosing a breast cancer in a subject by detecting TIP-2 antigen-bearing cancer cells which comprises:
a) administering to the subject an antibody directed to an epitope on TIP-2 antigen or a Fab fragment of such an antibody, wherein the epitope is recognized by the antibody or the Fab fragment and the antibody or Fab fragment is detectably labeled, under appropriate conditions such that the antibody or Fab fragment binds to TIP-2 antigen bearing breast cancer cells in the subject; and
b) determining the presence of any antibody-TIP-2 antigen complex or any Fab fragment-TIP-2 antigen complex by detecting the detectably labeled antibody or Fab fragment, the presence of the antibody-TIP-2 antigen complex or the Fab fragment-TIP-2 antigen complex being diagnostic of breast cancer so as to thereby diagnose breast cancer in the subject.

14. The method of claim 13, wherein the detectably labeled second antibody is labeled with a radioactive isotope, an enzyme, a dye, biotin, a fluorescent label or a chemiluminescent label.

15. The method of claim 13, wherein the antibody is a monoclonal antibody.

16. The method of claim 13, wherein the epitope is recognized by monoclonal antibody 27.F7 produced by the hybridoma designated 27.F7 (ATCC Designation No. PTA-1598).

17. The method of claim 13, wherein the epitope is recognized by monoclonal antibody 27.B1 produced by the hybridoma designated 27.B1 (ATCC Designation No. PTA-1599).

18. The method of claim 13, wherein in step (b) presence of the antibody or Fab fragment thereof bound to the surface of cells in the subject is detected wherein means for detecting the detectably labeled antibody or Fab fragment is an imaging device.

19. The method of claim 13, wherein the imaging device is a magnetic resonance imaging device or an X-ray immunoscintigraphy imaging device.

20. A method for monitoring progression of breast cancer, wherein the cancer cells are TIP-2 antigen-bearing breast cancer cells in a subject comprising:
a) administering to a subject diagnosed with breast cancer an antibody directed to an epitope on TIP-2 antigen or a Fab fragment of such an antibody, which epitope is recognized by the antibody or Fab fragment, and the antibody or Fab fragment is detectably labeled, under appropriate conditions so as to bind the antibody or the Fab fragment to TIP-2 antigen bearing cells in the subject;
b) determining the presence of detectably labeled antibody or Fab fragment bound to the surface of cells in the subject;
c) comparing the presence of the detectably labeled antibody or Fab fragment bound to cells in step (b) with the presence of detectably labeled antibody bound to cells at (i) diagnosis time or (ii) after treatment, wherein a greater presence of detectably labeled antibody or Fab fragment bound to cells in step (b) than at (i) diagnosis time or (ii) after treatment, indicates progression of the breast cancer in the subject and a lesser presence of detectably labeled antibody or Fab fragment bound to cells in step (b) than at (i) diagnosis time or (ii) after treatment indicates regression of the breast cancer in the subject.

* * * * *